United States Patent
Shoseyov et al.

(10) Patent No.: US 11,801,329 B2
(45) Date of Patent: Oct. 31, 2023

(54) DERMAL FILLERS AND APPLICATIONS THEREOF

(71) Applicant: CollPlant Ltd., Rehovot (IL)

(72) Inventors: Oded Shoseyov, Shoham (IL); Nadav Orr, Mazkeret Batya (IL); Jasmine Seror Maknouz, Tel-Aviv (IL); Revital Zarka, Mazkeret Batya (IL)

(73) Assignee: CollPlant Ltd., Rehovot (IL)

( * ) Notice: Subject to any disclaimer, the term of this patent is extended or adjusted under 35 U.S.C. 154(b) by 0 days.

(21) Appl. No.: 17/052,216

(22) PCT Filed: May 2, 2019

(86) PCT No.: PCT/IL2019/050492
§ 371 (c)(1),
(2) Date: Nov. 2, 2020

(87) PCT Pub. No.: WO2019/211854
PCT Pub. Date: Nov. 7, 2019

(65) Prior Publication Data
US 2021/0138113 A1     May 13, 2021

Related U.S. Application Data

(60) Provisional application No. 62/666,267, filed on May 3, 2018.

(51) Int. Cl.
*A61L 27/26*     (2006.01)
*A61L 27/36*     (2006.01)
(Continued)

(52) U.S. Cl.
CPC .............. *A61L 27/26* (2013.01); *A61K 8/042* (2013.01); *A61K 8/65* (2013.01); *A61K 8/735* (2013.01); *A61L 27/3687* (2013.01); *A61Q 19/08* (2013.01); *C08L 5/08* (2013.01); *C08L 89/04* (2013.01); *C12N 15/8257* (2013.01);
(Continued)

(58) Field of Classification Search
None
See application file for complete search history.

(56) References Cited

U.S. PATENT DOCUMENTS 3,121,049 A     2/1964     Tomio
3,131,130 A     4/1964     Oneson
(Continued)

FOREIGN PATENT DOCUMENTS

EP     0067553 A2     12/1982
EP     0194809 A1     9/1986
(Continued)

OTHER PUBLICATIONS

Gaudet, I.D. & Shreiber, D.I., Characterization of Methacrylated Type-I Collagen as a Dynamic, Photoactive Hydrogel, Biointerphases, 7 (2012) pp. 25-33. (Year: 2012).*
(Continued)

*Primary Examiner* — Dominic Lazaro

(57) ABSTRACT

The disclosure herein relates to photoinitiated dermal fillers, hyaluronic acid-rhCollagen double crosslinked dermal fillers and hyaluronic acid-rhCollagen semi interpenetrated network, each comprising plant-derived human collagen, as well as methods of using the same.

12 Claims, 61 Drawing Sheets

Specification includes a Sequence Listing.

(51) Int. Cl.
    *C08L 5/08* (2006.01)
    *C12N 15/82* (2006.01)
    *A61K 8/73* (2006.01)
    *A61K 8/65* (2006.01)
    *A61K 8/04* (2006.01)
    *A61Q 19/08* (2006.01)
    *C08L 89/04* (2006.01)

(52) U.S. Cl.
    CPC ...... *A61K 2800/59* (2013.01); *A61K 2800/81* (2013.01); *A61K 2800/91* (2013.01); *A61L 2400/06* (2013.01); *A61L 2430/34* (2013.01)

(56) References Cited

U.S. PATENT DOCUMENTS

| | | |
|---|---|---|
| 3,314,861 A | 4/1967 | Tadahiko |
| 3,530,037 A | 9/1970 | Nishihara |
| 3,934,852 A | 1/1976 | Weber et al. |
| 3,949,073 A | 4/1976 | Daniels et al. |
| 4,233,360 A | 11/1980 | Luck et al. |
| 4,488,911 A | 12/1984 | Luck et al. |
| 4,597,762 A | 7/1986 | Walter et al. |
| 4,855,237 A | 8/1989 | Morinaga et al. |
| 5,316,931 A | 5/1994 | Donson et al. |
| 5,316,942 A | 5/1994 | Fink |
| 5,670,369 A | 9/1997 | Fink et al. |
| 5,814,328 A | 9/1998 | Gunasekaran |
| 5,827,937 A | 10/1998 | Agerup |
| 5,854,382 A | 12/1998 | Loomis |
| 5,900,245 A | 5/1999 | Sawhney et al. |
| 5,997,895 A | 12/1999 | Narotam et al. |
| 6,051,248 A | 4/2000 | Sawhney et al. |
| 6,217,894 B1 | 4/2001 | Sawhney et al. |
| 6,352,710 B2 | 3/2002 | Sawhney et al. |
| 6,531,147 B2 | 3/2003 | Sawhney et al. |
| 6,605,294 B2 | 8/2003 | Sawhney |
| 6,617,431 B1 | 9/2003 | Gruber et al. |
| 7,238,364 B2 | 7/2007 | Sawhney et al. |
| 7,637,900 B2 | 12/2009 | Burgess |
| 7,648,713 B2 | 1/2010 | Sawhney et al. |
| 7,780,980 B2 | 8/2010 | Sawhney |
| 7,862,831 B2 | 1/2011 | Wang et al. |
| 7,897,165 B2 | 3/2011 | Elisseeff et al. |
| 8,038,665 B2 | 10/2011 | Burgess |
| 8,105,622 B2 | 1/2012 | Sawhney |
| 8,455,717 B2 | 6/2013 | Shoseyov et al. |
| 8,673,333 B2 | 3/2014 | Elisseeff et al. |
| 8,703,118 B2 | 4/2014 | Schroeder et al. |
| 8,759,487 B2 | 6/2014 | Shoseyov et al. |
| 8,883,182 B2 | 11/2014 | Ratcliffe et al. |
| 8,945,624 B2 | 2/2015 | Elisseeff et al. |
| 9,662,422 B2 | 5/2017 | Pollock et al. |
| 9,795,711 B2 | 10/2017 | Yu et al. |
| 9,821,086 B2 | 11/2017 | Yu et al. |
| 2002/0091251 A1* | 7/2002 | Zhao ................. A61P 37/04 536/53 |
| 2002/0098578 A1 | 7/2002 | Prockop et al. |
| 2002/0142391 A1 | 10/2002 | Kivirikko et al. |
| 2003/0096973 A1 | 5/2003 | Gruber |
| 2006/0100138 A1* | 5/2006 | Olsen ................. A61L 27/24 623/23.72 |
| 2007/0053987 A1 | 3/2007 | Bayer |
| 2007/0186312 A1* | 8/2007 | Shoseyov ........... C12N 9/0071 435/468 |
| 2009/0074868 A1* | 3/2009 | Elisseeff ............. A61K 8/8152 424/78.38 |
| 2009/0093755 A1 | 4/2009 | Schroeder et al. |
| 2009/0324722 A1 | 12/2009 | Elisseeff |
| 2010/0055184 A1 | 3/2010 | Zeitels et al. |
| 2010/0119451 A1 | 5/2010 | Sawhney |
| 2011/0002997 A1 | 1/2011 | Elisseeff et al. |
| 2013/0116188 A1 | 5/2013 | Pollock et al. |
| 2014/0052168 A1 | 2/2014 | Sawhney |
| 2016/0120955 A1 | 5/2016 | Gueta et al. |
| 2016/0184440 A1 | 6/2016 | Elisseeff |
| 2016/0193384 A1 | 7/2016 | Phopasc |
| 2018/0028719 A1 | 2/2018 | Yu et al. |

FOREIGN PATENT DOCUMENTS

| | | |
|---|---|---|
| EP | 0278667 A2 | 8/1988 |
| EP | 3253417 A1 | 12/2017 |
| EP | 2753647 B1 | 8/2018 |
| EP | 2550027 B2 | 3/2019 |
| JP | S-6314693 A | 1/1988 |
| JP | 2008-514225 | 5/2008 |
| JP | 2009-507103 | 2/2009 |
| JP | 2015-529268 | 10/2015 |
| WO | WO-1987006261 A1 | 10/1987 |
| WO | WO-1996029370 A2 | 9/1996 |
| WO | WO-2004029137 A2 | 4/2004 |
| WO | WO-2005034875 A2 | 4/2005 |
| WO | WO-2005035442 A1 | 4/2005 |
| WO | WO-2006035442 A2 | 4/2006 |
| WO | WO-2006036681 A2 | 4/2006 |
| WO | WO-2008098019 A2 | 8/2008 |
| WO | WO-2009017555 A1 | 2/2009 |
| WO | WO-2009018555 A1 | 2/2009 |
| WO | WO-2009053985 A1 | 4/2009 |
| WO | WO-2010021738 A2 | 2/2010 |
| WO | WO-2010053918 A1 * | 5/2010 ............. A61K 38/39 |
| WO | WO-2013067293 A1 | 5/2013 |
| WO | WO-2013106715 A1 | 7/2013 |
| WO | WO-2016057603 A1 | 4/2016 |
| WO | WO-2018225076 A1 | 12/2018 |

OTHER PUBLICATIONS

Alster, T. S. et al. (2000). Human-derived and new synthetic injectable materials for soft-tissue augmentation: current status and rule in cosmetic surgery. *Plastic and reconstructive surgery*, 105(7), 2515-2525.

Andres, B. M. et al. (2008). Treatment of tendinopathy: what works, what does not, and what is on the horizon. *Clinical Orthopaedics and Related Research*, 466(7), 1539-1554.

Baier Leach, J. et al. (2003). Photocrosslinked hyaluronic acid hydrogesl: natural, biodegradable tissue engineering scaffolds. *Biotechnology and bioengineering*, 82(5), 578-589.

Brinkman, W. T. et al. (2003). Photo-cross-linking of type I collagen gels in the presence of smooth muscle cells: mechanical properties, cell viability, and function. *Biomacromolecules*, 4(4), 890-895.

Bulleed, N. J. et al. (2000). Recombinant expression systems for the production of collagen. *Biochemical Society Transactions*, 28(4), 350-353.

Castrow II, F. F. et al. (1983). Injectable collagen implant-update. *Journal of the American Academy of Dermatology*, 9(6), 889-893.

Dawson, W. O. et al. (1989). A tobacco mosaic virus-hybrid expressess and loses an added gene. *Virology*, 172(1), 285-292.

Delong, J. M. et al. (2011). Update on platelet-rich plasma. *Current Orthopedic Practice*, 22(6), 514-523.

Di Matteo, B. et al. (2015). Platelet-rich plasma: evidence for the treatment of patellar and Achilles tendinopathy—a systematic review. *Musculoskeletal Surgery*, 99(1), 1-9.

Duggan, S. et al. (2015). Synthesis of mucoadhesive thiolated gelatin using a two-step reaction process. *European Journal of Pharmaceutics and Biopharmaceutics*, 91, 75-81.

Eckert, K. A. et al. (1991). DNA polymerase fidelity and the polymerase chain reaction. *Genome Research*, 1(1), 17-24.

Elisseeff, J. et al. (1999). Transdermal photopolymerization for minimally invasive implantation. *Proceedings of the National Academy of Sciences*, 96(6), 3104-3107.

French, R. et al. (1986). Bacterial gene inserted in an engineerred RNA virus: efficient expression in monocotyledonous plant cells. *Science*, 231(4743), 1294-1297.

Fromm, M. E. et al. (1986). Stable transformation of maize after gene transfer by electroporation. *Nature*, 319(6056), 791-793.

Gallie, D. R. et al. (1987). The 5'-leader sequence of tobacco mosaic virus RNA enhances the expression of foreign gene transcripts in vitro and in vivo. *Nucleic Acids Research*, 15(8), 3257-3273.

(56) References Cited

OTHER PUBLICATIONS

Gaudet, I. D. et al. (2012). Characterization of methacrylated type-I collagen as a dynamic, photactive hydrogel. *Biointerphases*, 7(1-4), 25.
Goldman, M. P. et al. (2007). A randomized trial to determine the influence of laster therapy, monopolar radiofrequency treatment, and intense pulsed light therapy administered immediately acid gel implantation. *Dermatologic Surgery*, 33(5) 535-542.
Habeeb, A. S. A. (1966). Determination of free amino groups in proteins by trinitrobenzenesulfonic acid. *Analytical Biochemistry*, 14(3), 328-336.
Hare, P. D. et al. (1997). Metabolic implications of stress-induced proline accumulation in plants. *Plant Growth Regulation*, 21(2), 79-102.
Harrison, S. et al. (2011). Platelet activation by collagen provides sustained release of anabolic cytokines. *The American Journal of Sports Medicine*, 39(4), 729-734.
Hillel, A. T. et al. (2012). Validation of a small animal model for soft tissue filler characterization. *Dermatologic Surgery*, 38(3), 471-478.
Horsch, R. B. et al. (1989). Leaf disc transformation. In *Plant Molecular Biology Manual* (pp. 63-71). Soringer, Dordrecht.
Hulmes, D. J. (2002). Building collagen molecules, fibrils, and suprafibrillar structures. *Journal of Structural Biology*, 137(1-2), 2-10.
Inkinen, K. (2003). Connective tissue formation in wound healing: An experimental study. *University of Helsinki, Faculty of Science, Department of Biosciences, Division of Biochemistry*, 1-107.
International Prelimary Report on Patentability (Chapter I of the PCT) dated Nov. 12, 2020, in the corresponding PCT International Application No. PCT/IL2019/050492, dated May 2, 2019.
International Search Report and Written Opinion of the International Searching Authority dated Jul. 16, 2019, in the corresponding PCT International Application No. PCT/IL2019/050492, dated May 2, 2019.
Kadler, K. (2004). Matrix loading: assembly of extracellular matrix collagen fibrils during embryogenesis. *Birth Defects Research Part C: Embryo Today: Reviews*, 72(1), 1-11.
Kadler, K. E. et al. (2007). Collagens at a glace. *Journal of Cell Science*, 120(12), 1955-1958.
Kajikawa, Y. et al. (2008). Platelet-rich plasma enhances the initial mobilization of circulation-derived cells for tendon healing. *Journal of Cellular Physiology*, 215(3), 837-845.
Kaux, J. F. et al. (2011). Current opinions on tendinopathy. Journal of Sports Science & Medicine, 10(2), 238.
Kaux, J. F. et al. (2012). Effects of platelet-rich plasma (PRP) on the healing of a chilles tendons of rats. *Wound Repair and Regeneration*, 20(5), 748-756.
Khan, K. M. et al. (1999). Histopathology of common tendinopathies. *Sports Meducube*, 27(6), 393-408.
Khoshnoodi, J. et al. (2006). Molecular recognition in the assembly of collagens: terminal noncollagenous domains are key recognition modules in the formation of triple helical protomers. *Journal of Biological Chemistry*, 281(50), 38117-3812.
Klee, H. et al. (1987). Agrobacterium-mediated plant ransformation and its further applications to plant biology. *Annual Review of Plant Physiology*, 38, 467-486.
Klein, T. M. et al. (1988). Factors influencing gene delivery into *Zea mays* cells by high-velocity microprojectiles. *Bio/technology*, 6(5), 559-563.
Kreger, S. T. et al. (2010). Polymerization and matrix physical properties as important design considerations for soluble collagen formulations. *Biopolymers: Original Research on Biomolecules*, 93(8), 690-707.
McCabe, D. E. et al. (1988). Stable transformation of soybean (*Glycine max*) by particle acceleration. *Bio/technology*, 6(8), 923-926.
Maffulli, N. et al. (2003). Types and epidemiology of tendinopathy. *Clinics in Sports Medicine*, 22(4), 675-692.
Majumdar, S. et al. (2016). Influence of collagen source on fibrillar architecture and properties of vitrified collagen membranes. *Journal of Biomedical Materials Research Part B: Applied Biomaterials*, 104(2), 300-307.
Merle, C. et al. (2002). Hydroxylated human homotrimeric collagen I in Agrobacterium tumefaciens-mediated transient expression and in transgenic tobacco plant. *FEBS Letters*, 515(1-3), 114-118.
Moraes, V. Y. et al. (2014). Platelet-rich therapies for musculoskeletal soft tissue injuries. *Cochrane Database of Systematic Reviews*, (4).
Neuhaus, G. et al. (1987). Transgenic rapeseed plants obtained by the microinjection of DNA into microspore-derived embryoids. *Theoretical and Applied Genetics*, 75(1), 30-36.
Neuhaus, G. et al. (1990). Plant transformation by microinjection techniques. *Physiologia Plantarum*, 79(1), 213-217.
Ohta, Y. (1986). High-efficiency genetic transformation of maize by a mixture of pollen and exogenous DNA. *Proceedings of the National Academy of Sciences*, 83(3), 715-719.
Olsen, D. et al. (2003). Recombinant collagen and gelatin for drug delivery. *Advanced Drug Delivery Reviews*, 55(12), 1547-1567.
Park, Y. D. et al. (2003). Photopolymerized hyaluronic acid-based hydrogels and interpenetrating networks. *Biomaterials*, 24(6), 893-900.
Potrykus, I. (1991). Gene transfer to plants: assessment of published approaches and results. *Annual Review of Plant Biology*, 42(1), 205-225.
Ross, E. V. (2006). Laser versus intense pulsed light: competing technologies in dermatology. *Lasers in Surgery and Medicine: The Official Journal of the American Society for Laser Medicine and Surgery*, 38(4), 261-272.
Ruggiero, F. et al. (200). Triple helix assembly and processing of human collagen produced in transgenic tobacco plants. *FEBS Letters*, 469(1), 132-136.
Sanford, J. C. (1900). Biolistic plant transformation. *Physiologia Plantarum*, 79(1), 206-209.
Sashidhar, R. B. et al. (1994). Quantitation of ϵ-amino group using amino acids as reference standards by trinitrobenzene sulfonic acids: A simple spectrophotometric method for the estimation of hapten to carrier protein ratio. *Journal of Immunological Methods*, 167(1-2), 121-127.
Shilo, S. et al. (2013). Cutaneous wound healing after treatment with plant-derived human recombinant collagen flowable gel. *Tissue Engineering Part A*, 19(13-14), 1519-1526.
Shimamoto, K. et al. (1989). Fertile transgenic rice plants regenerated from transformed protoplasts. *nature*, 338(6212), 274-276.
Shoseyov, O. et al. (2013). Human recombinant type I collagen produced in plants. *Tissue Engineering Par A*, 19(13-14), 1527-1533.
Shoseyov, O. et al. (2014). Human collagen produced in plants: more than just another molecule. *Bioengineered*, 5(1), 49-52.
Siegle, R. J. et al. (1984). Intradermal implatation of bovine collagen: humoral immune responses associated with clinical reactions. *Archives of Dermatology*, 120(2), 183-187.
Stein, H. et al. (2009). Production of bioactive, post-translationally modified, heterotrimeric, human recombinant type-I collagen in transgenic tobacco. *Biomacromolecules*, 10(9), 2640-2645.
Takamatsu, N., Ishikawa, M., Meshi, T., & Okada, Y. (1987), Expression of bacterial chloramphenicol acetyltransferase gene in tobacco plants mediated by TMV-RNA. *The EMBO Journal*, 6(2), 307-311.
Takamatsu, N. et al. (1990). Production of enkephalin in tobacco protoplasts using tobacco mosaic virus RNA vector. *FEBS Letters*, 269(1), 73-76.
Toriyama, K. et al. (1988). Transgenic rice plants after direct gene transfer into protoplasts. *Bio/technology*, 6(9), 1072-1074.
Van Engelen, F. A. et al. (1995). pBINPLUS: an improved plant transformation vector based on pBIN19. *Transgenic Research*, 4(4), 288-290.
Wang, C. et al. (2002). The third activity for lysyl hydroxylase 3: galactosylation of hydroxylysyl resides in collagens in vitro. *Matrix Biology*, 21(7), 559-566.

(56) References Cited

OTHER PUBLICATIONS

Willard, J. J. et al. (2013). Plant-derived human collagen scaffolds for skin tissue engineering. *Tissue Engineering Part A*, 19(13-14), 1507-1518.
Yaari, A. et al. (2013). Liquid crystalline human recombinant collagen: the challenge and the opportunity. *Tissue Engineering Part A*, 19(13-14), 1502-1506.
Yaari, A. et al. (2016). Wet spinning and drawing of human recombinant collagen. *ACS Biomaterials Science & Engineering*, 2(3), 349-360.
Yuan, T. et al. (2013). Augmenting tendon and ligament repair with platelet-rich plasma (PRP). *Muscles, Ligaments and Tendons Journal*, 3(3), 139.
Zhang, H. M. et al. (1988). Transgenic rice plants produced by electroporation—mediated plasmid uptake into protoplasts. *Plant Cell Reports*, 7(6), 379-384.
Zhang, J. et al. (2010). Platelet-rich plasma releasate promotes differentiation of tendon stem cells in acive tenocytes. *The American Journal of Sports Medicine*, 38(12), 2477-2486.
Zhou, D. et al. (2014). Visible light-curbale polymers for biomedical applications. *Science China Chemistry*, 57(4), 510-521.
Omlor et al. (2012). Injection of polymerized hyaluronic acid/collagen hydrogel matrix in an in vivo porcine disc degeneration model. European Spine Journal, 21(9), 1700-1708.
Communication Pursuant to Article 94(3) EPC dated Jan. 10, 2023 From the European Patent Office Re. Application No. 19725422.0. (4 Pages).
Notice of Reason(s) for Rejection dated Feb. 28, 2023 From the Japan Patent Office Re. Application No. 2020-561769. (6 pages).
Notification of Office Action and Search Report dated Nov. 16, 2022 From the China National Intellectual Property Administration Re. Application No. 2019800402852 and Its Summary in English. (24 Pages).
Communication Pursuant to Article 94(3) EPC dated May 9, 2023 From the European Patent Office Re. Application No. 19725422.0. (8 Pages).
Relat?rio de Busca e Parecer [Search Report and Opinion] dated Mar. 8, 2023 From the Servi?o P?blico Federal, Minisl?rio da Economia, Instituto Nacional da Propriedade industrial do Brasil Re. Application No. BR 11 2020 022438 3 (4 Pages).
Translation dated 13 Mar. 2023 of Notice of Reason(s) for Rejection dated Feb. 28, 2023 From the Japan Patent Office Re. Application No. 2020-561769. (5 pages).
Translation dated Mar. 24, 2023 of Relatório de Busca e Parecer [Search Report and Opinion] dated Mar. 8, 2023 From the Serviço Público Federal, Ministério da Economia, Instituto Nacional da Propriedade Industrial do Brasil Re. Application No. BR 11 2020 022438 3 (4 pages).
Notification of Office Action and Search Report dated May 6, 2023 From the China National Intellectual Property Administration Re. Application No. 2019800402852 and Its Summary in English. (26 Pages).
Requisition by the Examiner dated Jun. 30, 2023 From the Innovation, Science and Economic Development Canada, Canadian Intellectual Property Office Re. Application No. 3,099,139. (5 pages).

* cited by examiner

|  | Vacuole | Cytoplasm | Appoplasm |
|---|---|---|---|
| 2 | Cole a1 (I) / Cole a2 (I) | 1 — Cole a1 (I) / Cole a2 (I) | 7 — Cole a1 (I) / Cole a2 (I) |
| 3 | Cole a1 (I) / Cole a2 (I) + P4Hb / P4Ha | 5 — Cole a1 (I) / Cole a2 (I) + P4Hb / P4Ha | 8 — Cole a1 (I) / Cole a2 (I) + P4Hb / P4Ha |
| 4 | Cole a1 (I) / Cole a2 (I) + P4Hb / P4Hplant | 6 — Cole a1 (I) / Cole a2 (I) + P4Hb / P4Hplant | 9 — Cole a1 (I) / Cole a2 (I) + P4Hb / P4Hplant |
| 10 | Protease C / Protease N | 11 — Protease C / Protease N | 12 — Protease C / Protease N |
| 13 | Cole a1 (I) / Cole a2 (I) + P4Hb / P4Ha + LH3 | 14 — Cole a1 (I) / Cole a2 (I) + P4Hb / P4Ha + LH3 | 15 — Cole a1 (I) / Cole a2 (I) + P4Hb / P4Ha + LH3 |
| 20 | P4Hb / P4Ha + LH3 |  | 21 — P4Hb / P4Ha + LH3 |

Fig. 2

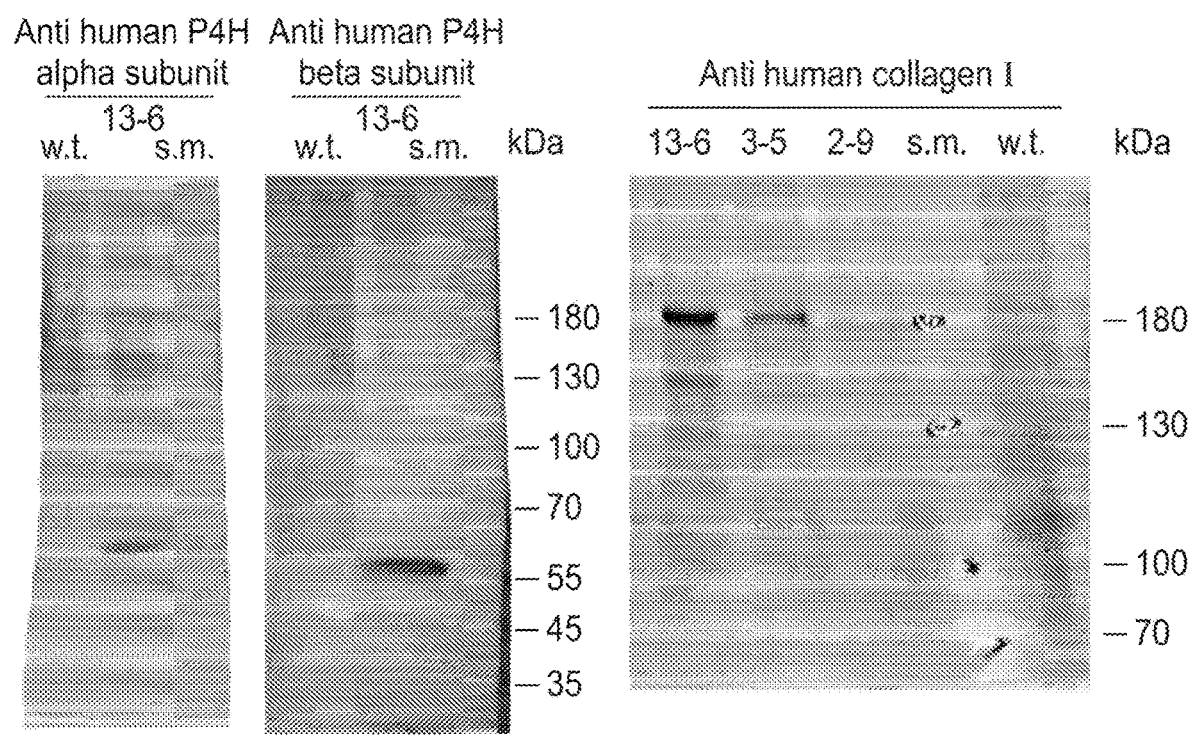
Fig. 8
Fig. 9
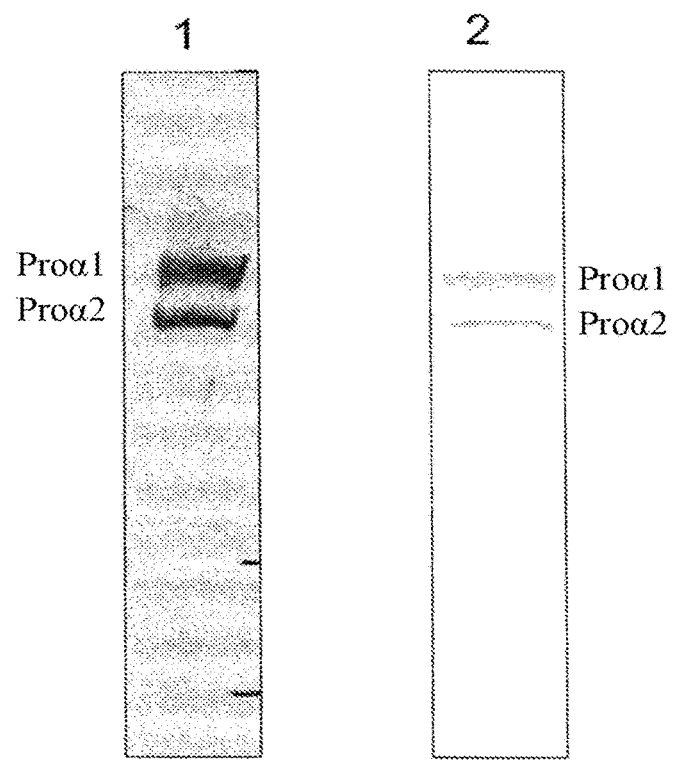

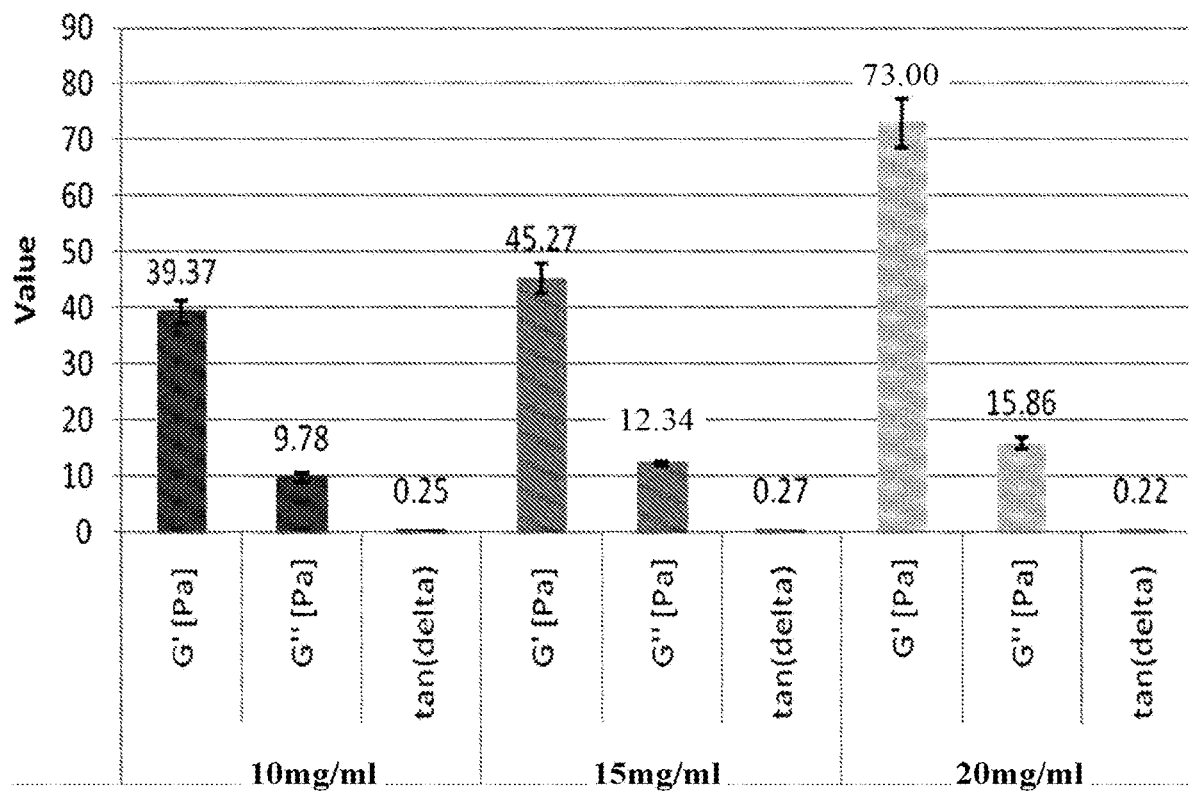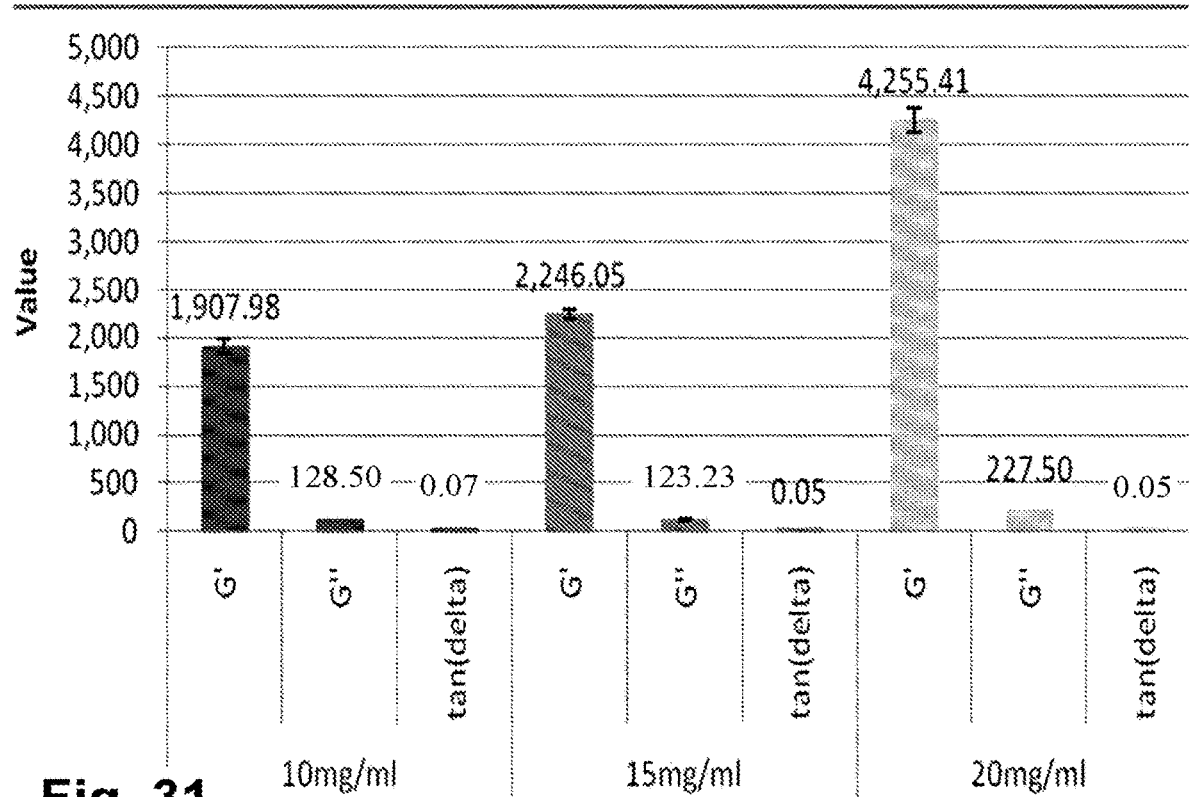
Fig. 31

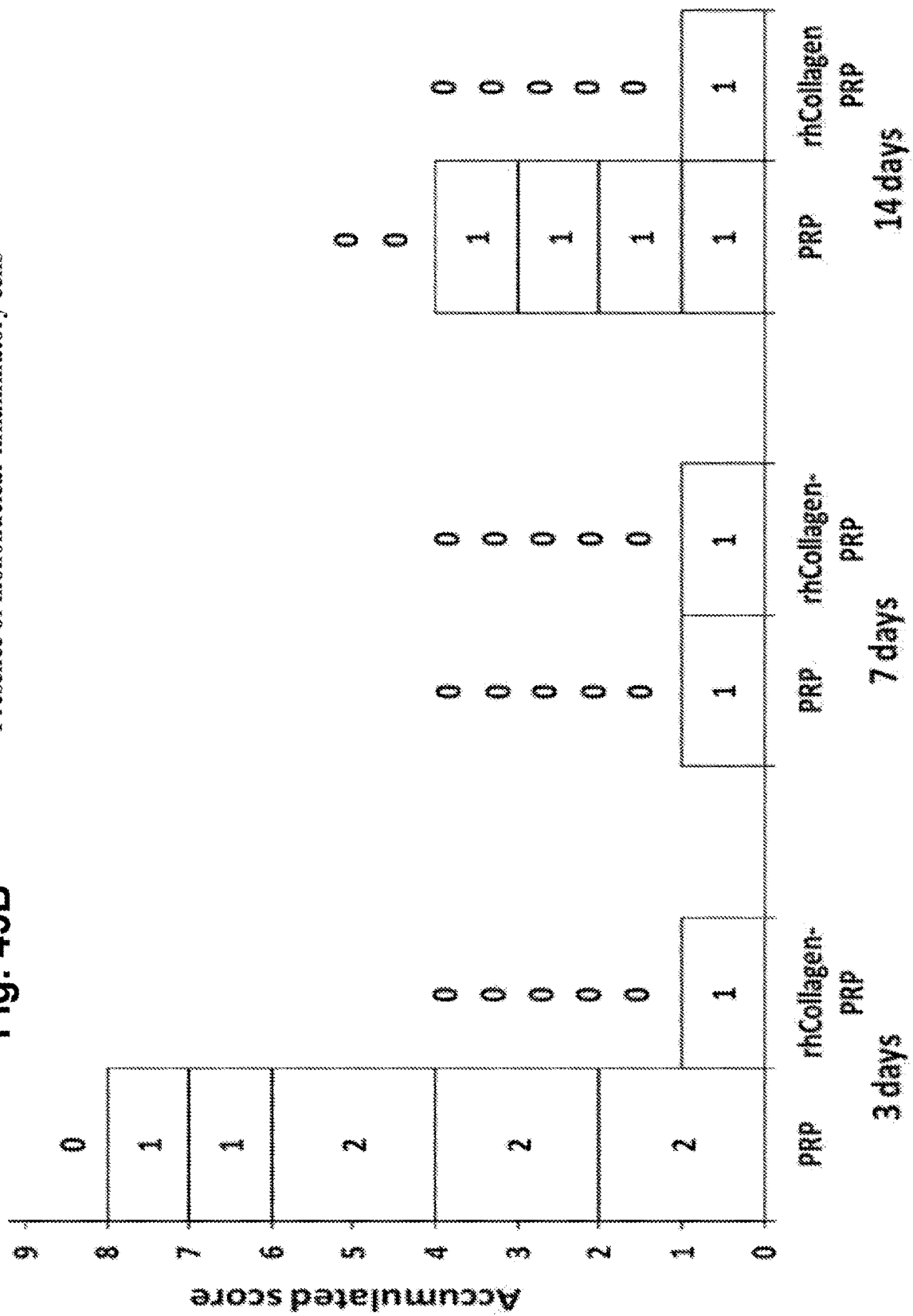

SEQUENCE LISTING

<160> NUMBER OF SEQ ID NOS: 42

<210> SEQ ID NO 1
<211> LENGTH: 4662
<212> TYPE: DNA
<213> ORGANISM: Artificial Sequence
<220> FEATURE:
<223> OTHER INFORMATION: Synthetic sequence containing the coding
      regions of the vacuolar signal sequence of barley gene for Thiol
      protease aleurain precursor fused to the human Collagen alpha 1(I)
      chain and flanking regions

<400> SEQUENCE: 1

```
gcgatgcatg taatgtcatg agccacatga tccaatggcc acaggaacgt aagaatgtag      60
atagatttga ttttgtccgt tagatagcaa acaacattat aaaaggtgtg tatcaatacg     120
aactaattca ctcattggat tcatagaagt ccattcctcc taagtatcta aaccatggct     180
cacgctcgtg ttctcctcct cgctctcgct gttttggcaa cagctgctgt ggctgtggct     240
tctagttctt cttttgctga ttcaaaccct attagacctg ttactgatag agcagcttcc     300
actttggctc aattgcaaga ggagggccag gttgagggcc aagatgagga tatccctcca     360
attacatgcg tgcaaaatgg cttgcgttac cacgataggg atgtgtggaa acctgaacct     420
tgtcgtatct gtgtgtgtga taacggcaag gtgctctgcg atgatgttat ctgcgatgag     480
acaaaaaatt gccctggcgc tgaagttcct gagggcgagt gttgccctgt gtgccctgat     540
ggttccgagt ccccaactga tcaggaaact actggcgtgg agggcccaaa aggagatact     600
ggtccacgtg gtcctagggg tccagcaggt cctccaggta gatgtggtat tccaggccag     660
cctggattgc caggaccacc aggcccacct ggcccaccag acctcctggg tcttggtgga     720
aatttcgctc acaactctct ttatggctat gatgagaagt caacaggtgg tatttccgtt     780
ccaggtccta tgggaccatc cggaccaaga ggtctcccag gtcctccagg tgctcctgga     840
cctcaaggct tcaaggacc tccaggcgaa ccaggagaac caggcgcttc tggaccaatg     900
ggcccaaggg gaccacctgg cccaccagga aaaaatggcg atgatggcga agctggaaag     960
cctggtcgtc ctggagagag aggtcctcct ggcccacagg gtgcaagagg cttgccagga    1020
actgctggct tgcctggaat gaagggacat aggggcttct ccggcctcga tggcgctaag    1080
ggtgatgctg ccctgctgg accaaagggc gagccaggtt cccctggaga aaacggtgct    1140
cctggacaaa tgggtcctcg tggacttcca ggagaaaggg gtcgtccagg cgctccagga    1200
ccagcaggtc taggggaaa cgatggtgca acaggcgctg ctggccctcc tggcccaact    1260
ggtcctgctg ccctccagg attcccaggc gcagttggag ctaaaggaga agcaggacca    1320
cagggcccta ggggttctga aggacctcag ggtgttagag gtgaaccagg tcctccaggc    1380
ccagctggag cagctggtcc agcaggaaat ccaggtgctg atggtcaacc tggagctaag    1440
ggcgctaatg gcgcaccagg tatcgcaggc gcaccaggtt ttcctggcgc tagaggccca    1500
agtggtcctc aaggaccagg tggaccacca ggtccaaaag gcaattctgg cgaacctggc    1560
gctccaggtt ctaaaggaga tactggtgct aaaggcgaac caggacctgt tggtgttcag    1620
ggtcctcctg gtcctgctgg agaagaagga aaaagaggtg ctcgtggaga accaggacca    1680
actggacttc ctggacctcc tggtgaacgt ggcggacctg ctcaagggg tttccctgga    1740 gctgatggag tggcaggtcc aaaaggccct gctggagaga gaggttcacc aggtccagct    1800
ggtcctaagg gctccctgg tgaagcaggt agaccaggcg aagcaggatt gccaggcgca    1860
aagggattga caggctctcc tggtagtcct ggcccagatg gaaaaacagg cccaccaggt    1920
```

```
ccagcaggac aagatggacg tccaggccca ccaggtcctc ctggagcaag ggacaagct      1980 ggcgttatgg gttttccagg acctaaaggt gctgctggag agccaggaaa ggcaggtgaa     2040
agaggagttc ctggtccacc aggagcagtg ggtcctgctg gcaaagatgg tgaagctgga     2100
gcacagggcc ctccaggccc tgctgggcca gctggcgaac gtggagaaca aggcccagct     2160
ggtagtccag gatttcaagg attgcctggc cctgctggcc tccaggaga agcaggaaaa      2220 cctggagaac aaggagttcc tggtgatttg ggagcacctg gaccttcagg agcacgtggt     2280
gaaagaggct tccctggcga gagggggtgtt caaggtccac caggtccagc aggacctaga    2340
ggtgctaatg gcgctcctgg caacgatgga gcaaaaggtg atgctggtgc tcctggcgca    2400
cctggaagtc agggtgctcc tggattgcaa ggaatgcctg gagagagggg tgctgctggc     2460
ttgccaggcc caagggcgat agggtgatt gctggaccaa aaggtgctga tggatcccca     2520
ggaaaagatg gagttcgtgg tcttactggc ccaatcggac ctccaggccc tgctggcgct    2580
ccaggtgata agggcgaaag tggcccaagt ggacctgctg gacctactgg tgctagaggt    2640
gcacctggtg atagggggtga acctggacca cctggtccag ctggtttttgc tggtcctcct    2700 ggagctgatg gacaacctgg cgcaaagggt gaaccaggtg atgctggcgc aaagggagat    2760
gctggtccac ctggacctgc tggtccagca ggcccccctg gccaatcgg taatgttgga     2820 gcaccaggtg ctaagggagc taggggttcc gctggtccac ctggagcaac aggatttcca    2880
ggcgctgctg gtagagttgg cccaccaggc ccatccggaa acgcaggccc tcctggtcct    2940
ccaggtcctg ctggcaagga gggtggcaaa ggaccaaggg gcgaaactgg ccctgctggt    3000
agacctggcg aagttggccc tcctggacca ccaggtccag caggagaaaa aggttccca      3060 ggagctgatg gcccagctgg tgctccagga actccaggcc ctcaaggtat gctggacag     3120 agaggcgttg tgggactccc tggtcaaagg ggagagagag gatttccagg cttgccagga    3180
cctagtggag aacctggaaa acaaggccca tcaggcgcta gtggagagcg tggacctcct    3240
ggccctatgg gacctcctgg attggctggc ccacctggcg aatcaggtcg tgaaggcgca    3300
ccaggcgcag aaggatcacc tggaagagat ggatccctg gtgctaaagg cgatcgtgga    3360
gaaactggtc cagcaggccc accaggcgca ccaggtgcac ctggcgctcc aggacctgtg    3420
ggaccagctg gaaaatccgg agataggggc gagacaggcc cagcaggacc agctggacct    3480
gttggccctg ctggcgctcg tggaccagca ggacctcaag gaccaagggg agataaggga    3540
gaaacaggcg aacaaggcga taggcattt aaggctcata ggggttttag tggctccag    3600 ggtcctcctg gcccacctgg atcaccagga gaacaggag catctggtgc ttccggccca    3660
gctggtccaa gaggaccctcc aggatcagct ggtgcacctg gaaagatgg tcttaacggt    3720 ctcccaggac caatcggccc tcaggacct agaggaagaa caggagatgc tggccctgtt    3780
ggccctccag gaccttcgg tcaccaggt ccacctggtc ctccatcagc tggattcgat    3840 ttttcattc ttccacagcc accacaagag aaagctcacg atggcggcag atattaccgt    3900
gctgatgatg ctaacgttgt tagggataga gatttggaag tggatacaac tttgaaatcc    3960
ctctcccagc aaattgaaaa cattagatct ccagaaggtt cacgtaaaa cccagctaga    4020 acatgtcgtg attttgaaaat gtgtcactcc gattgggaaaa gtggtaata ctggattgat    4080 ccaaatcagg gctgtaatct cgatgctatc aaagtttct gtaacatgga acaggcgaa     4140 acatgcgtttt atcctactca accttccgtg gctcagaaa attggtacat ctcaaaaaaat    4200 cctaaagata agaggcacgt ttggttcggt gaaagtatga ctgatggatt tcaatttgag    4260
tacggcggtc aaggtagtga tccagctgat gtggctattc aactcacatt tttgcgtctt    4320
```

-continued

```
atgtccacag aggcatcaca aaacatcact taccactgca aaaacagtgt ggcttatatg    4380
gatcaacaaa caggaaacct taagaaggct cttcttttga agggctcaaa cgagattgag    4440
attagagcag agggcaactc aaggtttact tattcagtta ctgttgatgg ctgcacttca    4500
catactggcg cttggggtaa aacagttatc gagtataaga ctacaaaaac atcaagactc    4560
ccaatcattg atgttgctcc tctcgatgtt ggcgctcctg atcaagagtt cggttttgat    4620
gtgggcccag tttgtttcct ctaatgagct cgcggccgca tc                      4662
```

<210> SEQ ID NO 2
<211> LENGTH: 4662
<212> TYPE: DNA
<213> ORGANISM: Artificial Sequence
<220> FEATURE:
<223> OTHER INFORMATION: Synthetic sequence of the vacuolar signal
      sequence of barley gene for Thiol protease aleurain precursor
      fused to the human Collagen alpha 1(I) chain and flanking regions
<220> FEATURE:
<221> NAME/KEY: CDS
<222> LOCATION: (175)..(4644)

<400> SEQUENCE: 2

```
gcgatgcatg taatgtcatg agccacatga tccaatggcc acaggaacgt aagaatgtag     60
atagatttga ttttgtccgt tagatagcaa acaacattat aaaaggtgtg tatcaatacg    120
aactaattca ctcattggat tcatagaagt ccattcctcc taagtatcta aacc atg     177
                                                                Met
                                                                  1 gct cac gct cgt gtt ctc ctc ctc gct ctc gct gtt ttg gca aca gct     225
Ala His Ala Arg Val Leu Leu Leu Ala Leu Ala Val Leu Ala Thr Ala
          5                  10                  15 gct gtg gct gtg gct tct agt tct tct ttt gct gat tca aac cct att     273
Ala Val Ala Val Ala Ser Ser Ser Ser Phe Ala Asp Ser Asn Pro Ile
     20                  25                  30 aga cct gtt act gat aga gca gct tcc act ttg gct caa ttg caa gag     321
Arg Pro Val Thr Asp Arg Ala Ala Ser Thr Leu Ala Gln Leu Gln Glu
 35                  40                  45 gag ggc cag gtt gag ggc caa gat gag gat atc cct cca att aca tgc     369
Glu Gly Gln Val Glu Gly Gln Asp Glu Asp Ile Pro Pro Ile Thr Cys
 50                  55                  60                  65 gtg caa aat ggc ttg cgt tac cac gat agg gat gtg tgg aaa cct gaa     417
Val Gln Asn Gly Leu Arg Tyr His Asp Arg Asp Val Trp Lys Pro Glu
                 70                  75                  80 cct tgt cgt atc tgt gtg tgt gat aac ggc aag gtg ctc tgc gat gat     465
Pro Cys Arg Ile Cys Val Cys Asp Asn Gly Lys Val Leu Cys Asp Asp
             85                  90                  95 gtt atc tgc gat gag aca aaa aat tgc cct ggc gct gaa gtt cct gag     513
Val Ile Cys Asp Glu Thr Lys Asn Cys Pro Gly Ala Glu Val Pro Glu
        100                 105                 110 ggc gag tgt tgc cct gtg tgc cct gat ggt tcc gag tcc cca act gat     561
Gly Glu Cys Cys Pro Val Cys Pro Asp Gly Ser Glu Ser Pro Thr Asp
    115                 120                 125 cag gaa act act ggc gtg gag ggc cca aaa gga gat act ggt cca cgt     609
Gln Glu Thr Thr Gly Val Glu Gly Pro Lys Gly Asp Thr Gly Pro Arg
130                 135                 140                 145 ggt cct agg ggt cca gca ggt cct cca ggt aga gat ggt att cca ggc     657
Gly Pro Arg Gly Pro Ala Gly Pro Pro Gly Arg Asp Gly Ile Pro Gly
                150                 155                 160 cag cct gga ttg cca gga cca cca ggc cca cct ggc cca cca gga cct     705
Gln Pro Gly Leu Pro Gly Pro Pro Gly Pro Pro Gly Pro Pro Gly Pro
            165                 170                 175
```

-continued

| | |
|---|---|
| cct ggt ctt ggt gga aat ttc gct cca caa ctc tct tat ggc tat gat<br>Pro Gly Leu Gly Gly Asn Phe Ala Pro Gln Leu Ser Tyr Gly Tyr Asp<br>           180                           185                     190 | 753 |
| gag aag tca aca ggt ggt att tcc gtt cca ggt cct atg gga cca tcc<br>Glu Lys Ser Thr Gly Gly Ile Ser Val Pro Gly Pro Met Gly Pro Ser<br>195                       200                       205 | 801 |
| gga cca aga ggt ctc cca ggt cct cca ggt gct cct gga cct caa ggc<br>Gly Pro Arg Gly Leu Pro Gly Pro Pro Gly Ala Pro Gly Pro Gln Gly<br>210                       215                      220                225 | 849 |
| ttt caa gga cct cca ggc gaa cca gga gaa cca ggc gct tct gga cca<br>Phe Gln Gly Pro Pro Gly Glu Pro Gly Glu Pro Gly Ala Ser Gly Pro<br>                       230                      235                   240 | 897 |
| atg ggc cca agg gga cca cct ggc cca cca gga aaa aat ggc gat gat<br>Met Gly Pro Arg Gly Pro Pro Gly Pro Pro Gly Lys Asn Gly Asp Asp<br>           245                           250                      255 | 945 |
| ggc gaa gct gga aag cct ggt cgt cct gga gag aga ggt cct cct ggc<br>Gly Glu Ala Gly Lys Pro Gly Arg Pro Gly Glu Arg Gly Pro Pro Gly<br>260                       265                      270 | 993 |
| cca cag ggt gca aga ggc ttg cca gga act gct ggc ttg cct gga atg<br>Pro Gln Gly Ala Arg Gly Leu Pro Gly Thr Ala Gly Leu Pro Gly Met<br>           275                           280                      285 | 1041 |
| aag gga cat agg ggc ttc tcc ggc ctc gat ggc gct aag ggt gat gct<br>Lys Gly His Arg Gly Phe Ser Gly Leu Asp Gly Ala Lys Gly Asp Ala<br>290                       295                      300                   305 | 1089 |
| ggc cct gct gga cca aag ggc gag cca ggt tcc cct gga gaa aac ggt<br>Gly Pro Ala Gly Pro Lys Gly Glu Pro Gly Ser Pro Gly Glu Asn Gly<br>                310                      315                      320 | 1137 |
| gct cct gga caa atg ggt cct cgt gga ctt cca gga gaa agg ggt cgt<br>Ala Pro Gly Gln Met Gly Pro Arg Gly Leu Pro Gly Glu Arg Gly Arg<br>               325                      330                      335 | 1185 |
| cca ggc gct cca gga cca gca ggt gct agg gga aac gat ggt gca aca<br>Pro Gly Ala Pro Gly Pro Ala Gly Ala Arg Gly Asn Asp Gly Ala Thr<br>           340                           345                      350 | 1233 |
| ggc gct gct gga cct cct ggc cca act ggt cct gct ggc cct cca gga<br>Gly Ala Ala Gly Pro Pro Gly Pro Thr Gly Pro Ala Gly Pro Pro Gly<br>355                       360                      365 | 1281 |
| ttc cca ggc gca gtt gga gct aaa gga gaa gca gga cca cag ggc cct<br>Phe Pro Gly Ala Val Gly Ala Lys Gly Glu Ala Gly Pro Gln Gly Pro<br>370                       375                      380                    385 | 1329 |
| agg ggt tct gaa gga cct cag ggt gtt aga ggt gaa cca ggt cct cca<br>Arg Gly Ser Glu Gly Pro Gln Gly Val Arg Gly Glu Pro Gly Pro Pro<br>                390                      395                      400 | 1377 |
| ggc cca gct gga gca gct ggt cca gca gga aat cca ggt gct gat ggt<br>Gly Pro Ala Gly Ala Ala Gly Pro Ala Gly Asn Pro Gly Ala Asp Gly<br>           405                           410                      415 | 1425 |
| caa cct gga gct aag ggc gct aat ggc gca cca ggt atc gca ggc gca<br>Gln Pro Gly Ala Lys Gly Ala Asn Gly Ala Pro Gly Ile Ala Gly Ala<br>               420                      425                      430 | 1473 |
| cca ggt ttt cct ggc gct aga ggc cca agt ggt cct caa gga cca ggt<br>Pro Gly Phe Pro Gly Ala Arg Gly Pro Ser Gly Pro Gln Gly Pro Gly<br>435                       440                      445 | 1521 |
| gga cca cca ggt cca aaa ggc aat tct ggc gaa cct ggc gct cca ggt<br>Gly Pro Pro Gly Pro Lys Gly Asn Ser Gly Glu Pro Gly Ala Pro Gly<br>450                       455                      460                    465 | 1569 |
| tct aaa gga gat act ggt gct aaa ggc gaa cca gga cct gtt ggt gtt<br>Ser Lys Gly Asp Thr Gly Ala Lys Gly Glu Pro Gly Pro Val Gly Val<br>               470                      475                    480 | 1617 |
| cag ggt cct cct ggt cct gct gga gaa gaa gga aaa aga ggt gct cgt<br>Gln Gly Pro Pro Gly Pro Ala Gly Glu Glu Gly Lys Arg Gly Ala Arg | 1665 |

-continued

```
                485                 490                 495
gga gaa cca gga cca act gga ctt cct gga cct cct ggt gaa cgt ggc    1713
Gly Glu Pro Gly Pro Thr Gly Leu Pro Gly Pro Pro Gly Glu Arg Gly
            500                 505                 510 gga cct ggc tca agg ggt ttc cct gga gct gat gga gtg gca ggt cca    1761
Gly Pro Gly Ser Arg Gly Phe Pro Gly Ala Asp Gly Val Ala Gly Pro
        515                 520                 525 aaa ggc cct gct gga gag aga ggt tca cca ggt cca gct ggt cct aag    1809
Lys Gly Pro Ala Gly Glu Arg Gly Ser Pro Gly Pro Ala Gly Pro Lys
530                 535                 540                 545 ggc tcc cct ggt gaa gca ggt aga cca ggc gaa gca gga ttg cca ggc    1857
Gly Ser Pro Gly Glu Ala Gly Arg Pro Gly Glu Ala Gly Leu Pro Gly
                550                 555                 560 gca aag gga ttg aca ggc tct cct ggt agt cct ggc cca gat gga aaa    1905
Ala Lys Gly Leu Thr Gly Ser Pro Gly Ser Pro Gly Pro Asp Gly Lys
            565                 570                 575 aca ggc cca cca ggt cca gca gga caa gat gga cgt cca ggc cca cca    1953
Thr Gly Pro Pro Gly Pro Ala Gly Gln Asp Gly Arg Pro Gly Pro Pro
        580                 585                 590 ggt cct cct gga gca agg gga caa gct ggc gtt atg ggt ttt cca gga    2001
Gly Pro Pro Gly Ala Arg Gly Gln Ala Gly Val Met Gly Phe Pro Gly
595                 600                 605 cct aaa ggt gct gct gga gag cca gga aag gca ggt gaa aga gga gtt    2049
Pro Lys Gly Ala Ala Gly Glu Pro Gly Lys Ala Gly Glu Arg Gly Val
610                 615                 620                 625 cct ggt cca cca gga gca gtg ggt cct gct ggc aaa gat ggt gaa gct    2097
Pro Gly Pro Pro Gly Ala Val Gly Pro Ala Gly Lys Asp Gly Glu Ala
                630                 635                 640 gga gca cag ggc cct cca ggc cct gct ggc cca gct ggc gaa cgt gga    2145
Gly Ala Gln Gly Pro Pro Gly Pro Ala Gly Pro Ala Gly Glu Arg Gly
            645                 650                 655 gaa caa ggc cca gct ggt agt cca gga ttt caa gga ttg cct ggc cct    2193
Glu Gln Gly Pro Ala Gly Ser Pro Gly Phe Gln Gly Leu Pro Gly Pro
        660                 665                 670 gct ggc cct cca gga gaa gca gga aaa cct gga gaa caa gga gtt cct    2241
Ala Gly Pro Pro Gly Glu Ala Gly Lys Pro Gly Glu Gln Gly Val Pro
675                 680                 685 ggt gat ttg gga gca cct gga cct tca gga gca cgt ggt gaa aga ggc    2289
Gly Asp Leu Gly Ala Pro Gly Pro Ser Gly Ala Arg Gly Glu Arg Gly
690                 695                 700                 705 ttc cct ggc gag agg ggt gtt caa ggt cca cca ggt cca gca gga cct    2337
Phe Pro Gly Glu Arg Gly Val Gln Gly Pro Pro Gly Pro Ala Gly Pro
                710                 715                 720 aga ggt gct aat ggc gct cct ggc aac gat gga gca aaa ggt gat gct    2385
Arg Gly Ala Asn Gly Ala Pro Gly Asn Asp Gly Ala Lys Gly Asp Ala
            725                 730                 735 ggt gct cct ggc gca cct gga agt cag ggt gct cct gga ttg caa gga    2433
Gly Ala Pro Gly Ala Pro Gly Ser Gln Gly Ala Pro Gly Leu Gln Gly
        740                 745                 750 atg cct gga gag agg ggt gct gct ggc ttg cca ggc cca aag ggc gat    2481
Met Pro Gly Glu Arg Gly Ala Ala Gly Leu Pro Gly Pro Lys Gly Asp
755                 760                 765 agg ggt gat gct gga cca aaa ggt gct gat gga tcc cca gga aaa gat    2529
Arg Gly Asp Ala Gly Pro Lys Gly Ala Asp Gly Ser Pro Gly Lys Asp
770                 775                 780                 785 gga gtt cgt ggt ctt act ggc cca atc gga cct cca ggc cct gct ggc    2577
Gly Val Arg Gly Leu Thr Gly Pro Ile Gly Pro Pro Gly Pro Ala Gly
                790                 795                 800 gct cca ggt gat aag ggc gaa agt ggc cca agt gga cct gct gga cct    2625
Ala Pro Gly Asp Lys Gly Glu Ser Gly Pro Ser Gly Pro Ala Gly Pro
```

```
Ala Pro Gly Asp Lys Gly Glu Ser Gly Pro Ser Gly Pro Ala Gly Pro
            805                 810                 815 act ggt gct aga ggt gca cct ggt gat agg ggt gaa cct gga cca cct      2673
Thr Gly Ala Arg Gly Ala Pro Gly Asp Arg Gly Glu Pro Gly Pro Pro
        820                 825                 830 ggt cca gct ggt ttt gct ggt cct cct gga gct gat gga caa cct ggc      2721
Gly Pro Ala Gly Phe Ala Gly Pro Pro Gly Ala Asp Gly Gln Pro Gly
            835                 840                 845 gca aag ggt gaa cca ggt gat gct ggc gca aag gga gat gct ggt cca      2769
Ala Lys Gly Glu Pro Gly Asp Ala Gly Ala Lys Gly Asp Ala Gly Pro
850                 855                 860                 865 cct gga cct gct ggt cca gca ggc ccc cct ggg cca atc ggt aat gtt      2817
Pro Gly Pro Ala Gly Pro Ala Gly Pro Pro Gly Pro Ile Gly Asn Val
                870                 875                 880 gga gca cca ggt gct aag gga gct agg ggt tcc gct ggt cca cct gga      2865
Gly Ala Pro Gly Ala Lys Gly Ala Arg Gly Ser Ala Gly Pro Pro Gly
            885                 890                 895 gca aca gga ttt cca ggc gct gct ggt aga gtt ggc cca cca ggc cca      2913
Ala Thr Gly Phe Pro Gly Ala Ala Gly Arg Val Gly Pro Pro Gly Pro
        900                 905                 910 tcc gga aac gca ggc cct cct ggt cct cca ggt cct gct ggc aag gag      2961
Ser Gly Asn Ala Gly Pro Pro Gly Pro Pro Gly Pro Ala Gly Lys Glu
    915                 920                 925 ggt ggc aaa gga cca agg ggc gaa act ggc cct gct ggt aga cct ggc      3009
Gly Gly Lys Gly Pro Arg Gly Glu Thr Gly Pro Ala Gly Arg Pro Gly
930                 935                 940                 945 gaa gtt ggc cct cct gga cca cca ggt cca gca gga gaa aaa ggt tcc      3057
Glu Val Gly Pro Pro Gly Pro Pro Gly Pro Ala Gly Glu Lys Gly Ser
                950                 955                 960 cca gga gct gat ggc cca gct ggt gct cca gga act cca ggc cct caa      3105
Pro Gly Ala Asp Gly Pro Ala Gly Ala Pro Gly Thr Pro Gly Pro Gln
            965                 970                 975 ggt att gct gga cag aga ggc gtt gtg gga ctc cct ggt caa agg gga      3153
Gly Ile Ala Gly Gln Arg Gly Val Val Gly Leu Pro Gly Gln Arg Gly
        980                 985                 990 gag aga gga ttt cca ggc ttg cca gga cct agt gga gaa cct gga aaa      3201
Glu Arg Gly Phe Pro Gly Leu Pro Gly Pro Ser Gly Glu Pro Gly Lys
    995                 1000                1005 caa ggc cca tca ggc gct agt gga gag cgt gga cct cct ggc cct          3246
Gln Gly Pro Ser Gly Ala Ser Gly Glu Arg Gly Pro Pro Gly Pro
1010                1015                1020 atg gga cct cct gga ttg gct ggc cca cct ggc gaa tca ggt cgt          3291
Met Gly Pro Pro Gly Leu Ala Gly Pro Pro Gly Glu Ser Gly Arg
1025                1030                1035 gaa ggc gca cca ggc gca gaa gga tca cct gga aga gat gga tcc          3336
Glu Gly Ala Pro Gly Ala Glu Gly Ser Pro Gly Arg Asp Gly Ser
1040                1045                1050 cct ggt gct aaa ggc gat cgt gga gaa act ggt cca gca ggc cca          3381
Pro Gly Ala Lys Gly Asp Arg Gly Glu Thr Gly Pro Ala Gly Pro
1055                1060                1065 cca ggc gca cca ggt gca cct ggc gct cca gga cct gtg gga cca          3426
Pro Gly Ala Pro Gly Ala Pro Gly Ala Pro Gly Pro Val Gly Pro
1070                1075                1080 gct gga aaa tcc gga gat agg ggc gag aca ggc cca gca gga cca          3471
Ala Gly Lys Ser Gly Asp Arg Gly Glu Thr Gly Pro Ala Gly Pro
1085                1090                1095 gct gga cct gtt ggc cct gct ggc gct cgt gga cca gca gga cct          3516
Ala Gly Pro Val Gly Pro Ala Gly Ala Arg Gly Pro Ala Gly Pro
1100                1105                1110
```

```
                                              -continued caa gga cca agg gga gat  aag gga gaa aca ggc  gaa caa ggc gat    3561
Gln Gly Pro Arg Gly Asp  Lys Gly Glu Thr Gly  Glu Gln Gly Asp
1115                1120                1125 agg ggc att aag ggt cat  agg ggt ttt agt ggc  ctc cag ggt cct    3606
Arg Gly Ile Lys Gly His  Arg Gly Phe Ser Gly  Leu Gln Gly Pro
1130                1135                1140 cct ggc cca cct gga tca  cca gga gaa cag gga  cca tct ggt gct    3651
Pro Gly Pro Pro Gly Ser  Pro Gly Glu Gln Gly  Pro Ser Gly Ala
1145                1150                1155 tcc ggc cca gct ggt cca  aga gga cct cca gga  tca gct ggt gca    3696
Ser Gly Pro Ala Gly Pro  Arg Gly Pro Pro Gly  Ser Ala Gly Ala
1160                1165                1170 cct gga aaa gat ggt ctt  aac ggt ctc cca gga  cca atc ggc cct    3741
Pro Gly Lys Asp Gly Leu  Asn Gly Leu Pro Gly  Pro Ile Gly Pro
1175                1180                1185 cca gga cct aga gga aga  aca gga gat gct ggc  cct gtt ggc cct    3786
Pro Gly Pro Arg Gly Arg  Thr Gly Asp Ala Gly  Pro Val Gly Pro
1190                1195                1200 cca gga cct cct ggt cca  cca ggt cca cct ggt  cct cca tca gct    3831
Pro Gly Pro Pro Gly Pro  Pro Gly Pro Pro Gly  Pro Pro Ser Ala
1205                1210                1215 gga ttc gat ttt tca ttt  ctt cca cag cca cca  caa gag aaa gct    3876
Gly Phe Asp Phe Ser Phe  Leu Pro Gln Pro Pro  Gln Glu Lys Ala
1220                1225                1230 cac gat ggc ggc aga tat  tac cgt gct gat gat  gct aac gtt gtt    3921
His Asp Gly Gly Arg Tyr  Tyr Arg Ala Asp Asp  Ala Asn Val Val
1235                1240                1245 agg gat aga gat ttg gaa  gtg gat aca act ttg  aaa tcc ctc tcc    3966
Arg Asp Arg Asp Leu Glu  Val Asp Thr Thr Leu  Lys Ser Leu Ser
1250                1255                1260 cag caa att gaa aac att  aga tct cca gaa ggt  tca cgt aaa aac    4011
Gln Gln Ile Glu Asn Ile  Arg Ser Pro Glu Gly  Ser Arg Lys Asn
1265                1270                1275 cca gct aga aca tgt cgt  gat ttg aaa atg tgt  cac tcc gat tgg    4056
Pro Ala Arg Thr Cys Arg  Asp Leu Lys Met Cys  His Ser Asp Trp
1280                1285                1290 aaa agt ggt gaa tac tgg  att gat cca aat cag  ggc tgt aat ctc    4101
Lys Ser Gly Glu Tyr Trp  Ile Asp Pro Asn Gln  Gly Cys Asn Leu
1295                1300                1305 gat gct atc aaa gtt ttc  tgt aac atg gaa aca  ggc gaa aca tgc    4146
Asp Ala Ile Lys Val Phe  Cys Asn Met Glu Thr  Gly Glu Thr Cys
1310                1315                1320 gtt tat cct act caa cct  tcc gtg gct cag aaa  aat tgg tac atc    4191
Val Tyr Pro Thr Gln Pro  Ser Val Ala Gln Lys  Asn Trp Tyr Ile
1325                1330                1335 tca aaa aat cct aaa gat  aag agg cac gtt tgg  ttc ggt gaa agt    4236
Ser Lys Asn Pro Lys Asp  Lys Arg His Val Trp  Phe Gly Glu Ser
1340                1345                1350 atg act gat gga ttt caa  ttt gag tac ggc ggt  caa ggt agt gat    4281
Met Thr Asp Gly Phe Gln  Phe Glu Tyr Gly Gly  Gln Gly Ser Asp
1355                1360                1365 cca gct gat gtg gct att  caa ctc aca ttt ttg  cgt ctt atg tcc    4326
Pro Ala Asp Val Ala Ile  Gln Leu Thr Phe Leu  Arg Leu Met Ser
1370                1375                1380 aca gag gca tca caa aac  atc act tac cac tgc  aaa aac agt gtg    4371
Thr Glu Ala Ser Gln Asn  Ile Thr Tyr His Cys  Lys Asn Ser Val
1385                1390                1395 gct tat atg gat caa caa  aca gga aac ctt aag  aag gct ctt ctt    4416
Ala Tyr Met Asp Gln Gln  Thr Gly Asn Leu Lys  Lys Ala Leu Leu
1400                1405                1410
```

-continued

```
ttg aag ggc tca aac gag att gag att aga gca gag ggc aac tca         4461
Leu Lys Gly Ser Asn Glu Ile Glu Ile Arg Ala Glu Gly Asn Ser
1415                1420                1425 agg ttt act tat tca gtt act gtt gat ggc tgc act tca cat act         4506
Arg Phe Thr Tyr Ser Val Thr Val Asp Gly Cys Thr Ser His Thr
1430                1435                1440 ggc gct tgg ggt aaa aca gtt atc gag tat aag act aca aaa aca         4551
Gly Ala Trp Gly Lys Thr Val Ile Glu Tyr Lys Thr Thr Lys Thr
1445                1450                1455 tca aga ctc cca atc att gat gtt gct cct ctc gat gtt ggc gct         4596
Ser Arg Leu Pro Ile Ile Asp Val Ala Pro Leu Asp Val Gly Ala
1460                1465                1470 cct gat caa gag ttc ggt ttt gat gtg ggc cca gtt tgt ttc ctc         4641
Pro Asp Gln Glu Phe Gly Phe Asp Val Gly Pro Val Cys Phe Leu
1475                1480                1485 taa tgagctcgcg gccgcatc                                              4662
```

<210> SEQ ID NO 3
<211> LENGTH: 1489
<212> TYPE: PRT
<213> ORGANISM: Artificial Sequence
<220> FEATURE:
<223> OTHER INFORMATION: Synthetic Construct

<400> SEQUENCE: 3

```
Met Ala His Ala Arg Val Leu Leu Ala Leu Ala Val Leu Ala Thr
1               5                   10                  15

Ala Ala Val Ala Val Ala Ser Ser Ser Phe Ala Asp Ser Asn Pro
            20                  25                  30

Ile Arg Pro Val Thr Asp Arg Ala Ala Ser Thr Leu Ala Gln Leu Gln
        35                  40                  45

Glu Glu Gly Gln Val Glu Gly Gln Asp Glu Asp Ile Pro Pro Ile Thr
    50                  55                  60

Cys Val Gln Asn Gly Leu Arg Tyr His Asp Arg Asp Val Trp Lys Pro
65                  70                  75                  80

Glu Pro Cys Arg Ile Cys Val Cys Asp Asn Gly Lys Val Leu Cys Asp
                85                  90                  95

Asp Val Ile Cys Asp Glu Thr Lys Asn Cys Pro Gly Ala Glu Val Pro
                100                 105                 110

Glu Gly Glu Cys Cys Pro Val Cys Pro Asp Gly Ser Glu Ser Pro Thr
            115                 120                 125

Asp Gln Glu Thr Thr Gly Val Glu Gly Pro Lys Gly Asp Thr Gly Pro
    130                 135                 140

Arg Gly Pro Arg Gly Pro Ala Gly Pro Pro Gly Arg Asp Gly Ile Pro
145                 150                 155                 160

Gly Gln Pro Gly Leu Pro Gly Pro Pro Gly Pro Pro Gly Pro Pro Gly
                165                 170                 175

Pro Pro Gly Leu Gly Gly Asn Phe Ala Pro Gln Leu Ser Tyr Gly Tyr
            180                 185                 190

Asp Glu Lys Ser Thr Gly Gly Ile Ser Val Pro Gly Pro Met Gly Pro
    195                 200                 205

Ser Gly Pro Arg Gly Leu Pro Gly Pro Pro Gly Ala Pro Gly Pro Gln
            210                 215                 220

Gly Phe Gln Gly Pro Pro Gly Glu Pro Gly Glu Pro Gly Ala Ser Gly
225                 230                 235                 240

Pro Met Gly Pro Arg Gly Pro Pro Gly Pro Pro Gly Lys Asn Gly Asp
```

```
                      245                 250                 255
Asp Gly Glu Ala Gly Lys Pro Gly Arg Pro Gly Glu Arg Gly Pro Pro
                260                 265                 270

Gly Pro Gln Gly Ala Arg Gly Leu Pro Gly Thr Ala Gly Leu Pro Gly
                275                 280                 285

Met Lys Gly His Arg Gly Phe Ser Gly Leu Asp Gly Ala Lys Gly Asp
                290                 295                 300

Ala Gly Pro Ala Gly Pro Lys Gly Glu Pro Gly Ser Pro Gly Glu Asn
305                 310                 315                 320

Gly Ala Pro Gly Gln Met Gly Pro Arg Gly Leu Pro Gly Glu Arg Gly
                325                 330                 335

Arg Pro Gly Ala Pro Gly Pro Ala Gly Ala Arg Gly Asn Asp Gly Ala
                340                 345                 350

Thr Gly Ala Ala Gly Pro Pro Gly Pro Thr Gly Pro Ala Gly Pro Pro
                355                 360                 365

Gly Phe Pro Gly Ala Val Gly Ala Lys Gly Glu Ala Gly Pro Gln Gly
                370                 375                 380

Pro Arg Gly Ser Glu Gly Pro Gln Gly Val Arg Gly Glu Pro Gly Pro
385                 390                 395                 400

Pro Gly Pro Ala Gly Ala Ala Gly Pro Ala Gly Asn Pro Gly Ala Asp
                405                 410                 415

Gly Gln Pro Gly Ala Lys Gly Ala Asn Gly Ala Pro Gly Ile Ala Gly
                420                 425                 430

Ala Pro Gly Phe Pro Gly Ala Arg Gly Pro Ser Gly Pro Gln Gly Pro
                435                 440                 445

Gly Gly Pro Pro Gly Pro Lys Gly Asn Ser Gly Glu Pro Gly Ala Pro
                450                 455                 460

Gly Ser Lys Gly Asp Thr Gly Ala Lys Gly Glu Pro Gly Pro Val Gly
465                 470                 475                 480

Val Gln Gly Pro Pro Gly Pro Ala Gly Glu Glu Gly Lys Arg Gly Ala
                485                 490                 495

Arg Gly Glu Pro Gly Pro Thr Gly Leu Pro Gly Pro Pro Gly Glu Arg
                500                 505                 510

Gly Gly Pro Gly Ser Arg Gly Phe Pro Gly Ala Asp Gly Val Ala Gly
                515                 520                 525

Pro Lys Gly Pro Ala Gly Glu Arg Gly Ser Pro Gly Pro Ala Gly Pro
                530                 535                 540

Lys Gly Ser Pro Gly Glu Ala Gly Arg Pro Gly Glu Ala Gly Leu Pro
545                 550                 555                 560

Gly Ala Lys Gly Leu Thr Gly Ser Pro Gly Ser Pro Gly Pro Asp Gly
                565                 570                 575

Lys Thr Gly Pro Pro Gly Pro Ala Gly Gln Asp Gly Arg Pro Gly Pro
                580                 585                 590

Pro Gly Pro Pro Gly Ala Arg Gly Gln Ala Gly Val Met Gly Phe Pro
                595                 600                 605

Gly Pro Lys Gly Ala Ala Gly Glu Pro Gly Lys Ala Gly Glu Arg Gly
                610                 615                 620

Val Pro Gly Pro Pro Gly Ala Val Gly Pro Ala Gly Lys Asp Gly Glu
625                 630                 635                 640

Ala Gly Ala Gln Gly Pro Pro Gly Pro Ala Gly Pro Ala Gly Glu Arg
                645                 650                 655

Gly Glu Gln Gly Pro Ala Gly Ser Pro Gly Phe Gln Gly Leu Pro Gly
                660                 665                 670
```

```
Pro Ala Gly Pro Pro Gly Glu Ala Gly Lys Pro Gly Glu Gln Gly Val
        675                 680                 685

Pro Gly Asp Leu Gly Ala Pro Gly Pro Ser Gly Ala Arg Gly Glu Arg
        690                 695                 700

Gly Phe Pro Gly Glu Arg Gly Val Gln Gly Pro Pro Gly Pro Ala Gly
705                 710                 715                 720

Pro Arg Gly Ala Asn Gly Ala Pro Gly Asn Asp Gly Ala Lys Gly Asp
                725                 730                 735

Ala Gly Ala Pro Gly Ala Pro Gly Ser Gln Gly Ala Pro Gly Leu Gln
            740                 745                 750

Gly Met Pro Gly Glu Arg Gly Ala Ala Gly Leu Pro Gly Pro Lys Gly
        755                 760                 765

Asp Arg Gly Asp Ala Gly Pro Lys Gly Ala Asp Gly Ser Pro Gly Lys
770                 775                 780

Asp Gly Val Arg Gly Leu Thr Gly Pro Ile Gly Pro Pro Gly Pro Ala
785                 790                 795                 800

Gly Ala Pro Gly Asp Lys Gly Glu Ser Gly Pro Ser Gly Pro Ala Gly
                805                 810                 815

Pro Thr Gly Ala Arg Gly Ala Pro Gly Asp Arg Gly Glu Pro Gly Pro
        820                 825                 830

Pro Gly Pro Ala Gly Phe Ala Gly Pro Pro Gly Ala Asp Gly Gln Pro
        835                 840                 845

Gly Ala Lys Gly Glu Pro Gly Asp Ala Gly Ala Lys Gly Asp Ala Gly
        850                 855                 860

Pro Pro Gly Pro Ala Gly Pro Ala Gly Pro Pro Gly Pro Ile Gly Asn
865                 870                 875                 880

Val Gly Ala Pro Gly Ala Lys Gly Ala Arg Gly Ser Ala Gly Pro Pro
                885                 890                 895

Gly Ala Thr Gly Phe Pro Gly Ala Ala Gly Arg Val Gly Pro Pro Gly
            900                 905                 910

Pro Ser Gly Asn Ala Gly Pro Pro Gly Pro Pro Gly Pro Ala Gly Lys
        915                 920                 925

Glu Gly Gly Lys Gly Pro Arg Gly Glu Thr Gly Pro Ala Gly Arg Pro
        930                 935                 940

Gly Glu Val Gly Pro Pro Gly Pro Pro Gly Pro Ala Gly Glu Lys Gly
945                 950                 955                 960

Ser Pro Gly Ala Asp Gly Pro Ala Gly Ala Pro Gly Thr Pro Gly Pro
                965                 970                 975

Gln Gly Ile Ala Gly Gln Arg Gly Val Val Gly Leu Pro Gly Gln Arg
            980                 985                 990

Gly Glu Arg Gly Phe Pro Gly Leu Pro Gly Pro Ser Gly Glu Pro Gly
        995                 1000                1005

Lys Gln Gly Pro Ser Gly Ala Ser Gly Glu Arg Gly Pro Pro Gly
        1010                1015                1020

Pro Met Gly Pro Pro Gly Leu Ala Gly Pro Pro Gly Glu Ser Gly
        1025                1030                1035

Arg Glu Gly Ala Pro Gly Ala Glu Gly Ser Pro Gly Arg Asp Gly
        1040                1045                1050

Ser Pro Gly Ala Lys Gly Asp Arg Gly Glu Thr Gly Pro Ala Gly
        1055                1060                1065

Pro Pro Gly Ala Pro Gly Ala Pro Gly Ala Pro Gly Pro Val Gly
        1070                1075                1080
```

```
Pro Ala Gly Lys Ser Gly Asp Arg Gly Glu Thr Gly Pro Ala Gly
    1085                1090                1095

Pro Ala Gly Pro Val Gly Pro Ala Gly Ala Arg Gly Pro Ala Gly
    1100                1105                1110

Pro Gln Gly Pro Arg Gly Asp Lys Gly Glu Thr Gly Glu Gln Gly
    1115                1120                1125

Asp Arg Gly Ile Lys Gly His Arg Gly Phe Ser Gly Leu Gln Gly
    1130                1135                1140

Pro Pro Gly Pro Pro Gly Ser Pro Gly Glu Gln Gly Pro Ser Gly
    1145                1150                1155

Ala Ser Gly Pro Ala Gly Pro Arg Gly Pro Pro Gly Ser Ala Gly
    1160                1165                1170

Ala Pro Gly Lys Asp Gly Leu Asn Gly Leu Pro Gly Pro Ile Gly
    1175                1180                1185

Pro Pro Gly Pro Arg Gly Arg Thr Gly Asp Ala Gly Pro Val Gly
    1190                1195                1200

Pro Pro Gly Pro Pro Gly Pro Pro Gly Pro Pro Gly Pro Pro Ser
    1205                1210                1215

Ala Gly Phe Asp Phe Ser Phe Leu Pro Gln Pro Pro Gln Glu Lys
    1220                1225                1230

Ala His Asp Gly Gly Arg Tyr Tyr Arg Ala Asp Asp Ala Asn Val
    1235                1240                1245

Val Arg Asp Arg Asp Leu Glu Val Asp Thr Thr Leu Lys Ser Leu
    1250                1255                1260

Ser Gln Gln Ile Glu Asn Ile Arg Ser Pro Glu Gly Ser Arg Lys
    1265                1270                1275

Asn Pro Ala Arg Thr Cys Arg Asp Leu Lys Met Cys His Ser Asp
    1280                1285                1290

Trp Lys Ser Gly Glu Tyr Trp Ile Asp Pro Asn Gln Gly Cys Asn
    1295                1300                1305

Leu Asp Ala Ile Lys Val Phe Cys Asn Met Glu Thr Gly Glu Thr
    1310                1315                1320

Cys Val Tyr Pro Thr Gln Pro Ser Val Ala Gln Lys Asn Trp Tyr
    1325                1330                1335

Ile Ser Lys Asn Pro Lys Asp Lys Arg His Val Trp Phe Gly Glu
    1340                1345                1350

Ser Met Thr Asp Gly Phe Gln Phe Glu Tyr Gly Gly Gln Gly Ser
    1355                1360                1365

Asp Pro Ala Asp Val Ala Ile Gln Leu Thr Phe Leu Arg Leu Met
    1370                1375                1380

Ser Thr Glu Ala Ser Gln Asn Ile Thr Tyr His Cys Lys Asn Ser
    1385                1390                1395

Val Ala Tyr Met Asp Gln Gln Thr Gly Asn Leu Lys Lys Ala Leu
    1400                1405                1410

Leu Leu Lys Gly Ser Asn Glu Ile Glu Ile Arg Ala Glu Gly Asn
    1415                1420                1425

Ser Arg Phe Thr Tyr Ser Val Thr Val Asp Gly Cys Thr Ser His
    1430                1435                1440

Thr Gly Ala Trp Gly Lys Thr Val Ile Glu Tyr Lys Thr Thr Lys
    1445                1450                1455

Thr Ser Arg Leu Pro Ile Ile Asp Val Ala Pro Leu Asp Val Gly
    1460                1465                1470

Ala Pro Asp Gln Glu Phe Gly Phe Asp Val Gly Pro Val Cys Phe
```

1475 1480 1485

Leu

<210> SEQ ID NO 4
<211> LENGTH: 4362
<212> TYPE: DNA
<213> ORGANISM: Artificial Sequence
<220> FEATURE:
<223> OTHER INFORMATION: Synthetic sequence containing the coding
      regions of the vacuolar signal sequence of barley gene for Thiol
      protease aleurain precursor fused to the human Collagen alpha 2(I)
      chain and flanking regions

<400> SEQUENCE: 4

```
gcgatgcatg taatgtcatg agccacatga tccaatggcc acaggaacgt aagaatgtag      60
atagatttga ttttgtccgt tagatagcaa acaacattat aaaaggtgtg tatcaatacg     120
aactaattca ctcattggat tcatagaagt ccattcctcc taagtatcta aaccatggct     180
cacgctcgtg ttctcctcct cgctctcgct gttttggcaa cagctgctgt ggctgtggct     240
tcaagttcta gttttgctga ttccaaccca attcgtccag ttactgatag agcagcttcc     300
actttggctc aattgcttca agaagaaact gtgaggaagg ccctgctgg cgataggggc      360 cctaggggcg aaaggggtcc accaggacct ccaggcaggg atggcgaaga tggtccaact     420
ggccctcctg gacctcctgg ccctccaggg ccaccggct tgggcggaaa cttcgcagct      480
caatacgatg gcaagggtgt tggtcttggt cctggtccta tgggcttgat gggacctaga     540
ggcccacctg gtgctgctgg tgctcctgga ccacagggtt tcagggacc agctggcgag      600 ccaggagagc caggccaaac aggaccagct ggtgcaaggg gacctgctgg acctcctgga     660
aaagctggtg aagatggtca cccaggcaaa ccaggacgtc ctggcgaaag aggtgttgtt     720
ggaccacaag gcgctagggg attccaggt acacctggat tgccaggttt taagggcatt     780
cgtggtcata acggcctcga tggattgaag ggacagcctg gcgcacctgg cgttaagggt     840
gaacctggag caccaggtga aaacggtact cctggccaga ctggtgcaag aggactccca     900
ggtgaaaggg gtagagttgg tgctcctgga cctgctggag ctaggggtag tgatggtagt     960
gttggtcctg tgggccctgc tggtccaatc ggttccgctg cccacctgg attcccaggc     1020 gctccaggac ctaaaggaga aatcggtgct gtgggtaacg caggtcctac tggtccagca     1080
ggtcctcgtg gagaagtggg gattgccagga cttctggtc cagtgggccc tccaggcaac     1140
cctggagcta acggcttgac aggagctaaa ggcgcagcag gactccctgg agtggctggc     1200
gcaccaggat tgcctggtcc aagggggtatc ccaggcccct tggcgcagc tggagctact     1260 ggtgcacgtg gacttgttgg cgaaccaggc cctgctggat caaaggcga gtctggaaat     1320 aagggagaac ctggttctgc tggacctcaa ggtcctcctg accttctgg agaagaagga     1380 aaaaggggac caaatggcga ggctggatca gcaggtccac caggaccacc tggacttcgt     1440 ggatccctg gtagtagagg acttccagg gctgatggta gagcaggcgt tatgggacca     1500
ccaggaagta gaggagcatc cggtccagca ggagttaggg gtcctaacgg agatgctggt     1560
agaccaggtg aaccaggtct tatgggccca aggggcctcc caggtagtcc aggaaatatc     1620 ggccctctg gaaaagaagg ccctgttgga cttccaggta ttgatggacg tcctggccct     1680
attggcccag caggtgcaag aggagaacct ggcaatattg gatttccagg accaaagggt     1740
ccaacaggcg atcctggaaa aaatggagat aagggtcatg ctggattggc aggcgcaagg     1800
ggcgctcctg gtccagatgg aaacaacggc gcacagggtc cacctggccc tcagggtgtt     1860
```

```
caaggcggaa aaggcgaaca aggcccagct ggaccaccag gctttcaagg cttgccagga   1920
ccaagtggtc cagcaggtga agttggcaag ccaggcgagc gtggacttca tggcgagttt   1980
ggactccctg gaccagcagg accaagggt gaaagaggcc ctcctggaga gagtggcgct    2040
gctggaccaa caggcccaat cggtagtaga ggtcctagtg gacctccagg cccagatgga   2100
aataagggtg aaccaggagt tgtgggcgct gttggaacag ctggtccttc aggaccatca   2160
ggactcccag gcgagagagg cgctgctggc attcctggag gaaaggtgaa aaaggcgaa    2220
cctggcctcc gtggcgaaat cggaaatcct ggacgtgatg gtgctcgtgg tgcacacggc   2280
gctgtgggcg ctccaggccc tgctggtgct actggtgata ggagagaggc tggcgcagct   2340
ggcccagcag gtcctgctgg cccaaggggt agtcctggtg aaagaggcga agttggacct   2400
gctggcccta acggctttgc tggccctgct ggagcagcag gtcaacctgg cgctaaaggt   2460
gaaaggggcg aaagggccc aaaaggtgaa atggcgttg tgggaccaac tggtccagtg     2520
ggcgcagctg gacctgctgg tccaaatgga ccaccaggac cagcaggtag tagaggagat   2580
ggtggacctc caggaatgac aggttttcca ggtgctgctg gtagaacagg acctcctggt   2640
cctagtggta tttctggtcc accaggacca ccaggtcctg ctggaaaaga aggattgagg   2700
ggtccacgtg gtgatcaagg accagtgggc agaactggtg aagttggcgc agtgggacca   2760
cctggttttg ctggagaaaa gggcccttct ggagaggcag gaacagctgg tcctcctggt   2820
acacctggac ctcaaggact ttgggtgca cctggtattc tcggattgcc aggaagtagg    2880
ggcgaacgtg gacttcctgg cgtggcagga gcagttggag aacctggccc tctcggaatc   2940
gcaggcccac caggcgcaag aggaccacca ggagctgttg gatcaccagg cgtgaatggt   3000
gcacctggcg aggctggtcg tgatggaaac ccaggaaatg atggcccacc aggaagagat   3060
ggtcaacctg gacacaaagg cgagagggc tacccaggaa atattggccc agttggtgct   3120
gctggcgcac caggcccaca cggtccagtt ggaccagcag gaaaacacgg taatcgtggc   3180
gaaacaggcc cttcaggccc agtgggacct gctggtgctg ttggcccaag aggaccatct   3240
ggacctcaag gcattagagg cgataaggga gagcctggcg aaaaaggacc tagaggcttg   3300
cctggtttta aaggacacaa cggtctccaa ggacttccag gtatcgctgg tcatcatgga   3360
gatcagggtg ctcctggatc agtgggtcca gcaggtccta gaggcccagc aggcccttcc   3420
ggtcagcag gaaaggatgg acgtactggc caccctggaa ctgtgggccc tgctggaatt   3480
agaggtcctc aaggtcatca gggccctgct ggccctccag gtccaccagg tcctccaggc   3540
ccaccaggag tttcaggtgg tggttacgat tttggttacg atggtgattt ttaccgtgct   3600
gatcaaccta gaagtgctcc ttctctccgt cctaaagatt atgaagttga tgctactttg   3660
aaatcactta acaaccagat tgagactctt ctcacacctg agggatcaag aaagaatcca   3720
gcacgtacat gccgtgatct cagacttagt cacccagagt ggtcaagtgg ctattattgg   3780
attgatccta atcagggttg tacaatggag gctatcaaag tttactgtga ttttccaact   3840
ggagagacat gtattagggc acaacctgag aacattccag ctaaaaattg gtatcgttcc   3900
tctaaagata agaaacatgt ttggctcgga gagactatta cgctggttc tcagttcgag   3960
tataatgttg agggcgttac ttctaaagag atggcaactc agctcgcttt tatgagattg   4020
ctcgctaact acgcatccca aaacatcact tatcactgca aaaattccat tgcatatatg   4080
gatgaggaga caggaaattt gaagaaagca gttattctcc aaggtagtaa cgatgttgag   4140
cttgtggctg agggaaatag tagattcact tacacagttt ggtggatgg atgctcaaag   4200
aaaactaatg agtggggcaa gacaatcatt gagtacaaga caaataagcc ttctaggctc   4260
```

```
ccatttctcg atattgcacc tcttgatatc ggaggagctg atcacgagtt ttttgttgat    4320
atcggacctg tttgttttaa gtaatgagct cgcggccgca tc                      4362

<210> SEQ ID NO 5
<211> LENGTH: 4362
<212> TYPE: DNA
<213> ORGANISM: Artificial Sequence
<220> FEATURE:
<223> OTHER INFORMATION: Synthetic sequence of the vacuolar signal
      sequence of barley gene for Thiol protease aleurain precursor
      fused to the human Collagen alpha 2(I) chain and flanking regions
<220> FEATURE:
<221> NAME/KEY: CDS
<222> LOCATION: (175)..(4344)

<400> SEQUENCE: 5
gcgatgcatg taatgtcatg agccacatga tccaatggcc acaggaacgt aagaatgtag     60
atagatttga ttttgtccgt tagatagcaa acaacattat aaaaggtgtg tatcaatacg    120
aactaattca ctcattggat tcatagaagt ccattcctcc taagtatcta aacc atg      177
                                                             Met
                                                              1 gct cac gct cgt gtt ctc ctc ctc gct ctc gct gtt ttg gca aca gct      225
Ala His Ala Arg Val Leu Leu Leu Ala Leu Ala Val Leu Ala Thr Ala
              5                  10                  15 gct gtg gct gtg gct tca agt tct agt ttt gct gat tcc aac cca att      273
Ala Val Ala Val Ala Ser Ser Ser Ser Phe Ala Asp Ser Asn Pro Ile
         20                  25                  30 cgt cca gtt act gat aga gca gct tcc act ttg gct caa ttg ctt caa      321
Arg Pro Val Thr Asp Arg Ala Ala Ser Thr Leu Ala Gln Leu Leu Gln
     35                  40                  45 gaa gaa act gtg agg aag ggc cct gct ggc gat agg ggc cct agg ggc      369
Glu Glu Thr Val Arg Lys Gly Pro Ala Gly Asp Arg Gly Pro Arg Gly
 50                  55                  60                  65 gaa agg ggt cca cca gga cct cca ggc agg gat ggc gaa gat ggt cca      417
Glu Arg Gly Pro Pro Gly Pro Pro Gly Arg Asp Gly Glu Asp Gly Pro
                 70                  75                  80 act ggc cct cct gga cct cct ggc cct cca ggg cca ccc ggc ttg ggc      465
Thr Gly Pro Pro Gly Pro Pro Gly Pro Pro Gly Pro Pro Gly Leu Gly
             85                  90                  95 gga aac ttc gca gct caa tac gat ggc aag ggt gtt ggt ctt ggt cct      513
Gly Asn Phe Ala Ala Gln Tyr Asp Gly Lys Gly Val Gly Leu Gly Pro
        100                 105                 110 ggt cct atg ggc ttg atg gga cct aga ggc cca cct ggt gct gct ggt      561
Gly Pro Met Gly Leu Met Gly Pro Arg Gly Pro Pro Gly Ala Ala Gly
    115                 120                 125 gct cct gga cca cag ggt ttt cag gga cca gct ggc gag cca gga gag      609
Ala Pro Gly Pro Gln Gly Phe Gln Gly Pro Ala Gly Glu Pro Gly Glu
130                 135                 140                 145 cca ggc caa aca gga cca gct ggt gca agg gga cct gct gga cct cct      657
Pro Gly Gln Thr Gly Pro Ala Gly Ala Arg Gly Pro Ala Gly Pro Pro
                150                 155                 160 gga aaa gct ggt gaa gat ggt cac cca ggc aaa cca gga cgt cct ggc      705
Gly Lys Ala Gly Glu Asp Gly His Pro Gly Lys Pro Gly Arg Pro Gly
            165                 170                 175 gaa aga ggt gtt gtt gga cca caa ggc gct agg gga ttt cca ggt aca      753
Glu Arg Gly Val Val Gly Pro Gln Gly Ala Arg Gly Phe Pro Gly Thr
        180                 185                 190 cct gga ttg cca ggt ttt aag ggc att cgt ggt cat aac ggc ctc gat      801
Pro Gly Leu Pro Gly Phe Lys Gly Ile Arg Gly His Asn Gly Leu Asp
    195                 200                 205
```

```
gga ttg aag gga cag cct ggc gca cct ggc gtt aag ggt gaa cct gga      849
Gly Leu Lys Gly Gln Pro Gly Ala Pro Gly Val Lys Gly Glu Pro Gly
210             215                 220                 225 gca cca ggt gaa aac ggt act cct ggc cag act ggt gca aga gga ctc      897
Ala Pro Gly Glu Asn Gly Thr Pro Gly Gln Thr Gly Ala Arg Gly Leu
            230                 235                 240 cca ggt gaa agg ggt aga gtt ggt gct cct gga cct gct gga gct agg      945
Pro Gly Glu Arg Gly Arg Val Gly Ala Pro Gly Pro Ala Gly Ala Arg
        245                 250                 255 ggt agt gat ggt agt gtt ggt cct gtg ggc cct gct ggt cca atc ggt      993
Gly Ser Asp Gly Ser Val Gly Pro Val Gly Pro Ala Gly Pro Ile Gly
    260                 265                 270 tcc gct ggc cca cct gga ttc cca ggc gct cca gga cct aaa gga gaa     1041
Ser Ala Gly Pro Pro Gly Phe Pro Gly Ala Pro Gly Pro Lys Gly Glu
275                 280                 285 atc ggt gct gtg ggt aac gca ggt cct act ggt cca gca ggt cct cgt     1089
Ile Gly Ala Val Gly Asn Ala Gly Pro Thr Gly Pro Ala Gly Pro Arg
290                 295                 300                 305 gga gaa gtg gga ttg cca gga ctt tct ggt cca gtg ggc cct cca ggc     1137
Gly Glu Val Gly Leu Pro Gly Leu Ser Gly Pro Val Gly Pro Pro Gly
            310                 315                 320 aac cct gga gct aac ggc ttg aca gga gct aaa ggc gca gca gga ctc     1185
Asn Pro Gly Ala Asn Gly Leu Thr Gly Ala Lys Gly Ala Ala Gly Leu
        325                 330                 335 cct gga gtg gct ggc gca cca gga ttg cct ggt cca agg ggt atc cca     1233
Pro Gly Val Ala Gly Ala Pro Gly Leu Pro Gly Pro Arg Gly Ile Pro
    340                 345                 350 ggc cct gtt ggc gca gct gga gct act ggt gca cgt gga ctt gtt ggc     1281
Gly Pro Val Gly Ala Ala Gly Ala Thr Gly Ala Arg Gly Leu Val Gly
355                 360                 365 gaa cca ggc cct gct gga tca aaa ggc gag tct gga aat aag gga gaa     1329
Glu Pro Gly Pro Ala Gly Ser Lys Gly Glu Ser Gly Asn Lys Gly Glu
370                 375                 380                 385 cct ggt tct gct gga cct caa ggt cct cct gga cct tct gga gaa gaa     1377
Pro Gly Ser Ala Gly Pro Gln Gly Pro Pro Gly Pro Ser Gly Glu Glu
            390                 395                 400 gga aaa agg gga cca aat ggc gag gct gga tca gca ggt cca cca gga     1425
Gly Lys Arg Gly Pro Asn Gly Glu Ala Gly Ser Ala Gly Pro Pro Gly
        405                 410                 415 cca cct gga ctt cgt gga tcc cct ggt agt aga gga ctt cca ggc gct     1473
Pro Pro Gly Leu Arg Gly Ser Pro Gly Ser Arg Gly Leu Pro Gly Ala
    420                 425                 430 gat ggt aga gca ggc gtt atg gga cca cca gga agt aga gga gca tcc     1521
Asp Gly Arg Ala Gly Val Met Gly Pro Pro Gly Ser Arg Gly Ala Ser
435                 440                 445 ggt cca gca gga gtt agg ggt cct aac gga gat gct ggt aga cca ggt     1569
Gly Pro Ala Gly Val Arg Gly Pro Asn Gly Asp Ala Gly Arg Pro Gly
450                 455                 460                 465 gaa cca ggt ctt atg ggc cca agg ggc ctc cca ggt agt cca gga aat     1617
Glu Pro Gly Leu Met Gly Pro Arg Gly Leu Pro Gly Ser Pro Gly Asn
            470                 475                 480 atc ggc cct gct gga aaa gaa ggc cct gtt gga ctt cca ggt att gat     1665
Ile Gly Pro Ala Gly Lys Glu Gly Pro Val Gly Leu Pro Gly Ile Asp
        485                 490                 495 gga cgt cct ggc cct att ggc cca gca ggt gca aga gga gaa cct ggc     1713
Gly Arg Pro Gly Pro Ile Gly Pro Ala Gly Ala Arg Gly Glu Pro Gly
    500                 505                 510 aat att gga ttt cca gga cca aag ggt cca aca ggc gat cct gga aaa     1761
Asn Ile Gly Phe Pro Gly Pro Lys Gly Pro Thr Gly Asp Pro Gly Lys
```

-continued

```
              515                 520                 525
aat gga gat aag ggt cat gct gga ttg gca ggc gca agg ggc gct cct    1809
Asn Gly Asp Lys Gly His Ala Gly Leu Ala Gly Ala Arg Gly Ala Pro
530                 535                 540                 545 ggt cca gat gga aac aac ggc gca cag ggt cca cct ggc cct cag ggt    1857
Gly Pro Asp Gly Asn Asn Gly Ala Gln Gly Pro Pro Gly Pro Gln Gly
                550                 555                 560 gtt caa ggc gga aaa ggc gaa caa ggc cca gct gga cca cca ggc ttt    1905
Val Gln Gly Gly Lys Gly Glu Gln Gly Pro Ala Gly Pro Pro Gly Phe
            565                 570                 575 caa ggc ttg cca gga cca agt ggt cca gca ggt gaa gtt ggc aag cca    1953
Gln Gly Leu Pro Gly Pro Ser Gly Pro Ala Gly Glu Val Gly Lys Pro
        580                 585                 590 ggc gag cgt gga ctt cat ggc gag ttt gga ctc cct gga cca gca gga    2001
Gly Glu Arg Gly Leu His Gly Glu Phe Gly Leu Pro Gly Pro Ala Gly
595                 600                 605 cca agg ggt gaa aga ggc cct cct gga gag agt ggc gct gct gga cca    2049
Pro Arg Gly Glu Arg Gly Pro Pro Gly Glu Ser Gly Ala Ala Gly Pro
610                 615                 620                 625 aca ggc cca atc ggt agt aga ggt cct agt gga cct cca ggc cca gat    2097
Thr Gly Pro Ile Gly Ser Arg Gly Pro Ser Gly Pro Pro Gly Pro Asp
                630                 635                 640 gga aat aag ggt gaa cca gga gtt gtg ggc gct gtt gga aca gct ggt    2145
Gly Asn Lys Gly Glu Pro Gly Val Val Gly Ala Val Gly Thr Ala Gly
            645                 650                 655 cct tca gga cca tca gga ctc cca ggc gag aga ggc gct gct ggc att    2193
Pro Ser Gly Pro Ser Gly Leu Pro Gly Glu Arg Gly Ala Ala Gly Ile
        660                 665                 670 cct gga gga aaa ggt gaa aaa ggc gaa cct ggc ctc cgt ggc gaa atc    2241
Pro Gly Gly Lys Gly Glu Lys Gly Glu Pro Gly Leu Arg Gly Glu Ile
675                 680                 685 gga aat cct gga cgt gat ggt gct cgt ggt gca cac ggc gct gtg ggc    2289
Gly Asn Pro Gly Arg Asp Gly Ala Arg Gly Ala His Gly Ala Val Gly
690                 695                 700                 705 gct cca ggc cct gct ggt gct act ggt gat aga gga gag gct ggc gca    2337
Ala Pro Gly Pro Ala Gly Ala Thr Gly Asp Arg Gly Glu Ala Gly Ala
                710                 715                 720 gct ggc cca gca ggt cct gct ggc cca agg ggt agt cct ggt gaa aga    2385
Ala Gly Pro Ala Gly Pro Ala Gly Pro Arg Gly Ser Pro Gly Glu Arg
            725                 730                 735 ggc gaa gtt gga cct gct ggc cct aac ggc ttt gct ggc cct gct gga    2433
Gly Glu Val Gly Pro Ala Gly Pro Asn Gly Phe Ala Gly Pro Ala Gly
        740                 745                 750 gca gca ggt caa cct ggc gct aaa ggt gaa agg ggc gga aag ggc cca    2481
Ala Ala Gly Gln Pro Gly Ala Lys Gly Glu Arg Gly Gly Lys Gly Pro
755                 760                 765 aaa ggt gaa aat ggc gtt gtg gga cca act ggt cca gtg ggc gca gct    2529
Lys Gly Glu Asn Gly Val Val Gly Pro Thr Gly Pro Val Gly Ala Ala
770                 775                 780                 785 gga cct gct ggt cca aat gga cca cca gga cca gca ggt agt aga gga    2577
Gly Pro Ala Gly Pro Asn Gly Pro Pro Gly Pro Ala Gly Ser Arg Gly
                790                 795                 800 gat ggt gga cct cca gga atg aca ggt ttt cca ggt gct gct ggt aga    2625
Asp Gly Gly Pro Pro Gly Met Thr Gly Phe Pro Gly Ala Ala Gly Arg
            805                 810                 815 aca gga cct cct ggt cct agt ggt att tct ggt cca cca gga cca cca    2673
Thr Gly Pro Pro Gly Pro Ser Gly Ile Ser Gly Pro Pro Gly Pro Pro
        820                 825                 830 ggt cct gct gga aaa gaa gga ttg agg ggt cca cgt ggt gat caa gga    2721
```

-continued

| | |
|---|---|
| Gly Pro Ala Gly Lys Glu Gly Leu Arg Gly Pro Arg Gly Asp Gln Gly<br>    835                  840                    845 | |
| cca gtg ggc aga act ggt gaa gtt ggc gca gtg gga cca cct ggt ttt<br>Pro Val Gly Arg Thr Gly Glu Val Gly Ala Val Gly Pro Pro Gly Phe<br>850                  855                  860                  865 | 2769 |
| gct gga gaa aag ggc cct tct gga gag gca gga aca gct ggt cct cct<br>Ala Gly Glu Lys Gly Pro Ser Gly Glu Ala Gly Thr Ala Gly Pro Pro<br>                  870                  875                  880 | 2817 |
| ggt aca cct gga cct caa gga ctt ttg ggt gca cct ggt att ctc gga<br>Gly Thr Pro Gly Pro Gln Gly Leu Leu Gly Ala Pro Gly Ile Leu Gly<br>                885                  890                  895 | 2865 |
| ttg cca gga agt agg ggc gaa cgt gga ctt cct ggc gtg gca gga gca<br>Leu Pro Gly Ser Arg Gly Glu Arg Gly Leu Pro Gly Val Ala Gly Ala<br>           900                  905                  910 | 2913 |
| gtt gga gaa cct ggc cct ctc gga atc gca ggc cca ggc gca aga<br>Val Gly Glu Pro Gly Pro Leu Gly Ile Ala Gly Pro Pro Gly Ala Arg<br>           915                  920                  925 | 2961 |
| gga cca cca gga gct gtt gga tca cca ggc gtg aat ggt gca cct ggc<br>Gly Pro Pro Gly Ala Val Gly Ser Pro Gly Val Asn Gly Ala Pro Gly<br>930                  935                  940                  945 | 3009 |
| gag gct ggt cgt gat gga aac cca gga aat gat ggc cca cca gga aga<br>Glu Ala Gly Arg Asp Gly Asn Pro Gly Asn Asp Gly Pro Pro Gly Arg<br>                  950                  955                  960 | 3057 |
| gat ggt caa cct gga cac aaa ggc gag agg ggc tac cca gga aat att<br>Asp Gly Gln Pro Gly His Lys Gly Glu Arg Gly Tyr Pro Gly Asn Ile<br>           965                  970                  975 | 3105 |
| ggc cca gtt ggt gct gct ggc gca cca ggc cca cac ggt cca gtt gga<br>Gly Pro Val Gly Ala Ala Gly Ala Pro Gly Pro His Gly Pro Val Gly<br>                  980                  985                  990 | 3153 |
| cca gca gga aaa cac ggt aat cgt ggc gaa aca ggc cct tca ggc cca<br>Pro Ala Gly Lys His Gly Asn Arg Gly Glu Thr Gly Pro Ser Gly Pro<br>           995                  1000                1005 | 3201 |
| gtg gga cct gct ggt gct gtt ggc cca aga gga cca tct gga cct<br>Val Gly Pro Ala Gly Ala Val Gly Pro Arg Gly Pro Ser Gly Pro<br>1010                  1015                1020 | 3246 |
| caa ggc att aga ggc gat aag gga gag cct ggc gaa aaa gga cct<br>Gln Gly Ile Arg Gly Asp Lys Gly Glu Pro Gly Glu Lys Gly Pro<br>1025                  1030                1035 | 3291 |
| aga ggc ttg cct ggt ttt aaa gga cac aac ggt ctc caa gga ctt<br>Arg Gly Leu Pro Gly Phe Lys Gly His Asn Gly Leu Gln Gly Leu<br>1040                  1045                1050 | 3336 |
| cca ggt atc gct ggt cat cat gga gat cag ggt gct cct gga tca<br>Pro Gly Ile Ala Gly His His Gly Asp Gln Gly Ala Pro Gly Ser<br>1055                  1060                1065 | 3381 |
| gtg ggt cca gca ggt cct aga ggc cca gca ggc cct tcc ggt cca<br>Val Gly Pro Ala Gly Pro Arg Gly Pro Ala Gly Pro Ser Gly Pro<br>1070                  1075                1080 | 3426 |
| gca gga aag gat gga cgt act ggc cac cct gga act gtg ggc cct<br>Ala Gly Lys Asp Gly Arg Thr Gly His Pro Gly Thr Val Gly Pro<br>1085                  1090                1095 | 3471 |
| gct gga att aga ggt cct caa ggt cat cag ggc cct gct ggc cct<br>Ala Gly Ile Arg Gly Pro Gln Gly His Gln Gly Pro Ala Gly Pro<br>1100                  1105                1110 | 3516 |
| cca ggt cca cca ggt cct cca ggc cca cca gga gtt tca ggt ggt<br>Pro Gly Pro Pro Gly Pro Pro Gly Pro Pro Gly Val Ser Gly Gly<br>1115                  1120                1125 | 3561 |
| ggt tac gat ttt ggt tac gat ggt gat ttt tac cgt gct gat caa<br>Gly Tyr Asp Phe Gly Tyr Asp Gly Asp Phe Tyr Arg Ala Asp Gln<br>1130                  1135                1140 | 3606 |

| | | | | | | | | | | | | | | |
|---|---|---|---|---|---|---|---|---|---|---|---|---|---|---|
| cct | aga | agt | gct | cct | tct | ctc | cgt | cct | aaa | gat | tat | gaa | gtt | gat | 3651 |
| Pro | Arg | Ser | Ala | Pro | Ser | Leu | Arg | Pro | Lys | Asp | Tyr | Glu | Val | Asp | |
| 1145 | | | | 1150 | | | | | 1155 | | | | | | |
| gct | act | ttg | aaa | tca | ctt | aac | aac | cag | att | gag | act | ctt | ctc | aca | 3696 |
| Ala | Thr | Leu | Lys | Ser | Leu | Asn | Asn | Gln | Ile | Glu | Thr | Leu | Leu | Thr | |
| 1160 | | | | | 1165 | | | | | 1170 | | | | | |
| cct | gag | gga | tca | aga | aag | aat | cca | gca | cgt | aca | tgc | cgt | gat | ctc | 3741 |
| Pro | Glu | Gly | Ser | Arg | Lys | Asn | Pro | Ala | Arg | Thr | Cys | Arg | Asp | Leu | |
| 1175 | | | | | 1180 | | | | | 1185 | | | | | |
| aga | ctt | agt | cac | cca | gag | tgg | tca | agt | ggc | tat | tat | tgg | att | gat | 3786 |
| Arg | Leu | Ser | His | Pro | Glu | Trp | Ser | Ser | Gly | Tyr | Tyr | Trp | Ile | Asp | |
| 1190 | | | | 1195 | | | | | 1200 | | | | | | |
| cct | aat | cag | ggt | tgt | aca | atg | gag | gct | atc | aaa | gtt | tac | tgt | gat | 3831 |
| Pro | Asn | Gln | Gly | Cys | Thr | Met | Glu | Ala | Ile | Lys | Val | Tyr | Cys | Asp | |
| 1205 | | | | 1210 | | | | | 1215 | | | | | | |
| ttt | cca | act | gga | gag | aca | tgt | att | agg | gca | caa | cct | gag | aac | att | 3876 |
| Phe | Pro | Thr | Gly | Glu | Thr | Cys | Ile | Arg | Ala | Gln | Pro | Glu | Asn | Ile | |
| 1220 | | | | 1225 | | | | | 1230 | | | | | | |
| cca | gct | aaa | aat | tgg | tat | cgt | tcc | tct | aaa | gat | aag | aaa | cat | gtt | 3921 |
| Pro | Ala | Lys | Asn | Trp | Tyr | Arg | Ser | Ser | Lys | Asp | Lys | Lys | His | Val | |
| 1235 | | | | 1240 | | | | | 1245 | | | | | | |
| tgg | ctc | gga | gag | act | att | aac | gct | ggt | tct | cag | ttc | gag | tat | aat | 3966 |
| Trp | Leu | Gly | Glu | Thr | Ile | Asn | Ala | Gly | Ser | Gln | Phe | Glu | Tyr | Asn | |
| 1250 | | | | 1255 | | | | | 1260 | | | | | | |
| gtt | gag | ggc | gtt | act | tct | aaa | gag | atg | gca | act | cag | ctc | gct | ttt | 4011 |
| Val | Glu | Gly | Val | Thr | Ser | Lys | Glu | Met | Ala | Thr | Gln | Leu | Ala | Phe | |
| 1265 | | | | 1270 | | | | | 1275 | | | | | | |
| atg | aga | ttg | ctc | gct | aac | tac | gca | tcc | caa | aac | atc | act | tat | cac | 4056 |
| Met | Arg | Leu | Leu | Ala | Asn | Tyr | Ala | Ser | Gln | Asn | Ile | Thr | Tyr | His | |
| 1280 | | | | 1285 | | | | | 1290 | | | | | | |
| tgc | aaa | aat | tcc | att | gca | tat | atg | gat | gag | gag | aca | gga | aat | ttg | 4101 |
| Cys | Lys | Asn | Ser | Ile | Ala | Tyr | Met | Asp | Glu | Glu | Thr | Gly | Asn | Leu | |
| 1295 | | | | 1300 | | | | | 1305 | | | | | | |
| aag | aaa | gca | gtt | att | ctc | caa | ggt | agt | aac | gat | gtt | gag | ctt | gtg | 4146 |
| Lys | Lys | Ala | Val | Ile | Leu | Gln | Gly | Ser | Asn | Asp | Val | Glu | Leu | Val | |
| 1310 | | | | 1315 | | | | | 1320 | | | | | | |
| gct | gag | gga | aat | agt | aga | ttc | act | tac | aca | gtt | ttg | gtg | gat | gga | 4191 |
| Ala | Glu | Gly | Asn | Ser | Arg | Phe | Thr | Tyr | Thr | Val | Leu | Val | Asp | Gly | |
| 1325 | | | | 1330 | | | | | 1335 | | | | | | |
| tgc | tca | aag | aaa | act | aat | gag | tgg | ggc | aag | aca | atc | att | gag | tac | 4236 |
| Cys | Ser | Lys | Lys | Thr | Asn | Glu | Trp | Gly | Lys | Thr | Ile | Ile | Glu | Tyr | |
| 1340 | | | | 1345 | | | | | 1350 | | | | | | |
| aag | aca | aat | aag | cct | tct | agg | ctc | cca | ttt | ctc | gat | att | gca | cct | 4281 |
| Lys | Thr | Asn | Lys | Pro | Ser | Arg | Leu | Pro | Phe | Leu | Asp | Ile | Ala | Pro | |
| 1355 | | | | 1360 | | | | | 1365 | | | | | | |
| ctt | gat | atc | gga | gga | gct | gat | cac | gag | ttt | ttt | gtt | gat | atc | gga | 4326 |
| Leu | Asp | Ile | Gly | Gly | Ala | Asp | His | Glu | Phe | Phe | Val | Asp | Ile | Gly | |
| 1370 | | | | 1375 | | | | | 1380 | | | | | | |
| cct | gtt | tgt | ttt | aag | taa | tgagctcgcg | gccgcatc | | | | | | | | 4362 |
| Pro | Val | Cys | Phe | Lys | | | | | | | | | | | |
| 1385 | | | | | | | | | | | | | | | |

<210> SEQ ID NO 6
<211> LENGTH: 1389
<212> TYPE: PRT
<213> ORGANISM: Artificial Sequence
<220> FEATURE:
<223> OTHER INFORMATION: Synthetic Construct

<400> SEQUENCE: 6

Met Ala His Ala Arg Val Leu Leu Leu Ala Leu Ala Val Leu Ala Thr

-continued

```
1               5                   10                  15
Ala Ala Val Ala Val Ala Ser Ser Ser Ser Phe Ala Asp Ser Asn Pro
            20                  25                  30
Ile Arg Pro Val Thr Asp Arg Ala Ala Ser Thr Leu Ala Gln Leu Leu
            35                  40                  45
Gln Glu Glu Thr Val Arg Lys Gly Pro Ala Gly Asp Arg Gly Pro Arg
50                  55                  60
Gly Glu Arg Gly Pro Pro Gly Pro Pro Gly Arg Asp Gly Glu Asp Gly
65                  70                  75                  80
Pro Thr Gly Pro Pro Gly Pro Pro Gly Pro Pro Gly Pro Pro Gly Leu
                85                  90                  95
Gly Gly Asn Phe Ala Ala Gln Tyr Asp Gly Lys Gly Val Gly Leu Gly
            100                 105                 110
Pro Gly Pro Met Gly Leu Met Gly Pro Arg Gly Pro Pro Gly Ala Ala
            115                 120                 125
Gly Ala Pro Gly Pro Gln Gly Phe Gln Gly Pro Ala Gly Glu Pro Gly
            130                 135                 140
Glu Pro Gly Gln Thr Gly Pro Ala Gly Ala Arg Gly Pro Ala Gly Pro
145                 150                 155                 160
Pro Gly Lys Ala Gly Glu Asp Gly His Pro Gly Lys Pro Gly Arg Pro
                165                 170                 175
Gly Glu Arg Gly Val Val Gly Pro Gln Gly Ala Arg Gly Phe Pro Gly
            180                 185                 190
Thr Pro Gly Leu Pro Gly Phe Lys Gly Ile Arg Gly His Asn Gly Leu
            195                 200                 205
Asp Gly Leu Lys Gly Gln Pro Gly Ala Pro Gly Val Lys Gly Glu Pro
            210                 215                 220
Gly Ala Pro Gly Glu Asn Gly Thr Pro Gly Gln Thr Gly Ala Arg Gly
225                 230                 235                 240
Leu Pro Gly Glu Arg Gly Arg Val Gly Ala Pro Gly Pro Ala Gly Ala
                245                 250                 255
Arg Gly Ser Asp Gly Ser Val Gly Pro Val Gly Pro Ala Gly Pro Ile
                260                 265                 270
Gly Ser Ala Gly Pro Pro Gly Phe Pro Gly Ala Pro Gly Pro Lys Gly
            275                 280                 285
Glu Ile Gly Ala Val Gly Asn Ala Gly Pro Thr Gly Pro Ala Gly Pro
            290                 295                 300
Arg Gly Glu Val Gly Leu Pro Gly Leu Ser Gly Pro Val Gly Pro Pro
305                 310                 315                 320
Gly Asn Pro Gly Ala Asn Gly Leu Thr Gly Ala Lys Gly Ala Ala Gly
                325                 330                 335
Leu Pro Gly Val Ala Gly Ala Pro Gly Leu Pro Gly Pro Arg Gly Ile
            340                 345                 350
Pro Gly Pro Val Gly Ala Ala Gly Ala Thr Gly Ala Arg Gly Leu Val
            355                 360                 365
Gly Glu Pro Gly Pro Ala Gly Ser Lys Gly Glu Ser Gly Asn Lys Gly
            370                 375                 380
Glu Pro Gly Ser Ala Gly Pro Gln Gly Pro Pro Gly Pro Ser Gly Glu
385                 390                 395                 400
Glu Gly Lys Arg Gly Pro Asn Gly Glu Ala Gly Ser Ala Gly Pro Pro
                405                 410                 415
Gly Pro Pro Gly Leu Arg Gly Ser Pro Gly Ser Arg Gly Leu Pro Gly
            420                 425                 430
```

```
Ala Asp Gly Arg Ala Gly Val Met Gly Pro Pro Gly Ser Arg Gly Ala
        435                 440                 445

Ser Gly Pro Ala Gly Val Arg Gly Pro Asn Gly Asp Ala Gly Arg Pro
    450                 455                 460

Gly Glu Pro Gly Leu Met Gly Arg Gly Leu Pro Gly Ser Pro Gly
465                 470                 475                 480

Asn Ile Gly Pro Ala Gly Lys Glu Gly Pro Val Gly Leu Pro Gly Ile
                485                 490                 495

Asp Gly Arg Pro Gly Pro Ile Gly Pro Ala Gly Ala Arg Gly Glu Pro
            500                 505                 510

Gly Asn Ile Gly Phe Pro Gly Pro Lys Gly Pro Thr Gly Asp Pro Gly
        515                 520                 525

Lys Asn Gly Asp Lys Gly His Ala Gly Leu Ala Gly Ala Arg Gly Ala
    530                 535                 540

Pro Gly Pro Asp Gly Asn Asn Gly Ala Gln Gly Pro Pro Gly Pro Gln
545                 550                 555                 560

Gly Val Gln Gly Gly Lys Gly Glu Gln Gly Pro Ala Gly Pro Pro Gly
                565                 570                 575

Phe Gln Gly Leu Pro Gly Pro Ser Gly Pro Ala Gly Glu Val Gly Lys
            580                 585                 590

Pro Gly Glu Arg Gly Leu His Gly Glu Phe Gly Leu Pro Gly Pro Ala
        595                 600                 605

Gly Pro Arg Gly Glu Arg Gly Pro Pro Gly Glu Ser Gly Ala Ala Gly
    610                 615                 620

Pro Thr Gly Pro Ile Gly Ser Arg Gly Pro Ser Gly Pro Pro Gly Pro
625                 630                 635                 640

Asp Gly Asn Lys Gly Glu Pro Gly Val Val Gly Ala Val Gly Thr Ala
                645                 650                 655

Gly Pro Ser Gly Pro Ser Gly Leu Pro Gly Glu Arg Gly Ala Ala Gly
            660                 665                 670

Ile Pro Gly Gly Lys Gly Glu Lys Gly Glu Pro Gly Leu Arg Gly Glu
        675                 680                 685

Ile Gly Asn Pro Gly Arg Asp Gly Ala Arg Gly Ala His Gly Ala Val
    690                 695                 700

Gly Ala Pro Gly Pro Ala Gly Ala Thr Gly Asp Arg Gly Glu Ala Gly
705                 710                 715                 720

Ala Ala Gly Pro Ala Gly Pro Ala Gly Pro Arg Gly Ser Pro Gly Glu
                725                 730                 735

Arg Gly Glu Val Gly Pro Ala Gly Pro Asn Gly Phe Ala Gly Pro Ala
            740                 745                 750

Gly Ala Ala Gly Gln Pro Gly Ala Lys Gly Glu Arg Gly Gly Lys Gly
        755                 760                 765

Pro Lys Gly Glu Asn Gly Val Val Gly Pro Thr Gly Pro Val Gly Ala
    770                 775                 780

Ala Gly Pro Ala Gly Pro Asn Gly Pro Pro Gly Pro Ala Gly Ser Arg
785                 790                 795                 800

Gly Asp Gly Gly Pro Pro Gly Met Thr Gly Phe Pro Gly Ala Ala Gly
                805                 810                 815

Arg Thr Gly Pro Pro Gly Pro Ser Gly Ile Ser Gly Pro Pro Gly Pro
            820                 825                 830

Pro Gly Pro Ala Gly Lys Glu Gly Leu Arg Gly Pro Arg Gly Asp Gln
        835                 840                 845
```

-continued

Gly Pro Val Gly Arg Thr Gly Glu Val Gly Ala Val Gly Pro Pro Gly
850                 855                 860

Phe Ala Gly Glu Lys Gly Pro Ser Gly Glu Ala Gly Thr Ala Gly Pro
865                 870                 875                 880

Pro Gly Thr Pro Gly Pro Gln Gly Leu Leu Gly Ala Pro Gly Ile Leu
                885                 890                 895

Gly Leu Pro Gly Ser Arg Gly Glu Arg Gly Leu Pro Gly Val Ala Gly
                900                 905                 910

Ala Val Gly Glu Pro Gly Pro Leu Gly Ile Ala Gly Pro Pro Gly Ala
                915                 920                 925

Arg Gly Pro Pro Gly Ala Val Gly Ser Pro Gly Val Asn Gly Ala Pro
930                 935                 940

Gly Glu Ala Gly Arg Asp Gly Asn Pro Gly Asn Asp Gly Pro Pro Gly
945                 950                 955                 960

Arg Asp Gly Gln Pro Gly His Lys Gly Glu Arg Gly Tyr Pro Gly Asn
                965                 970                 975

Ile Gly Pro Val Gly Ala Ala Gly Ala Pro Gly Pro His Gly Pro Val
                980                 985                 990

Gly Pro Ala Gly Lys His Gly Asn Arg Gly Glu Thr Gly Pro Ser Gly
                995                 1000                1005

Pro Val Gly Pro Ala Gly Ala Val Gly Pro Arg Gly Pro Ser Gly
1010                1015                1020

Pro Gln Gly Ile Arg Gly Asp Lys Gly Glu Pro Gly Glu Lys Gly
1025                1030                1035

Pro Arg Gly Leu Pro Gly Phe Lys Gly His Asn Gly Leu Gln Gly
1040                1045                1050

Leu Pro Gly Ile Ala Gly His His Gly Asp Gln Gly Ala Pro Gly
1055                1060                1065

Ser Val Gly Pro Ala Gly Pro Arg Gly Pro Ala Gly Pro Ser Gly
1070                1075                1080

Pro Ala Gly Lys Asp Gly Arg Thr Gly His Pro Gly Thr Val Gly
1085                1090                1095

Pro Ala Gly Ile Arg Gly Pro Gln Gly His Gln Gly Pro Ala Gly
1100                1105                1110

Pro Pro Gly Pro Pro Gly Pro Pro Gly Pro Pro Gly Val Ser Gly
1115                1120                1125

Gly Gly Tyr Asp Phe Gly Tyr Asp Gly Asp Phe Tyr Arg Ala Asp
1130                1135                1140

Gln Pro Arg Ser Ala Pro Ser Leu Arg Pro Lys Asp Tyr Glu Val
1145                1150                1155

Asp Ala Thr Leu Lys Ser Leu Asn Asn Gln Ile Glu Thr Leu Leu
1160                1165                1170

Thr Pro Glu Gly Ser Arg Lys Asn Pro Ala Arg Thr Cys Arg Asp
1175                1180                1185

Leu Arg Leu Ser His Pro Glu Trp Ser Ser Gly Tyr Tyr Trp Ile
1190                1195                1200

Asp Pro Asn Gln Gly Cys Thr Met Glu Ala Ile Lys Val Tyr Cys
1205                1210                1215

Asp Phe Pro Thr Gly Glu Thr Cys Ile Arg Ala Gln Pro Glu Asn
1220                1225                1230

Ile Pro Ala Lys Asn Trp Tyr Arg Ser Ser Lys Asp Lys Lys His
1235                1240                1245

Val Trp Leu Gly Glu Thr Ile Asn Ala Gly Ser Gln Phe Glu Tyr

```
              1250                1255                1260

Asn Val Glu Gly Val Thr Ser Lys Glu Met Ala Thr Gln Leu Ala
    1265                1270                1275

Phe Met Arg Leu Leu Ala Asn Tyr Ala Ser Gln Asn Ile Thr Tyr
    1280                1285                1290

His Cys Lys Asn Ser Ile Ala Tyr Met Asp Glu Glu Thr Gly Asn
    1295                1300                1305

Leu Lys Lys Ala Val Ile Leu Gln Gly Ser Asn Asp Val Glu Leu
    1310                1315                1320

Val Ala Glu Gly Asn Ser Arg Phe Thr Tyr Thr Val Leu Val Asp
    1325                1330                1335

Gly Cys Ser Lys Lys Thr Asn Glu Trp Gly Lys Thr Ile Ile Glu
    1340                1345                1350

Tyr Lys Thr Asn Lys Pro Ser Arg Leu Pro Phe Leu Asp Ile Ala
    1355                1360                1365

Pro Leu Asp Ile Gly Gly Ala Asp His Glu Phe Val Asp Ile
    1370                1375                1380

Gly Pro Val Cys Phe Lys
    1385

<210> SEQ ID NO 7
<211> LENGTH: 127
<212> TYPE: DNA
<213> ORGANISM: Artificial Sequence
<220> FEATURE:
<223> OTHER INFORMATION: Synthetic sequence containing the coding region
      of the appoplast signal of Arabidopsis thaliana endo-1,4-beta-
      glucanase and flanking regions

<400> SEQUENCE: 7
gccatggcta ggaagtcttt gattttccca gtgattcttc ttgctgtgct tctttctct       60 ccacctattt actctgctgg acacgattat agggatgctc ttaggaagtc atctatggct     120
caattgc                                                                127

<210> SEQ ID NO 8
<211> LENGTH: 127
<212> TYPE: DNA
<213> ORGANISM: Artificial Sequence
<220> FEATURE:
<223> OTHER INFORMATION: Synthetic sequence of the appoplast signal of
      Arabidopsis thaliana endo-1,4-beta-glucanase and flanking regions
<220> FEATURE:
<221> NAME/KEY: CDS
<222> LOCATION: (10)..(120)

<400> SEQUENCE: 8 gccatggct agg aag tct ttg att ttc cca gtg att ctt ctt gct gtg ctt     51
          Arg Lys Ser Leu Ile Phe Pro Val Ile Leu Leu Ala Val Leu
            1               5                  10 ctt ttc tct cca cct att tac tct gct gga cac gat tat agg gat gct       99
Leu Phe Ser Pro Pro Ile Tyr Ser Ala Gly His Asp Tyr Arg Asp Ala
 15              20                  25                  30 ctt agg aag tca tct atg gct caattgc                                   127
Leu Arg Lys Ser Ser Met Ala
                35

<210> SEQ ID NO 9
<211> LENGTH: 37
<212> TYPE: PRT
<213> ORGANISM: Artificial Sequence
<220> FEATURE:
```

<223> OTHER INFORMATION: Synthetic Construct

<400> SEQUENCE: 9

Arg Lys Ser Leu Ile Phe Pro Val Ile Leu Ala Val Leu Leu Phe
1               5                   10                  15

Ser Pro Pro Ile Tyr Ser Ala Gly His Asp Tyr Arg Asp Ala Leu Arg
            20                  25                  30

Lys Ser Ser Met Ala
        35

<210> SEQ ID NO 10
<211> LENGTH: 1037
<212> TYPE: DNA
<213> ORGANISM: Artificial Sequence
<220> FEATURE:
<223> OTHER INFORMATION: Chrysanthemum rbcS1 promoter and 5' UTR

<400> SEQUENCE: 10

```
aaatggcgcg ccaagcttag acaaacaccc cttgttatac aaagaatttc gctttacaaa      60
atcaaattcg agaaaataat atatgcacta ataagatca ttcggatcca atctaaccaa      120
ttacgatacg ctttgggtac acttgatttt tgtttcagta gttacatata tcttgtttta     180
tatgctatct ttaaggatct tcactcaaag actatttgtt gatgttcttg atggggctcg     240
gaagatttga tatgatacac tctaatcttt aggagatacc agccaggatt atattcagta    300
agacaatcaa attttacgtg ttcaaactcg ttatctttc atttaatgga tgagccagaa     360
tctctataga atgattgcaa tcgagaatat gttcggccga tatcccttg ttggcttcaa     420 tattctacat atcacacaag aatcgaccgt attgtaccct ctttccataa aggaacacac    480
agtatgcaga tgcttttttc ccacatgcag taacataggt attcaaaaat ggctaaaaga    540
agttggataa caaattgaca actatttcca tttctgttat ataaatttca caacacacaa    600
aagcccgtaa tcaagagtct gcccatgtac gaaataactt ctattatttg gtattgggcc   660
taagcccagc tcagagtacg tgggggtacc acatatagga aggtaacaaa atactgcaag    720
atagccccat aacgtaccag cctctcctta ccacgaagag ataagatata agacccaccc    780
tgccacgtgt cacatcgtca tggtggtaa tgataaggga ttacatcctt ctatgtttgt    840
ggacatgatg catgtaatgt catgagccac atgatccaat ggccacagga acgtaagaat   900
gtagatagat ttgattttgt ccgttagata gcaaacaaca ttataaaagg tgtgtatcaa    960
tacgaactaa ttcactcatt ggattcatag aagtccattc ctcctaagta tctaaacata   1020
tgcaattgtc gactaaa                                                   1037
```

<210> SEQ ID NO 11
<211> LENGTH: 975
<212> TYPE: DNA
<213> ORGANISM: Artificial Sequence
<220> FEATURE:
<223> OTHER INFORMATION: Chrysanthemum rbcS1 3'UTR and terminator

<400> SEQUENCE: 11

```
aaaaggatcc gcggccgcat aagttttact atttaccaag acttttgaat attaaccttc     60
ttgtaacgag tcggttaaat ttgattgttt agggttttgt attattttt tttggtcttt    120 taattcatca ctttaattcc ctaattgtct gttcatttcg ttgtttgttt ccggatcgat    180
aatgaaatgt aagagatatc atatataaat aataaattgt cgtttcatat ttgcaatctt    240
tttttacaaa cctttaatta attgtatgta tgacattttc ttcttgttat attaggggga    300
```

| | |
|---|---|
| aataatgtta aataaaagta caaaataaac tacagtacat cgtactgaat aaattaccta | 360 |
| gccaaaaagt acacctttcc atatacttcc tacatgaagg cattttcaac attttcaaat | 420 |
| aaggaatgct acaaccgcat aataacatcc acaaattttt ttataaaata acatgtcaga | 480 |
| cagtgattga aagattttat tatagtttcg ttatcttctt ttctcattaa gcgaatcact | 540 |
| acctaacacg tcattttgtg aaatattttt tgaatgtttt tatatagttg tagcattcct | 600 |
| cttttcaaat tagggtttgt ttgagatagc atttcagccg gttcatacaa cttaaaagca | 660 |
| tactctaatg ctggaaaaaa gactaaaaaa tcttgtaagt tagcgcagaa tattgaccca | 720 |
| aattatatac acacatgacc ccatatagag actaattaca cttttaacca ctaataatta | 780 |
| ttactgtatt ataacatcta ctaattaaac ttgtgagttt ttgctagaat tattatcata | 840 |
| tatactaaaa ggcaggaacg caaacattgc cccggtactg tagcaactac ggtagacgca | 900 |
| ttaattgtct atagtggacg cattaattaa ccaaaaccgc ctcttttcccc ttcttcttga | 960 |
| agcttgagct ctttt | 975 |

<210> SEQ ID NO 12
<211> LENGTH: 1633
<212> TYPE: DNA
<213> ORGANISM: Artificial Sequence
<220> FEATURE:
<223> OTHER INFORMATION: Synthetic sequence containing the coding
regions of the vacuolar signal sequence of barley gene for Thiol
protease aleurain precursor fused to the human Prolyl
4-hydroxylase beta subunit and flanking regions

<400> SEQUENCE: 12

| | |
|---|---|
| ctcgagtaaa ccatggctca tgctagggtt ttgcttttgg ctcttgctgt tcttgctact | 60 |
| gctgctgttg ctgtggcttc ttcttcatct ttcgctgatt ctaacccaat taggccagtg | 120 |
| actgatagag ctgcttctac tcttgctcaa ttggtcgaca tggatgctcc agaagaggag | 180 |
| gatcacgttc ttgtgcttag gaagtctaac ttcgctgaag ctcttgctgc tcacaagtac | 240 |
| cttcttgtgg agttttatgc tccttggtgc ggacattgca aagctcttgc tccagagtat | 300 |
| gctaaggctg ctggaaagtt gaaggctgag ggatctgaaa ttaggcttgc taaagtggat | 360 |
| gctactgagg agtctgatct tgctcaacag tacggagtta ggggatacccc aactattaag | 420 |
| ttcttcagga acggagatac tgcttctcca aaggagtata ctgctggaag ggaggctgat | 480 |
| gatattgtga actggcttaa gaagagaact ggaccagctg ctactactct tccagatgga | 540 |
| gctgctgctg aatctcttgt ggagtcatct gaggtggcag tgattggatt cttcaaggat | 600 |
| gtggagtctg attctgctaa gcagttcctt caagctgctg aggctattga tgatattcca | 660 |
| ttcggaatta cttctaactc tgatgtgttc tctaagtacc agcttgataa ggatggagtg | 720 |
| gtgcttttca gaaaattcga tgagggaagg aacaatttcg agggagaggt gacaaaggag | 780 |
| aaccttcttg atttcattaa gcacaaccag cttccacttg tgattgagtt cactgagcag | 840 |
| actgctccaa agattttcgg aggagagatt aagactcaca ttcttctttt ccttccaaag | 900 |
| tctgtgtctg attacgatgg aaagttgtct aacttcaaga ctgctgctga gtctttcaag | 960 |
| ggaaagattc ttttcatttt cattgattct gatcacactg ataaccagag gattcttgag | 1020 |
| ttcttcggac ttaagaagga gagtgcccca gctgttaggc ttattactct tgaggaggag | 1080 |
| atgactaagt acaagccaga gtctgaagaa cttactgctg agaggattac tgagttctgc | 1140 |
| cacagattcc ttgagggaaa gattaagcca caccttatgt ctcaagagct tccagaggat | 1200 |
| tgggataagc agccagttaa ggtgttggtg ggtaaaaact cgaggatgt ggctttcgat | 1260 |

-continued

```
gagaagaaga acgtgttcgt ggagttctac gcaccttggt gtggtcactg taagcagctt    1320
gctccaattt gggataagtt gggagagact tacaaggatc acgagaacat tgtgattgct    1380
aagatggatt ctactgctaa cgaggtggag gctgttaagg ttcactcttt cccaactttg    1440
aagttcttcc cagcttctgc tgataggact gtgattgatt acaacggaga aaggactctt    1500
gatggattca agaagttcct tgagtctgga ggacaagatg gagctggaga tgatgatgat    1560
cttgaggatt tggaagaagc tgaggagcca gatatggagg aggatgatga tcagaaggct    1620
gtgtgatgag ctc                                                      1633
```

<210> SEQ ID NO 13
<211> LENGTH: 537
<212> TYPE: PRT
<213> ORGANISM: Artificial Sequence
<220> FEATURE:
<223> OTHER INFORMATION: Synthetic sequence containing the vacuolar
    signal sequence of barley gene for Thiol protease aleurain
    precursor fused to the human Prolyl 4-hydroxylase beta subunit and
    flanking regions

<400> SEQUENCE: 13

```
Met Ala His Ala Arg Val Leu Leu Leu Ala Leu Ala Val Leu Ala Thr
1               5                   10                  15

Ala Ala Val Ala Val Ala Ser Ser Ser Phe Ala Asp Ser Asn Pro
            20                  25                  30

Ile Arg Pro Val Thr Asp Arg Ala Ala Ser Thr Leu Ala Gln Leu Val
        35                  40                  45

Asp Met Asp Ala Pro Glu Glu Glu Asp His Val Leu Val Leu Arg Lys
    50                  55                  60

Ser Asn Phe Ala Glu Ala Leu Ala Ala His Lys Tyr Leu Leu Val Glu
65                  70                  75                  80

Phe Tyr Ala Pro Trp Cys Gly His Cys Lys Ala Leu Ala Pro Glu Tyr
                85                  90                  95

Ala Lys Ala Ala Gly Lys Leu Lys Ala Glu Gly Ser Glu Ile Arg Leu
            100                 105                 110

Ala Lys Val Asp Ala Thr Glu Glu Ser Asp Leu Ala Gln Gln Tyr Gly
        115                 120                 125

Val Arg Gly Tyr Pro Thr Ile Lys Phe Phe Arg Asn Gly Asp Thr Ala
    130                 135                 140

Ser Pro Lys Glu Tyr Thr Ala Gly Arg Glu Ala Asp Asp Ile Val Asn
145                 150                 155                 160

Trp Leu Lys Lys Arg Thr Gly Pro Ala Ala Thr Thr Leu Pro Asp Gly
                165                 170                 175

Ala Ala Ala Glu Ser Leu Val Glu Ser Ser Glu Val Ala Val Ile Gly
            180                 185                 190

Phe Phe Lys Asp Val Glu Ser Asp Ser Ala Lys Gln Phe Leu Gln Ala
        195                 200                 205

Ala Glu Ala Ile Asp Asp Ile Pro Phe Gly Ile Thr Ser Asn Ser Asp
    210                 215                 220

Val Phe Ser Lys Tyr Gln Leu Asp Lys Asp Gly Val Val Leu Phe Lys
225                 230                 235                 240

Lys Phe Asp Glu Gly Arg Asn Asn Phe Glu Gly Glu Val Thr Lys Glu
                245                 250                 255

Asn Leu Leu Asp Phe Ile Lys His Asn Gln Leu Pro Leu Val Ile Glu
            260                 265                 270

Phe Thr Glu Gln Thr Ala Pro Lys Ile Phe Gly Gly Glu Ile Lys Thr
```

```
                275                 280                 285
His Ile Leu Leu Phe Leu Pro Lys Ser Val Ser Asp Tyr Asp Gly Lys
    290                 295                 300
Leu Ser Asn Phe Lys Thr Ala Ala Glu Ser Phe Lys Gly Lys Ile Leu
305                 310                 315                 320
Phe Ile Phe Ile Asp Ser Asp His Thr Asp Asn Gln Arg Ile Leu Glu
                325                 330                 335
Phe Phe Gly Leu Lys Lys Glu Glu Cys Pro Ala Val Arg Leu Ile Thr
            340                 345                 350
Leu Glu Glu Glu Met Thr Lys Tyr Lys Pro Glu Ser Glu Glu Leu Thr
            355                 360                 365
Ala Glu Arg Ile Thr Glu Phe Cys His Arg Phe Leu Glu Gly Lys Ile
        370                 375                 380
Lys Pro His Leu Met Ser Gln Glu Leu Pro Glu Asp Trp Asp Lys Gln
385                 390                 395                 400
Pro Val Lys Val Leu Val Gly Lys Asn Phe Glu Asp Val Ala Phe Asp
                405                 410                 415
Glu Lys Lys Asn Val Phe Val Glu Phe Tyr Ala Pro Trp Cys Gly His
            420                 425                 430
Cys Lys Gln Leu Ala Pro Ile Trp Asp Lys Leu Gly Glu Thr Tyr Lys
        435                 440                 445
Asp His Glu Asn Ile Val Ile Ala Lys Met Asp Ser Thr Ala Asn Glu
    450                 455                 460
Val Glu Ala Val Lys Val His Ser Phe Pro Thr Leu Lys Phe Phe Pro
465                 470                 475                 480
Ala Ser Ala Asp Arg Thr Val Ile Asp Tyr Asn Gly Glu Arg Thr Leu
                485                 490                 495
Asp Gly Phe Lys Lys Phe Leu Glu Ser Gly Gly Gln Asp Gly Ala Gly
            500                 505                 510
Asp Asp Asp Asp Leu Glu Asp Leu Glu Glu Ala Glu Glu Pro Asp Met
        515                 520                 525
Glu Glu Asp Asp Asp Gln Lys Ala Val
    530                 535

<210> SEQ ID NO 14
<211> LENGTH: 1723
<212> TYPE: DNA
<213> ORGANISM: Artificial Sequence
<220> FEATURE:
<223> OTHER INFORMATION: Synthetic sequence containing the coding
      regions of the vacuolar signal sequence of barley gene for Thiol
      protease aleurain precursor fused to the human Prolyl
      4-hydroxylase alpha-1 subunit and flanking regions

<400> SEQUENCE: 14
ctcgagtaaa ccatggctca tgctagggtt ttgcttttgg ctcttgctgt tcttgctact      60
gctgctgttg ctgtggcttc ttcttcatct ttcgctgatt ctaacccaat taggccagtg    120
actgatagag ctgcttctac tcttgctcaa ttggtcgaca tgcacccagg attcttcact    180
tctattggac agatgactga tcttattcac actgagaagg atcttgtgac ttctcttaag    240
gattacatta aggctgagga ggataagttg gagcagatta agaagtgggc tgagaagttg    300
gataggctta cttctactgc tacaaaagat ccagagggat tcgttggtca tccagtgaac    360
gctttcaagt tgatgaagag gcttaacact gagtggagtg agcttgagaa ccttgtgctt    420
aaggatatgt ctgatggatt catttctaac cttactattc agaggcagta cttcccaaat    480
```

```
gatgaggatc aagtgggagc tgctaaggct cttcttaggc ttcaggatac ttacaacctt      540
gatactgata caatttctaa gggaaacctt ccaggagtta agcacaagtc tttccttact      600
gctgaggatt gcttcgagct tggaaaggtt gcatacactg aggctgatta ctaccacact      660
gagctttgga tggaacaagc tcttaggcaa cttgatgagg agagatttc tactattgat       720 aaggtgtcag tgcttgatta ccttttcttac gctgtgtacc agcagggtga tcttgataag     780
gctcttttgc ttactaagaa gttgcttgag cttgatccag aacatcagag ggctaacgga      840
aaccttaagt acttcgagta cattatggct aaggaaaagg atgtgaacaa gtctgcttct     900
gatgatcagt ctgatcaaaa gactactcca aagaagaagg gagtggctgt tgattatctt     960
cctgagaggc agaagtatga tgttgtgt aggggagagg gtattaagat gactccaagg       1020
aggcagaaga agttgttctg caggtatcac gatggaaaca ggaacccaaa gttcattctt     1080
gctccagcta agcaagaaga tgagtgggat aagccaagga ttattaggtt ccacgatatt     1140
atttctgatg ctgagattga gattgtgaag gatcttgcta agccaagact taggagggct     1200
actatttcta accctattac tggtgatctt gagactgtgc actacaggat ttctaagtct     1260
gcttggcttt ctggatacga gaacccagtg gtgtct

-continued

```
Ser Glu Leu Glu Asn Leu Val Leu Lys Asp Met Ser Asp Gly Phe Ile
    130                 135                 140
Ser Asn Leu Thr Ile Gln Arg Gln Tyr Phe Pro Asn Asp Glu Asp Gln
145                 150                 155                 160
Val Gly Ala Ala Lys Ala Leu Leu Arg Leu Gln Asp Thr Tyr Asn Leu
                165                 170                 175
Asp Thr Asp Thr Ile Ser Lys Gly Asn Leu Pro Gly Val Lys His Lys
            180                 185                 190
Ser Phe Leu Thr Ala Glu Asp Cys Phe Glu Leu Gly Lys Val Ala Tyr
        195                 200                 205
Thr Glu Ala Asp Tyr Tyr His Thr Glu Leu Trp Met Glu Gln Ala Leu
    210                 215                 220
Arg Gln Leu Asp Glu Gly Glu Ile Ser Thr Ile Asp Lys Val Ser Val
225                 230                 235                 240
Leu Asp Tyr Leu Ser Tyr Ala Val Tyr Gln Gln Gly Asp Leu Asp Lys
                245                 250                 255
Ala Leu Leu Leu Thr Lys Lys Leu Leu Glu Leu Asp Pro Glu His Gln
            260                 265                 270
Arg Ala Asn Gly Asn Leu Lys Tyr Phe Glu Tyr Ile Met Ala Lys Glu
        275                 280                 285
Lys Asp Val Asn Lys Ser Ala Ser Asp Asp Gln Ser Asp Gln Lys Thr
    290                 295                 300
Thr Pro Lys Lys Lys Gly Val Ala Val Asp Tyr Leu Pro Glu Arg Gln
305                 310                 315                 320
Lys Tyr Glu Met Leu Cys Arg Gly Glu Gly Ile Lys Met Thr Pro Arg
                325                 330                 335
Arg Gln Lys Lys Leu Phe Cys Arg Tyr His Asp Gly Asn Arg Asn Pro
            340                 345                 350
Lys Phe Ile Leu Ala Pro Ala Lys Gln Glu Asp Glu Trp Asp Lys Pro
        355                 360                 365
Arg Ile Ile Arg Phe His Asp Ile Ile Ser Asp Ala Glu Ile Glu Ile
    370                 375                 380
Val Lys Asp Leu Ala Lys Pro Arg Leu Arg Arg Ala Thr Ile Ser Asn
385                 390                 395                 400
Pro Ile Thr Gly Asp Leu Glu Thr Val His Tyr Arg Ile Ser Lys Ser
                405                 410                 415
Ala Trp Leu Ser Gly Tyr Glu Asn Pro Val Val Ser Arg Ile Asn Met
            420                 425                 430
Arg Ile Gln Asp Leu Thr Gly Leu Asp Val Ser Thr Ala Glu Glu Leu
        435                 440                 445
Gln Val Ala Asn Tyr Gly Val Gly Gly Gln Tyr Glu Pro His Phe Asp
    450                 455                 460
Phe Ala Arg Lys Asp Glu Pro Asp Ala Phe Lys Glu Leu Gly Thr Gly
465                 470                 475                 480
Asn Arg Ile Ala Thr Trp Leu Phe Tyr Met Ser Asp Val Ser Ala Gly
                485                 490                 495
Gly Ala Thr Val Phe Pro Glu Val Gly Ala Ser Val Trp Pro Lys Lys
            500                 505                 510
Gly Thr Ala Val Phe Trp Tyr Asn Leu Phe Ala Ser Gly Glu Gly Asp
        515                 520                 525
Tyr Ser Thr Arg His Ala Ala Cys Pro Val Leu Val Gly Asn Lys Trp
    530                 535                 540
Val Ser Asn Lys Trp Leu His Glu Arg Gly Gln Glu Phe Arg Arg Pro
```

```
                   545                 550                 555                 560

Cys Thr Leu Ser Glu Leu Glu
                565

<210> SEQ ID NO 16
<211> LENGTH: 928
<212> TYPE: DNA
<213> ORGANISM: Artificial Sequence
<220> FEATURE:
<223> OTHER INFORMATION: Synthetic sequence containing the coding
      regions of the vacuolar signal sequence of barley gene for Thiol
      protease aleurain precursor fused to the plant Prolyl
      4-hydroxylase Plant and flanking regions

<400> SEQUENCE: 16
ctcgagtaaa ccatggctca tgctagggtt ttgcttttgg ctcttgctgt tcttgctact      60
gctgctgttg ctgtggcttc ttcttcatct ttcgctgatt ctaacccaat taggccagtg     120
actgatagag ctgcttctac tcttgctcaa ttggtcgaca tgcttggtat tctttctctt     180
ccaaacgcta acaggaactc ttctaagact aacgatctta ctaacattgt gaggaagtct     240
gagacttctt ctggagatga ggagggaaat ggagaaagat gggtggaagt gatttcttgg     300
gagccaaggg ctgttgttta ccacaacttc cttactaatg aggagtgcga gcaccttatt     360
tctcttgcta agccatctat ggtgaagtct actgtggtgg atgagaaaac tggaggatct     420
aaggattcaa gagtgaggac ttcatctggt actttcctta ggaggggaca tgatgaagtt     480
gtggaagtta ttgagaagag gatttctgat ttcactttca ttccagtgga gaacggagaa     540
ggacttcaag ttcttcacta ccaagtggga caaaagtacg agccacacta cgattacttc     600
cttgatgagt caacactaa gaacggagga cagaggattg ctactgtgct tatgtacctt     660
tctgatgtgg atgatggagg agagactgtt tttccagctg ctaggggaaa catttctgct     720
gttccttggt ggaacgagct ttctaagtgt ggaaaggagg actttctgt gcttccaaag     780 aaaagggatg ctcttctttt ctggaacatg aggccagatg cttctcttga tccatcttct     840
cttcatggag gatgcccagt tgttaaggga aacaagtggt catctactaa gtggttccac     900
gtgcacgagt tcaaggtgta atgagctc                                        928

<210> SEQ ID NO 17
<211> LENGTH: 302
<212> TYPE: PRT
<213> ORGANISM: Artificial Sequence
<220> FEATURE:
<223> OTHER INFORMATION: Synthetic sequence containing the vacuolar
      signal sequence of barley gene for Thiol protease aleurain
      precursor fused to the plant Prolyl 4-hydroxylase Plant and
      flanking regions

<400> SEQUENCE: 17

Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
                20                  25                  30

Ile Arg Pro Val Thr Asp Arg Ala Ala Ser Thr Leu Ala Gln Leu Val
            35                  40                  45

Asp Met Leu Gly Ile Leu Ser Leu Pro Asn Ala Asn Arg Asn Ser Ser
        50                  55                  60

Lys Thr Asn Asp Leu Thr Asn Ile Val Arg Lys Ser Glu Thr Ser Ser
65                  70                  75                  80

Gly Asp Glu Glu Gly Asn Gly Glu Arg Trp Val Glu Val Ile Ser Trp
```

```
                    85                  90                  95
Glu Pro Arg Ala Val Val Tyr His Asn Phe Leu Thr Asn Glu Glu Cys
                100                 105                 110

Glu His Leu Ile Ser Leu Ala Lys Pro Ser Met Val Lys Ser Thr Val
            115                 120                 125

Val Asp Glu Lys Thr Gly Gly Ser Lys Asp Ser Arg Val Arg Thr Ser
        130                 135                 140

Ser Gly Thr Phe Leu Arg Arg Gly His Asp Glu Val Val Glu Val Ile
145                 150                 155                 160

Glu Lys Arg Ile Ser Asp Phe Thr Phe Ile Pro Val Glu Asn Gly Glu
                165                 170                 175

Gly Leu Gln Val Leu His Tyr Gln Val Gly Gln Lys Tyr Glu Pro His
                180                 185                 190

Tyr Asp Tyr Phe Leu Asp Glu Phe Asn Thr Lys Asn Gly Gly Gln Arg
                195                 200                 205

Ile Ala Thr Val Leu Met Tyr Leu Ser Asp Val Asp Asp Gly Gly Glu
        210                 215                 220

Thr Val Phe Pro Ala Ala Arg Gly Asn Ile Ser Ala Val Pro Trp Trp
225                 230                 235                 240

Asn Glu Leu Ser Lys Cys Gly Lys Glu Gly Leu Ser Val Leu Pro Lys
                245                 250                 255

Lys Arg Asp Ala Leu Leu Phe Trp Asn Met Arg Pro Asp Ala Ser Leu
                260                 265                 270

Asp Pro Ser Ser Leu His Gly Gly Cys Pro Val Val Lys Gly Asn Lys
                275                 280                 285

Trp Ser Ser Thr Lys Trp Phe His Val His Glu Phe Lys Val
            290                 295                 300

<210> SEQ ID NO 18
<211> LENGTH: 2689
<212> TYPE: DNA
<213> ORGANISM: Artificial Sequence
<220> FEATURE:
<223> OTHER INFORMATION: Synthetic sequence containing the coding
      regions of the human Procollagen C-proteinase and flanking regions

<400> SEQUENCE: 18
agatctatcg atgcatgcca tggtaccgcg ccatggctca attggctgca acatcaaggc      60
ctgaaagagt ttggccagat ggtgttattc ctttcgttat tggtggaaac tttactggat     120
ctcagagagc agtttttaga caagctatga gacattggga aaagcacact tgtgtgacat     180
tccttgaaag gactgatgaa gattcttata ttgtgttcac ataccgtcca tgtggatgct     240
gctcatatgt tggtagaagg ggaggaggtc acaagcaatt tctattgga aaaaactgcg      300 ataagttcgg aattgtggtg catgaattgg gacatgttgt tggtttctgg cacgaacaca     360
caaggccaga tagggatagg cacgtgtcta ttgtgaggga aaacattcag ccaggtcaag     420
agtacaattt tcttaagatg gaacctcaag aggtggaatc tctcggagag acttacgact     480
tcgactccat catgcactac gcaaggaata cttttcagcag gggcatcttc ttggatacca     540
ttgtgcctaa gtacgaggtg aacggcgtta agccacctat tggtcaaagg actaggctct     600
ctaagggtga tattgcacag gctaggaagc tctacaaatg tccagcatgc ggagaaactc     660
ttcaggattc cactggcaac ttctcatctc cagagtaccc aaacggatac tctgctcata     720
tgcactgtgt ttggaggatc tcagtgactc ctggagagaa gatcatcctc aacttcactt     780
ccctcgatct ctatcgttct aggctctgtt ggtacgacta tgtggaagtg agagatggct     840
```

```
tctggagaaa ggctccactt agaggaaggt tctgcggatc taaacttcct gagccaatcg      900
tgtctactga ttccagattg tgggtggagt tcaggtcctc ttctaattgg gttggcaagg      960
gcttttttgc tgtgtacgag gctatttgtg gcggcgacgt gaaaaaggac tacggacata    1020
ttcaaagtcc aaattaccca gatgattacc gtccttcaaa agtgtgtatt tggaggattc    1080
aagtgagtga gggtttccat gttggattga cattccaatc tttcgaaatt gagagacacg    1140
attcatgcgc atacgattat ttggaagtga gagatggaca ctctgaatct tctacactta    1200
ttggaaggta ctgcggttat gagaaacctg atgatattaa gtctacttct agtaggttgt    1260
ggcttaaatt tgtgtcagat ggttctatta acaaggctgg tttcgcagtg aacttcttca    1320
aggaagtgga tgaatgctca agacctaaca gaggaggatg tgagcaaaga tgccttaaca    1380
ctttgggaag ttacaagtgt tcttgcgatc ctggatacga gttggctcct gataagagaa    1440
gatgcgaagc tgcttgcggt ggttttttga caaaattgaa cggatctatt acttctcctg    1500
gatggccaaa agagtaccca cctaataaga attgcatttg gcagcttgtt gcacctactc    1560
agtaccgtat ttcattgcaa ttcgattttt tcgagactga gggtaatgat gtgtgcaagt    1620
acgatttcgt ggaagtgaga tcaggtctta ctgctgatag taaattgcac ggaaagttct    1680
gcggatctga aaaccagaa gtgattacat cacagtacaa caatatgagg gtggagttca    1740
aatctgataa tactgtttct aaaaaaggtt ttaaggcaca tttcttttct gataaggacg    1800
agtgctctaa agataatggt ggttgccagc aggattgcgt gaacacattc ggttcatatg    1860
agtgccaatg ccgtagtgga tttgttcttc acgataacaa acatgattgc aaagaggcag    1920
gttgcgatca caaggtgaca tctacttcag gtactatcac atctccaaac tggcctgata    1980
agtatccttc aaaaaaagaa tgtacatggg caatttcttc tacaccaggt cataggggta    2040
agttgacatt catggagatg gatattgaga gtcaaccaga gtgcgcttat gatcatcttg    2100
aggtgttcga tggaagggat gctaaggctc ctgttcttgg tagattctgt ggtagtaaaa    2160
agccagaacc agtgcttgca acaggatcta ggatgttcct tagattctac tctgataact    2220
cagttcagag gaaaggattc caagctagtc acgcaactga atgcggtgga caagttagag    2280
cagatgttaa gactaaggat ctttactcac acgcacagtt cggagataac aactaccctg    2340
gaggagttga ttgcgagtgg gttattgtgg ctgaagaggg atacggagtt gagcttgttt    2400
tccagacatt cgaggtggag gaggaaactg attgcggtta cgattatatg gaactttttg    2460
atggatacga tagtactgct ccaagacttg gaaggtattg tggtagtggt ccaccagaag    2520
aggtgtactc agctggagat agtgttcttg ttaagttcca cagtgatgat acaattacta    2580 agaaggggatt ccatcttaga tatacttcaa ctaagtttca ggatactctt cattctagga    2640
agtaatgagc tcgcggccgc atccaagctt ctgcagacgc gtcgacgtc               2689
```

<210> SEQ ID NO 19
<211> LENGTH: 870
<212> TYPE: PRT
<213> ORGANISM: Artificial Sequence
<220> FEATURE:
<223> OTHER INFORMATION: Synthetic sequence containing the human
      Procollagen C-proteinase and flanking regions

<400> SEQUENCE: 19

Met Ala Gln Leu Ala Ala Thr Ser Arg Pro Glu Arg Val Trp Pro Asp
1               5                   10                  15

Gly Val Ile Pro Phe Val Ile Gly Gly Asn Phe Thr Gly Ser Gln Arg
            20                  25                  30

```
Ala Val Phe Arg Gln Ala Met Arg His Trp Glu Lys His Thr Cys Val
         35                  40                  45

Thr Phe Leu Glu Arg Thr Asp Glu Asp Ser Tyr Ile Val Phe Thr Tyr
 50                  55                  60

Arg Pro Cys Gly Cys Ser Tyr Val Gly Arg Arg Gly Gly Pro
 65              70                  75                  80

Gln Ala Ile Ser Ile Gly Lys Asn Cys Asp Lys Phe Gly Ile Val Val
                 85                  90                  95

His Glu Leu Gly His Val Val Gly Phe Trp His Glu His Thr Arg Pro
                100                 105                 110

Asp Arg Asp Arg His Val Ser Ile Val Arg Glu Asn Ile Gln Pro Gly
                115                 120                 125

Gln Glu Tyr Asn Phe Leu Lys Met Glu Pro Gln Glu Val Glu Ser Leu
        130                 135                 140

Gly Glu Thr Tyr Asp Phe Asp Ser Ile Met His Tyr Ala Arg Asn Thr
145                 150                 155                 160

Phe Ser Arg Gly Ile Phe Leu Asp Thr Ile Val Pro Lys Tyr Glu Val
                165                 170                 175

Asn Gly Val Lys Pro Pro Ile Gly Gln Arg Thr Arg Leu Ser Lys Gly
                180                 185                 190

Asp Ile Ala Gln Ala Arg Lys Leu Tyr Lys Cys Pro Ala Cys Gly Glu
                195                 200                 205

Thr Leu Gln Asp Ser Thr Gly Asn Phe Ser Ser Pro Glu Tyr Pro Asn
        210                 215                 220

Gly Tyr Ser Ala His Met His Cys Val Trp Arg Ile Ser Val Thr Pro
225                 230                 235                 240

Gly Glu Lys Ile Ile Leu Asn Phe Thr Ser Leu Asp Leu Tyr Arg Ser
                245                 250                 255

Arg Leu Cys Trp Tyr Asp Tyr Val Glu Val Arg Asp Gly Phe Trp Arg
                260                 265                 270

Lys Ala Pro Leu Arg Gly Arg Phe Cys Gly Ser Lys Leu Pro Glu Pro
        275                 280                 285

Ile Val Ser Thr Asp Ser Arg Leu Trp Val Glu Phe Arg Ser Ser Ser
        290                 295                 300

Asn Trp Val Gly Lys Gly Phe Phe Ala Val Tyr Glu Ala Ile Cys Gly
305                 310                 315                 320

Gly Asp Val Lys Lys Asp Tyr Gly His Ile Gln Ser Pro Asn Tyr Pro
                325                 330                 335

Asp Asp Tyr Arg Pro Ser Lys Val Cys Ile Trp Arg Ile Gln Val Ser
                340                 345                 350

Glu Gly Phe His Val Gly Leu Thr Phe Gln Ser Phe Glu Ile Glu Arg
                355                 360                 365

His Asp Ser Cys Ala Tyr Asp Tyr Leu Glu Val Arg Asp Gly His Ser
        370                 375                 380

Glu Ser Ser Thr Leu Ile Gly Arg Tyr Cys Gly Tyr Glu Lys Pro Asp
385                 390                 395                 400

Asp Ile Lys Ser Thr Ser Ser Arg Leu Trp Leu Lys Phe Val Ser Asp
                405                 410                 415

Gly Ser Ile Asn Lys Ala Gly Phe Ala Val Asn Phe Lys Glu Val
                420                 425                 430

Asp Glu Cys Ser Arg Pro Asn Arg Gly Gly Cys Glu Gln Arg Cys Leu
        435                 440                 445
```

```
Asn Thr Leu Gly Ser Tyr Lys Cys Ser Cys Asp Pro Gly Tyr Glu Leu
    450                 455                 460
Ala Pro Asp Lys Arg Arg Cys Glu Ala Ala Cys Gly Gly Phe Leu Thr
465                 470                 475                 480
Lys Leu Asn Gly Ser Ile Thr Ser Pro Gly Trp Pro Lys Glu Tyr Pro
                485                 490                 495
Pro Asn Lys Asn Cys Ile Trp Gln Leu Val Ala Pro Thr Gln Tyr Arg
            500                 505                 510
Ile Ser Leu Gln Phe Asp Phe Phe Glu Thr Glu Gly Asn Asp Val Cys
        515                 520                 525
Lys Tyr Asp Phe Val Glu Val Arg Ser Gly Leu Thr Ala Asp Ser Lys
    530                 535                 540
Leu His Gly Lys Phe Cys Gly Ser Glu Lys Pro Glu Val Ile Thr Ser
545                 550                 555                 560
Gln Tyr Asn Asn Met Arg Val Glu Phe Lys Ser Asp Asn Thr Val Ser
                565                 570                 575
Lys Lys Gly Phe Lys Ala His Phe Phe Ser Asp Lys Asp Glu Cys Ser
            580                 585                 590
Lys Asp Asn Gly Gly Cys Gln Gln Asp Cys Val Asn Thr Phe Gly Ser
        595                 600                 605
Tyr Glu Cys Gln Cys Arg Ser Gly Phe Val Leu His Asp Asn Lys His
    610                 615                 620
Asp Cys Lys Glu Ala Gly Cys Asp His Lys Val Thr Ser Thr Ser Gly
625                 630                 635                 640
Thr Ile Thr Ser Pro Asn Trp Pro Asp Lys Tyr Pro Ser Lys Lys Glu
                645                 650                 655
Cys Thr Trp Ala Ile Ser Ser Thr Pro Gly His Arg Val Lys Leu Thr
            660                 665                 670
Phe Met Glu Met Asp Ile Glu Ser Gln Pro Glu Cys Ala Tyr Asp His
        675                 680                 685
Leu Glu Val Phe Asp Gly Arg Asp Ala Lys Ala Pro Val Leu Gly Arg
    690                 695                 700
Phe Cys Gly Ser Lys Lys Pro Glu Pro Val Leu Ala Thr Gly Ser Arg
705                 710                 715                 720
Met Phe Leu Arg Phe Tyr Ser Asp Asn Ser Val Gln Arg Lys Gly Phe
                725                 730                 735
Gln Ala Ser His Ala Thr Glu Cys Gly Gly Gln Val Arg Ala Asp Val
            740                 745                 750
Lys Thr Lys Asp Leu Tyr Ser His Ala Gln Phe Gly Asp Asn Asn Tyr
        755                 760                 765
Pro Gly Gly Val Asp Cys Glu Trp Val Ile Val Ala Glu Glu Gly Tyr
    770                 775                 780
Gly Val Glu Leu Val Phe Gln Thr Phe Glu Val Glu Glu Glu Thr Asp
785                 790                 795                 800
Cys Gly Tyr Asp Tyr Met Glu Leu Phe Asp Gly Tyr Asp Ser Thr Ala
                805                 810                 815
Pro Arg Leu Gly Arg Tyr Cys Gly Ser Gly Pro Pro Glu Glu Val Tyr
            820                 825                 830
Ser Ala Gly Asp Ser Val Leu Val Lys Phe His Ser Asp Asp Thr Ile
        835                 840                 845
Thr Lys Lys Gly Phe His Leu Arg Tyr Thr Ser Thr Lys Phe Gln Asp
    850                 855                 860
Thr Leu His Ser Arg Lys
```

<210> SEQ ID NO 20
<211> LENGTH: 2912
<212> TYPE: DNA
<213> ORGANISM: Artificial Sequence
<220> FEATURE:
<223> OTHER INFORMATION: Synthetic sequence containing the coding
regions of the human Procollagen I N-proteinase and flanking
regions

<400> SEQUENCE: 20

| | | | | | |
|---|---|---|---|---|---|
| gcgccatggc | tcaattgagg | agaagggcta | ggagacacgc | agctgatgat | gattacaaca | 60 |
| ttgaagtttt | gcttggtgtt | gatgatagtg | tggtgcaatt | ccacggaaaa | gagcatgttc | 120 |
| agaaatatct | tttgacactt | atgaatattg | tgaacgaaat | ctaccatgat | gagtctttgg | 180 |
| gagcacacat | taacgtggtt | cttgtgagga | ttattcttct | ttcatacggt | aaatctatgt | 240 |
| cacttattga | gattggaaac | ccttctcagt | ctcttgagaa | tgtgtgcaga | tgggcatacc | 300 |
| ttcaacagaa | gcctgatact | ggacacgatg | agtatcacga | tcacgctatt | ttccttacaa | 360 |
| ggcaggattt | cggtccaagt | ggaatgcaag | gatatgctcc | tgttactggt | atgtgccacc | 420 |
| ctgttaggtc | ttgtacactt | aaccacgagg | atggttttc | atctgctttc | gtggtggctc | 480 |
| atgagacagg | tcatgttttg | ggaatggaac | atgatggaca | gggtaataga | tgtggagatg | 540 |
| aagtgagact | tggttcaatt | atggctcctc | ttgttcaagc | tgcttttcat | aggttccact | 600 |
| ggagtaggtg | ttcacagcaa | gagttgagta | gataccttca | ttcttacgat | tgcttgcttg | 660 |
| atgatccatt | tgctcatgat | tggccagctt | tgcctcaact | tcctggattg | cactactcta | 720 |
| tgaacgagca | gtgcagattt | gatttcggtc | ttggttacat | gatgtgcaca | gctttcagga | 780 |
| ctttcgatcc | atgcaaacag | ttgtggtgtt | cacacccaga | taacccatat | ttctgtaaaa | 840 |
| caaaaaagg | tccaccactt | gatggtacta | tgtgcgcacc | tggaaagcac | tgcttcaagg | 900 |
| gacactgcat | ttggcttact | cctgatattc | ttaaaaggga | tggatcatgg | ggagcttggt | 960 |
| ctccattcgg | aagttgctca | agaacttgcg | gaacaggtgt | taagtttaga | actaggcagt | 1020 |
| gcgataatcc | acaccctgct | aatggtggta | gaacttgctc | tggacttgct | tacgatttc | 1080 |
| agttgtgttc | taggcaagat | tgccctgata | gtcttgctga | ttttagagaa | gagcaatgta | 1140 |
| gacagtggga | tctttacttt | gagcacggcg | acgctcagca | ccactggctt | ccacacgagc | 1200 |
| atagagatgc | aaaagaaagg | tgtcacccttt | attgcgagag | tagagagact | ggagaggtgg | 1260 |
| tgtcaatgaa | gagaatggtg | cacgatggta | caaggtgttc | ttataaggat | gcattctctt | 1320 |
| tgtgtgtgag | gggagattgc | aggaaagtgg | gttgtgatgg | agtgattgga | tctagtaagc | 1380 |
| aagaagataa | gtgcggagtg | tgcggaggag | ataactctca | ttgcaaggtt | gtgaaaggaa | 1440 |
| cttttacaag | atcaccaaaa | aaacacggtt | acattaagat | gttcgaaatt | cctgctggag | 1500 |
| caaggcattt | gcttattcag | gaagtggatg | caacatctca | ccacttggca | gtgaaaaacc | 1560 |
| ttgagactgg | aaaattcatt | ttgaacgagg | agaacgatgt | tgatgcatct | agtaagactt | 1620 |
| tcattgcaat | gggtgttgaa | tgggagtata | gggatgagga | tggaagggaa | acacttcaaa | 1680 |
| caatgggtcc | tcttcatgga | acaattactg | tgttggtgat | tccagtggga | gatacaaggg | 1740 |
| tgtcattgac | atacaagtat | atgattcacg | aggatagtct | taacgttgat | gataacaacg | 1800 |
| ttttggaaga | agattctgtg | gtttacgagt | gggctcttaa | gaaatggtca | ccttgctcta | 1860 |
| agccatgtgg | tggaggaagt | cagttcacta | agtatggttg | taggaggagg | cttgatcata | 1920 |
| agatggttca | tagggatttt | gcgcagcac | ttagtaagcc | aaaggcaatt | aggagggctt | 1980 |

```
gtaaccctca agaatgctca caaccagttt gggtgacagg agagtgggag ccatgttcac    2040
aaacatgcgg aagaactgga atgcaagtta gatcagttag atgcattcaa cctcttcatg    2100
ataacactac aagaagtgtg cacgcaaaac actgtaacga tgctaggcca gagagtagaa    2160
gagcttgctc tagggaactt tgccctggta gatggagggc aggaccttgg agtcagtgct    2220
ctgtgacatg tggaaacggt actcaggaaa gacctgttcc atgtagaact gctgatgata    2280
gtttcggaat ttgtcaggag gaaaggccag aaacagctag gacttgtaga cttgaccttt    2340
gtcctaggaa tatttctgat cctagtaaaa aatcatacgt ggtgcaatgg ttgagtaggc    2400
cagatccaga ttcaccaatt aggaagattt cttcaaaagg acactgccag ggtgataaga    2460
gtattttctg cagaatggaa gttcttagta ggtactgttc tattccaggt tataacaaac    2520
tttcttgtaa gagttgcaac ttgtataaca atcttactaa cgtggagggt agaattgaac    2580
ctccaccagg aaagcacaac gatattgatg tgtttatgcc tactcttcct gtgccaacag    2640
ttgcaatgga agttagacct tctccatcta ctccacttga ggtgccactt aatgcatcaa    2700
gtactaacgc tactgaggat cacccagaga ctaacgcagt tgatgagcct tataagattc    2760
acggacttga ggatgaggtt cagccaccaa accttattcc taggaggcca agtccttacg    2820
aaaaaactag aaatcagagg attcaggagc ttattgatga gatgaggaaa aaggagatgc    2880
ttggaaagtt ctaatgagct cgcggccgca tc                                  2912
```

<210> SEQ ID NO 21
<211> LENGTH: 962
<212> TYPE: PRT
<213> ORGANISM: Artificial Sequence
<220> FEATURE:
<223> OTHER INFORMATION: Synthetic sequence containing the human
      Procollagen I N-proteinase and flanking regions

<400> SEQUENCE: 21

```
Met Ala Gln Leu Arg Arg Arg Ala Arg Arg His Ala Ala Asp Asp Asp
1               5                   10                  15

Tyr Asn Ile Glu Val Leu Leu Gly Val Asp Asp Ser Val Val Gln Phe
            20                  25                  30

His Gly Lys Glu His Val Gln Lys Tyr Leu Leu Thr Leu Met Asn Ile
        35                  40                  45

Val Asn Glu Ile Tyr His Asp Glu Ser Leu Gly Ala His Ile Asn Val
    50                  55                  60

Val Leu Val Arg Ile Ile Leu Leu Ser Tyr Gly Lys Ser Met Ser Leu
65                  70                  75                  80

Ile Glu Ile Gly Asn Pro Ser Gln Ser Leu Glu Asn Val Cys Arg Trp
                85                  90                  95

Ala Tyr Leu Gln Gln Lys Pro Asp Thr Gly His Asp Glu Tyr His Asp
            100                 105                 110

His Ala Ile Phe Leu Thr Arg Gln Asp Phe Gly Pro Ser Gly Met Gln
        115                 120                 125

Gly Tyr Ala Pro Val Thr Gly Met Cys His Pro Val Arg Ser Cys Thr
    130                 135                 140

Leu Asn His Glu Asp Gly Phe Ser Ser Ala Phe Val Val Ala His Glu
145                 150                 155                 160

Thr Gly His Val Leu Gly Met Glu His Asp Gly Gln Gly Asn Arg Cys
                165                 170                 175

Gly Asp Glu Val Arg Leu Gly Ser Ile Met Ala Pro Leu Val Gln Ala
            180                 185                 190
```

```
Ala Phe His Arg Phe His Trp Ser Arg Cys Ser Gln Gln Glu Leu Ser
        195                 200                 205

Arg Tyr Leu His Ser Tyr Asp Cys Leu Leu Asp Asp Pro Phe Ala His
        210                 215                 220

Asp Trp Pro Ala Leu Pro Gln Leu Pro Gly Leu His Tyr Ser Met Asn
225                 230                 235                 240

Glu Gln Cys Arg Phe Asp Phe Gly Leu Gly Tyr Met Met Cys Thr Ala
                245                 250                 255

Phe Arg Thr Phe Asp Pro Cys Lys Gln Leu Trp Cys Ser His Pro Asp
            260                 265                 270

Asn Pro Tyr Phe Cys Lys Thr Lys Lys Gly Pro Pro Leu Asp Gly Thr
        275                 280                 285

Met Cys Ala Pro Gly Lys His Cys Phe Lys Gly His Cys Ile Trp Leu
    290                 295                 300

Thr Pro Asp Ile Leu Lys Arg Asp Gly Ser Trp Gly Ala Trp Ser Pro
305                 310                 315                 320

Phe Gly Ser Cys Ser Arg Thr Cys Gly Thr Gly Val Lys Phe Arg Thr
                325                 330                 335

Arg Gln Cys Asp Asn Pro His Pro Ala Asn Gly Gly Arg Thr Cys Ser
            340                 345                 350

Gly Leu Ala Tyr Asp Phe Gln Leu Cys Ser Arg Gln Asp Cys Pro Asp
        355                 360                 365

Ser Leu Ala Asp Phe Arg Glu Glu Gln Cys Arg Gln Trp Asp Leu Tyr
    370                 375                 380

Phe Glu His Gly Asp Ala Gln His His Trp Leu Pro His Glu His Arg
385                 390                 395                 400

Asp Ala Lys Glu Arg Cys His Leu Tyr Cys Glu Ser Arg Glu Thr Gly
                405                 410                 415

Glu Val Val Ser Met Lys Arg Met Val His Asp Gly Thr Arg Cys Ser
            420                 425                 430

Tyr Lys Asp Ala Phe Ser Leu Cys Val Arg Gly Asp Cys Arg Lys Val
        435                 440                 445

Gly Cys Asp Gly Val Ile Gly Ser Ser Lys Gln Glu Asp Lys Cys Gly
    450                 455                 460

Val Cys Gly Gly Asp Asn Ser His Cys Lys Val Val Lys Gly Thr Phe
465                 470                 475                 480

Thr Arg Ser Pro Lys Lys His Gly Tyr Ile Lys Met Phe Glu Ile Pro
                485                 490                 495

Ala Gly Ala Arg His Leu Leu Ile Gln Glu Val Asp Ala Thr Ser His
            500                 505                 510

His Leu Ala Val Lys Asn Leu Glu Thr Gly Lys Phe Ile Leu Asn Glu
        515                 520                 525

Glu Asn Asp Val Asp Ala Ser Ser Lys Thr Phe Ile Ala Met Gly Val
    530                 535                 540

Glu Trp Glu Tyr Arg Asp Glu Asp Gly Arg Glu Thr Leu Gln Thr Met
545                 550                 555                 560

Gly Pro Leu His Gly Thr Ile Thr Val Leu Val Ile Pro Val Gly Asp
                565                 570                 575

Thr Arg Val Ser Leu Thr Tyr Lys Tyr Met Ile His Glu Asp Ser Leu
            580                 585                 590

Asn Val Asp Asp Asn Asn Val Leu Glu Glu Asp Ser Val Val Tyr Glu
        595                 600                 605
```

```
Trp Ala Leu Lys Lys Trp Ser Pro Cys Ser Lys Pro Cys Gly Gly Gly
            610                 615                 620
Ser Gln Phe Thr Lys Tyr Gly Cys Arg Arg Leu Asp His Lys Met
625                 630                 635                 640
Val His Arg Gly Phe Cys Ala Ala Leu Ser Lys Pro Lys Ala Ile Arg
                645                 650                 655
Arg Ala Cys Asn Pro Gln Glu Cys Ser Gln Pro Val Trp Val Thr Gly
            660                 665                 670
Glu Trp Glu Pro Cys Ser Gln Thr Cys Gly Arg Thr Gly Met Gln Val
            675                 680                 685
Arg Ser Val Arg Cys Ile Gln Pro Leu His Asp Asn Thr Thr Arg Ser
690                 695                 700
Val His Ala Lys His Cys Asn Asp Ala Arg Pro Glu Ser Arg Arg Ala
705                 710                 715                 720
Cys Ser Arg Glu Leu Cys Pro Gly Arg Trp Arg Ala Gly Pro Trp Ser
                725                 730                 735
Gln Cys Ser Val Thr Cys Gly Asn Gly Thr Gln Glu Arg Pro Val Pro
            740                 745                 750
Cys Arg Thr Ala Asp Asp Ser Phe Gly Ile Cys Gln Glu Glu Arg Pro
            755                 760                 765
Glu Thr Ala Arg Thr Cys Arg Leu Gly Pro Cys Pro Arg Asn Ile Ser
770                 775                 780
Asp Pro Ser Lys Lys Ser Tyr Val Val Gln Trp Leu Ser Arg Pro Asp
785                 790                 795                 800
Pro Asp Ser Pro Ile Arg Lys Ile Ser Ser Lys Gly His Cys Gln Gly
                805                 810                 815
Asp Lys Ser Ile Phe Cys Arg Met Glu Val Leu Ser Arg Tyr Cys Ser
            820                 825                 830
Ile Pro Gly Tyr Asn Lys Leu Ser Cys Lys Ser Cys Asn Leu Tyr Asn
            835                 840                 845
Asn Leu Thr Asn Val Glu Gly Arg Ile Glu Pro Pro Gly Lys His
    850                 855                 860
Asn Asp Ile Asp Val Phe Met Pro Thr Leu Pro Val Pro Thr Val Ala
865                 870                 875                 880
Met Glu Val Arg Pro Ser Pro Ser Thr Pro Leu Glu Val Pro Leu Asn
                885                 890                 895
Ala Ser Ser Thr Asn Ala Thr Glu Asp His Pro Glu Thr Asn Ala Val
            900                 905                 910
Asp Glu Pro Tyr Lys Ile His Gly Leu Glu Asp Glu Val Gln Pro Pro
            915                 920                 925
Asn Leu Ile Pro Arg Arg Pro Ser Pro Tyr Glu Lys Thr Arg Asn Gln
930                 935                 940
Arg Ile Gln Glu Leu Ile Asp Glu Met Arg Lys Lys Glu Met Leu Gly
945                 950                 955                 960
Lys Phe

<210> SEQ ID NO 22
<211> LENGTH: 2888
<212> TYPE: DNA
<213> ORGANISM: Artificial Sequence
<220> FEATURE:
<223> OTHER INFORMATION: Synthetic sequence containing the coding
      regions of the vacuolar signal sequence of barley gene for Thiol
      protease aleurain precursor fused to the human Lysyl hydroxylase 3
      and flanking regions
```

<400> SEQUENCE: 22

```
gcgaattcgc tagctatcac tgaaaagaca gcaagacaat ggtgtctcga tgcaccagaa      60
ccacatcttt gcagcagatg tgaagcagcc agagtggtcc acaagacgca ctcagaaaag     120
gcatcttcta ccgacacaga aaagacaac cacagctcat catccaacat gtagactgtc     180
gttatgcgtc ggctgaagat aagactgacc ccaggccagc actaaagaag aaataatgca     240
agtggtccta gctccacttt agctttaata attatgtttc attattattc tctgcttttg     300
ctctctatat aaagagcttg tattttcatt tgaaggcaga ggcgaacaca cacacagaac     360
ctccctgctt acaaaccaga tcttaaacca tggctcacgc tagggttttg cttcttgctc     420
ttgctgttct tgctactgct gctgttgctg tggcttcttc aagttctttc gctgattcta     480
acccaattag gccagtgact gatagagctg cttctactct tgctcaattg agatctatgt     540
ctgatagacc aaggggaagg gatccagtta atccagagaa gttgcttgtg attactgtgg     600
ctactgctga gactgaagga taccttagat tccttaggag tgctgagttc ttcaactaca     660
ctgtgaggac tcttggactt ggagaagaat ggagggagg agatgttgct agaactgttg     720
gaggaggaca gaaagtgaga tggcttaaga aagagatgga gaagtacgct gatagggagg     780
atatgattat tatgttcgtg gattcttacg atgtgattct tgctggatct ccaactgagc     840
ttttgaagaa attcgttcag tctggatcta ggcttctttt ctctgctgag tcttttgtt     900
ggccagaatg gggacttgct gagcaatatc agaagtggg aactgaaag agattcctta     960
actctggagg attcattgga ttcgctacta ctattcacca gattgtgagg cagtggaagt    1020
acaaggatga cgatgatgat cagcttttct acactaggct ttaccttgat ccaggactta    1080
gggagaagtt gtctcttaac cttgatcaca agtctaggat tttccagaac cttaacggtg    1140
ctcttgatga ggttgtgctt aagttcgata ggaacagagt gaggattagg aacgtggctt    1200
acgatactct tcctattgtg gtgcatggaa acggaccaac aaaactccag cttaactacc    1260
ttggaaacta cgttccaaac ggatggactc cagaaggagg atgtggattc tgcaatcagg    1320
ataggagaac tcttccagga ggacaaccac caccaagagt tttccttgct gtgttcgttg    1380
aacagccaac tccattcctt ccaagattcc ttcagaggct tcttcttttg gattacccac    1440
cagataggt gacacttttc cttcacaaca acgaggtttt ccacgagcca cacattgctg    1500
attcttggcc acagcttcag gatcatttct ctgctgtgaa gttggttggt ccagaagaag    1560
ctctttctcc aggagaagct agggatatgg ctatggattt gtgcaggcag gatccagagt    1620
gcgagttcta cttctctctt gatgctgatg ctgtgcttac taaccttcag actcttagga    1680
ttcttattga ggagaacagg aaagtgattg ctccaatgct ttctaggcac ggaaagttgt    1740
ggtctaattt ctgggggtgct cttttctcctg atgagtacta cgctagatca gaggactacg    1800
tggagcttgt tcagagaaag agagtgggag tttggaacgt tccttatatt tctcaggctt    1860
acgtgattag gggagatact cttaggatgg agcttccaca gagggatgtt ttctctggat    1920
ctgatactga tccagatatg gctttctgca agtctttcag ggataaggga attttccttc    1980
accttctaa ccagcatgag ttcggaagat tgcttgctac ttcaagatac gatactgagc    2040
accttcatcc tgatctttgg cagatttcg ataacccagt ggattggaag gagcagtaca    2100
ttcacgagaa ctactctagg gctcttgaag gagaaggaat tgtggagcaa ccatgcccag    2160
atgtttactg gttcccactt cttttctgagc aaatgtgcga tgagcttgtt gctgagatgg    2220
agcattacgg acaatggagt ggaggtagac atgaggattc taggcttgct ggaggatacg    2280
agaacgttcc aactgtggat attcacatga agcaagtggg atacgaggat caatggcttc    2340
```

-continued

```
agcttcttag gacttatgtg ggaccaatga ctgagtctct tttcccagga taccacacta    2400
aggctagggc tgttatgaac ttcgttgtga ggtatcgtcc agatgagcaa ccatctctta    2460
ggccacacca cgattcttct actttcactc ttaacgtggc tcttaaccac aagggacttg    2520
attatgaggg aggaggatgc cgtttcctta gatacgattg cgtgatttct tcaccaagaa    2580
agggatgggc tcttcttcat ccaggaaggc ttactcatta ccacgaggga cttccaacta    2640
cttggggaac tagatatatt atggtgtctt tcgtggatcc atgactgctt taatgagata    2700
tgcgagacgc ctatgatcgc atgatatttg ctttcaattc tgttgtgcac gttgtaaaaa    2760
acctgagcat gtgtagctca gatccttacc gccggtttcg gttcattcta atgaatatat    2820
cacccgttac tatcgtattt ttatgaataa tattctccgt tcaatttact gattgtccag    2880
aattcgcg                                                              2888
```

<210> SEQ ID NO 23
<211> LENGTH: 764
<212> TYPE: PRT
<213> ORGANISM: Artificial Sequence
<220> FEATURE:
<223> OTHER INFORMATION: Synthetic sequence containing the vacuolar
      signal sequence of barley gene for Thiol protease aleurain
      precursor fused to the human Lysyl hydroxylase 3 and flanking
      regions

<400> SEQUENCE: 23

```
Met Ala His Ala Arg Val Leu Leu Leu Ala Leu Ala Val Leu Ala Thr
1               5                   10                  15

Ala Ala Val Ala Val Ala Ser Ser Ser Phe Ala Asp Ser Asn Pro
            20                  25                  30

Ile Arg Pro Val Thr Asp Arg Ala Ala Ser Thr Leu Ala Gln Leu Arg
        35                  40                  45

Ser Met Ser Asp Arg Pro Arg Gly Arg Asp Pro Val Asn Pro Glu Lys
    50                  55                  60

Leu Leu Val Ile Thr Val Ala Thr Ala Glu Thr Glu Gly Tyr Leu Arg
65                  70                  75                  80

Phe Leu Arg Ser Ala Glu Phe Phe Asn Tyr Thr Val Arg Thr Leu Gly
                85                  90                  95

Leu Gly Glu Glu Trp Arg Gly Gly Asp Val Ala Arg Thr Val Gly Gly
            100                 105                 110

Gly Gln Lys Val Arg Trp Leu Lys Lys Glu Met Glu Lys Tyr Ala Asp
        115                 120                 125

Arg Glu Asp Met Ile Ile Met Phe Val Asp Ser Tyr Asp Val Ile Leu
    130                 135                 140

Ala Gly Ser Pro Thr Glu Leu Leu Lys Lys Phe Val Gln Ser Gly Ser
145                 150                 155                 160

Arg Leu Leu Phe Ser Ala Glu Ser Phe Cys Trp Pro Glu Trp Gly Leu
                165                 170                 175

Ala Glu Gln Tyr Pro Glu Val Gly Thr Gly Lys Arg Phe Leu Asn Ser
            180                 185                 190

Gly Gly Phe Ile Gly Phe Ala Thr Thr Ile His Gln Ile Val Arg Gln
        195                 200                 205

Trp Lys Tyr Lys Asp Asp Asp Asp Gln Leu Phe Tyr Thr Arg Leu
    210                 215                 220

Tyr Leu Asp Pro Gly Leu Arg Glu Lys Leu Ser Leu Asn Leu Asp His
225                 230                 235                 240
```

```
Lys Ser Arg Ile Phe Gln Asn Leu Asn Gly Ala Leu Asp Glu Val Val
            245                 250                 255

Leu Lys Phe Asp Arg Asn Arg Val Arg Ile Arg Asn Val Ala Tyr Asp
        260                 265                 270

Thr Leu Pro Ile Val Val His Gly Asn Gly Pro Thr Lys Leu Gln Leu
    275                 280                 285

Asn Tyr Leu Gly Asn Tyr Val Pro Asn Gly Trp Thr Pro Glu Gly Gly
290                 295                 300

Cys Gly Phe Cys Asn Gln Asp Arg Arg Thr Leu Pro Gly Gly Gln Pro
305                 310                 315                 320

Pro Pro Arg Val Phe Leu Ala Val Phe Val Glu Gln Pro Thr Pro Phe
                325                 330                 335

Leu Pro Arg Phe Leu Gln Arg Leu Leu Leu Leu Asp Tyr Pro Pro Asp
            340                 345                 350

Arg Val Thr Leu Phe Leu His Asn Asn Glu Val Phe His Glu Pro His
        355                 360                 365

Ile Ala Asp Ser Trp Pro Gln Leu Gln Asp His Phe Ser Ala Val Lys
    370                 375                 380

Leu Val Gly Pro Glu Glu Ala Leu Ser Pro Gly Glu Ala Arg Asp Met
385                 390                 395                 400

Ala Met Asp Leu Cys Arg Gln Asp Pro Glu Cys Glu Phe Tyr Phe Ser
                405                 410                 415

Leu Asp Ala Asp Ala Val Leu Thr Asn Leu Gln Thr Leu Arg Ile Leu
            420                 425                 430

Ile Glu Glu Asn Arg Lys Val Ile Ala Pro Met Leu Ser Arg His Gly
        435                 440                 445

Lys Leu Trp Ser Asn Phe Trp Gly Ala Leu Ser Pro Asp Glu Tyr Tyr
    450                 455                 460

Ala Arg Ser Glu Asp Tyr Val Glu Leu Val Gln Arg Lys Arg Val Gly
465                 470                 475                 480

Val Trp Asn Val Pro Tyr Ile Ser Gln Ala Tyr Val Ile Arg Gly Asp
                485                 490                 495

Thr Leu Arg Met Glu Leu Pro Gln Arg Asp Val Phe Ser Gly Ser Asp
            500                 505                 510

Thr Asp Pro Asp Met Ala Phe Cys Lys Ser Phe Arg Asp Lys Gly Ile
        515                 520                 525

Phe Leu His Leu Ser Asn Gln His Glu Phe Gly Arg Leu Leu Ala Thr
    530                 535                 540

Ser Arg Tyr Asp Thr Glu His Leu His Pro Asp Leu Trp Gln Ile Phe
545                 550                 555                 560

Asp Asn Pro Val Asp Trp Lys Glu Gln Tyr Ile His Glu Asn Tyr Ser
                565                 570                 575

Arg Ala Leu Glu Gly Glu Gly Ile Val Glu Gln Pro Cys Pro Asp Val
            580                 585                 590

Tyr Trp Phe Pro Leu Leu Ser Glu Gln Met Cys Asp Glu Leu Val Ala
        595                 600                 605

Glu Met Glu His Tyr Gly Gln Trp Ser Gly Gly Arg His Glu Asp Ser
    610                 615                 620

Arg Leu Ala Gly Gly Tyr Glu Asn Val Pro Thr Val Asp Ile His Met
625                 630                 635                 640

Lys Gln Val Gly Tyr Glu Asp Gln Trp Leu Gln Leu Leu Arg Thr Tyr
                645                 650                 655

Val Gly Pro Met Thr Glu Ser Leu Phe Pro Gly Tyr His Thr Lys Ala
```

```
                660               665               670
Arg Ala Val Met Asn Phe Val Arg Tyr Arg Pro Asp Glu Gln Pro
            675               680               685

Ser Leu Arg Pro His His Asp Ser Thr Phe Thr Leu Asn Val Ala
        690               695               700

Leu Asn His Lys Gly Leu Asp Tyr Glu Gly Gly Cys Arg Phe Leu
705               710               715               720

Arg Tyr Asp Cys Val Ile Ser Ser Pro Arg Lys Gly Trp Ala Leu Leu
                725               730               735

His Pro Gly Arg Leu Thr His Tyr His Glu Gly Leu Pro Thr Thr Trp
            740               745               750

Gly Thr Arg Tyr Ile Met Val Ser Phe Val Asp Pro
            755               760

<210> SEQ ID NO 24
<211> LENGTH: 45
<212> TYPE: PRT
<213> ORGANISM: Artificial Sequence
<220> FEATURE:
<223> OTHER INFORMATION: Vacuole signal sequence of barley gene for
      Thiol protease aleurain precursor

<400> SEQUENCE: 24

Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30

Ile Arg Pro Val Thr Asp Arg Ala Ala Ser Thr Leu Ala
        35                  40                  45

<210> SEQ ID NO 25
<211> LENGTH: 24
<212> TYPE: DNA
<213> ORGANISM: Artificial Sequence
<220> FEATURE:
<223> OTHER INFORMATION: Single strand DNA oligonucleotide

<400> SEQUENCE: 25
atcaccagga gaacagggac catc                                               24

<210> SEQ ID NO 26
<211> LENGTH: 29
<212> TYPE: DNA
<213> ORGANISM: Artificial Sequence
<220> FEATURE:
<223> OTHER INFORMATION: Single strand DNA oligonucleotide

<400> SEQUENCE: 26
tccacttcca aatctctatc cctaacaac                                          29

<210> SEQ ID NO 27
<211> LENGTH: 23
<212> TYPE: DNA
<213> ORGANISM: Artificial Sequence
<220> FEATURE:
<223> OTHER INFORMATION: Single strand DNA oligonucleotide

<400> SEQUENCE: 27
aggcattaga ggcgataagg gag                                                23

<210> SEQ ID NO 28
<211> LENGTH: 27
```

```
<212> TYPE: DNA
<213> ORGANISM: Artificial Sequence
<220> FEATURE:
<223> OTHER INFORMATION: Single strand DNA oligonucleotide

<400> SEQUENCE: 28
tcaatccaat aatagccact tgaccac                                         27

<210> SEQ ID NO 29
<211> LENGTH: 102
<212> TYPE: DNA
<213> ORGANISM: Artificial Sequence
<220> FEATURE:
<223> OTHER INFORMATION: pBINPLUS multiple cloning site

<400> SEQUENCE: 29
atgaccatga ttacgccaag ctggcgcgcc aagcttgcat gcctgcaggt cgactctaga    60
ggatccccgg gtaccgagct cgaattctta attaacaatt ca                      102

<210> SEQ ID NO 30
<211> LENGTH: 1464
<212> TYPE: PRT
<213> ORGANISM: Homo sapiens

<400> SEQUENCE: 30

Met Phe Ser Phe Val Asp Leu Arg Leu Leu Leu Leu Leu Ala Ala Thr
 1               5                  10                  15

Ala Leu Leu Thr His Gly Gln Glu Glu Gly Gln Val Glu Gly Gln Asp
                20                  25                  30

Glu Asp Ile Pro Pro Ile Thr Cys Val Gln Asn Gly Leu Arg Tyr His
            35                  40                  45

Asp Arg Asp Val Trp Lys Pro Glu Pro Cys Arg Ile Cys Val Cys Asp
        50                  55                  60

Asn Gly Lys Val Leu Cys Asp Asp Val Ile Cys Asp Glu Thr Lys Asn
 65                  70                  75                  80

Cys Pro Gly Ala Glu Val Pro Glu Gly Glu Cys Cys Pro Val Cys Pro
                85                  90                  95

Asp Gly Ser Glu Ser Pro Thr Asp Gln Glu Thr Thr Gly Val Glu Gly
                100                 105                 110

Pro Lys Gly Asp Thr Gly Pro Arg Gly Pro Arg Gly Pro Ala Gly Pro
            115                 120                 125

Pro Gly Arg Asp Gly Ile Pro Gly Gln Pro Gly Leu Pro Gly Pro Pro
        130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
                180                 185                 190

Pro Gly Ala Pro Gly Pro Gln Gly Phe Gln Gly Pro Pro Gly Glu Pro
            195                 200                 205

Gly Glu Pro Gly Ala Ser Gly Pro Met Gly Pro Arg Gly Pro Pro Gly
        210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
                245                 250                 255
```

```
Gly Thr Ala Gly Leu Pro Gly Met Lys Gly His Arg Gly Phe Ser Gly
            260                 265                 270

Leu Asp Gly Ala Lys Gly Asp Ala Gly Pro Ala Gly Pro Lys Gly Glu
        275                 280                 285

Pro Gly Ser Pro Gly Glu Asn Gly Ala Pro Gly Gln Met Gly Pro Arg
    290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
            340                 345                 350

Gly Glu Ala Gly Pro Gln Gly Pro Arg Gly Ser Glu Gly Pro Gln Gly
        355                 360                 365

Val Arg Gly Glu Pro Gly Pro Pro Gly Pro Ala Gly Ala Ala Gly Pro
    370                 375                 380

Ala Gly Asn Pro Gly Ala Asp Gly Gln Pro Gly Ala Lys Gly Ala Asn
385                 390                 395                 400

Gly Ala Pro Gly Ile Ala Gly Ala Pro Gly Phe Pro Gly Ala Arg Gly
                405                 410                 415

Pro Ser Gly Pro Gln Gly Pro Gly Gly Pro Pro Gly Pro Lys Gly Asn
            420                 425                 430

Ser Gly Glu Pro Gly Ala Pro Gly Ser Lys Gly Asp Thr Gly Ala Lys
        435                 440                 445

Gly Glu Pro Gly Pro Val Gly Val Gln Gly Pro Pro Gly Pro Ala Gly
    450                 455                 460

Glu Glu Gly Lys Arg Gly Ala Arg Gly Glu Pro Gly Pro Thr Gly Leu
465                 470                 475                 480

Pro Gly Pro Pro Gly Glu Arg Gly Pro Gly Ser Arg Gly Phe Pro
                485                 490                 495

Gly Ala Asp Gly Val Ala Gly Pro Lys Gly Pro Ala Gly Glu Arg Gly
            500                 505                 510

Ser Pro Gly Pro Ala Gly Pro Lys Gly Ser Pro Gly Glu Ala Gly Arg
        515                 520                 525

Pro Gly Glu Ala Gly Leu Pro Gly Ala Lys Gly Leu Thr Gly Ser Pro
    530                 535                 540

Gly Ser Pro Gly Pro Asp Gly Lys Thr Gly Pro Pro Gly Pro Ala Gly
545                 550                 555                 560

Gln Asp Gly Arg Pro Gly Pro Pro Gly Pro Pro Gly Ala Arg Gly Gln
                565                 570                 575

Ala Gly Val Met Gly Phe Pro Gly Pro Lys Gly Ala Ala Gly Glu Pro
            580                 585                 590

Gly Lys Ala Gly Glu Arg Gly Val Pro Gly Pro Pro Gly Ala Val Gly
        595                 600                 605

Pro Ala Gly Lys Asp Gly Glu Ala Gly Ala Gln Gly Pro Pro Gly Pro
    610                 615                 620

Ala Gly Pro Ala Gly Glu Arg Gly Glu Gln Gly Pro Ala Gly Ser Pro
625                 630                 635                 640

Gly Phe Gln Gly Leu Pro Gly Pro Ala Gly Pro Pro Gly Glu Ala Gly
                645                 650                 655

Lys Pro Gly Glu Gln Gly Val Pro Gly Asp Leu Gly Ala Pro Gly Pro
            660                 665                 670

Ser Gly Ala Arg Gly Glu Arg Gly Phe Pro Gly Glu Arg Gly Val Gln
```

-continued

```
            675                 680                 685

Gly Pro Pro Gly Pro Ala Gly Pro Arg Gly Ala Asn Gly Ala Pro Gly
    690                 695                 700

Asn Asp Gly Ala Lys Gly Asp Ala Gly Ala Pro Gly Ala Pro Gly Ser
705                 710                 715                 720

Gln Gly Ala Pro Gly Leu Gln Gly Met Pro Gly Glu Arg Gly Ala Ala
                725                 730                 735

Gly Leu Pro Gly Pro Lys Gly Asp Arg Gly Asp Ala Gly Pro Lys Gly
                740                 745                 750

Ala Asp Gly Ser Pro Gly Lys Asp Gly Val Arg Gly Leu Thr Gly Pro
            755                 760                 765

Ile Gly Pro Pro Gly Pro Ala Gly Ala Pro Gly Asp Lys Gly Glu Ser
            770                 775                 780

Gly Pro Ser Gly Pro Ala Gly Pro Thr Gly Ala Arg Gly Ala Pro Gly
785                 790                 795                 800

Asp Arg Gly Glu Pro Gly Pro Pro Gly Pro Ala Gly Phe Ala Gly Pro
                805                 810                 815

Pro Gly Ala Asp Gly Gln Pro Gly Ala Lys Gly Glu Pro Gly Asp Ala
                820                 825                 830

Gly Ala Lys Gly Asp Ala Gly Pro Pro Gly Pro Ala Gly Pro Ala Gly
            835                 840                 845

Pro Pro Gly Pro Ile Gly Asn Val Gly Ala Pro Gly Ala Lys Gly Ala
            850                 855                 860

Arg Gly Ser Ala Gly Pro Pro Gly Ala Thr Gly Phe Pro Gly Ala Ala
865                 870                 875                 880

Gly Arg Val Gly Pro Pro Gly Pro Ser Gly Asn Ala Gly Pro Pro Gly
                885                 890                 895

Pro Pro Gly Pro Ala Gly Lys Glu Gly Gly Lys Gly Pro Arg Gly Glu
                900                 905                 910

Thr Gly Pro Ala Gly Arg Pro Gly Glu Val Gly Pro Pro Gly Pro Pro
            915                 920                 925

Gly Pro Ala Gly Glu Lys Gly Ser Pro Gly Ala Asp Gly Pro Ala Gly
            930                 935                 940

Ala Pro Gly Thr Pro Gly Pro Gln Gly Ile Ala Gly Gln Arg Gly Val
945                 950                 955                 960

Val Gly Leu Pro Gly Gln Arg Gly Glu Arg Gly Phe Pro Gly Leu Pro
                965                 970                 975

Gly Pro Ser Gly Glu Pro Gly Lys Gln Gly Pro Ser Gly Ala Ser Gly
            980                 985                 990

Glu Arg Gly Pro Pro Gly Pro Met Gly Pro Pro Gly Leu Ala Gly Pro
            995                 1000                1005

Pro Gly Glu Ser Gly Arg Glu Gly Ala Pro Gly Ala Glu Gly Ser
    1010                1015                1020

Pro Gly Arg Asp Gly Ser Pro Gly Ala Lys Gly Asp Arg Gly Glu
    1025                1030                1035

Thr Gly Pro Ala Gly Pro Pro Gly Ala Pro Gly Ala Pro Gly Ala
    1040                1045                1050

Pro Gly Pro Val Gly Pro Ala Gly Lys Ser Gly Asp Arg Gly Glu
    1055                1060                1065

Thr Gly Pro Ala Gly Pro Ala Gly Pro Val Gly Pro Val Gly Ala
    1070                1075                1080

Arg Gly Pro Ala Gly Pro Gln Gly Pro Arg Gly Asp Lys Gly Glu
    1085                1090                1095
```

-continued

```
Thr Gly Glu Gln Gly Asp Arg Gly Ile Lys Gly His Arg Gly Phe
    1100                1105                1110

Ser Gly Leu Gln Gly Pro Pro Gly Pro Pro Gly Ser Pro Gly Glu
    1115                1120                1125

Gln Gly Pro Ser Gly Ala Ser Gly Pro Ala Gly Pro Arg Gly Pro
    1130                1135                1140

Pro Gly Ser Ala Gly Ala Pro Gly Lys Asp Gly Leu Asn Gly Leu
    1145                1150                1155

Pro Gly Pro Ile Gly Pro Pro Gly Pro Arg Gly Arg Thr Gly Asp
    1160                1165                1170

Ala Gly Pro Val Gly Pro Pro Gly Pro Pro Gly Pro Pro Gly Pro
    1175                1180                1185

Pro Gly Pro Pro Ser Ala Gly Phe Asp Phe Ser Phe Leu Pro Gln
    1190                1195                1200

Pro Pro Gln Glu Lys Ala His Asp Gly Gly Arg Tyr Tyr Arg Ala
    1205                1210                1215

Asp Asp Ala Asn Val Val Arg Asp Arg Asp Leu Glu Val Asp Thr
    1220                1225                1230

Thr Leu Lys Ser Leu Ser Gln Gln Ile Glu Asn Ile Arg Ser Pro
    1235                1240                1245

Glu Gly Ser Arg Lys Asn Pro Ala Arg Thr Cys Arg Asp Leu Lys
    1250                1255                1260

Met Cys His Ser Asp Trp Lys Ser Gly Glu Tyr Trp Ile Asp Pro
    1265                1270                1275

Asn Gln Gly Cys Asn Leu Asp Ala Ile Lys Val Phe Cys Asn Met
    1280                1285                1290

Glu Thr Gly Glu Thr Cys Val Tyr Pro Thr Gln Pro Ser Val Ala
    1295                1300                1305

Gln Lys Asn Trp Tyr Ile Ser Lys Asn Pro Lys Asp Lys Arg His
    1310                1315                1320

Val Trp Phe Gly Glu Ser Met Thr Asp Gly Phe Gln Phe Glu Tyr
    1325                1330                1335

Gly Gly Gln Gly Ser Asp Pro Ala Asp Val Ala Ile Gln Leu Thr
    1340                1345                1350

Phe Leu Arg Leu Met Ser Thr Glu Ala Ser Gln Asn Ile Thr Tyr
    1355                1360                1365

His Cys Lys Asn Ser Val Ala Tyr Met Asp Gln Gln Thr Gly Asn
    1370                1375                1380

Leu Lys Lys Ala Leu Leu Leu Gln Gly Ser Asn Glu Ile Glu Ile
    1385                1390                1395

Arg Ala Glu Gly Asn Ser Arg Phe Thr Tyr Ser Val Thr Val Asp
    1400                1405                1410

Gly Cys Thr Ser His Thr Gly Ala Trp Gly Lys Thr Val Ile Glu
    1415                1420                1425

Tyr Lys Thr Thr Lys Thr Ser Arg Leu Pro Ile Ile Asp Val Ala
    1430                1435                1440

Pro Leu Asp Val Gly Ala Pro Asp Gln Glu Phe Gly Phe Asp Val
    1445                1450                1455

Gly Pro Val Cys Phe Leu
    1460

<210> SEQ ID NO 31
<211> LENGTH: 1366
```

<212> TYPE: PRT
<213> ORGANISM: Homo sapiens

<400> SEQUENCE: 31

```
Met Leu Ser Phe Val Asp Thr Arg Thr Leu Leu Leu Ala Val Thr
1               5                   10                  15

Leu Cys Leu Ala Thr Cys Gln Ser Leu Gln Glu Glu Thr Val Arg Lys
                20                  25                  30

Gly Pro Ala Gly Asp Arg Gly Pro Arg Gly Glu Arg Gly Pro Pro Gly
            35                  40                  45

Pro Pro Gly Arg Asp Gly Glu Asp Gly Pro Thr Gly Pro Pro Gly Pro
50                  55                  60

Pro Gly Pro Pro Gly Pro Pro Gly Leu Gly Gly Asn Phe Ala Ala Gln
65                  70                  75                  80

Tyr Asp Gly Lys Gly Val Gly Leu Gly Pro Gly Pro Met Gly Leu Met
                85                  90                  95

Gly Pro Arg Gly Pro Pro Gly Ala Ala Gly Ala Pro Gly Pro Gln Gly
            100                 105                 110

Phe Gln Gly Pro Ala Gly Glu Pro Gly Glu Pro Gly Gln Thr Gly Pro
            115                 120                 125

Ala Gly Ala Arg Gly Pro Ala Gly Pro Pro Gly Lys Ala Gly Glu Asp
            130                 135                 140

Gly His Pro Gly Lys Pro Gly Arg Pro Gly Glu Arg Gly Val Val Gly
145                 150                 155                 160

Pro Gln Gly Ala Arg Gly Phe Pro Gly Thr Pro Gly Leu Pro Gly Phe
                165                 170                 175

Lys Gly Ile Arg Gly His Asn Gly Leu Asp Gly Leu Lys Gly Gln Pro
            180                 185                 190

Gly Ala Pro Gly Val Lys Gly Glu Pro Gly Ala Pro Gly Glu Asn Gly
            195                 200                 205

Thr Pro Gly Gln Thr Gly Ala Arg Gly Leu Pro Gly Glu Arg Gly Arg
            210                 215                 220

Val Gly Ala Pro Gly Pro Ala Gly Ala Arg Gly Ser Asp Gly Ser Val
225                 230                 235                 240

Gly Pro Val Gly Pro Ala Gly Pro Ile Gly Ser Ala Gly Pro Pro Gly
                245                 250                 255

Phe Pro Gly Ala Pro Gly Pro Lys Gly Glu Ile Gly Ala Val Gly Asn
            260                 265                 270

Ala Gly Pro Ala Gly Pro Ala Gly Pro Arg Gly Glu Val Gly Leu Pro
            275                 280                 285

Gly Leu Ser Gly Pro Val Gly Pro Pro Gly Asn Pro Gly Ala Asn Gly
            290                 295                 300

Leu Thr Gly Ala Lys Gly Ala Ala Gly Leu Pro Gly Val Ala Gly Ala
305                 310                 315                 320

Pro Gly Leu Pro Gly Pro Arg Gly Ile Pro Gly Pro Val Gly Ala Ala
                325                 330                 335

Gly Ala Thr Gly Ala Arg Gly Leu Val Gly Glu Pro Gly Pro Ala Gly
            340                 345                 350

Ser Lys Gly Glu Ser Gly Asn Lys Gly Glu Pro Gly Ser Ala Gly Pro
            355                 360                 365

Gln Gly Pro Pro Gly Pro Ser Gly Glu Glu Gly Lys Arg Gly Pro Asn
            370                 375                 380

Gly Glu Ala Gly Ser Ala Gly Pro Pro Gly Pro Pro Gly Leu Arg Gly
385                 390                 395                 400
```

```
Ser Pro Gly Ser Arg Gly Leu Pro Gly Ala Asp Gly Arg Ala Gly Val
            405                 410                 415

Met Gly Pro Pro Gly Ser Arg Gly Ala Ser Gly Pro Ala Gly Val Arg
            420                 425                 430

Gly Pro Asn Gly Asp Ala Gly Arg Pro Gly Glu Pro Gly Leu Met Gly
            435                 440                 445

Pro Arg Gly Leu Pro Gly Ser Pro Gly Asn Ile Gly Pro Ala Gly Lys
450                 455                 460

Glu Gly Pro Val Gly Leu Pro Gly Ile Asp Gly Arg Pro Gly Pro Ile
465                 470                 475                 480

Gly Pro Ala Gly Ala Arg Gly Glu Pro Gly Asn Ile Gly Phe Pro Gly
            485                 490                 495

Pro Lys Gly Pro Thr Gly Asp Pro Gly Lys Asn Gly Asp Lys Gly His
            500                 505                 510

Ala Gly Leu Ala Gly Ala Arg Gly Ala Pro Gly Pro Asp Gly Asn Asn
            515                 520                 525

Gly Ala Gln Gly Pro Pro Gly Pro Gln Gly Val Gln Gly Gly Lys Gly
            530                 535                 540

Glu Gln Gly Pro Ala Gly Pro Pro Gly Phe Gln Gly Leu Pro Gly Pro
545                 550                 555                 560

Ser Gly Pro Ala Gly Glu Val Gly Lys Pro Gly Glu Arg Gly Leu His
            565                 570                 575

Gly Glu Phe Gly Leu Pro Gly Pro Ala Gly Pro Arg Gly Glu Arg Gly
            580                 585                 590

Pro Pro Gly Glu Ser Gly Ala Ala Gly Pro Thr Gly Pro Ile Gly Ser
            595                 600                 605

Arg Gly Pro Ser Gly Pro Pro Gly Pro Asp Gly Asn Lys Gly Glu Pro
            610                 615                 620

Gly Val Val Gly Ala Val Gly Thr Ala Gly Pro Ser Gly Pro Ser Gly
625                 630                 635                 640

Leu Pro Gly Glu Arg Gly Ala Ala Gly Ile Pro Gly Gly Lys Gly Glu
            645                 650                 655

Lys Gly Glu Pro Gly Leu Arg Gly Glu Ile Gly Asn Pro Gly Arg Asp
            660                 665                 670

Gly Ala Arg Gly Ala Pro Gly Ala Val Gly Ala Pro Gly Pro Ala Gly
            675                 680                 685

Ala Thr Gly Asp Arg Gly Glu Ala Gly Ala Ala Gly Pro Ala Gly Pro
            690                 695                 700

Ala Gly Pro Arg Gly Ser Pro Gly Glu Arg Gly Glu Val Gly Pro Ala
705                 710                 715                 720

Gly Pro Asn Gly Phe Ala Gly Pro Ala Gly Ala Ala Gly Gln Pro Gly
            725                 730                 735

Ala Lys Gly Glu Arg Gly Ala Lys Gly Pro Lys Gly Glu Asn Gly Val
            740                 745                 750

Val Gly Pro Thr Gly Pro Val Gly Ala Ala Gly Pro Ala Gly Pro Asn
            755                 760                 765

Gly Pro Pro Gly Pro Ala Gly Ser Arg Gly Asp Gly Gly Pro Pro Gly
            770                 775                 780

Met Thr Gly Phe Pro Gly Ala Ala Gly Arg Thr Gly Pro Pro Gly Pro
785                 790                 795                 800

Ser Gly Ile Ser Gly Pro Pro Gly Pro Pro Gly Pro Ala Gly Lys Glu
            805                 810                 815
```

-continued

Gly Leu Arg Gly Pro Arg Gly Asp Gln Gly Pro Val Gly Arg Thr Gly
            820                 825                 830

Glu Val Gly Ala Val Gly Pro Pro Gly Phe Ala Gly Glu Lys Gly Pro
            835                 840                 845

Ser Gly Glu Ala Gly Thr Ala Gly Pro Pro Gly Thr Pro Gly Pro Gln
        850                 855                 860

Gly Leu Leu Gly Ala Pro Gly Ile Leu Gly Leu Pro Gly Ser Arg Gly
865                 870                 875                 880

Glu Arg Gly Leu Pro Gly Val Ala Gly Ala Val Gly Glu Pro Gly Pro
                885                 890                 895

Leu Gly Ile Ala Gly Pro Pro Gly Ala Arg Gly Pro Pro Gly Ala Val
            900                 905                 910

Gly Ser Pro Gly Val Asn Gly Ala Pro Gly Glu Ala Gly Arg Asp Gly
            915                 920                 925

Asn Pro Gly Asn Asp Gly Pro Pro Gly Arg Asp Gly Gln Pro Gly His
        930                 935                 940

Lys Gly Glu Arg Gly Tyr Pro Gly Asn Ile Gly Pro Val Gly Ala Ala
945                 950                 955                 960

Gly Ala Pro Gly Pro His Gly Pro Val Gly Pro Ala Gly Lys His Gly
                965                 970                 975

Asn Arg Gly Glu Thr Gly Pro Ser Gly Pro Val Gly Pro Ala Gly Ala
            980                 985                 990

Val Gly Pro Arg Gly Pro Ser Gly  Pro Gln Gly Ile Arg  Gly Asp Lys
            995                 1000                 1005

Gly Glu  Pro Gly Glu Lys Gly  Pro Arg Gly Leu Pro  Gly Leu Lys
    1010                1015                 1020

Gly His  Asn Gly Leu Gln Gly  Leu Pro Gly Ile Ala  Gly His His
    1025                1030                 1035

Gly Asp  Gln Gly Ala Pro Gly  Ser Val Gly Pro Ala  Gly Pro Arg
    1040                1045                 1050

Gly Pro  Ala Gly Pro Ser Gly  Pro Ala Gly Lys Asp  Gly Arg Thr
    1055                1060                 1065

Gly His  Pro Gly Thr Val Gly  Pro Ala Gly Ile Arg  Gly Pro Gln
    1070                1075                 1080

Gly His  Gln Gly Pro Ala Gly  Pro Pro Gly Pro Pro  Gly Pro Pro
    1085                1090                 1095

Gly Pro  Pro Gly Val Ser Gly  Gly Gly Tyr Asp Phe  Gly Tyr Asp
    1100                1105                 1110

Gly Asp  Phe Tyr Arg Ala Asp  Gln Pro Arg Ser Ala  Pro Ser Leu
    1115                1120                 1125

Arg Pro  Lys Asp Tyr Glu Val  Asp Ala Thr Leu Lys  Ser Leu Asn
    1130                1135                 1140

Asn Gln  Ile Glu Thr Leu Leu  Thr Pro Glu Gly Ser  Arg Lys Asn
    1145                1150                 1155

Pro Ala  Arg Thr Cys Arg Asp  Leu Arg Leu Ser His  Pro Glu Trp
    1160                1165                 1170

Ser Ser  Gly Tyr Tyr Trp Ile  Asp Pro Asn Gln Gly  Cys Thr Met
    1175                1180                 1185

Asp Ala  Ile Lys Val Tyr Cys  Asp Phe Ser Thr Gly  Glu Thr Cys
    1190                1195                 1200

Ile Arg  Ala Gln Pro Glu Asn  Ile Pro Ala Lys Asn  Trp Tyr Arg
    1205                1210                 1215

Ser Ser  Lys Asp Lys Lys His  Val Trp Leu Gly Glu  Thr Ile Asn

```
                    1220                1225                1230
Ala Gly Ser Gln Phe Glu Tyr Asn Val Glu Gly Val Thr Ser Lys
        1235                1240                1245
Glu Met Ala Thr Gln Leu Ala Phe Met Arg Leu Leu Ala Asn Tyr
        1250                1255                1260
Ala Ser Gln Asn Ile Thr Tyr His Cys Lys Asn Ser Ile Ala Tyr
        1265                1270                1275
Met Asp Glu Glu Thr Gly Asn Leu Lys Lys Ala Val Ile Leu Gln
        1280                1285                1290
Gly Ser Asn Asp Val Glu Leu Val Ala Glu Gly Asn Ser Arg Phe
        1295                1300                1305
Thr Tyr Thr Val Leu Val Asp Gly Cys Ser Lys Lys Thr Asn Glu
        1310                1315                1320
Trp Gly Lys Thr Ile Ile Glu Tyr Lys Thr Asn Lys Pro Ser Arg
        1325                1330                1335
Leu Pro Phe Leu Asp Ile Ala Pro Leu Asp Ile Gly Gly Ala Asp
        1340                1345                1350
Gln Glu Phe Phe Val Asp Ile Gly Pro Val Cys Phe Lys
        1355                1360                1365

<210> SEQ ID NO 32
<211> LENGTH: 5927
<212> TYPE: DNA
<213> ORGANISM: Homo sapiens

<400> SEQUENCE: 32
tcgtcggagc agacgggagt ttctcctcgg ggtcggagca ggaggcacgc ggagtgtgag      60
gccacgcatg agcggacgct aaccccctcc ccagccacaa agagtctaca tgtctagggt     120
ctagacatgt tcagctttgt ggacctccgg ctcctgctcc tcttagcggc caccgccctc     180
ctgacgcacg gccaagagga aggccaagtc gagggccaag acgaagacat cccaccaatc     240
acctgcgtac agaacggcct caggtaccat gaccgagacg tgtggaaacc cgagccctgc     300
cggatctgcg tctgcgacaa cggcaaggtg ttgtgcgatg acgtgatctg tgacgagacc     360
aagaactgcc ccggcgccga agtccccgag ggcgagtgct gtcccgtctg ccccgacggc     420
tcagagtcac ccaccgacca agaaaccacc ggcgtcgagg gacccaaggg agacactggc     480
ccccgaggcc caagggggacc cgcaggcccc cctggccgag atggcatccc tggacagcct     540
ggacttcccg gacccccggg accccccgga cctcccggac ccctggcct cggaggaaac     600 tttgctcccc agctgtctta tggctatgat gagaaatcaa ccggaggaat ttccgtgcct     660
ggccccatgg gtccctctgg tcctcgtggt ctccctggcc ccctggtgc acctggtccc     720 caaggcttcc aaggtccccc tggtgagcct ggcgagcctg gagcttcagg tcccatgggt     780
ccccgaggtc ccccaggtcc cctggaaag aatggagatg atgggggaagc tggaaaacct     840 ggtcgtcctg gtgagcgtgg gcctcctggg cctcagggtg ctcgaggatt gcccggaaca     900
gctggcctcc ctggaatgaa gggacacaga ggtttcagtg gtttggatgg tgccaaggga     960
gatgctggtc ctgctggtcc taagggtgag cctggcagcc ctggtgaaaa tggagctcct    1020
ggtcagatgg gccccgtgg cctgcctggt gagagaggtc gccctggagc cctggccct    1080 gctggtgctc gtggaaatga tggtgctact ggtgctgccg gcccctgg tcccaccggc    1140 cccgctggtc ctctggcctt ccctggtgct gttggtgcta agggtgaagc tggtccccaa    1200
gggccccgag gctctgaagg tccccagggt gtgcgtggtg agcctggccc cctggccct    1260
```

```
gctggtgctg ctggccctgc tggaaaccct ggtgctgatg acagcctggt gctaaaggt    1320
gccaatggtg ctcctggtat tgctggtgct cctggcttcc ctggtgcccg aggcccctct    1380
ggaccccagg gccccggcgg ccctcctggt cccaagggta acagcggtga acctggtgct    1440
cctggcagca aggagacact ggtgctaagg ggagagcctg ccctgttgg tgttcaagga    1500
cccccctggcc ctgctggaga ggaaggaaag cgaggagctc gaggtgaacc cggacccact    1560
ggcctgcccg acccctgg cgagcgtggt ggacctggta gccgtggttt ccctggcgca    1620
gatggtgttg ctggtcccaa gggtcccgct ggtgaacgtg gttctcctgg ccctgctggc    1680
cccaaaggat ctcctggtga agctggtcgt cccggtgaag ctggtctgcc tggtgccaag    1740
ggtctgactg gaagccctgg cagccctggt cctgatggca aaactggccc cctggtccc    1800
gccggtcaag atggtcgccc cggacccca ggcccacctg gtgccgtgg tcaggctggt    1860
gtgatgggat ccctggacc taaaggtgct gctggagagc ccggcaaggc tggagagcga    1920
ggtgttcccg acccctgg cgctgtcggt cctgctggca agatggaga ggctggagct    1980
cagggacccc ctggccctgc tggtcccgct ggcgagagag gtgaacaagg ccctgctggc    2040
tccccccggat tccagggtct ccctggtcct gctggtcctc caggtgaagc aggcaaacct    2100
ggtgaacagg gtgttcctgg agaccttggc gcccctggcc cctctggagc aagaggcgag    2160
agaggtttcc ctggcgagcg tggtgtgcaa ggtccccctg gtcctgctgg tccccgaggg    2220
gccaacggtg ctcccggcaa cgatggtgct aagggtgatg ctggtgcccc tggagctccc    2280
ggtagccagg gcgcccctgg ccttcaggga atgcctggtg aacgtggtgc agctggtctt    2340
ccagggccta aggtgacag aggtgatgct ggtcccaaag gtgctgatgg ctctcctggc    2400
aaagatggcg tccgtggtct gactggcccc attggtcctc ctggcccctg tggtgcccct    2460
ggtgacaagg gtgaaagtgg tcccagcggc cctgctggtc ccactggagc tcgtggtgcc    2520
cccggagacc gtggtgagcc tggtcccccc ggccctgctg gctttgctgg ccccctggt    2580
gctgacggcc aacctggtgc taaaggcgaa cctggtgatg ctggtgctaa aggcgatgct    2640
ggtcccctg gcctgccgg accgctgga ccccctggcc ccattggtaa tgttggtgct    2700
cctggagcca aggtgctcg cggcagcgct ggtccccctg gtgctactgg tttccctggt    2760
gctgctggcc gagtcggtcc tcctggcccc tctggaaatg ctggaccccc tggccctcct    2820
ggtcctgctg gcaaagaagg cggcaaaggt cccgtggtg agactggccc tgctggacgt    2880
cctggtgaag ttggtccccc tggtccccct ggccctgctg gcgagaaagg atcccctggt    2940
gctgatggtc ctgctggtgc tcctggtact cccgggcctc aaggtattgc tggacagcgt    3000
ggtgtggtcg gcctgcctgg tcagagagga gagagaggct ccctggtct tcctggcccc    3060
tctggtgaac ctggcaaaca aggtccctct ggagcaagtg gtgaacgtgg tccccctggt    3120
cccatgggcc cccctggatt ggctggaccc cctggtgaat ctggacgtga ggggctcct    3180
ggtgccgaag ttcccctgg acgagacggt tctcctggcg ccaagggtga ccgtggtgag    3240
accggccccg ctggaccccc tggtgctcct ggtgctcctg gtgcccctgg cccgttggc    3300
cctgctggca agtggtga tcgtggtgag actggtcctg ctggtcccgc cggtcctgtc    3360
ggccctgttg gcgcccgtgg ccccgccgga cccaaggcc ccgtggtga aagggtgag    3420
acaggcgaac agggcgacag aggcataaag ggtcaccgtg gcttctctgg cctccagggt    3480
cccccctggcc ctcctggctc tcctggtgaa caaggtccct ctggagcctc tggtcctgct    3540
ggtccccgag gtccccctgg ctctgctggt gctcctggca aagatggact caacggtctc    3600
cctggccca ttgggccccc tggtcctcgc ggtcgcactg gtgatgctgg tcctgttggt    3660
```

```
cccccggcc ctcctggacc tcctggtccc cctggtcctc ccagcgctgg tttcgacttc    3720
agcttcctgc cccagccacc tcaagagaag gctcacgatg gtggccgcta ctaccgggct    3780
gatgatgcca atgtggttcg tgaccgtgac ctcgaggtgg acaccaccct caagagcctg    3840
agccagcaga tcgagaacat ccggagccca gagggcagcc gcaagaaccc cgcccgcacc    3900
tgccgtgacc tcaagatgtg ccactctgac tggaagagtg gagagtactg gattgacccc    3960
aaccaaggct gcaacctgga tgccatcaaa gtcttctgca acatggagac tggtgagacc    4020
tgcgtgtacc ccactcagcc cagtgtggcc cagaagaact ggtacatcag caagaacccc    4080
aaggacaaga ggcatgtctg gttcggcgag agcatgaccg atggattcca gttcgagtat    4140
ggcggccagg gctccgaccc tgccgatgtg gccatccagc tgaccttcct gcgcctgatg    4200
tccaccgagg cctcccagaa catcacctac cactgcaaga acagcgtggc ctacatggac    4260
cagcagactg gcaacctcaa gaaggccctg ctcctccagg gctccaacga gatcgagatc    4320
cgcgccgagg gcaacagccg cttcacctac agcgtcactg tcgatggctg cacgagtcac    4380
accggagcct ggggcaagac agtgattgaa tacaaaacca ccaagacctc ccgcctgccc    4440
atcatcgatg tggccccctt ggacgttggt gccccagacc aggaattcgg cttcgacgtt    4500
ggccctgtct gcttcctgta aactccctcc atcccaacct ggctccctcc cacccaacca    4560
actttccccc caacccggaa acagacaagc aacccaaact gaaccccctc aaaagccaaa    4620
aaatgggaga caatttcaca tggactttgg aaaatatttt tttcctttgc attcatctct    4680
caaacttagt ttttatcttt gaccaaccga acatgaccaa aaaccaaaag tgcattcaac    4740
cttaccaaaa aaaaaaaaaa aaaagaata aataataac ttttaaaaa aggaagcttg    4800 gtccacttgc ttgaagaccc atgcgggggt aagtcccttt ctgcccgttg ggcttatgaa    4860
accccaatgc tgcccttttct gctcctttct ccacaccccc cttggggcct cccctccact    4920
ccttcccaaa tctgtctccc cagaagacac aggaaacaat gtattgtctg cccagcaatc    4980
aaaggcaatg ctcaaacacc caagtggccc ccaccctcag cccgctcctg cccgcccagc    5040 accccaggc cctgggggac ctggggttct cagactgcca agaagccctt gccatctggc    5100
gctcccatgg ctcttgcaac atctccccctt cgttttttgag ggggtcatgc cgggggagcc    5160
accagcccct cactgggttc ggaggagagt caggaagggc cacgacaaag cagaaacatc    5220
ggatttgggg aacgcgtgtc aatcccttgt gccgcagggc tgggcgggag agactgttct    5280
gttccttgtg taactgtgtt gctgaaagac tacctcgttc ttgtcttgat gtgtcaccgg    5340
ggcaactgcc tggggcggg gatggggggca gggtggaagc ggctccccat tttataccaa    5400
aggtgctaca tctatgtgat gggtggggtg gggagggaat cactggtgct atagaaattg    5460
agatgccccc ccaggccagc aaatgttcct ttttgttcaa agtctatttt tattccttga    5520 tattttctt tttttttttt ttttttgtg gatgggact tgtgaatttt tctaaaggtg    5580
ctatttaaca tgggaggaga gcgtgtgcgg ctccagccca gcccgctgct cactttccac    5640
cctctctcca cctgcctctg gcttctcagg cctctgctct ccgacctctc tcctctgaaa    5700
ccctcctcca cagctgcagc ccatcctccc ggctccctcc tagtctgtcc tgcgtcctct    5760
gtccccgggt ttcagagaca acttcccaaa gcacaaagca gttttccccc ctaggggtgg    5820
gaggaagcaa aagactctgt acctattttg tatgtgtata ataatttgag atgttttta    5880 ttattttgat tgctggaata aagcatgtgg aaatgaccca aacataa             5927
```

<210> SEQ ID NO 33

```
<211> LENGTH: 5411
<212> TYPE: DNA
<213> ORGANISM: Homo sapiens

<400> SEQUENCE: 33
gtgtcccata gtgtttccaa acttggaaag ggcgggggag ggcgggagga tgcggagggc      60
ggaggtatgc agacaacgag tcagagtttc cccttgaaag cctcaaaagt gtccacgtcc     120
tcaaaaagaa tggaaccaat ttaagaagcc agccccgtgg ccacgtccct tcccccattc     180
gctccctcct ctgcgccccc gcaggctcct cccagctgtg gctgcccggg ccccagccc     240 cagccctccc attggtggag gcccttttgg aggcaccta gggccaggga aacttttgcc     300
gtataaatag ggcagatccg ggctttatta ttttagcacc acggcagcag gaggtttcgg     360
ctaagttgga ggtactggcc acgactgcat gcccgcgccc gccaggtgat acctccgccg     420
gtgacccagg ggctctgcga cacaaggagt ctgcatgtct aagtgctaga catgctcagc     480
tttgtggata cgcggacttt gttgctgctt gcagtaacct tatgcctagc aacatgccaa     540
tctttacaag aggaaactgt aagaaagggc ccagccggag atagaggacc acgtggagaa     600 agggtccac caggcccccc aggcagagat ggtgaagatg gtcccacagg ccctcctggt     660
ccacctggtc ctcctggccc ccctggtctc ggtgggaact ttgctgctca gtatgatgga     720 aaggagttg gacttggccc tggaccaatg ggcttaatgg gacctagagg cccacctggt     780
gcagctggag ccccaggccc tcaaggtttc caaggacctg ctggtgagcc tggtgaacct     840
ggtcaaactg gtcctgcagg tgctcgtggt ccagctggcc ctcctggcaa ggctggtgaa     900
gatggtcacc ctgaaaaacc cggacgacct ggtgagagag agttgttgg accacagggt     960 gctcgtggtt tccctggaac tcctggactt cctggcttca aaggcattag gggacacaat    1020
ggtctggatg gattgaaggg acagcccggt gctcctggtg tgaagggtga acctggtgcc    1080
cctggtgaaa atgaactcc aggtcaaaca ggagcccgtg ggcttcctgg tgagagagga    1140
cgtgttggtg cccctggccc agctggtgcc cgtggcagta tggaagtgt gggtcccgtg    1200 ggtcctgctg gtcccattgg gtctgctggc cctccaggct tcccaggtgc cctggcccc    1260 aagggtgaaa ttggagctgt tggtaacgct ggtcctgctg gtcccgccgg tccccgtggt    1320
gaagtgggtc ttccaggcct ctccggcccc gttggacctc ctggtaatcc tggagcaaac    1380
ggccttactg gtgccaaggg tgctgctggc cttcccggcg ttgctgggc tcccggcctc    1440 cctggacccc gcggtattcc tggccctgtt ggtgctgccg gtgctactgg tgccagagga    1500
cttgttggtg agcctggtcc agctggctcc aaaggagaga gcggtaacaa gggtgagccc    1560
ggctctgctg ggccccaagg tcctcctggt cccagtggtg aagaaggaaa agagaggccct    1620 aatggggaag ctggatctgc cggccctcca ggacctcctg ggctgagagg tagtcctggt    1680
tctcgtggtc ttcctggagc tgatggcaga gctggcgtca tgggccctcc tggtagtcgt    1740
ggtgcaagtg gccctgctgg agtccgagga cctaatggag atgctggtcg ccctgggggag    1800 cctggtctca tgggacccag aggtcttcct ggttcccctg gaaatatcgg cccgctgga    1860 aaagaaggtc ctgtcggcct ccctggcatc gacggcaggc ctggcccaat tggcccagct    1920
ggagcaagag gagagcctgg caacattgga ttccctggac ccaaaggccc cactggtgat    1980
cctggcaaaa acggtgataa aggtcatgct ggtcttgctg gtgctcgggg tgctccaggt    2040
cctgatggaa acaatggtgc tcagggacct cctggaccac agggtgttca aggtggaaaa    2100
ggtgaacagg gtccccctgg tcctccagge ttccagggtc tgcctggccc ctcaggtccc    2160
gctggtgaag ttggcaaacc aggagaaagg ggtctccatg gtgagtttgg tctccctggt    2220
```

```
cctgctggtc caagagggga acgcggtccc ccaggtgaga gtggtgctgc cggtcctact   2280
ggtcctattg gaagccgagg tccttctgga cccccagggc ctgatggaaa caagggtgaa   2340
cctggtgtgg ttggtgctgt gggcactgct ggtccatctg gtcctagtgg actcccagga   2400
gagaggggtg ctgctggcat acctggaggc aagggagaaa agggtgaacc tggtctcaga   2460
ggtgaaattg gtaaccctgg cagagatggt gctcgtggtg ctcctggtgc tgtaggtgcc   2520
cctggtcctg ctggagccac aggtgaccgg ggcgaagctg gggctgctgg tcctgctggt   2580
cctgctggtc tcggggaagc cctggtgaaa cgtggtgagg tcggtcctgc tggccccaat   2640
ggatttgctg gtcctgctgg tgctgctggt caacctggtg ctaaaggaga aagaggagcc   2700
aaagggccta agggtgaaaa cggtgttgtt ggtcccacag gccccgttgg agctgctggc   2760
ccagctggtc caaatggtcc cccggtcct gctggaagtc gtggtgatgg aggcccccct   2820
ggtatgactg gtttccctgg tgctgctgga cggactggtc ccccaggacc ctctggtatt   2880
tctggccctc ctggtccccc tggtcctgct gggaaagaag gcttcgtgg tcctcgtggt   2940
gaccaaggtc cagttggccg aactggagaa gtaggtgcag ttggtcccc tggcttcgct   3000
ggtgagaagg gtccctctgg agaggctggt actgctggac ctcctggcac tccaggtcct   3060
cagggtcttc ttggtgctcc tggtattctg gtctccctg gctcgagagg tgaacgtggt   3120
ctaccaggtg ttgctggtgc tgtgggtgaa cctggtcctc ttggcattgc cggccctcct   3180
ggggcccgtg gtcctcctgg tgctgtgggt agtcctggag tcaacggtgc tcctggtgaa   3240
gctggtcgta tggcaaccc tgggaacgat ggtcccccag gtcgcgatgg tcaacccgga   3300
cacaagggag agcgcggtta ccctggcaat attggtcccg ttggtgctgc aggtgcacct   3360
ggtcctcatg gccccgtggg tcctgctggc aaacatggaa accgtggtga aactggtcct   3420
tctggtcctg ttggtcctgc tggtgctgtt ggcccaagag gtcctagtgg cccacaaggc   3480
attcgtggcg ataagggaga gcccggtgaa aaggggccca gagtgtctcc tggcttaaag   3540
ggacacaatg gattgcaagg tctgcctggt atcgctggtc accatggtga tcaaggtgct   3600
cctggctccg tgggtcctgc tggtcctagg ggccctgctg gtccttctgg ccctgctgga   3660
aaagatggtc gcactggaca tcctggtaca gttggacctg ctggcattcg aggccctcag   3720
ggtcaccaag gccctgctgg cccccctggt cccctggcc ctcctggacc tccaggtgta   3780
agcggtggtg gttatgactt tggttacgat ggagacttct acagggctga ccagcctcgc   3840
tcagcacctt ctctcagacc caaggactat gaagttgatg ctactctgaa gtctctcaac   3900
aaccagattg agacccttct tactcctgaa ggctctagaa agaacccagc tcgcacatgc   3960
cgtgacttga gactcagcca cccagagtgg agcagtggtt actactggat tgaccctaac   4020
caaggatgca ctatgatgc tatcaaagta tactgtgatt tctctactgg cgaaacctgt   4080
atccgggccc aacctgaaaa catcccagcc aagaactggt ataggagctc caaggacaag   4140
aaacacgtct ggctaggaga aactatcaat gctggcagcc agtttgaata taatgtagaa   4200
ggagtgactt ccaaggaaat ggctacccaa cttgccttca tgcgcctgct ggccaactat   4260
gcctctcaga acatcaccta ccactgcaag aacagcattg catacatgga tgaggagact   4320
ggcaacctga aaaaggctgt cattctacag ggctctaatg atgttgaact tgttgctgag   4380
ggcaacagca ggttcactta cactgttctt gtagatggct gctctaaaaa gacaaatgaa   4440
tggggaaaga caatcattga atacaaaaca aataagccat cacgcctgcc cttccttgat   4500
attgcacctt tggacatcgg tggtgctgac caggaattct ttgtggacat tggcccagtc   4560
```

-continued

```
tgtttcaaat aaatgaactc aatctaaatt aaaaaagaaa gaaatttgaa aaaactttct   4620
ctttgccatt tcttcttctt ctttttaac tgaaagctga atccttccat ttcttctgca   4680
catctacttg cttaaattgt gggcaaaaga gaaaaagaag gattgatcag agcattgtgc   4740
aatacagttt cattaactcc ttcccccgct cccccaaaaa tttgaatttt tttttcaaca   4800
ctcttacacc tgttatggaa aatgtcaacc tttgtaagaa aaccaaaata aaaattgaaa   4860
aataaaaacc ataaacattt gcaccacttg tggcttttga atatcttcca cagagggaag   4920
tttaaaaccc aaacttccaa aggtttaaac tacctcaaaa cactttccca tgagtgtgat   4980
ccacattgtt aggtgctgac ctagacagag atgaactgag gtccttgttt tgttttgttc   5040
ataatacaaa ggtgctaatt aatagtattt cagatacttg aagaatgttg atggtgctag   5100
aagaatttga gaagaaatac tcctgtattg agttgtatcg tgtggtgtat tttttaaaaa   5160
atttgattta gcattcatat tttccatctt attcccaatt aaaagtatgc agattatttg   5220
cccaaatctt cttcagattc agcatttgtt ctttgccagt ctcattttca tcttcttcca   5280
tggttccaca gaagctttgt ttcttgggca agcagaaaaa ttaaattgta cctattttgt   5340
atatgtgaga tgtttaaata aattgtgaaa aaaatgaaat aaagcatgtt tggttttcca   5400
aaagaacata t                                                        5411

<210> SEQ ID NO 34
<211> LENGTH: 1633
<212> TYPE: DNA
<213> ORGANISM: Artificial Sequence
<220> FEATURE:
<223> OTHER INFORMATION: Synthetic sequence containing the coding
      regions of the vascular signal sequence of barley gene for Thiol
      protease aleurain precursor fused to the human Prolyl
      4-hydroxylase beta subunit and flanking regions

<400> SEQUENCE: 34
ctcgagtaaa ccatggctca tgctagggtt ttgcttttgg ctcttgctgt tcttgctact     60
gctgctgttg ctgtggcttc ttcttcatct ttcgctgatt ctaacccaat taggccagtg    120
actgatagag ctgcttctac tcttgctcaa ttggtcgaca tggatgctcc agaagaggag    180
gatcacgttc ttgtgcttag gaagtctaac ttcgctgaag ctcttgctgc tcacaagtac    240
cttcttgtgg agttttatgc tccttggtgc ggacattgca aagctcttgc tccagagtat    300
gctaaggctg ctggaaagtt gaaggctgag ggatctgaaa ttaggcttgc taaagtggat    360
gctactgagg agtctgatct tgctcaacag tacggagtta ggggataccc aactattaag    420
ttcttcagga acggagatac tgcttctcca aaggagtata ctgctggaag ggaggctgat    480
gatattgtga actggcttaa gaagagaact ggaccagctg ctactactct tccagatgga    540
gctgctgctg aatctcttgt ggagtcatct gaggtggcag tgattggatt cttcaaggat    600
gtggagtctg attctgctaa gcagttcctt caagctgctg aggctattga tgatattcca    660
ttcggaatta cttctaactc tgatgtgttc tctaagtacc agcttgataa ggatggagtg    720
gtgcttttca agaaattcga tgagggaagg aacaatttcg agggagaggt gacaaaggag    780
aaccttcttg atttcattaa gcacaaccag cttccacttg tgattgagtt cactgagcag    840
actgctccaa agattttcgg aggagagatt aagactcaca ttcttctttt ccttccaaag    900
tctgtgtctg attacgatgg aaagttgtct aacttcaaga ctgctgctga gtctttcaag    960
ggaaagattc ttttcatttt cattgattct gatcacactg ataaccagag gattcttgag   1020
ttcttcggac ttaagaagga agagtgccca gctgttaggc ttattactct tgaggaggag   1080
```

```
atgactaagt acaagccaga gtctgaagaa cttactgctg agaggattac tgagttctgc    1140
cacagattcc ttgagggaaa gattaagcca caccttatgt ctcaagagct tccagaggat    1200
tgggataagc agccagttaa ggtgttggtg ggtaaaaact tcgaggatgt ggctttcgat    1260
gagaagaaga acgtgttcgt ggagttctac gcaccttggt gtggtcactg taagcagctt    1320
gctccaattt gggataagtt gggagagact acaaggatc acgagaacat tgtgattgct    1380
aagatggatt ctactgctaa cgaggtggag gctgttaagg ttcactcttt cccaactttg    1440
aagttcttcc cagcttctgc tgataggact gtgattgatt acaacggaga aaggactctt    1500
gatggattca agaagttcct tgagtctgga ggacaagatg gagctggaga tgatgatgat    1560
cttgaggatt tggaagaagc tgaggagcca gatatggagg aggatgatga tcagaaggct    1620
gtgtgatgag ctc                                                       1633
```

<210> SEQ ID NO 35
<211> LENGTH: 1723
<212> TYPE: DNA
<213> ORGANISM: Artificial Sequence
<220> FEATURE:
<223> OTHER INFORMATION: Synthetic sequence containing the coding
      regions of the vascular signal sequence of barley gene for Thiol
      protease aleurain precursor fused to the human Prolyl
      4-hydroxylase alpha-1 subunit and flanking regions

<400> SEQUENCE: 35

```
ctcgagtaaa ccatggctca tgctagggtt ttgcttttgg ctcttgctgt tcttgctact     60
gctgctgttg ctgtggcttc ttcttcatct ttcgctgatt ctaacccaat taggccagtg    120
actgatagag ctgcttctac tcttgctcaa ttggtcgaca tgcacccagg attcttcact    180
tctattggac agatgactga tcttattcac actgagaagg atcttgtgac ttctcttaag    240
gattacatta aggctgagga ggataagttg gagcagatta agaagtgggc tgagaagttg    300
gataggctta cttctactgc tacaaaagat ccagagggat tcgttggtca tccagtgaac    360
gctttcaagt tgatgaagag gcttaacact gagtggagtg agcttgagaa ccttgtgctt    420
aaggatatgt ctgatggatt catttctaac cttactattc agaggcagta cttcccaaat    480
gatgaggatc aagtgggagc tgctaaggct cttcttaggc ttcaggatac ttacaacctt    540
gatactgata caatttctaa gggaaacctt ccaggagtta agcacaagtc tttccttact    600
gctgaggatt gcttcgagct tggaaaggtt gcatacactg aggctgatta ctaccacact    660
gagctttgga tggaacaagc tcttaggcaa cttgatgagg agagatttc tactattgat    720 aaggtgtcag tgcttgatta ccttttcttac gctgtgtacc agcagggtga tcttgataag    780 gctctttttgc ttactaagaa gttgcttgag cttgatccag aacatcagag ggctaacgga    840
aaccttaagt acttcgagta cattatggct aaggaaaagg atgtgaacaa gtctgcttct    900
gatgatcagt ctgatcaaaa gactactcca agaagaagg agtggctgt tgattatctt     960 cctgagaggc agaagtatga gatgttgtgt aggggagagg gtattaagat gactccaagg   1020
aggcagaaga agttgttctg caggtatcac gatggaaaca ggaacccaaa gttcattctt   1080
gctccagcta agcaagaaga tgagtgggat aagccaagga ttattaggtt ccacgatatt   1140
atttctgatg ctgagattga gattgtgaag gatcttgcta agccaagact taggagggct   1200
actatttcta accctattac tggtgatctt gagactgtgc actacaggat ttctaagtct   1260
gcttggcttt ctggatacga gaacccagtg gtgtctagga ttaacatgag gattcaggat   1320
cttactggac ttgatgtgtc tactgctgag gagcttcaag ttgctaacta cggagttgga   1380
```

-continued

```
ggacaatatg agccacactt cgatttcgct aggaaggatg agccagatgc tttttaaggag   1440 cttggaactg gaaacaggat tgctacttgg ctttttctaca tgtctgatgt ttctgctgga   1500
ggagctactg ttttcccaga agtgggagct tctgtttggc caaagaaggg aactgctgtg   1560
ttctggtaca accttttcgc ttctggagag ggagattact ctactaggca tgctgcttgc   1620
ccagttcttg ttggaaacaa gtgggtgtca aacaagtggc ttcatgagag gggacaagag   1680
tttagaaggc catgcactct ttctgagctt gagtgatgag ctc                      1723
```

<210> SEQ ID NO 36
<211> LENGTH: 1489
<212> TYPE: PRT
<213> ORGANISM: Homo sapiens

<400> SEQUENCE: 36

```
Met Ala His Ala Arg Val Leu Leu Ala Leu Ala Val Leu Ala Thr
1               5                   10                  15

Ala Ala Val Ala Val Ala Ser Ser Ser Phe Ala Asp Ser Asn Pro
                20                  25                  30

Ile Arg Pro Val Thr Asp Arg Ala Ala Ser Thr Leu Ala Gln Leu Gln
        35                  40                  45

Glu Glu Gly Gln Val Glu Gly Gln Asp Glu Asp Ile Pro Pro Ile Thr
    50                  55                  60

Cys Val Gln Asn Gly Leu Arg Tyr His Asp Arg Asp Val Trp Lys Pro
65                  70                  75                  80

Glu Pro Cys Arg Ile Cys Val Cys Asp Asn Gly Lys Val Leu Cys Asp
                85                  90                  95

Asp Val Ile Cys Asp Glu Thr Lys Asn Cys Pro Gly Ala Glu Val Pro
            100                 105                 110

Glu Gly Glu Cys Cys Pro Val Cys Pro Asp Gly Ser Glu Ser Pro Thr
        115                 120                 125

Asp Gln Glu Thr Thr Gly Val Glu Gly Pro Lys Gly Asp Thr Gly Pro
    130                 135                 140

Arg Gly Pro Arg Gly Pro Ala Gly Pro Pro Gly Arg Asp Gly Ile Pro
145                 150                 155                 160

Gly Gln Pro Gly Leu Pro Gly Pro Pro Gly Pro Pro Gly Pro Pro Gly
                165                 170                 175

Pro Pro Gly Leu Gly Gly Asn Phe Ala Pro Gln Leu Ser Tyr Gly Tyr
            180                 185                 190

Asp Glu Lys Ser Thr Gly Gly Ile Ser Val Pro Gly Pro Met Gly Pro
        195                 200                 205

Ser Gly Pro Arg Gly Leu Pro Gly Pro Pro Gly Ala Pro Gly Pro Gln
    210                 215                 220

Gly Phe Gln Gly Pro Pro Gly Glu Pro Gly Pro Gly Ala Ser Gly
225                 230                 235                 240

Pro Met Gly Pro Arg Gly Pro Pro Gly Pro Pro Gly Lys Asn Gly Asp
                245                 250                 255

Asp Gly Glu Ala Gly Lys Pro Gly Arg Pro Gly Glu Arg Gly Pro Pro
            260                 265                 270

Gly Pro Gln Gly Ala Arg Gly Leu Pro Gly Thr Ala Gly Leu Pro Gly
        275                 280                 285

Met Lys Gly His Arg Gly Phe Ser Gly Leu Asp Gly Ala Lys Gly Asp
    290                 295                 300

Ala Gly Pro Ala Gly Pro Lys Gly Glu Pro Gly Ser Pro Gly Glu Asn
305                 310                 315                 320
```

```
Gly Ala Pro Gly Gln Met Gly Pro Arg Gly Leu Pro Gly Glu Arg Gly
                325                 330                 335

Arg Pro Gly Ala Pro Gly Pro Ala Gly Ala Arg Gly Asn Asp Gly Ala
                340                 345                 350

Thr Gly Ala Ala Gly Pro Pro Gly Pro Thr Gly Pro Ala Gly Pro Pro
                355                 360                 365

Gly Phe Pro Gly Ala Val Gly Ala Lys Gly Glu Ala Gly Pro Gln Gly
            370                 375                 380

Pro Arg Gly Ser Glu Gly Pro Gln Gly Val Arg Gly Glu Pro Gly Pro
385                 390                 395                 400

Pro Gly Pro Ala Gly Ala Ala Gly Pro Ala Gly Asn Pro Gly Ala Asp
                405                 410                 415

Gly Gln Pro Gly Ala Lys Gly Ala Asn Gly Ala Pro Gly Ile Ala Gly
                420                 425                 430

Ala Pro Gly Phe Pro Gly Ala Arg Gly Pro Ser Gly Pro Gln Gly Pro
                435                 440                 445

Gly Gly Pro Pro Gly Pro Lys Gly Asn Ser Gly Glu Pro Gly Ala Pro
            450                 455                 460

Gly Ser Lys Gly Asp Thr Gly Ala Lys Gly Glu Pro Gly Pro Val Gly
465                 470                 475                 480

Val Gln Gly Pro Pro Gly Pro Ala Gly Glu Glu Gly Lys Arg Gly Ala
                485                 490                 495

Arg Gly Glu Pro Gly Pro Thr Gly Leu Pro Gly Pro Pro Gly Glu Arg
                500                 505                 510

Gly Gly Pro Gly Ser Arg Gly Phe Pro Gly Ala Asp Gly Val Ala Gly
            515                 520                 525

Pro Lys Gly Pro Ala Gly Glu Arg Gly Ser Pro Gly Pro Ala Gly Pro
            530                 535                 540

Lys Gly Ser Pro Gly Glu Ala Gly Arg Pro Gly Glu Ala Gly Leu Pro
545                 550                 555                 560

Gly Ala Lys Gly Leu Thr Gly Ser Pro Gly Ser Pro Gly Pro Asp Gly
                565                 570                 575

Lys Thr Gly Pro Pro Gly Pro Ala Gly Gln Asp Gly Arg Pro Gly Pro
                580                 585                 590

Pro Gly Pro Pro Gly Ala Arg Gly Gln Ala Gly Val Met Gly Phe Pro
            595                 600                 605

Gly Pro Lys Gly Ala Ala Gly Glu Pro Gly Lys Ala Gly Glu Arg Gly
            610                 615                 620

Val Pro Gly Pro Pro Gly Ala Val Gly Pro Ala Gly Lys Asp Gly Glu
625                 630                 635                 640

Ala Gly Ala Gln Gly Pro Pro Gly Pro Ala Gly Pro Ala Gly Glu Arg
                645                 650                 655

Gly Glu Gln Gly Pro Ala Gly Ser Pro Gly Phe Gln Gly Leu Pro Gly
                660                 665                 670

Pro Ala Gly Pro Pro Gly Glu Ala Gly Lys Pro Gly Glu Gln Gly Val
            675                 680                 685

Pro Gly Asp Leu Gly Ala Pro Gly Pro Ser Gly Ala Arg Gly Glu Arg
            690                 695                 700

Gly Phe Pro Gly Glu Arg Gly Val Gln Gly Pro Pro Gly Pro Ala Gly
705                 710                 715                 720

Pro Arg Gly Ala Asn Gly Ala Pro Gly Asn Asp Gly Ala Lys Gly Asp
                725                 730                 735
```

```
Ala Gly Ala Pro Gly Ala Pro Gly Ser Gln Gly Ala Pro Gly Leu Gln
            740                 745                 750

Gly Met Pro Gly Glu Arg Gly Ala Ala Gly Leu Pro Gly Pro Lys Gly
            755                 760                 765

Asp Arg Gly Asp Ala Gly Pro Lys Gly Ala Asp Gly Ser Pro Gly Lys
            770                 775                 780

Asp Gly Val Arg Gly Leu Thr Gly Pro Ile Gly Pro Pro Gly Pro Ala
785                 790                 795                 800

Gly Ala Pro Gly Asp Lys Gly Glu Ser Gly Pro Ser Gly Pro Ala Gly
            805                 810                 815

Pro Thr Gly Ala Arg Gly Ala Pro Gly Asp Arg Gly Glu Pro Gly Pro
            820                 825                 830

Pro Gly Pro Ala Gly Phe Ala Gly Pro Pro Gly Ala Asp Gly Gln Pro
            835                 840                 845

Gly Ala Lys Gly Glu Pro Gly Asp Ala Gly Ala Lys Gly Asp Ala Gly
            850                 855                 860

Pro Pro Gly Pro Ala Gly Pro Ala Gly Pro Pro Gly Pro Ile Gly Asn
865                 870                 875                 880

Val Gly Ala Pro Gly Ala Lys Gly Ala Arg Gly Ser Ala Gly Pro Pro
            885                 890                 895

Gly Ala Thr Gly Phe Pro Gly Ala Ala Gly Arg Val Gly Pro Pro Gly
            900                 905                 910

Pro Ser Gly Asn Ala Gly Pro Pro Gly Pro Pro Gly Pro Ala Gly Lys
            915                 920                 925

Glu Gly Gly Lys Gly Pro Arg Gly Glu Thr Gly Pro Ala Gly Arg Pro
930                 935                 940

Gly Glu Val Gly Pro Pro Gly Pro Pro Gly Pro Ala Gly Glu Lys Gly
945                 950                 955                 960

Ser Pro Gly Ala Asp Gly Pro Ala Gly Ala Pro Gly Thr Pro Gly Pro
            965                 970                 975

Gln Gly Ile Ala Gly Gln Arg Gly Val Val Gly Leu Pro Gly Gln Arg
            980                 985                 990

Gly Glu Arg Gly Phe Pro Gly Leu Pro Gly Pro Ser Gly Glu Pro Gly
            995                 1000                1005

Lys Gln Gly Pro Ser Gly Ala Ser Gly Glu Arg Gly Pro Pro Gly
            1010                1015                1020

Pro Met Gly Pro Pro Gly Leu Ala Gly Pro Pro Gly Glu Ser Gly
            1025                1030                1035

Arg Glu Gly Ala Pro Gly Ala Glu Gly Ser Pro Gly Arg Asp Gly
            1040                1045                1050

Ser Pro Gly Ala Lys Gly Asp Arg Gly Glu Thr Gly Pro Ala Gly
            1055                1060                1065

Pro Pro Gly Ala Pro Gly Ala Pro Gly Ala Pro Gly Pro Val Gly
            1070                1075                1080

Pro Ala Gly Lys Ser Gly Asp Arg Gly Glu Thr Gly Pro Ala Gly
            1085                1090                1095

Pro Ala Gly Pro Val Gly Pro Ala Gly Ala Arg Gly Pro Ala Gly
            1100                1105                1110

Pro Gln Gly Pro Arg Gly Asp Lys Gly Glu Thr Gly Glu Gln Gly
            1115                1120                1125

Asp Arg Gly Ile Lys Gly His Arg Gly Phe Ser Gly Leu Gln Gly
            1130                1135                1140

Pro Pro Gly Pro Pro Gly Ser Pro Gly Glu Gln Gly Pro Ser Gly
```

```
                   1145                1150                1155
Ala Ser Gly Pro Ala Gly Pro Arg Gly Pro Pro Gly Ser Ala Gly
            1160                1165                1170

Ala Pro Gly Lys Asp Gly Leu Asn Gly Leu Pro Gly Pro Ile Gly
        1175                1180                1185

Pro Pro Gly Pro Arg Gly Arg Thr Gly Asp Ala Gly Pro Val Gly
    1190                1195                1200

Pro Pro Gly Pro Pro Gly Pro Gly Pro Pro Gly Pro Pro Gly Pro Ser
1205                1210                1215

Ala Gly Phe Asp Phe Ser Phe Leu Pro Gln Pro Gln Glu Lys
        1220                1225                1230

Ala His Asp Gly Gly Arg Tyr Tyr Arg Ala Asp Asp Ala Asn Val
        1235                1240                1245

Val Arg Asp Arg Asp Leu Glu Val Asp Thr Thr Leu Lys Ser Leu
        1250                1255                1260

Ser Gln Gln Ile Glu Asn Ile Arg Ser Pro Glu Gly Ser Arg Lys
        1265                1270                1275

Asn Pro Ala Arg Thr Cys Arg Asp Leu Lys Met Cys His Ser Asp
        1280                1285                1290

Trp Lys Ser Gly Glu Tyr Trp Ile Asp Pro Asn Gln Gly Cys Asn
        1295                1300                1305

Leu Asp Ala Ile Lys Val Phe Cys Asn Met Glu Thr Gly Glu Thr
        1310                1315                1320

Cys Val Tyr Pro Thr Gln Pro Ser Val Ala Gln Lys Asn Trp Tyr
        1325                1330                1335

Ile Ser Lys Asn Pro Lys Asp Lys Arg His Val Trp Phe Gly Glu
        1340                1345                1350

Ser Met Thr Asp Gly Phe Gln Phe Glu Tyr Gly Gly Gln Gly Ser
        1355                1360                1365

Asp Pro Ala Asp Val Ala Ile Gln Leu Thr Phe Leu Arg Leu Met
        1370                1375                1380

Ser Thr Glu Ala Ser Gln Asn Ile Thr Tyr His Cys Lys Asn Ser
        1385                1390                1395

Val Ala Tyr Met Asp Gln Gln Thr Gly Asn Leu Lys Lys Ala Leu
        1400                1405                1410

Leu Leu Lys Gly Ser Asn Glu Ile Glu Ile Arg Ala Glu Gly Asn
        1415                1420                1425

Ser Arg Phe Thr Tyr Ser Val Thr Val Asp Gly Cys Thr Ser His
        1430                1435                1440

Thr Gly Ala Trp Gly Lys Thr Val Ile Glu Tyr Lys Thr Thr Lys
        1445                1450                1455

Thr Ser Arg Leu Pro Ile Ile Asp Val Ala Pro Leu Asp Val Gly
        1460                1465                1470

Ala Pro Asp Gln Glu Phe Gly Phe Asp Val Gly Pro Val Cys Phe
        1475                1480                1485

Leu
```

<210> SEQ ID NO 37
<211> LENGTH: 1389
<212> TYPE: PRT
<213> ORGANISM: Homo sapiens

<400> SEQUENCE: 37

Met Ala His Ala Arg Val Leu Leu Leu Ala Leu Ala Val Leu Ala Thr

-continued

```
1               5                   10                  15
Ala Ala Val Ala Val Ala Ser Ser Ser Phe Ala Asp Ser Asn Pro
                20                  25                  30
Ile Arg Pro Val Thr Asp Arg Ala Ser Thr Leu Ala Gln Leu Leu
            35                  40                  45
Gln Glu Glu Thr Val Arg Lys Gly Pro Ala Gly Asp Arg Gly Pro Arg
    50                  55                  60
Gly Glu Arg Gly Pro Pro Gly Pro Pro Gly Arg Asp Gly Glu Asp Gly
65                  70                  75                  80
Pro Thr Gly Pro Pro Gly Pro Pro Gly Pro Pro Gly Pro Pro Gly Leu
                85                  90                  95
Gly Gly Asn Phe Ala Ala Gln Tyr Asp Gly Lys Gly Val Gly Leu Gly
                100                 105                 110
Pro Gly Pro Met Gly Leu Met Gly Pro Arg Gly Pro Pro Gly Ala Ala
                115                 120                 125
Gly Ala Pro Gly Pro Gln Gly Phe Gln Gly Pro Ala Gly Glu Pro Gly
            130                 135                 140
Glu Pro Gly Gln Thr Gly Pro Ala Gly Ala Arg Gly Pro Ala Gly Pro
145                 150                 155                 160
Pro Gly Lys Ala Gly Glu Asp Gly His Pro Gly Lys Pro Gly Arg Pro
                165                 170                 175
Gly Glu Arg Gly Val Val Gly Pro Gln Gly Ala Arg Gly Phe Pro Gly
                180                 185                 190
Thr Pro Gly Leu Pro Gly Phe Lys Gly Ile Arg Gly His Asn Gly Leu
            195                 200                 205
Asp Gly Leu Lys Gly Gln Pro Gly Ala Pro Gly Val Lys Gly Glu Pro
    210                 215                 220
Gly Ala Pro Gly Glu Asn Gly Thr Pro Gly Gln Thr Gly Ala Arg Gly
225                 230                 235                 240
Leu Pro Gly Glu Arg Gly Arg Val Gly Ala Pro Gly Pro Ala Gly Ala
                245                 250                 255
Arg Gly Ser Asp Gly Ser Val Gly Pro Val Gly Pro Ala Gly Pro Ile
                260                 265                 270
Gly Ser Ala Gly Pro Pro Gly Phe Pro Gly Ala Pro Gly Pro Lys Gly
            275                 280                 285
Glu Ile Gly Ala Val Gly Asn Ala Gly Pro Thr Gly Pro Ala Gly Pro
            290                 295                 300
Arg Gly Glu Val Gly Leu Pro Gly Leu Ser Gly Pro Val Gly Pro Pro
305                 310                 315                 320
Gly Asn Pro Gly Ala Asn Gly Leu Thr Gly Ala Lys Gly Ala Ala Gly
                325                 330                 335
Leu Pro Gly Val Ala Gly Ala Pro Gly Leu Pro Gly Pro Arg Gly Ile
                340                 345                 350
Pro Gly Pro Val Gly Ala Ala Gly Ala Thr Gly Ala Arg Gly Leu Val
                355                 360                 365
Gly Glu Pro Gly Pro Ala Gly Ser Lys Gly Glu Ser Gly Asn Lys Gly
            370                 375                 380
Glu Pro Gly Ser Ala Gly Pro Gln Gly Pro Pro Gly Pro Ser Gly Glu
385                 390                 395                 400
Glu Gly Lys Arg Gly Pro Asn Gly Glu Ala Gly Ser Ala Gly Pro Pro
                405                 410                 415
Gly Pro Pro Gly Leu Arg Gly Ser Pro Gly Ser Arg Gly Leu Pro Gly
                420                 425                 430
```

```
Ala Asp Gly Arg Ala Gly Val Met Gly Pro Pro Gly Ser Arg Gly Ala
        435                 440                 445

Ser Gly Pro Ala Gly Val Arg Gly Pro Asn Gly Asp Ala Gly Arg Pro
450                 455                 460

Gly Glu Pro Gly Leu Met Gly Pro Arg Gly Leu Pro Gly Ser Pro Gly
465                 470                 475                 480

Asn Ile Gly Pro Ala Gly Lys Glu Gly Pro Val Gly Leu Pro Gly Ile
                485                 490                 495

Asp Gly Arg Pro Gly Pro Ile Gly Pro Ala Gly Ala Arg Gly Glu Pro
            500                 505                 510

Gly Asn Ile Gly Phe Pro Gly Pro Lys Gly Pro Thr Gly Asp Pro Gly
        515                 520                 525

Lys Asn Gly Asp Lys Gly His Ala Gly Leu Ala Gly Ala Arg Gly Ala
530                 535                 540

Pro Gly Pro Asp Gly Asn Asn Gly Ala Gln Gly Pro Pro Gly Pro Gln
545                 550                 555                 560

Gly Val Gln Gly Gly Lys Gly Glu Gln Gly Pro Ala Gly Pro Pro Gly
                565                 570                 575

Phe Gln Gly Leu Pro Gly Pro Ser Gly Pro Ala Gly Glu Val Gly Lys
            580                 585                 590

Pro Gly Glu Arg Gly Leu His Gly Glu Phe Gly Leu Pro Gly Pro Ala
        595                 600                 605

Gly Pro Arg Gly Glu Arg Gly Pro Pro Gly Glu Ser Gly Ala Ala Gly
610                 615                 620

Pro Thr Gly Pro Ile Gly Ser Arg Gly Pro Ser Gly Pro Pro Gly Pro
625                 630                 635                 640

Asp Gly Asn Lys Gly Glu Pro Gly Val Val Gly Ala Val Gly Thr Ala
                645                 650                 655

Gly Pro Ser Gly Pro Ser Gly Leu Pro Gly Glu Arg Gly Ala Ala Gly
            660                 665                 670

Ile Pro Gly Gly Lys Gly Glu Lys Gly Glu Pro Gly Leu Arg Gly Glu
        675                 680                 685

Ile Gly Asn Pro Gly Arg Asp Gly Ala Arg Gly Ala His Gly Ala Val
        690                 695                 700

Gly Ala Pro Gly Pro Ala Gly Ala Thr Gly Asp Arg Gly Glu Ala Gly
705                 710                 715                 720

Ala Ala Gly Pro Ala Gly Pro Ala Gly Pro Arg Gly Ser Pro Gly Glu
                725                 730                 735

Arg Gly Glu Val Gly Pro Ala Gly Pro Asn Gly Phe Ala Gly Pro Ala
            740                 745                 750

Gly Ala Ala Gly Gln Pro Gly Ala Lys Gly Glu Arg Gly Gly Lys Gly
        755                 760                 765

Pro Lys Gly Glu Asn Gly Val Val Gly Pro Thr Gly Pro Val Gly Ala
770                 775                 780

Ala Gly Pro Ala Gly Pro Asn Gly Pro Pro Gly Pro Ala Gly Ser Arg
785                 790                 795                 800

Gly Asp Gly Gly Pro Pro Gly Met Thr Gly Phe Pro Gly Ala Ala Gly
                805                 810                 815

Arg Thr Gly Pro Pro Gly Pro Ser Gly Ile Ser Gly Pro Pro Gly Pro
            820                 825                 830

Pro Gly Pro Ala Gly Lys Glu Gly Leu Arg Gly Pro Arg Gly Asp Gln
        835                 840                 845
```

```
Gly Pro Val Gly Arg Thr Gly Glu Val Gly Ala Val Gly Pro Pro Gly
            850                 855                 860

Phe Ala Gly Glu Lys Gly Pro Ser Gly Glu Ala Gly Thr Ala Gly Pro
865                 870                 875                 880

Pro Gly Thr Pro Gly Pro Gln Gly Leu Leu Gly Ala Pro Gly Ile Leu
                885                 890                 895

Gly Leu Pro Gly Ser Arg Gly Glu Arg Gly Leu Pro Gly Val Ala Gly
                900                 905                 910

Ala Val Gly Glu Pro Gly Pro Leu Gly Ile Ala Gly Pro Gly Ala
        915                 920                 925

Arg Gly Pro Pro Gly Ala Val Gly Ser Pro Gly Val Asn Gly Ala Pro
    930                 935                 940

Gly Glu Ala Gly Arg Asp Gly Asn Pro Gly Asn Asp Gly Pro Pro Gly
945                 950                 955                 960

Arg Asp Gly Gln Pro Gly His Lys Gly Glu Arg Gly Tyr Pro Gly Asn
                965                 970                 975

Ile Gly Pro Val Gly Ala Ala Gly Ala Pro Gly Pro His Gly Pro Val
                980                 985                 990

Gly Pro Ala Gly Lys His Gly Asn  Arg Gly Glu Thr Gly  Pro Ser Gly
                995                 1000                1005

Pro Val  Gly Pro Ala Gly Ala  Val Gly Pro Arg Gly  Pro Ser Gly
    1010                1015                1020

Pro Gln  Gly Ile Arg Gly Asp  Lys Gly Glu Pro Gly  Glu Lys Gly
    1025                1030                1035

Pro Arg  Gly Leu Pro Gly Phe  Lys Gly His Asn Gly  Leu Gln Gly
    1040                1045                1050

Leu Pro  Gly Ile Ala Gly His  His Gly Asp Gln Gly  Ala Pro Gly
    1055                1060                1065

Ser Val  Gly Pro Ala Gly Pro  Arg Gly Pro Ala Gly  Pro Ser Gly
    1070                1075                1080

Pro Ala  Gly Lys Asp Gly Arg  Thr Gly His Pro Gly  Thr Val Gly
    1085                1090                1095

Pro Ala  Gly Ile Arg Gly Pro  Gln Gly His Gln Gly  Pro Ala Gly
    1100                1105                1110

Pro Pro  Gly Pro Pro Gly Pro  Pro Gly Pro Pro Gly  Val Ser Gly
    1115                1120                1125

Gly Gly  Tyr Asp Phe Gly Tyr  Asp Gly Asp Phe Tyr  Arg Ala Asp
    1130                1135                1140

Gln Pro  Arg Ser Ala Pro Ser  Leu Arg Pro Lys Asp  Tyr Glu Val
    1145                1150                1155

Asp Ala  Thr Leu Lys Ser Leu  Asn Asn Gln Ile Glu  Thr Leu Leu
    1160                1165                1170

Thr Pro  Glu Gly Ser Arg Lys  Asn Pro Ala Arg Thr  Cys Arg Asp
    1175                1180                1185

Leu Arg  Leu Ser His Pro Glu  Trp Ser Ser Gly Tyr  Tyr Trp Ile
    1190                1195                1200

Asp Pro  Asn Gln Gly Cys Thr  Met Glu Ala Ile Lys  Val Tyr Cys
    1205                1210                1215

Asp Phe  Pro Thr Gly Glu Thr  Cys Ile Arg Ala Gln  Pro Glu Asn
    1220                1225                1230

Ile Pro  Ala Lys Asn Trp Tyr  Arg Ser Ser Lys Asp  Lys Lys His
    1235                1240                1245

Val Trp  Leu Gly Glu Thr Ile  Asn Ala Gly Ser Gln  Phe Glu Tyr
```

Asn Val Glu Gly Val Thr Ser Lys Glu Met Ala Thr Gln Leu Ala
1265                1270                1275

Phe Met Arg Leu Leu Ala Asn Tyr Ala Ser Gln Asn Ile Thr Tyr
1280                1285                1290

His Cys Lys Asn Ser Ile Ala Tyr Met Asp Glu Glu Thr Gly Asn
1295                1300                1305

Leu Lys Lys Ala Val Ile Leu Gln Gly Ser Asn Asp Val Glu Leu
1310                1315                1320

Val Ala Glu Gly Asn Ser Arg Phe Thr Tyr Thr Val Leu Val Asp
1325                1330                1335

Gly Cys Ser Lys Lys Thr Asn Glu Trp Gly Lys Thr Ile Ile Glu
1340                1345                1350

Tyr Lys Thr Asn Lys Pro Ser Arg Leu Pro Phe Leu Asp Ile Ala
1355                1360                1365

Pro Leu Asp Ile Gly Gly Ala Asp His Glu Phe Val Asp Ile
1370                1375                1380

Gly Pro Val Cys Phe Lys
    1385

<210> SEQ ID NO 38
<211> LENGTH: 2888
<212> TYPE: DNA
<213> ORGANISM: Artificial Sequence
<220> FEATURE:
<223> OTHER INFORMATION: Synthetic sequence containing the coding
      regions of the vascular signal sequence of barley gene for Thiol
      protease aleurain precursor fused to the human Lysyl hydroxylase 3
      and flanking regions

<400> SEQUENCE: 38

| | | | | | |
|---|---|---|---|---|---|
| gcgaattcgc | tagctatcac | tgaaaagaca | gcaagacaat | ggtgtctcga | tgcaccagaa | 60 |
| ccacatcttt | gcagcagatg | tgaagcagcc | agagtggtcc | acaagacgca | ctcagaaaag | 120 |
| gcatcttcta | ccgacacaga | aaaagacaac | cacagctcat | catccaacat | gtagactgtc | 180 |
| gttatgcgtc | ggctgaagat | aagactgacc | ccaggccagc | actaaagaag | aaataatgca | 240 |
| agtggtccta | gctccacttt | agctttaata | attatgtttc | attattattc | tctgcttttg | 300 |
| ctctctatat | aaagagcttg | tattttcatt | tgaaggcaga | ggcgaacaca | cacacagaac | 360 |
| ctccctgctt | acaaaccaga | tcttaaacca | tggctcacgc | tagggttttg | cttcttgctc | 420 |
| ttgctgttct | tgctactgct | gctgttgctg | tggcttcttc | aagttctttc | gctgattcta | 480 |
| acccaattag | gccagtgact | gatagagctg | cttctactct | tgctcaattg | agatctatgt | 540 |
| ctgatagacc | aaggggaagg | gatccagtta | atccagagaa | gttgcttgtg | attactgtgg | 600 |
| ctactgctga | gactgaagga | taccttagat | tccttaggag | tgctgagttc | ttcaactaca | 660 |
| ctgtgaggac | tcttggactt | ggagaagaat | ggaggggagg | agatgttgct | agaactgttg | 720 |
| gaggaggaca | gaaagtgaga | tggcttaaga | agagatggga | gaagtacgct | gatagggagg | 780 |
| atatgattat | tatgttcgtg | gattcttacg | atgtgattct | tgctggatct | ccaactgagc | 840 |
| ttttgaagaa | attcgttcag | tctggatcta | ggcttctttt | ctctgctgag | tcttttttgtt | 900 |
| ggccagaatg | gggacttgct | gagcaatatc | agaagtggg | aactggaaag | agattcctta | 960 |
| actctggagg | attcattgga | ttcgctacta | ctattcacca | gattgtgagg | cagtggaagt | 1020 |
| acaaggatga | cgatgatgat | cagcttttct | acactaggct | ttaccttgat | ccaggactta | 1080 |
| gggagaagtt | gtctcttaac | cttgatcaca | agtctaggat | tttccagaac | cttaacggtg | 1140 |

```
ctcttgatga ggttgtgctt aagttcgata ggaacagagt gaggattagg aacgtggctt    1200
acgatactct tcctattgtg gtgcatggaa acggaccaac aaaactccag cttaactacc    1260
ttggaaacta cgttccaaac ggatggactc cagaaggagg atgtggattc tgcaatcagg    1320
ataggagaac tcttccagga ggacaaccac caccaagagt tttccttgct gtgttcgttg    1380
aacagccaac tccattcctt ccaagattcc ttcagaggct tcttcttttg gattacccac    1440
cagatagggt gacactttc cttcacaaca cgaggtttt ccacgagcca cacattgctg      1500
attcttggcc acagcttcag gatcatttct ctgctgtgaa gttggttggt ccagaagaag    1560
ctctttctcc aggagaagct agggatatgg ctatggattt gtgcaggcag gatccagagt    1620
gcgagttcta cttctctctt gatgctgatg ctgtgcttac taaccttcag actcttagga    1680
ttcttattga ggagaacagg aaagtgattg ctccaatgct ttctaggcac ggaaagttgt    1740
ggtctaattt ctggggtgct ctttctcctg atgagtacta cgctagatca gaggactacg    1800
tggagcttgt tcagagaaag agagtgggag tttggaacgt tccttatatt tctcaggctt    1860
acgtgattag gggagatact cttaggatgg agcttccaca gagggatgtt ttctctggat    1920
ctgatactga tccagatatg gctttctgca agtctttcag ggataaggga attttccttc    1980
acctttctaa ccagcatgag ttcggaagat tgcttgctac ttcaagatac gatactgagc    2040
accttcatcc tgatctttgg cagattttcg ataacccagt ggattggaag gagcagtaca    2100
ttcacgagaa ctactctagg gctcttgaag agaaggaat tgtggagcaa ccatgcccag      2160
atgtttactg gttcccactt ctttctgagc aaatgtgcga tgagcttgtt gctgagatgg    2220
agcattacgg acaatggagt ggaggtagac atgaggattc taggcttgct ggaggatacg    2280
agaacgttcc aactgtggat attcacatga agcaagtggg atacgaggat caatggcttc    2340
agcttcttag gacttatgtg ggaccaatga ctgagtctct tttcccagga taccacacta    2400
aggctagggc tgttatgaac ttcgttgtga ggtatcgtcc agatgagcaa ccatctctta    2460
ggccacacca cgattcttct actttcactc ttaacgtggc tcttaaccac aagggacttg    2520
attatgaggg aggaggatgc cgtttcctta gatacgattg cgtgatttct tcaccaagaa    2580
agggatgggc tcttcttcat ccaggaaggc ttactcatta ccacgaggga cttccaacta    2640
cttggggaac tagatatatt atggtgtctt tcgtggatcc atgactgctt taatgagata    2700
tgcgagacgc ctatgatcgc atgatatttg cttcaattc tgttgtgcac gttgtaaaaa     2760
acctgagcat gtgtagctca gatccttacc gccggtttcg gttcattcta atgaatatat    2820
cacccgttac tatcgtattt ttatgaataa tattctccgt tcaatttact gattgtccag    2880
aattcgcg                                                              2888
```

<210> SEQ ID NO 39
<211> LENGTH: 2689
<212> TYPE: DNA
<213> ORGANISM: Artificial Sequence
<220> FEATURE:
<223> OTHER INFORMATION: Synthetic sequence containing the coding
      regions of the human Procollagen C-proteinase and flanking regions

<400> SEQUENCE: 39

```
agatctatcg atgcatgcca tggtaccgcg ccatggctca attggctgca acatcaaggc      60
ctgaaagagt ttggccagat ggtgttattc ctttcgttat tggtggaaac tttactggat     120
ctcagagagc agttttttaga caagctatga gacattggga aaagcacact tgtgtgacat     180
tccttgaaag gactgatgaa gattcttata ttgtgttcac ataccgtcca tgtggatgct     240
```

```
gctcatatgt tggtagaagg ggaggaggtc cacaagcaat ttctattgga aaaaactgcg    300
ataagttcgg aattgtggtg catgaattgg gacatgttgt tggtttctgg cacgaacaca    360
caaggccaga tagggatagg cacgtgtcta ttgtgaggga aaacattcag ccaggtcaag    420
agtacaattt tcttaagatg gaacctcaag aggtggaatc tctcggagag acttacgact    480
tcgactccat catgcactac gcaaggaata ctttcagcag gggcatcttc ttggatacca    540
ttgtgcctaa gtacgaggtg aacggcgtta agccacctat tggtcaaagg actaggctct    600
ctaagggtga tattgcacag gctaggaagc tctacaaatg tccagcatgc ggagaaactc    660
ttcaggattc cactggcaac ttctcatctc cagagtaccc aaacggatac tctgctcata    720
tgcactgtgt ttggaggatc tcagtgactc ctggagagaa gatcatcctc aacttcactt    780
ccctcgatct ctatcgttct aggctctgtt ggtacgacta tgtggaagtg agagatggct    840
tctggagaaa ggctccactt agaggaaggt tctgcggatc taaacttcct gagccaatcg    900
tgtctactga ttccagattg tgggtggagt tcaggtcctc ttctaattgg gttggcaagg    960
gcttttttgc tgtgtacgag gctatttgtg gcggcgacgt gaaaaaggac tacggacata   1020
ttcaaagtcc aaattaccca gatgattacc gtccttcaaa agtgtgtatt tggaggattc   1080
aagtgagtga gggtttccat gttggattga cattccaatc tttcgaaatt gagagacacg   1140
attcatgcgc atacgattat ttggaagtga gagatggaca ctctgaatct tctacactta   1200
ttggaaggta ctgcggttat gagaaacctg atgatattaa gtctacttct agtaggttgt   1260
ggcttaaatt tgtgtcagat ggttctatta caaaggctgg tttcgcagtg aacttcttca   1320
aggaagtgga tgaatgctca agacctaaca gaggaggatg tgagcaaaga tgccttaaca   1380
ctttgggaag ttacaagtgt tcttgcgatc ctggatacga gttggctcct gataagagaa   1440
gatgcgaagc tgcttgcggt ggttttttga caaaattgaa cggatctatt acttctcctg   1500
gatggccaaa agagtaccca cctaataaga attgcatttg gcagcttgtt gcacctactc   1560
agtaccgtat ttcattgcaa ttcgatttt tcgagactga gggtaatgat gtgtgcaagt   1620
acgatttcgt ggaagtgaga tcaggtctta ctgctgatag taaattgcac ggaaaagttct   1680 gcggatctga aaaaccagaa gtgattacat cacagtacaa caatatgagg gtggagttca   1740
aatctgataa tactgtttct aaaaaaggtt ttaaggcaca tttcttttct gataaggacg   1800
agtgctctaa agataatggt ggttgccagc aggattgcgt gaacacattc ggttcatatg   1860
agtgccaatg ccgtagtgga tttgttcttc acgataacaa acatgattgc aaagaggcag   1920
gttgcgatca caaggtgaca tctacttcag gtactatcac atctccaaac tggcctgata   1980
agtatccttc aaaaaaagaa tgtacatggg caatttcttc tacaccaggt catagggtta   2040
agttgacatt catggagatg gatattgaga gtcaaccaga gtgcgcttat gatcatcttg   2100
aggtgttcga tggaagggat gctaaggctc ctgttcttgg tagattctgt ggtagtaaaa   2160
agccagaacc agtgccttgca acaggatcta ggatgttcct tagattctac tctgataact   2220
cagttcagag gaaaggattc caagctagtc acgcaactga atgcggtgga caagttagag   2280
cagatgttaa gactaaggat ctttactcac acgcacagtt cggagataac aactaccctg   2340
gaggagttga ttgcgagtgg gttattgtgg ctgaagaggg atacgagtt gagcttgttt   2400 tccagacatt cgaggtggag gaggaaactg attgcggtta cgattatatg gaacttttg   2460 atggatacga tagtactgct ccaagacttg gaaggtattg tggtagtggt ccaccagaag   2520
aggtgtactc agctggagat agtgttcttg ttaagttcca cagtgatgat acaattacta   2580
```

```
agaagggatt ccatcttaga tatacttcaa ctaagtttca ggatactctt cattctagga      2640
agtaatgagc tcgcggccgc atccaagctt ctgcagacgc gtcgacgtc                 2689

<210> SEQ ID NO 40
<211> LENGTH: 2912
<212> TYPE: DNA
<213> ORGANISM: Artificial Sequence
<220> FEATURE:
<223> OTHER INFORMATION: Synthetic sequence containing the coding
      regions of the human Procollagen I N-proteinase and flanking
      regions

<400> SEQUENCE: 40
gcgccatggc tcaattgagg agaagggcta ggagacacgc agctgatgat gattacaaca       60
ttgaagtttt gcttggtgtt gatgatagtg tggtgcaatt ccacggaaaa gagcatgttc      120
agaaatatct tttgacactt atgaatattg tgaacgaaat ctaccatgat gagtctttgg      180
gagcacacat taacgtggtt cttgtgagga ttattcttct ttcatacggt aaatctatgt      240
cacttattga gattggaaac ccttctcagt ctccttgaga tgtgtgcaga tgggcatacc      300
ttcaacagaa gcctgatact ggacacgatg agtatcacga tcacgctatt ttccttacaa      360
ggcaggattt cggtccaagt ggaatgcaag atatgctcc tgttactggt atgtgccacc       420
ctgttaggtc ttgtacactt aaccacgagg atggttttc atctgctttc gtggtggctc      480
atgagacagg tcatgttttg ggaatggaac atgatggaca gggtaataga gtggagatg       540 aagtgagact tggttcaatt atggctcctc ttgttcaagc tgcttttcat aggttccact      600
ggagtaggtg ttcacagcaa gagttgagta gataccttca ttcttacgat gcttgcttg      660 atgatccatt tgctcatgat tggccagctt tgcctcaact tcctggattg cactactcta     720
tgaacgagca gtgcagattt gatttcggtc ttggttacat gatgtgcaca gctttcagga    780
ctttcgatcc atgcaaacag ttgtggtgtt cacacccaga taacccatat ttctgtaaaa    840
caaaaaaagg tccaccactt gatggtacta tgtgcgcacc tggaaagcac tgcttcaagg    900
gacactgcat ttggcttact cctgatattc ttaaaaggga tggatcatgg ggagcttggt    960
ctccattcgg aagttgctca gaacttgcg gaacaggtgt taagtttaga actaggcagt     1020
gcgataatcc acaccctgct aatggtggta gaacttgctc tggacttgct tacgattttc    1080
agttgtgttc taggcaagat tgccctgata gtcttgctga ttttagagaa gagcaatgta    1140
gacagtggga tctttacttt gagcacggcg acgctcagca ccactggctt ccacacgagc    1200
atagagatgc aaaagaaagg tgtcaccttt attgcgagag tagagagact ggagaggtgg    1260
tgtcaatgaa gagaatggtg cacgatggta caaggtgttc ttataaggat gcattctctt    1320
tgtgtgtgag gggagattgc aggaaagtgg ttgtgatgg agtgattgga tctagtaagc     1380
aagaagataa gtgcggagtg tgcggaggag ataactctca ttgcaaggtt gtgaaggaa     1440 cttttacaag atcaccaaaa aaacacggtt acattaagat gttcgaaatt cctgctggag    1500
caaggcattt gcttattcag gaagtggatg caacatctca ccacttggca gtgaaaaacc    1560
ttgagactgg aaaattcatt ttgaacgagg agaacgatgt tgatgcatct agtaagactt    1620
tcattgcaat gggtgttgaa tgggagtata gggatgagga tggaagggaa acacttcaaa    1680
caatgggtcc tcttcatgga acaattactg tgttggtgat tccagtggga gatacaaggg    1740
tgtcattgac atacaagtat atgattcacg aggatagtct taacgttgat gataacaacg    1800
ttttggaaga agattctgtg gtttacgagt gggctcttaa gaaatggtca ccttgctcta    1860
agccatgtgg tggaggaagt cagttcacta agtatggttg taggaggagg cttgatcata    1920
```

```
agatggttca tagggatttt tgcgcagcac ttagtaagcc aaaggcaatt aggagggctt    1980
gtaaccctca agaatgctca caaccagttt gggtgacagg agagtgggag ccatgttcac    2040
aaacatgcgg aagaactgga atgcaagtta gatcagttag atgcattcaa cctcttcatg    2100
ataacactac aagaagtgtg cacgcaaaac actgtaacga tgctaggcca gagagtagaa    2160
gagcttgctc tagggaactt tgccctggta gatggagggc aggaccttgg agtcagtgct    2220
ctgtgacatg tggaaacggt actcaggaaa gacctgttcc atgtagaact gctgatgata    2280
gtttcggaat ttgtcaggag gaaaggccag aaacagctag gacttgtaga cttggacctt    2340
gtcctaggaa tatttctgat cctagtaaaa aatcatacgt ggtgcaatgg ttgagtaggc    2400
cagatccaga ttcaccaatt aggaagattt cttcaaaagg acactgccag ggtgataaga    2460
gtattttctg cagaatggaa gttcttagta ggtactgttc tattccaggt tataacaaac    2520
tttcttgtaa gagttgcaac ttgtataaca atcttactaa cgtggagggt agaattgaac    2580
ctccaccagg aaagcacaac gatattgatg tgtttatgcc tactcttcct gtgccaacag    2640
ttgcaatgga agttagacct tctccatcta ctccacttga ggtgccactt aatgcatcaa    2700
gtactaacgc tactgaggat cacccagaga ctaacgcagt tgatgagcct tataagattc    2760
acggacttga ggatgaggtt cagccaccaa accttattcc taggaggcca agtccttacg    2820
aaaaaactag aaatcagagg attcaggagc ttattgatga gatgaggaaa aaggagatgc    2880
ttggaaagtt ctaatgagct cgcggccgca tc                                  2912

<210> SEQ ID NO 41
<211> LENGTH: 4467
<212> TYPE: DNA
<213> ORGANISM: Homo sapiens

<400> SEQUENCE: 41
atggctcacg ctcgtgttct cctcctcgct ctcgctgttt tggcaacagc tgctgtggct      60
gtggcttcta gttcttcttt tgctgattca aaccctatta gacctgttac tgatagagca     120
gcttccactt tggctcaatt gcaagaggag ggccaggttg agggccaaga tgaggatatc     180
cctccaatta catgcgtgca aaatggcttg cgttaccacg atagggatgt gtggaaacct     240
gaaccttgtc gtatctgtgt gtgtgataac ggcaaggtgc tctgcgatga tgttatctgc     300
gatgagacaa aaaattgccc tggcgctgaa gttcctgagg gcgagtgttg ccctgtgtgc     360
cctgatggtt ccgagtcccc aactgatcag gaaactactg gcgtggaggg cccaaaagga     420
gatactggtc cacgtggtcc taggggtcca gcaggtcctc caggtagaga tggtattcca     480
ggccagcctg gattgccagg accaccaggc ccacctggcc caccaggacc tcctggtctt     540
ggtggaaatt tcgctccaca actctcttat ggctatgatg agaagtcaac aggtggtatt     600
tccgttccag gtcctatggg accatccgga ccaagaggtc tcccaggtcc tccaggtgct     660 cctggaccte aaggctttca aggacctcca ggcgaaccag agaaccaggc gcttctggaa     720
ccaatgggcc caaggggacc acctggccca ccaggaaaaa atggcgatga tggcgaagct     780
ggaaagcctg gtcgtcctgg agagagaggt cctcctggcc acagggtgc aagaggcttg     840 ccaggaactc ctggcttgcc tggaatgaag ggacataggg gcttctccgg cctcgatggc     900
gctaagggtg atgctggccc tgctggacca agggcgagc aggttccccc tggagaaaac     960
ggtgctcctg gacaaatggg tcctcgtgga cttccaggag aaaggggtcg tccaggcgct    1020
ccaggaccag caggtgctag gggaaacgat ggtgcaacag gcgctgctgg ccctcctggc    1080
```

```
ccaactggtc ctgctggccc tccaggattc ccaggcgcag ttggagctaa aggagaagca    1140
ggaccacagg gccctagggg ttctgaagga cctcagggtg ttagaggtga accaggtcct    1200
ccaggcccag ctggagcagc tggtccagca ggaaatccag gtgctgatgg tcaacctgga    1260
gctaagggcg ctaatggcgc accaggtatc gcaggcgcac caggttttcc tggcgctaga    1320
ggcccaagtg gtcctcaagg accaggtgga ccaccaggtc aaaaggcaa ttctggcgaa     1380 cctggcgctc caggttctaa aggagatact ggtgctaaag gcgaaccagg acctgttggt    1440
gttcagggtc ctcctggtcc tgctggagaa gaaggaaaaa gaggtgctcg tggagaacca    1500
ggaccaactg gacttcctgg acctcctggt gaacgtggcg gacctggctc aagggttttc    1560
cctggagctg atggagtggc aggtccaaaa ggccctgctg gagagagagg ttcaccaggt    1620
ccagctggtc ctaagggctc ccctggtgaa gcagtagac caggcgaagc aggattgcca     1680
ggcgcaaagg gattgacagg ctctcctggt agtcctggcc cagatggaaa aacaggccca    1740
ccaggtccag caggacaaga tggacgtcca ggcccaccag gtcctcctgg agcaaggga    1800 caagctggcg ttatgggttt tccaggacct aaaggtgctg ctggagagcc aggaaaggca    1860
ggtgaaagag gagttcctgg tccaccagga gcagtgggtc ctgctggcaa agatggtgaa    1920
gctggagcac agggccctcc aggccctgct ggcccagctg gcgaacgtgg agaacaaggc    1980
ccagctggta gtccaggatt tcaaggattg cctggccctg ctggccctcc aggagaagca    2040
ggaaaacctg gagaacaagg agttcctggt gatttgggag cacctggacc ttcaggagca    2100
cgtggtgaaa gaggcttccc tggcgagagg ggtgttcaag gtccaccagg tccagcagga    2160
cctagaggtg ctaatggcgc tcctggcaac gatggagcaa aggtgatgc tggtgctcct     2220 ggcgcacctg gaagtcaggg tgctcctgga ttgcaaggaa tgcctggaga gaggggtgct    2280
gctggcttgc caggcccaaa gggcgatagg ggtgatgctg accaaaagg tgctgatgga    2340 tccccaggaa aagatggagt tcgtggtctt actggcccaa tcggacctcc aggccctgct    2400
ggcgctccag gtgataaggg cgaaagtggc ccaagtggac ctgctggacc tactggtgct    2460
agaggtgcac ctggtgatag gggtgaacct ggaccacctg gtccagctgg ttttgctggt    2520
cctcctggag ctgatggaca acctggcgca aaggtgaac caggtgatgc tggcgcaaag    2580
ggagatgctg gtccacctgg acctgctggt ccagcaggcc cccctgggcc aatcggtaat    2640
gttggagcac aggtgctaa gggagctagg ggttccgctg gtccacctgg agcaacagga    2700
tttccaggcg ctgctggtag agttggccca ccaggcccat ccggaaacgc aggccctcct    2760
ggtcctccag gtcctgctgg caaggagggt ggcaaaggac caaggggcga aactggcccct   2820 gctggtagac ctggcgaagt tggccctcct ggaccaccag gtccagcagg agaaaaaggt    2880
tccccaggag ctgatggccc agctggtgct ccaggaactc caggccctca ggtattgct    2940 ggacagagag gcgttgtggg actccctggt caaaggggag agagaggatt ccaggcttg     3000 ccaggaccta gtggagaacc tggaaaacaa ggcccatcag gcgctagtgg agagcgtgga    3060
cctcctggcc ctatgggacc tcctggattg gctggcccac ctggcgaatc aggtcgtgaa    3120
ggcgcaccag gcgcagaagg atcacctgga agagatggat ccctggtgc taaaggcgat    3180 cgtggagaaa ctggtccagc aggcccacca ggcgcaccag gtcacctgg cgctccagga    3240 cctgtgggac cagctggaaa atccggagat aggggcgaga caggcccagc aggaccagct    3300
ggacctgttg ccctgctgg cgctcgtgga ccagcaggac ctcaaggacc aaggggagat    3360 aaggagaaa caggcgaaca aggcgatagg ggcattaagg gtcataggg ttttagtggc     3420 ctccagggtc ctcctggccc acctggatca ccaggagaac aggaccatc tggtgcttcc     3480
```

```
ggcccagctg gtccaagagg acctccagga tcagctggtg cacctggaaa agatggtctt   3540
aacggtctcc caggaccaat cggccctcca ggacctagga gaagaacagg agatgctggc   3600
cctgttggcc ctccaggacc tcctggtcca ccaggtccac ctggtcctcc atcagctgga   3660
ttcgattttt catttcttcc acagccacca caagagaaag ctcacgatgg cggcagatat   3720
taccgtgctg atgatgctaa cgttgttagg gatagagatt tggaagtgga tacaactttg   3780
aaatccctct cccagcaaat tgaaaacatt agatctccag aaggttcacg taaaaaccca   3840
gctagaacat gtcgtgattt gaaaatgtgt cactccgatt ggaaaagtgg tgaatactgg   3900
attgatccaa atcagggctg taatctcgat gctatcaaag ttttctgtaa catggaaaca   3960
ggcgaaacat gcgtttatcc tactcaacct tccgtggctc agaaaaattg gtacatctca   4020
aaaaatccta aagataagag gcacgttttgg ttcggtgaaa gtatgactga tggatttcaa   4080
tttgagtacg gcggtcaagg tagtgatcca gctgatgtgg ctattcaact cacattttg   4140 cgtcttatgt ccacagaggc atcacaaaac atcacttacc actgcaaaaa cagtgtggct   4200
tatatggatc aacaaacagg aaaccttaag aaggctcttc ttttgaaggg ctcaaacgag   4260
attgagatta gagcagaggg caactcaagg tttacttatt cagttactgt tgatggctgc   4320
acttcacata ctggcgcttg ggtaaaaaca gttatcgagt ataagactac aaaaacatca   4380
agactcccaa tcattgatgt tgctcctctc gatgttggcg ctcctgatca agagttcggt   4440
tttgatgtgg gcccagtttg tttcctc                                      4467

<210> SEQ ID NO 42
<211> LENGTH: 4167
<212> TYPE: DNA
<213> ORGANISM: Homo sapiens

<400> SEQUENCE: 42
atggctcacg ctcgtgttct cctcctcgct ctcgctgttt tggcaacagc tgctgtggct     60
gtggcttcaa gttctagttt tgctgattcc aacccaattc gtccagttac tgatagagca    120
gcttccactt tggctcaatt gcttcaagaa gaaactgtga ggaagggccc tgctggcgat    180
aggggcccta ggggcgaaag gggtccacca ggacctccag gcaggatgg cgaagatggt    240 ccaactggcc ctcctggacc tcctggccct cagggccac ccggcttggg cggaaacttc    300
gcagctcaat acgatggcaa gggtgttggt cttggtcctg gtcctatggg cttgatggga    360
cctagaggcc cacctggtgc tgctggtgct cctggaccac agggttttca gggaccagct    420
ggcgagccag gagagccagg ccaaacagga ccagctggtg caaggggacc tgctggacct    480
cctggaaaag ctggtgaaga tggtcaccca ggcaaaccag gacgtcctgg cgaaagaggt    540
gttgttggac acaaggcgc taggggattt ccaggtacac ctggattgcc aggttttaag    600
ggcattcgtg gtcataacgg cctcgatgga ttgaagggac agcctggcgc acctggcgtt    660
aagggtgaac tggagcacc aggtgaaaac ggtactcctg ccagactggg tgcaagagga    720
ctcccaggtg aaaggggtag agttggtgct cctggacctg ctggagctag ggtagtgat    780 ggtagtgttg gtcctgtggg ccctgctggt ccaatcggtt ccgctggccc acctggattc    840
ccaggcgctc caggacctaa aggagaaatc ggtgctgtgg gtaacgcagg tcctactggt    900
ccagcaggtc ctcgtggaga agtgggattg ccaggactttt ctggtccagt gggccctcca    960
ggcaaccctg gagctaacgg cttgacagga gctaaaggcg cagcaggact ccctggagtg   1020
gctggcgcac aggattgcc tggtccaagg ggtatcccag gccctgttgg cgcagctgga   1080
```

```
gctactggtg cacgtggact tgttggcgaa ccaggccctg ctggatcaaa aggcgagtct   1140
ggaaataagg gagaacctgg ttctgctgga cctcaaggtc ctcctggacc ttctggagaa   1200
gaaggaaaaa ggggaccaaa tggcgaggct ggatcagcag gtccaccagg accacctgga   1260
cttcgtggat cccctggtag tagaggactt ccaggcgctg atggtagagc aggcgttatg   1320
ggaccaccag gaagtagagg agcatccggt ccagcaggag ttaggggtcc taacggagat   1380
gctggtagac caggtgaacc aggtcttatg ggcccaaggg gcctcccagg tagtccagga   1440
aatatcggcc ctgctggaaa agaaggccct gttggacttc caggtattga tggacgtcct   1500
ggccctattg gcccagcagg tgcaagagga gaacctggca atattggatt tccaggacca   1560
aagggtccaa caggcgatcc tggaaaaaat ggagataagg gtcatgctgg attggcaggc   1620
gcaaggggcg ctcctggtcc agatggaaac aacggcgcac agggtccacc tggccctcag   1680
ggtgttcaag gcggaaaagg cgaacaaggc ccagctggac caccaggctt tcaaggcttg   1740
ccaggaccaa gtggtccagc aggtgaagtt ggcaagccag gcgagcgtgg acttcatggc   1800
gagtttggac tccctggacc agcaggacca aggggtgaaa gaggccctcc tggagagagt   1860
ggcgctgctg gaccaacagg cccaatcggt agtagaggtc ctagtggacc tccaggccca   1920
gatggaaata gggtgaacc aggagttgtg ggcgctgttg aacagctgg tccttcagga   1980 ccatcaggac tcccaggcga gagaggcgct gctggcattc tggaggaaa aggtgaaaaa   2040 ggcgaacctg gcctccgtgg cgaaatcgga atcctggac gtgatggtgc tcgtggtgca   2100
cacggcgctg tgggcgctcc aggccctgct ggtgctactg gtgatagagg agaggctggc   2160
gcagctggcc cagcaggtcc tgctggccca agggggtagtc ctggtgaaag aggcgaagtt   2220
ggacctgctg gccctaacgg ctttgctggc cctgctggag cagcaggtca acctggcgct   2280
aaaggtgaaa ggggcggaaa gggcccaaaa ggtgaaaatg gcgttgtggg accaactggt   2340
ccagtgggcg cagctggacc tgctggtcca aatggaccac caggaccagc aggtagtaga   2400
ggagatggtg gacctccagg aatgacaggt tttccaggtg ctgctggtag aacaggacct   2460
cctggtccta gtggtatttc tggtccacca ggaccaccag gtcctgctgg aaaagaagga   2520
ttgaggggtc cacgtggtga tcaaggacca gtgggcagaa ctggtgaagt tggcgcagtg   2580
ggaccacctg gttttgctgg agaaaagggc ccttctggag aggcaggaac agctggtcct   2640
cctggtacac ctggacctca aggacttttg gtgcacctg gtattctcgg attgccagga   2700
agtaggggcg aacgtggact tcctggcgtg gcaggagcag ttggagaacc tggccctctc   2760
ggaatcgcag gccaccagg cgcaagagga ccaccaggag ctgttggatc accaggcgtg   2820
aatggtgcac ctggcgaggc tggtcgtgat ggaaacccag gaaatgatgg cccaccagga   2880
agagatggtc aacctggaca caaggcgag aggggctacc caggaaatat tggcccagtt   2940
ggtgctgctg gcgcaccagg cccacacggt ccagttggac cagcaggaaa acacggtaat   3000
cgtggcgaaa caggccttc aggcccagtg ggacctgctg gtgctgttgg cccaagagga   3060
ccatctggac ctcaaggcat tagaggcgat aaggagagc ctggcgaaaa aggacctaga   3120
ggcttgcctg gttttaaagg acacaacggt ctccaaggac ttccaggtat cgctggtcat   3180
catggagatc agggtgctcc tggatcagtg ggtccagcag gtcctagagg cccagcaggc   3240
ccttccggtc cagcaggaaa ggatggacgt actggccacc ctggaactgt gggccctgct   3300
ggaattagag gtcctcaagg tcatcagggc cctgctggcc ctccaggtcc accaggtcct   3360
ccaggcccac aggagtttc aggtggtggt tacgattttg gttacgatgg tgatttttac   3420
cgtgctgatc aacctagaag tgctcccttct ctccgtccta aagattatga agttgatgct   3480
```

-continued

```
actttgaaat cacttaacaa ccagattgag actcttctca cacctgaggg atcaagaaag    3540
aatccagcac gtacatgccg tgatctcaga cttagtcacc cagagtggtc aagtggctat    3600
tattggattg atcctaatca gggttgtaca atggaggcta tcaaagttta ctgtgatttt    3660
ccaactggag agacatgtat tagggcacaa cctgagaaca ttccagctaa aaattggtat    3720
cgttcctcta aagataagaa acatgtttgg ctcggagaga ctattaacgc tggttctcag    3780
ttcgagtata atgttgaggg cgttacttct aaagagatgg caactcagct cgcttttatg    3840
agattgctcg ctaactacgc atcccaaaac atcacttatc actgcaaaaa ttccattgca    3900
tatatggatg aggagacagg aaatttgaag aaagcagtta ttctccaagg tagtaacgat    3960
gttgagcttg tggctgaggg aaatagtaga ttcacttaca cagttttggt ggatggatgc    4020
tcaaagaaaa ctaatgagtg gggcaagaca atcattgagt acaagacaaa taagccttct    4080
aggctcccat ttctcgatat tgcacctctt gatatcggag gagctgatca cgagtttttt    4140
gttgatatcg gacctgtttg ttttaag                                        4167
```

DERMAL FILLERS AND APPLICATIONS THEREOF

CROSS-REFERENCE TO RELATED APPLICATIONS

This application is a National Phase Application of PCT International Application Number PCT/IL2019/050492, International filing date May 2, 2019, which claims the benefit of U.S. Provisional Application Ser. No. 62/666,267 filed May 3, 2018, which is hereby incorporated by reference in its entirety.

SEQUENCE LISTING STATEMENT

The instant application contains a Sequence Listing which has been submitted electronically in ASCII format and is hereby incorporated by reference in its entirety. Said ASCII copy, created on May 2, 2019, is named P-578412-US-SQL-02MAY19.txt and is 230 KB in size.

FIELD OF DISCLOSURE

Disclosed herein are photoinitiated and double cross-linked dermal fillers comprising plant-derived human collagen, and cellular growth promoting scaffolds, as well as methods of using the dermal fillers in some instances, for soft tissue augmentation.

BACKGROUND

Collagens are the main proteins responsible for the structural integrity of vertebrates and many other multicellular organisms. Collagen comprises the main component of connective tissue and is the most abundant protein in mammals, comprising approximately 30% of the protein found in the body. Loss or deterioration of collagen can occur as the result of aging or injury (Olsen et al, Adv Drug Deliv Rev. 2003 Nov. 28; 55(12):1547-67).

One common aspect of aging is the development of lines, fine lines, or wrinkles. Treatments involving the use of tissue-extracted collagen have been used to reduce or eliminate lines, fine lines, or wrinkles. Similar treatments have been used to reduce scars.

Collagen is also a component of tendons. Tendinopathy, a common injury usually associated with sports and physical activities, is associated with degeneration and disordered arrangement of the tendon's collagen fibers. Healing of injured tendons requires an orchestrated activity of specific cells and an extended presence of relevant growth factors (GFs) at the vicinity of the injury. Tendinopathy is nowadays the leading reason for consultation for a musculoskeletal complaint (Kaux et al. (January 2011) J. Sport. Sci. Med. January: 238-253). Tendinopathy refers to a variety of painful conditions that develop in and around tendons and ligaments which are likely arising from an imbalance between pathological changes due to tendon overuse and the consequent regenerative responses (Andres et al. (2008) Clin. Orthop. Relat. Res. 466:1539-1554). Tendinopathy is associated with degeneration and disordered arrangement of collagen (Maffulli et al. (2003) Clin. Sport. Med. 22:675-692), sometimes associated with fibers micro tears, increase in vascularity and presence of a mild inflammation (Khan et al. (1999) Sport. Med. 27(6):393-408). Clinically, it is characterized by onset of tendon stiffness, activity-related pain, decrease in functionality and sometimes localized swelling (Kaux 2011; Andres 2008). Collagen fibers present unequal and irregular crimping, loosening, and increased waviness instead of the normal tight, parallel, bundled appearance (Mafulli 2003). As the population remains active at older ages, the incidence rate of tendon injuries is expected to rise in the coming decades. A wide variety of treatments for tendinopathy are available, including physiotherapy, pharmacological treatments and combination thereof, however, clinical results are not satisfactory, and recurrence of symptoms is common (Kaux 2011). Injection of autologous platelet rich plasma (PRP) for the treatment of tendinopathy received wide attention in the last decades (Delong et al. (2016) Curr. Orthpaedic Pract. 22:514-523; Kaux et al. (2012) Wound Repair Regen. 20:748-756; Yuan et al. (2013) Muscles. Ligaments Tendons J. 3(3):139-49; Di Matteo et al. (2015) Musculoskelet. Surg. 99(1):1-9). PRP is the plasma fraction of blood containing high concentration of platelets. Upon injection to the injured site, platelets release various types of growth factors (GFs) which are thought to promote the healing process. Among the PRP-associated GFs vasculo-endothelial growth factor (VEGF), transforming beta growth factor (TGF-beta), platelet derived growth factor (PDGF), platelet derived epidermal growth factor (PDEGF), fibroblast growth factors (bFGF), epidermal growth factors (EGF) and hepatocyte growth factors (HGF) have been reported (Delong 2016; Yuan 2013; Harrison et al. (2011) Am. J. Sports Med. 39(4):729-734). Many in vitro studies and in vivo models show that PRP treatments enhance collagen expression and extracellular matrix production, stimulate angiogenesis and increase cell migration, differentiation and proliferation, thus supporting the healing of tendon injuries (Yuan 2013; Kajikawa et al. (2008) J. Cell. Physiol. 215(3):837-845; Zhang et al. (2010) Am. J. Sports Med. 38(12):2477-2486). However, clear clinical evidences of the efficacy of PRP treatment is limited (Delong 2016; Yuan 2013; Moraes et al. (2014)).

Collagen serves as the predominant component and primary structural-mechanical determinant of most tissue extra cellular matrix (ECM) [see, for example, Kadler K. Birth Defects Res C Embryo Today. 2004; 72:1-11; Kadler K E, Baldock C, Bella J, Boot-Handford R P. J Cell Sci. 2007; 120:1955-1958; Kreger S T. Biopolymers. 2010 93(8): 690-707]. Tropocollagen typically consists of three left-handed helices (usually two identical helices and a third distinct helix) of procollagen joining to form a right-handed triple-helical tropocollagen, resulting on the formation of fibrils.

The conformation and most of the properties of native collagen are determined by the triple helix domain which composes more than 95% of the molecule. This domain consists of three alpha chains, each containing approximately 1,000 amino acids, wrapped in a rope-like fashion to form a tight, triple helix structure. The triple helix is wound in such a way that peptide bonds linking adjacent amino acids are buried within the interior of the molecule, such that the collagen molecules are resistant to attack by proteases, such as pepsin.

Type I collagen represents the prototypical fibrillar collagen and is the major collagen type in most tissues, including bone, tendon, skin, aorta, and lung. Type I collagen fibers provide for great tensile strength and limited extensibility. The most abundant molecular form of type I collagen is a heterotrimer composed of two different alpha chains [alpha 1(I)]2 and alpha 2(I) (Inkinen, Connective Tissue Formation in Wound Healing an Experimental Study, Academic Dissertation, September 2003. University of Helsinki, Faculty of Science, Department of Biosciences, Division of Biochemistry).

In all of the fibrillar collagen molecules, the three polypeptide chains are constructed from a repeating Gly-X-Y triplet, where X and Y can be any amino acid but are frequently the imino acids proline and hydroxyproline. Collagen is particularly rich in glycine, proline, and hydroxyproline amino acid residues, and the protein sequence of a strand of collagen often has a repeating amino acid sequence. Procollagen is modified by the addition of hydroxyl groups on proline and lysine residues. These hydroxylation reactions are catalyzed, respectively, by prolyl-4-hydroxylase and lysyl-hydroxylase. Hydroxyl groups on the lysine residues are then glycosylated, and the triple helix is subsequently formed.

An important feature of fibril-forming collagens is that they are synthesized as precursor procollagens containing globular N- and C-terminal extension propeptides. The biosynthesis of procollagen is a complex process involving a number of different post-translational modifications including proline and lysine hydroxylation, N-linked and O-linked glycosylation and both intra- and inter-chain disulphide-bond formation. The enzymes carrying out these modifications act in a coordinated fashion to ensure the folding and assembly of a correctly aligned and thermally stable triple-helical molecule.

The triconstituent polypeptide chains are assembled within the rough endoplasmic reticulum (RER) to form procollagen. As the polypeptide chain is co-translationally translocated across the membrane of the endoplasmic reticulum (ER), prolyl-4-hydroxylase (P4H)-dependent hydroxylation of proline and lysine residues occurs within the Gly-X-Y repeat region. The stability of the final triple-helical structure of collagen is highly dependent on the P4H-mediated hydroxylation of collagen chains. Lysyl hydroxylase (LH, EC 1.14.11.4), galactosyltransferase (EC 2.4.1.50) and glucosyltransferase (EC 2.4.1.66) are enzymes involved in posttranslational modifications of collagens. They sequentially modify lysyl residues in specific positions to hydroxylysyl, galactosylhydroxylysyl and glucosylgalactosyl hydroxylysyl residues. These structures are unique to collagens and essential for their functional activity (Wang et al. (2002) Matrix Biology, 21(7): 559-566). A single human enzyme, lysyl hydroxylase 3 (LH3) can catalyze all three consecutive steps in hydroxylysine linked carbohydrate formation (Wang et al. (2002) Matrix Biology, 21(7): 559-566). Once the polypeptide chain is fully translocated into the lumen of the endoplasmic reticulum the three pro-alpha chains then associate via their C-propeptides to form a trimeric molecule where the Gly-X-Y repeat region forms a nucleation point at its C-terminal end, ensuring correct alignment of the chains. The Gly-X-Y region then folds in a C-to-N direction to form a triple helix (Khoshnoodi et al. (2006) J. Biol. Chem. 281:38117-38121).

The temporal relationship between polypeptide chain modification and triple-helix formation is crucial as hydroxylation of proline residues is required to ensure stability of the triple helix at body temperature, once formed, the triple helix no longer serves as a substrate for the hydroxylation enzyme. The C-propeptides (and to a lesser extent the N-propeptides) keep the procollagen soluble during its passage out of the cell (Bulleid et al. (2000) Biochem. Socy. Transact., 28(4): 350-353). Following or during secretion of procollagen molecules into the extracellular matrix, propeptides are removed by procollagen N- and C-proteinases, thereby triggering spontaneous self-assembly of collagen molecules into fibrils (Hulmes, 2002, J. Struct. Biol. January-February; 137(1-2):2-10). Removal of the propeptides by procollagen N- and C-proteinases lowers the solubility of procollagen by >10000-fold and is necessary to initiate the self-assembly of collagen into fibers at 37° C. Crucial to this assembly process are the short telopeptides which are the non-triple-helical remnants of the N- and C-terminal propeptides remaining after digestion with N/C proteinases. These peptides act to ensure correct covalent registration of the collagen molecules within the fibril structure and lower the critical concentration for self-assembly (Bulleid et al. (2000) Biochem. Socy. Transact., 28(4): 350-353) through their cross-linkable aldehydes.

Native collagen is generally present in connective tissue as telopeptide-containing collagen molecules packed side by side in the form of fibrils. Each longitudinal course is composed of molecules aligned in end-to-end dispositions with slight longitudinal spaces staggered relative to the next successive laterally adjacent longitudinal course. In this way, gaps are generated between facing end regions of successive molecules in a given longitudinal course and bound by the staggered sides of the molecules in the parallel longitudinal courses laterally adjacent thereto.

Dispersal and solubilization of native animal collagen can be achieved using various proteolytic enzymes which disrupt the intermolecular bonds and remove the immunogenic non-helical telopeptides without affecting the basic, rigid triple-helical structure which imparts the desired characteristics of collagen (see U.S. Pat. Nos. 3,934,852; 3,121,049; 3,131,130; 3,314,861; 3,530,037; 3,949,073; 4,233,360 and 4,488,911 for general methods for preparing purified soluble collagen). The resulting soluble atelocollagen can be subsequently purified by repeated precipitation at low pH and high ionic strength, followed by washing and re-solublization at low pH. Nevertheless, the soluble preparation is typically contaminated with crosslinked collagen chains which decrease the homogeneity of the protein preparation.

Due to its unique characteristics and diverse profile in human body functions, collagen has been selected from a variety of biocompatible materials for use in tissue repair to support structural integrity, induce cellular infiltration and promote tissue regeneration. Among the 5 major collagen types, Type I collagen is the most abundant form of collagen in the human body.

Type I collagen can self-assemble into a fibrillar hydrogel capable of supporting tissue cells through bioactive adhesion sites. Addition of methacrylate groups to the collagen creates collagen methacrylate (CMA), which is more resistant to degradation (Gaudet et al. Biointerphases (2012) 7:25-33). Thiolation of collagen can improve cohesion and mucoadhesion and affects swelling ability (Duggan et al., Eur. J. Pharm. Biopharm. (April 2015) 91:75-81).

Collagen's unique properties have contributed to its use in regenerative medicine products. Collagen provides biomaterials with characteristics necessary for a myriad of applications including pharmaceutical (haemostatic compresses, sponges, healing dressings), medical (prostheses such as cardiac valves, tendons and ligaments, skin substitutes, filling agents), odontological (gum implants/gum disease) and cosmetic (additive, anti-wrinkling agent, microcontainer for perfumed substances). The collagen-based products manufactured in all of the aforementioned markets require vast amounts of raw collagen materials for their production.

Human and animal-derived collagens, such as from cadaver or animal sources (bovine, porcine, or equine), and collagen-based products have been used for application, injection, implantation, and oral ingestion. Uses include pre-molding into desired shapes for repair or partial replacement of damaged bone or cartilage structures, injections into damaged joints, and injections as dermal fillers.

The use of animal-derived collagen (including human-derived collagen) is problematic due to the possible risks of contamination by non-conventional infectious agents. While the risks raised by bacterial or viral contamination can be fully controlled, prions are less containable and present considerable health risks. These infectious agents which appear to have a protein-like nature, are involved in the development of degenerative animal encephalopathy (sheep trembling disease, bovine spongiform encephalopathy) and human encephalopathy (Creutzfeld-Jacob disease, Gerstmann-Straussler syndrome, and kuru disease). Other diseases (e.g., acquired immune deficiency syndrome [AIDS], hepatitis, rabies, some cancers) may also be transmitted to the recipient. Due to the lengthy time before onset of the encephalopathies and some of the other diseases, formal controls are difficult to conduct. (See generally, Castrow et al. (1983) J. Am. Acad. Dermatol. 9(6):889-93; Siegle et al. (1984) Arch. Dermatol. 120(2):183-187.)

Moreover, in some patients, treatment with human or animal collagen triggers cellular or humoral immune responses, including allergies. In addition, the quality of the collagen generally decreases with the age of the source cadaver or organism or may decrease subject to other factors. In addition, the extraction process causes significant structural damage which compromises its biological and mechanical functions (Stein et al. (2009) Biomacromolecules 10(9):2640-2645; Shilo et al. (2013) Tissue Eng. Part A 19(13-14):1519-1526; Shoseyov et al. (2013) Tiss. Eng. Part A 19(13-14):1527).

Plants expressing collagen chains are known in the art (see, e.g., WO 2005/035442; U.S. Pat. No. 6,617,431; US Publ. 2002/0098578; US Publ. 2002/0142391; Merle et al. (2002) FEBS Letters 515: 114-118; Ruggiero et al. (Mar. 3, 2000) FEBS Lett. 469(1):132-6). Although such plants can be used to produce collagen chains as well as collagen, such chains are incorrectly hydroxylated and thus self-assembly thereof, whether in planta or not, leads to collagen which is inherently unstable. For example, although plants are capable of synthesizing hydroxyproline-containing proteins the prolyl hydroxylase that is responsible for synthesis of hydroxyproline in plant cells exhibits relatively loose substrate sequence specificity as compared with mammalian P4H and thus, production of collagen containing hydroxyproline only in the Y position of Gly-X-Y triplets requires plant co-expression of collagen and P4H genes (Olsen et al. (2003) Adv. Drug Deliv. Rev., 55(12): 1547-1567).

Processing of animal-derived "insoluble collagen" with plant-derived proteases, such as ficin and/or papain, is also known in the art (U.S. Pat. Nos. 4,597,762, 5,670,369, 5,316,942, 5,997,895 and 5,814,328).

An attempt to produce human collagens that rely on the hydroxylation machinery naturally present in plants resulted in collagen that is poor in proline hydroxylation (Merle et al. (2002) FEBS Letters 515: 114-118). Such collagen melts or loses its triple helical structure at temperatures below 30° C. Co-expression of collagen and prolyl-hydroxylase results with stable hydroxylated collagen that is biologically relevant for applications at body temperatures (Merle et al. (2002) FEBS Letters 515: 114-118).

Hydroxylysins of a human collagen expressed in tobacco form less than 2% of the hydroxylysins found in a bovine collagen (0.04% of residues/1.88% of residues). This suggests that plant endogenic Lysyl hydroxylase is unable to sufficiently hydroxylate lysines in collagen.

Recent developments in technology have resulted in the development of a system for the purification of naïve human Type I collagen (rhCollagen) (COLLPLANT™, Israel; also available at SIGMA-ALDRICH®, St. Louis, MO, USA) by introducing into tobacco plants, five human genes encoding heterotrimeric type I collagen [see, for example, Stein H. (2009) Biomacromolecules 10:2640-5; Yaari et al. (2013) Tiss. Eng. Part A 19(13/14): 1502-1506; Willard et al. (2013) Tiss. Eng. Part A 19(13/14): 1507-1518; Shilo et al. (2013) Tiss. Eng. Part A 19(13/14): 1519-1526; Shoseyov et al. (2013) Tissue Eng. Part A 19:1527-1533; and Shoseyov et al. (January/February 2014) Bioengineered 5:1.1-4]. The protein is purified to homogeneity through a cost-effective industrial process taking advantage of collagen's unique properties. See also WO 2006/035442, WO 2009/053985, and patents and patent applications deriving therefrom, all of which are incorporated by reference as if fully set forth herein.

Compared with tissue-extracted collagen, which can become partially denatured and be stripped of cell binding domains, plant-derived human collagen Type I has a more consistent structure and a greater number of cell binding domains (Shoseyov et al. (January/February 2014) Bioengineered 5:1.1-4; Majumdar et al. (2015) J. Biomed. Mater. Res. Part B: Appl. Biomater. 104B: 300-307). rhCollagen can form functional three-dimensional (3D) matrices and scaffolding, with applications in additive manufacturing (AM), a process in which a 3D object is manufactured in a layer wise manner utilizing a computer model of the objects, via 3D bio-printing. Moreover, rhCollagen generally lacks the immunogenicity and disease transfer problems of tissue-extracted collagen.

Methods of producing collagen in a plant by expressing at least one type of a collagen alpha chain and enabling its accumulation in a subcellular compartment devoid of endogenous P4H activity are available (U.S. Pat. No. 8,455,717), as are methods of generating atelocollagen from a non-animal cell-derived human telopeptide-comprising collagen via treatment with a protease (U.S. Pat. No. 8,759,487).

Type I collagen and rhCollagen are considered candidates for use as a major component of a building material in 3D-bioprinting. Scaffolding of various types has been used for cosmetic and other reconstructive applications.

In addition, there has been an increase in the use of dermal fillers for soft tissue augmentation, e.g., the reduction of wrinkles. One possible method for the use of dermal fillers includes injection of a polymerizable dermal filler material into the desired area, followed by the contouring or molding of the filler into the desired conformation. Polymerization and cross-linking of the material by one of various methods can transform the monomers in the injected material to form polymers and chains, which can form networks, retaining the desired molded conformation. There are a number of methods to form polymers and to crosslink polymers. One method involves light-reactive reagents and light-induced reactions which create reactive species in a monomer solution. See, e.g., U.S. Pat. Nos. 9,795,711; 8,945,624; 6,352,710; and US Publ. 2009/0324722, as well as Elisseeff et al. (March 1999) Proc. Natl. Acad. Sci. USA 96: 3104-3107.

However, at least some of these approaches continue to focus on tissue-derived collagens or non-collagen polymers (e.g., poly(vinyl alcohol), hyaluronic acid, or polyethylene glycol). Moreover, the use of tissue extracted collagen is limited due to its sensitivity to temperature and ionic strength which drives spontaneous gel formation at temperatures higher than 20° C., under physiological conditions [see, for example, PureCol, Advanced BioMatrix, Inc.]. The typical temperature-dependent formation of gel of tissue extracted-collagens hampers significantly the precise fluidity. Keeping the collagens at low temperature until application is a possible solution for this phenomenon but implies a serious technical limitation. Another solution is the use of gelatin, the denatured form of collagen which does not become gel-like under these conditions. However, gelatin lacks the genuine tissue and cell interactions of native collagen and thus crucial biological functions are lost. Moreover, the viscosity makes it more difficult to be injected under the dermis using fine-gauge needles and also makes it more difficult to spread and mold it into smaller cavities.

Thus, there is a demand for, and it would be highly desirable and advantageous to have, improved injectable dermal fillers with tunable rheological and mechanical properties, and methods and uses thereof.

SUMMARY

Disclosed herein in one aspect is a double crosslinked dermal filler comprising:
(a) a plant-derived human collagen; and
(b) a crosslinked hyaluronic acid;
wherein the plant-derived human collagen is crosslinked to the crosslinked hyaluronic acid.

In a related aspect, the plant-derived human collagen comprises
(a) type 1 recombinant human collagen (rhCollagen); or
(b) the crosslinked hyaluronic acid comprises crosslinked and non-crosslinked hyaluronic acid; or
(c) a combination thereof.

In a related aspect, the crosslinker linking the crosslinked hyalurinoic acid differs from the crosslinker linking the plant-derived human collagen with the crosslinked hyaluronic acid; or the ratio of crosslinked hyaluronic acid to the plant-derived human collagen comprises a range between 4:1 to 1:2; or a combination thereof. In a further related aspect, the crosslinker crosslinking hyaluronic acid and the crosslinker crosslinking the plant-derived human collagen are independently selected from 1,4-butanediol diglycidyl ether (BBDE), 1-[3-(Dimethylamino)propyl]-3-ethylcarbodiimide methiodide (EDC), N,N'-dicyclohexylcarbodiimide (DCC), N,N'-diisopropylcarbodiimide (DIC).

Disclosed herein in one aspect, is a method of preparing a double crosslinked dermal filler comprising plant-derived human collagen crosslinked to crosslinked hyaluronic acid, comprising the steps of
(a) crosslinking hyaluronic acid;
(b) neutralizing the crosslinked hyaluronic acid;
(c) neutralizing the plant-derived human collagen;
(d) mixing the neutralized crosslinked hyaluronic acid with the neutralized plant-derived human collagen;
(e) addition of lower molecular weight hyaluronic acid (MW HA);
(f) crosslinking the mix of crosslinked hyaluronic acid and plant-derived human collagen; and
(g) dialyzing double crosslinked crosslinked hyaluronic acid-plant-derived human collagen dermal filler.

In a related aspect, the plant-derived human collagen comprises type 1 recombinant human collagen (rhCollagen); or the crosslinker linking the crosslinked hyalurinoic acid of step (a_ differs from the crosslinker linking the plant-derived human collagen with the crosslinked hyaluronic acid of step (e); or a combination thereof. In a related aspect, the ratio of crosslinked hyaluronic acid to the plant-derived human collagen comprises a range between 4:1 to 1:2; or the crosslinker crosslinking hyaluronic acid and the crosslinker crosslinking the plant-derived human collagen are independently selected from 1,4-butanediol diglycidyl ether (BBDE), 1-[3-(Dimethylamino)propyl]-3-ethylcarbodiimide methiodide (EDC), N,N'-dicyclohexylcarbodiimide (DCC), N,N'-diisopropylcarbodiimide (DIC); or a combination thereof.

In addition, disclosed herein in one aspect, is a method of filling a tissue space under an epidermis comprising:
(a) introducing a polymerizable solution into the tissue space, wherein the polymerizable solution comprises:
(i) a cross-linkable, plant-derived human collagen;
(ii) a hyaluronic acid (HA) or modified derivative thereof, a poly(vinyl alcohol) (PVA) or modified derivative thereof, a polyethylene glycol (PEG) or modified derivative thereof, oxidized cellulose (OC) or a modified derivate thereof, polymethylmethacrylate (PMMA) microspheres or a modified derivative thereof, tricalcium phosphate (TCP) or a modified derivative thereof, calcium hydroxylapatite (CaHA) or a modified derivative thereof, carboxymethylcellulose or a modified derivative thereof, crystalline nanocellulose (CNC) or a modified derivative thereof, or a combination thereof; and
(iii) a photoinitiator; and
(b) applying light to the surface of the epidermis superficial to said space to induce polymerization.

In a related aspect, the polymerizable solution components are introduced into the tissue space independently at about the same location and about the same time, wherein the cross-linkable, plant-derived human collagen and the photoinitiatior are introduced together and independently from said hyaluronic acid (HA) or modified derivative thereof, said poly(vinyl alcohol) (PVA) or modified derivative thereof, said polyethylene glycol (PEG) or modified derivative thereof, oxidized cellulose (OC) or said modified derivate thereof, polymethylmethacrylate (PMMA) microspheres or said modified derivative thereof, tricalcium phosphate (TCP) or said modified derivative thereof, calcium hydroxylapatite (CaHA) or said modified derivative thereof, carboxymethylcellulose or said modified derivative thereof, crystalline nanocellulose (CNC) or said modified derivative thereof, or said combination thereof, are introduced into the tissue space independently at about the same time. In another related aspect, the method further includes a step of molding or sculpting the polymerizable solution or the components of the polymerizable solution, into a desired configuration in the tissue space, wherein said step is concomitant with, or subsequent to, the step of applying light.

In another related aspect, the polymerizable solution components are introduced into the tissue space together as a mixture, wherein the cross-linkable, plant-derived human collagen and the photoinitiatior are introduced together with said hyaluronic acid (HA) or modified derivative thereof, or said poly(vinyl alcohol) (PVA) or modified derivative thereof, or said polyethylene glycol (PEG) or modified derivative thereof, or said oxidized cellulose (OC) or said modified derivate thereof, or said polymethylmethacrylate (PMMA) microspheres or said modified derivative thereof, or said tricalcium phosphate (TCP) or said modified derivative thereof, or said calcium hydroxylapatite (CaHA) or said modified derivative thereof, or said carboxymethylcellulose or said modified derivative thereof, or said crystalline nanocellulose (CNC) or said modified derivative thereof, or a combination thereof.

In another related aspect, the polymerizable solution components are introduced into the tissue space independent from one another, wherein the cross-linkable, plant-derived human collagen and the photoinitiatior are introduced together and independently from said hyaluronic acid (HA) or modified derivative thereof, or said poly(vinyl alcohol)

(PVA) or modified derivative thereof, or said polyethylene glycol (PEG) or modified derivative thereof, or said oxidized cellulose (OC) or said modified derivate thereof, or said polymethylmethacrylate (PMMA) microspheres or said modified derivative thereof, or said tricalcium phosphate (TCP) or said modified derivative thereof, or said calcium hydroxylapatite (CaHA) or said modified derivative thereof, or said carboxymethylcellulose or said modified derivative thereof, or said crystalline nanocellulose (CNC) or said modified derivative thereof, or said combination thereof.

In another related aspect, following introduction into the tissue space, the method further includes a step of molding or sculpting the polymerizable solution or the components of the polymerizable solution, into a desired configuration in the tissue space, wherein said step is concomitant with, or subsequent to, the step of applying light.

In another related aspect, the method is non-therapeutic, and the molding or sculpting step reduces lines, folds, fine lines, wrinkles, or scars, or a combination thereof.

In another related aspect,
(a) the cross-linkable, plant-derived human collagen is methacrylated or thiolated type 1 human recombinant collagen (rhcollagen); or
(b) the modified derivative of hyaluronic acid (HA), poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a methacrylated or thiolated derivative; or
(c) the hyaluronic acid (HA), poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a crosslinked hyaluronic acid (HA), crosslinked poly(vinyl alcohol) (PVA), crosslinked polyethylene glycol (PEG), crosslinked oxidized cellulose (OC), crosslinked polymethylmethacrylate (PMMA) microspheres, crosslinked tricalcium phosphate (TCP), crosslinked calcium hydroxylapatite (CaHA), crosslinked carboxymethylcellulose, or crosslinked crystalline nanocellulose (CNC); or
(d) a combination of (a) and (b), or (a) and (c).

In a further related aspect, when MA-rhCollagen is selected, and hyaluronic acid or a derivative thereof, or crosslinked hyaluronic acid is selected, the ratio of HA to MA-rhCollagen is 1:1, 2:1, 3:1, 4:1, 5:1, 6:1, 1:2, 1:3, 1:4, 1:5, 1:6, or 0:1.

Disclosed herein, in one aspect is a method of filling a tissue space under an epidermis comprising introducing a double crosslinked dermal filler into the tissue space, wherein the double crosslinked dermal filler comprises:
(a) a plant-derived human collagen; and
(b) a crosslinked hyaluronic acid (HA) or modified crosslinked derivative thereof, a crosslinked poly(vinyl alcohol) (PVA) or modified crosslinked derivative thereof, a crosslinked polyethylene glycol (PEG) or modified crosslinked derivative thereof, crosslinked oxidized cellulose (OC) or a modified crosslinked derivate thereof, crosslinked polymethylmethacrylate (PMMA) microspheres or a modified crosslinked derivative thereof, crosslinked tricalcium phosphate (TCP) or a modified crosslinked derivative thereof, crosslinked calcium hydroxylapatite (CaHA) or a modified crosslinked derivative thereof, crosslinked carboxymethylcellulose or a modified crosslinked derivative thereof, crosslinked crystalline nanocellulose (CNC) or a modified crosslinked derivative thereof, or a combination thereof;
wherein the plant-derive human collagen is crosslinked to the crosslinked crosslinked hyaluronic acid (HA) or modified crosslinked derivative thereof, a crosslinked poly(vinyl alcohol) (PVA) or modified crosslinked derivative thereof, a crosslinked polyethylene glycol (PEG) or modified crosslinked derivative thereof, crosslinked oxidized cellulose (OC) or a modified crosslinked derivate thereof, crosslinked polymethylmethacrylate (PMMA) microspheres or a modified crosslinked derivative thereof, crosslinked tricalcium phosphate (TCP) or a modified crosslinked derivative thereof, crosslinked calcium hydroxylapatite (CaHA) or a modified crosslinked derivative thereof, crosslinked carboxymethylcellulose or a modified crosslinked derivative thereof, crosslinked crystalline nanocellulose (CNC) or a modified crosslinked derivative thereof.

In a related aspect, the plant-derived human collagen is type 1 human recombinant collagen (rhcollagen), or an MA or Thiolated derivative thereof; or the modified derivative of hyaluronic acid (HA), poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a methacrylated or thiolated derivative; or a combination thereof.

In another related aspect, when crosslinked HA is selected, the ratio of crosslinked HA to the plant-derived human collagen is 1:1, 2:1, 3:1, 4:1, 5:1, 6:1, 1:2, 1:3, 1:4, 1:5, 1:6, or 0:1.

In a related aspect, the method is non-therapeutic, and reduces lines, folds, fine lines, wrinkles, or scars, or a combination thereof.

Disclosed herein in one aspect, is a polymerizable or non-polymerizable solution for use for tissue augmentation, wherein
(a) the polymerizable solution comprises a cross-linkable, plant-derived human collagen and a photoinitiator to induce polymerization prior to, on concomitant with, application of visible light, or
(b) the non-polymerizable solution comprises a double crosslinked dermal filler comprising a plant-derived human collagen, and a crosslinked hyaluronic acid or a crosslinked PVA, or a crosslinked PGE, or a crosslinked OC, wherein the plant-derived human collagen is crosslinked to the crosslinked hyaluronic acid or crosslinked PVA, or a crosslinked PGE, or a crosslinked OC;
and said use comprises injecting said polymerizable or non-polymerizable solution into a tissue space under an epidermis, followed by molding or sculpting the polymerizable or non-polymerizable solution into a desired configuration to reduce lines, folds, fine lines, wrinkles, or scars.

In a related aspect, the cross-linkable, plant-derived human collagen is methacrylated or thiolated; or the polymerizable solution further comprises a hyaluronic acid (HA) or a modified derivative thereof or a photopolymerizable modified derivative thereof, a poly(vinyl alcohol) (PVA) or a modified derivative thereof or a photopolymerizable modified derivative thereof, a polyethylene glycol (PEG) or a modified derivative thereof or a photopolymerizable modified derivative thereof, polymethylmethacrylate (PMMA) microspheres or a modified derivative thereof or a photopolymerizable modified derivative thereof, tricalcium phosphate (TCP) or a modified derivative thereof or a photopolymerizable modified derivative thereof, calcium a hydroxylapatite (CaHA) or a modified derivative thereof or a photopolymerizable modified derivative thereof, a carboxymethylcellulose or a modified derivative thereof or a photopolymerizable modified derivative thereof, a crystalline nanocellulose (CNC) or a modified derivative thereof or a photopolymerizable modified derivative thereof, or a combination thereof, wherein optionally the derivative thereof comprises a methacrylated or thiolated derivative; or a combination thereof.

In another related aspect, the tissue augmentation is required as a result of any medical or dental (gum implants/ gum disease) condition. In a further related aspect, the tissue augmentation reduces lines, folds, fine lines, wrinkles, or scars, or a combination thereof.

Disclosed herein in one aspect, is a method of inducing a cellular growth promoting scaffold in a tissue space under an epidermis comprising introducing a solution into the tissue space, the solution comprising:
(a) a plant-derived human collagen; and
(b) at least one growth factor or source thereof;
wherein said method promotes healing or replacement of a collagen-comprising tissue.

In a related aspect, the plant-derived collagen comprises type 1 recombinant human collagen (rhCollagen); or the source of the at least one growth factor comprises a plasma or a platelet-rich plasma; or the collagen-comprising tissue comprises skin; or any combination thereof.

In another related aspect, the method is non-therapeutic and the cellular growth promoting scaffold fills in tissue space reducing lines, folds, fine lines, wrinkles, or scars, or a combination thereof.

Disclosed herein in one aspect, is a solution for use inducing a cellular growth promoting scaffold, the solution comprising a plant-derived human collagen and at least one growth factor or source thereof, wherein the use comprises injecting said solution into a tissue space under an epidermis and wherein said use is for promoting healing or replacement due to degradation or injury of a collagen-comprising skin tissue.

In a related aspect, the plant-derived collagen comprises type 1 recombinant human collagen (rhCollagen); or the source of the at least one growth factor comprises a plasma or a platelet-rich plasma; or the collagen-comprising tissue comprises skin; or any combination thereof.

In another related aspect, the rhCollagen comprises a methacrylate or thiol derivative thereof.

In a related aspect, the solution used in the method further comprises a hyaluronic acid (HA) or modified derivative thereof, a poly(vinyl alcohol) (PVA) or modified derivative thereof, a polyethylene glycol (PEG) or modified derivative thereof, oxidized cellulose (OC) or a modified derivate thereof, polymethylmethacrylate (PMMA) microspheres or a modified derivative thereof, tricalcium phosphate (TCP) or a modified derivative thereof, calcium hydroxylapatite (CaHA) or a modified derivative thereof, carboxymethylcellulose or a modified derivative thereof, crystalline nanocellulose (CNC) or a modified derivative thereof, or a combination thereof, and a photoinitiator to induce polymerization prior to, on concomitant with, application of visible light; or a crosslinked hyaluronic acid or a crosslinked PVA, or a crosslinked PGE, or a crosslinked OC, wherein the plant-derived human collagen is crosslinked to the crosslinked hyaluronic acid or crosslinked PVA, or a crosslinked PGE, or a crosslinked OC.

In a related aspect, the method is non-therapeutic and the cellular growth promoting scaffold fills in tissue space reducing lines, folds, fine lines, wrinkles, or scars, or a combination thereof.

Disclosed herein is a solution for use inducing a cellular growth promoting scaffold, the solution comprising a plant-derived human collagen and at least one growth factor or source thereof, wherein the use comprises injecting said solution into a tissue space under an epidermis and wherein said use is for promoting healing or replacement due to degradation or injury of a collagen-comprising tissue.

In a related aspect, the source of the at least one growth factor comprises a plasma or a platelet-rich plasma; or the plant-derived collagen comprises type 1 recombinant human collagen (rhCollagen); or the collagen-comprising tissue comprises skin; or a combination thereof.

In another related aspect, the solution for use further comprises a hyaluronic acid (HA) or modified derivative thereof, a poly(vinyl alcohol) (PVA) or modified derivative thereof, a polyethylene glycol (PEG) or modified derivative thereof, oxidized cellulose (OC) or a modified derivate thereof, polymethylmethacrylate (PMMA) microspheres or a modified derivative thereof, tricalcium phosphate (TCP) or a modified derivative thereof, calcium hydroxylapatite (CaHA) or a modified derivative thereof, carboxymethylcellulose or a modified derivative thereof, crystalline nanocellulose (CNC) or a modified derivative thereof, or a combination thereof, and a photoinitiator to induce polymerization prior to, on concomitant with, application of visible light; or a crosslinked hyaluronic acid or a crosslinked PVA, or a crosslinked PGE, or a crosslinked OC, wherein the plant-derived human collagen is crosslinked to the crosslinked hyaluronic acid or crosslinked PVA, or a crosslinked PGE, or a crosslinked OC.

Disclosed herein in one aspect, is a method of filling a tissue space under an epidermis comprising: (a) introducing a polymerizable solution into the tissue space, wherein the polymerizable solution comprises: (i) a cross-linkable, plant-derived human collagen; and (ii) a photoinitiator; and applying light to the surface of the epidermis superficial to said space to induce polymerization.

In a related aspect, the polymerizable solution further includes a step of molding or sculpting the polymerizable solution into a desired configuration in the tissue space, wherein said step is concomitant with, or subsequent to, the step of applying light.

In another related aspect, the method is non-therapeutic, and the molding or sculpting step reduces lines, folds, fine lines, wrinkles, or scars, or a combination thereof.

In another related aspect, the cross-linkable, plant-derived human collagen is methacrylated or thiolated type 1 human recombinant collagen (rhcollagen).

Other objects, features and advantages of the present invention will become clear from the following description and drawings.

BRIEF DESCRIPTION OF THE DRAWINGS

FIG. 1a shows a cloning scheme of type I collagen alpha I chain or type II collagen alpha 2 chain into a plant expression vector in accordance with some embodiments of the present invention; FIG. 1b shows a cloning scheme of the enzyme prolyl-4-hydroxylase (P4H) into a plant expression vector in accordance with some embodiments of the present invention; FIG. 1c shows a cloning scheme proteinase C or proteinase N into a plant expression vector in accordance with some embodiments of the present invention; FIG. 1d shows a cloning scheme of Lysyl hydroxylase 3 (LH3) into a plant expression vector in accordance with some embodiments of the present invention.

FIG. 2 illustrates various co-transformations approaches used previously. Each expression cassette is represented by the short name of the coding sequence. The coding sequences are specified in Table 1. Each co-transformation was performed by two pBINPLUS binary vectors. Each rectangle represents a single pBINPLUS vector carrying one, two or three expression cassettes. Promoter and terminators are specified in Example 1.

In FIG. 6a, total soluble protein from tobacco 2-9 (expressing only col alpha1 and no P4H) and 3-5 (expressing both col alpha 1+2 and human P4H alpha and beta subunits) were subjected to heat treatment (15 minutes in 38° C. or 43° C.) followed by Trypsin digestion (20 minutes at room temperature [RT]) and tested with anti-Collagen I antibody in a Western blot procedure. Positive controls were samples of 500 ng human collagen I+total soluble proteins of w.t. tobacco. In FIG. 6b, total soluble proteins were extracted from transgenic tobacco 13-6 (expressing collagen I alpha 1 and alpha 2 chains—pointed by arrows, human P4H alpha and beta subunits and human LH3) and subjected to heat treatment (20 minutes in 33° C., 38° C., or 42° C.), immediately cooled on ice to prevent reassembly of triple helix and incubated with pepsin for 30 minutes in room temperature (about 22° C.) followed by testing with anti-Collagen I antibody ((#AB745 from Chemicon Inc.) in a standard Western blot procedure. Positive control was sample of 50 ng human collagen I (#CC050 from Chemicon Inc., extracted from human placenta by pepsin digestion) which was added to total soluble proteins extracted from wild-type (w.t., wt) tobacco.

FIG. 8 is a previous Western blot analysis of transgenic plants generated by co-transformations 2, 3 and 13. Total soluble protein was extracted from tobacco co-transformants and tested with anti-human P4H alpha and beta and anti-Collagen I antibodies.

FIG. 9 is a previous Western blot analysis of (lane 1) cross breeding vacuolar targeted plants A (2-300+20-279) grown under normal light regimen; and 13-652 vacuolar targeted plants grown for 8 days in the dark. All plants express exogenous col1, col2, P4H-alpha and P4H-beta as well as LH3 (PCR validated).

FIG. 31 shows storage and loss moduli and tan phase shift angle of rhCollagen-MA formulation at different concentrations before (upper graph) and after (lower graph) photocrosslinking.

FIG. 33A shows the upstream isolation and processing of procollagen and collagen (steps A-H). FIGS. 33B-33C show two phases of downstream processing (respectively, steps I-M and steps N-P & Z).

FIGS. 43A-43C show histopathological scoring of Achilles tendons in a rat model of tendinopathy treated with PRP or rhCollagen/PRP matrix. (A) Mature fibrosis, (B) presence of mononuclear inflammatory cells and (C) presence of immature granulation tissue.

DETAILED DESCRIPTION

Figure 1A:
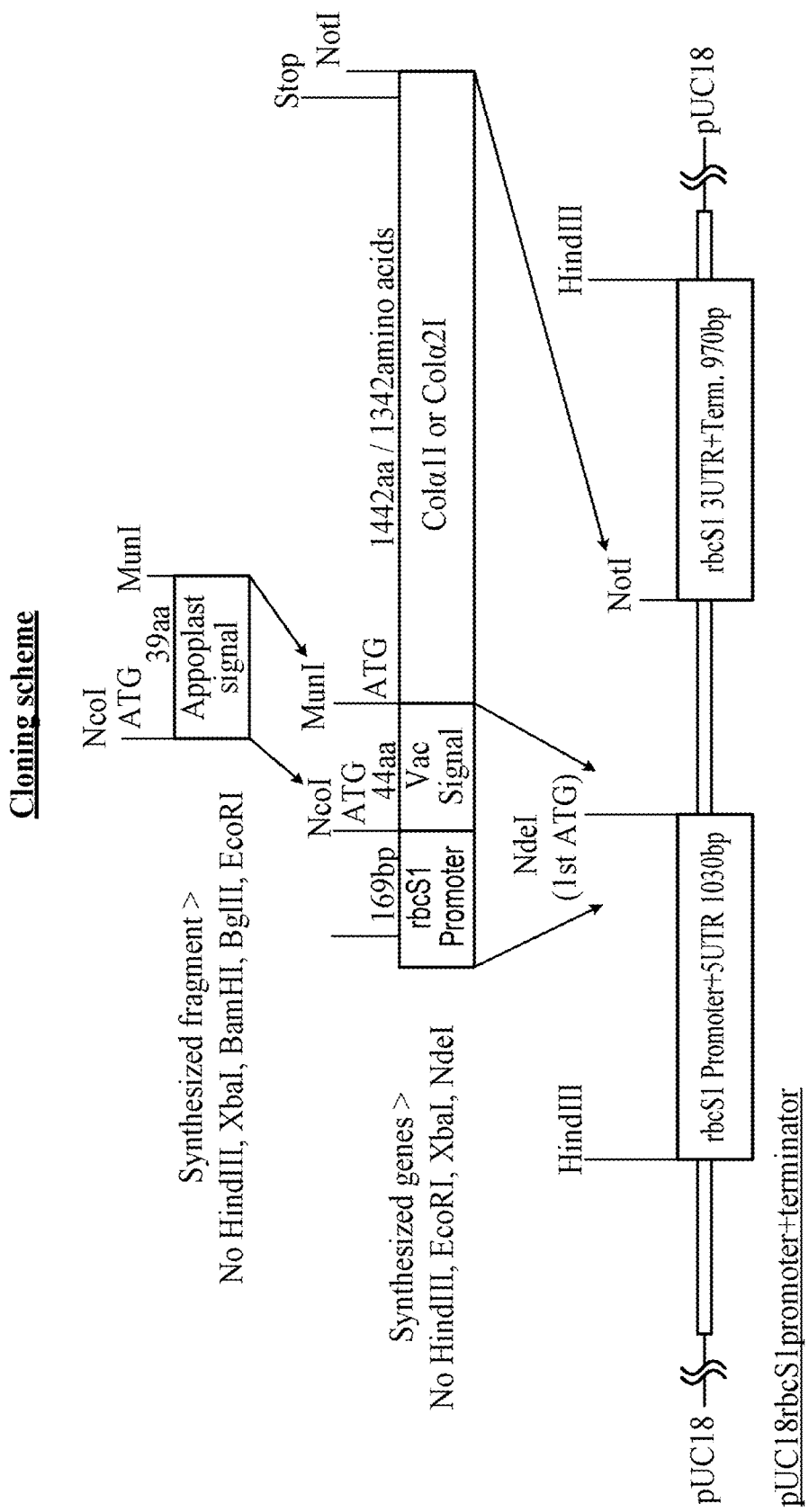
FIGS. 1a-d illustrate construction of various expression cassettes and vectors previously used to transform test plants. All of the coding sequences synthesized as a part of the study were optimized for expression in tobacco.

Disclosed herein are photoinitiated dermal fillers and double crosslinked dermal fillers, and cellular growth promoting scaffolds, and methods of using the same, for example but not limited to, for soft tissue augmentation.

Collagen-producing plants can be used to produce collagen chains as well as collagen, but such chains are incorrectly hydroxylated and thus self-assembly thereof, whether in planta or not, leads to collagen which is inherently unstable in contrast to the plant-derived human collagen of the present application.

While reducing the present polymerizable and double crosslinked solutions, and methods of use, to practice, the practitioners have devised a plant expression approach which ensures correct hydroxylation of collagen chains and thus enables in-planta production of collagen which closely mimics the characteristics (e.g. molecular structure, temperature stability, cellular interactions) of human type I collagen.

In one aspect, disclosed herein is a method of filling a tissue space under an epidermis comprising:
  (a) introducing a polymerizable solution into the tissue space, the polymerizable solution comprising:
    (i) a cross-linkable, plant-derived human collagen; and
    (ii) a photoinitiator; and
  (b) applying light to the surface of the epidermis superficial to said space to induce polymerization.

In a particular embodiment, the method further comprises, prior to, or concomitant with, the step of applying light, molding or sculpting the polymerizable solution into a desired configuration in the tissue space. In another particular embodiment, the molding or sculpting step reduces lines, folds, fine lines, wrinkles, or scars.

In yet another particular embodiment, the polymer solution further comprises a filler comprising a hyaluronic acid (HA) or a modified derivative thereof, a poly(vinyl alcohol) (PVA) or a modified derivative thereof, polyethylene glycol (PEG) or a modified derivative thereof, oxidized cellulose (OC) or a modified derivative thereof, or a combination thereof. In one particular embodiment, the isolated plant-derived human collagen is optionally formulated, such as with hyaluronic acid (HA), poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, crystalline nanocellulose (CNC) or a combination thereof.

Modified derivatives include, but are not limited to, photopolymerizable versions of, e.g., HA, PVA, PEG, or OC. Modifications include, but are not limited to, methacrylation or thiolation. In yet another particular embodiment, the light source is selected from light-emitting diode (LED), laser, xenon lamp, and the like.

In some embodiments, in formulations disclosed herein methacrylate rhCollagen crosslinks under illumination conditions only to itself. In some embodiments, in formulations disclosed herein methacrylate rhCollagen crosslinks under illumination conditions to thiolated rhCollagen. In some embodiments, in formulations disclosed herein methacrylate rhCollagen crosslinks under illumination conditions to any MA/thiolated additive. In some embodiments, in formulations disclosed herein methacrylate rhCollagen crosslinks under illumination conditions to methacrylated HA. In some embodiments, in formulations disclosed herein methacrylate rhCollagen crosslinks under illumination conditions to thiolated HA. In some embodiments, in formulations disclosed herein methacrylate rhCollagen crosslinks under illumination conditions to methacrylated PVA. In some embodiments, in formulations disclosed herein methacrylate rhCollagen crosslinks under illumination conditions to thiolated PVA. In some embodiments, in formulations disclosed herein methacrylate rhCollagen crosslinks under illumination conditions to methacrylated PEG. In some embodiments, in formulations disclosed herein methacrylate rhCollagen crosslinks under illumination conditions to thiolated PEG. In some embodiments, in formulations disclosed herein methacrylate rhCollagen crosslinks under illumination conditions to methacrylated OC. In some embodiments, in formulations disclosed herein methacrylate rhCollagen crosslinks under illumination conditions to thiolated OC.

A skilled artisan would appreciate that a photocurable formulation is actually a semi IPN before curing and becomes an IPN (interpenetrated network) after curing. An IPN may encompass two entangled networks, each one crosslinked to itself and not crosslinked to the other.

In some embodiments, crosslinked formulation includes a ratio of non-modified rhCollagen to tune the stiffness following crosslinking (with light) without reducing the final total amount of rhCollagen, as non modified rhCollagen cannot crosslink under illumination, therefore does not enhance the final stiffness. Methacrylated HA may also be added to this final formulation.

Figure 49:
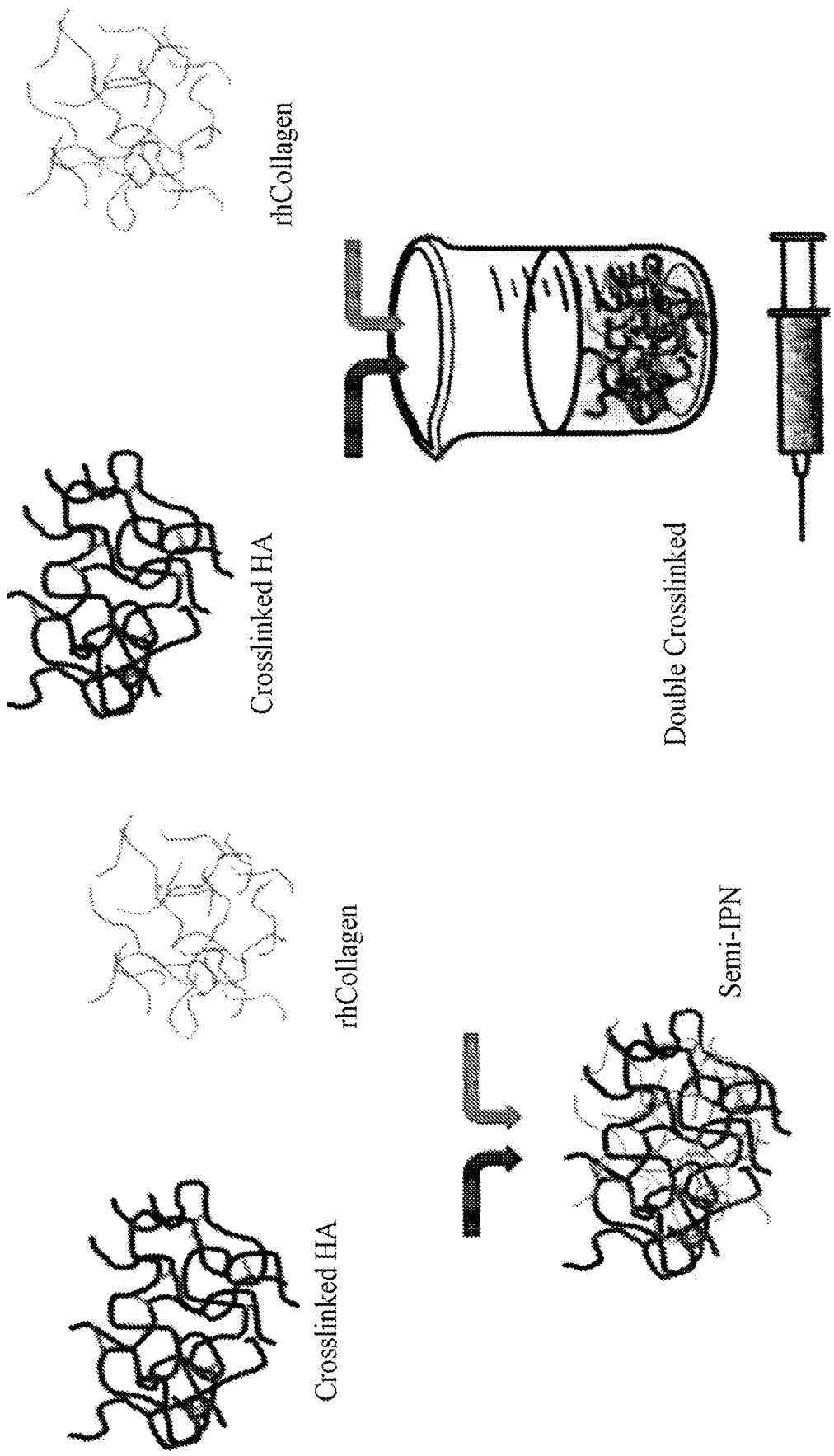
FIG. 49 shows two examples of Dermal Filler components. On the left-side is a schematic of a semi-interpenetrated dermal filler comprising crosslinked hyaluronic acid (HA) and rhCollagen. On the right-side is a schematic of the double crosslinked dermal filler comprising crosslinked hyaluronic acid and rhCollagen, wherein the crosslinked HA is further crosslinked to the rhCollagen. Light grey bars indicate the HA-crosslinker, blackstrands represent the HA, the rhcollagen is represented as thin grey strands, and the second crosslinker, cross linking crosslinked HA with rhCollagen, as black circles.

In some embodiments, the HA or MA-HA may be crossedlinked to itself using a crosslinker, for example but not limited to BDDE, as described in Example 23. In some embodiments, the crosslinker crosslinking HA or MA-HA comprises Divinyl Sulfone (DVS) or glutaraldehyde. In certain embodiments, the BDDE crosslinked HA or MA-HA is not further crosslinked to rhCollagen or MA-rhCollagen, creating what is called an interpenetrated network (FIG. 49 left-hand side).

In still another particular embodiment, the plant-derived collagen comprises rhCollagen. In another particular embodiment, the plant-derived collagen is obtained from a genetically modified plant. In another particular embodiment, the genetically modified plant is a genetically modified plant selected from the group consisting of tobacco, maize, alfalfa, rice, potato, soybean, tomato, wheat, barley, canola, carrot, and cotton. In particular, the genetically modified plant is a tobacco plant.

In still another particular embodiment, the genetically modified plant comprises an expressible sequence of at least one gene sequence of human deoxyribonucleic acid (DNA) selected from the group consisting of: COL1, COL2, P4H-alpha, P4H-beta, and LH3. In another particular embodiment, the plant-derived human collagen comprises at least modified one human collagen alpha-1 chain as set forth in SEQ ID NO: 3 and as expressed in the genetically modified plant; and at least one modified human collagen alpha-2 chain as set forth in SEQ ID NO: 6 and as expressed in the genetically modified plant; and wherein the genetically modified plant further expresses an exogenous prolyl-4-hydroxylase (P4H). In another particular embodiment, the method further comprises expressing an exogenous polypeptide selected from the group consisting of lysyl hydroxylase (LH), protease N, and protease C. In yet another particular embodiment, the human collagen alpha-1 chain is encoded by a sequence as set forth in SEQ ID NO: 1. In another particular embodiment, the human collagen alpha-2 chain is encoded by a sequence as set further in SEQ ID NO: 4.

In still another embodiment, the exogenous P4H is a mammalian P4H. In particular, the exogenous P4H is a human P4H. In yet another embodiment, the method further comprises targeting the human collagen alpha-1 to a vacuole of the plant or the genetically modified plant and digesting it with ficin. In yet another embodiment, the method further comprises targeting the human collagen alpha-2 to a vacuole of the plant or the genetically modified plant and digesting it with ficin.

In still another embodiment, the plant-derived human collagen is atelocollagen. In another embodiment, the plant-derived human collagen is atelocollagen having an amino acid (AA) sequence derived from SEQ ID NO: 1 and SEQ ID NO: 4. Atelocollagen is derived by enzymatic digestion (e.g., with ficin) of procollagen, which is the product of SEQ ID NO: 1 and SEQ ID NO: 4.

In yet another embodiment, the photoinitiator induces polymerization of the polymerizable solution in response to visible light. In particular, the visible light has a wavelength of 390-800 nm. In particular, the photoinitiator is selected from the group consisting of Eosyn Y+triethanolamine, riboflavin, and the like.

In another embodiment, the photoinitiator induces polymerization of the polymerizable solution in response to ultraviolet (uv) light. In particular, the photoinitiator is selected from the group consisting of lithium phenyl-2,4,6-trimethylbenzoylphosphinate (LAP) or 1-[4 2-hydroxy-1-[4-(2-hydroxyethoxy)phenyl]-2-methylpropan-1-one (IRGACURE® 2959).

In another embodiment, the photoinitiator induces polymerization of the polymerizable solution in response to infrared light.

In still another embodiment, the polymerizable solution is introduced into the tissue space via a hollow needle or canula in the range of 27 gauge to 33 gauge.

In still another embodiment, the polymerizable solution in the tissue space is molded or sculpted into the desired configuration via manual massage. In another embodiment, the polymerizable solution in the tissue space is molded or sculpted into the desired configuration using a molding or sculpting implement.

In still another embodiment, the polymerizable solution in the tissue space is essentially non-gellable at room temperature. In another embodiment, the polymerizable solution in the tissue space is essentially non-gellable at 37° C. In yet another embodiment, the polymerizable solution comprising the plant-derived human collagen has a reduced viscosity at room temperature in comparison with an analogous polymerizable solution comprising a tissue-extracted human or animal-derived collagen, for example but not limited to bovine or procine or equine collagen in the same concentration and formulation. In another embodiment, the polymerizable solution comprising the plant-derived human collagen has a reduced viscosity at 37° C. in comparison with an analogous polymerizable solution comprising a tissue-extracted human or animal-derived collagen in the same concentration and formulation.

As used throughout, the term "animal-derived collagen" may encompass bovine or procine or equine collagen or rat tail collagen and is in contrast to human derived collagen.

In still another embodiment, the polymerizable solution comprising the plant-derived human collagen is introduced into the tissue space with a reduced force at room temperature as compared with an analogous polymerizable solution comprising a tissue-extracted human or animal-derived collagen in the same concentration and formulation. In still another embodiment, the polymerizable solution comprising the plant-derived human collagen is introduced into the tissue space with a reduced force at 37° C. as compared with an analogous polymerizable solution comprising a tissued-extracted human or animal-derived collagen in the same concentration and formulation.

In another aspect, disclosed herein is a use of a polymerizable solution injected into a tissue space under an epidermis to reduce lines, folds, fine lines, wrinkles, or scars, the polymerizable solution comprising a methacrylated or thiolated cross-linkable, plant-derived human collagen and a photoinitiator to induce polymerization prior to, on concomitant with, application of visible light, and molding or sculpting the polymerizable solution into a desired configuration to reduce lines, folds, fine lines, wrinkles, or scars. In a particular embodiment, the polymer solution further comprises a filler comprising a hyaluronic acid (HA) or a modified derivative thereof, a poly(vinyl alcohol) (PVA) or a modified derivative thereof, polyethylene glycol (PEG) or a modified derivative thereof, oxidized cellulose (OC) or a modified derivative thereof, polymethylmethacrylate (PMMA) microspheres or a modified derivative thereof, tricalcium phosphate (TCP) or a modified derivative thereof, calcium hydroxylapatite (CaHA) or a modified derivative thereof, carboxymethylcellulose or a modified derivative thereof, crystalline nanocellulose (CNC) or a modified derivative thereof, or a combination of any of these.

Modified derivatives include, but are not limited to, photopolymerizable versions of, e.g., HA, PVA, PEG, OC, PMMA, TCP, CaHA, carboxymethylceullose, or CNC. Modifications include, but are not limited to, methacrylation or thiolation.

In another aspect, disclosed herein is a method of filling a tissue space under an epidermis comprising:
  (a) introducing a polymerizable solution into the tissue space, the polymerizable solution comprising a cross-linkable, plant-derived human collagen.

The instant technology relates, in part, to cosmetic and medical collagen-based polymerizable fillers that form a moldable composition, polymerizable on photoactivation with a light source, such as a visible light source. The polymerizable filler comprises a cross-linkable, plant-derived human collagen along with a photoinitiator.

The present technology of interest has the advantage of permitting in situ formation of a custom, contoured dermal filler or implant, typically without invasive surgical intervention or general anesthesia. Generally, the collagen-based polymerizable solution is introduced into a tissue space under the skin (that is, under the epidermis), and polymerization is induced by exposure to visible light applied to the skin surface, that is, from outside of the body or outside of the skin, or to the epidermis.

The in situ polymerization methods provide cosmetic and medical corrective and/or enhancement procedures using a polymerizable solution comprising a polymer component capable of forming an insoluble crosslinked crosslinking network on activation with a visible light source.

In some embodiments, a dermal filler or cellular growth promoting scaffold disclosed herein is for cosmetic use. In some embodiments, a dermal filler or cellular growth promoting scaffold disclosed herein is for medical corrective use. In some embodiments, a dermal filler or cellular growth promoting scaffold disclosed herein is for use in an enhancement procedure, for example but not limited to tissue augmentation. In some embodiments, a double crosslinked dermal filler disclosed herein is for cosmetic use. In some embodiments, a double crosslinked dermal filler disclosed herein is for medical corrective use. In some embodiments, a double crosslinked dermal filler disclosed herein is required as a result of a medical or or dental (gum implants/gum disease) condition. In some embodiments, a double crosslinked dermal filler disclosed herein is required as a result of a medical condition requiring skin augmentation. In some embodiments, a double crosslinked dermal filler disclosed herein is for use in an enhancement procedure, for example but not limited to tissue augmentation. In some embodiments, a photocurable dermal filler disclosed herein is for cosmetic use. In some embodiments, a photocurable dermal filler disclosed herein is for medical corrective use. In some embodiments, a photocurable dermal filler disclosed herein is required as a result of a medical or or dental (gum implants/gum disease) condition. In some embodiments, a photocurable dermal filler disclosed herein is required as a result of a medical condition requiring skin augmentation. In some embodiments, a photocurable dermal filler disclosed herein is for use in an enhancement procedure, for example but not limited to tissue augmentation. In some embodiments, a cellular growth promoting scaffold disclosed herein is for cosmetic use. In some embodiments, a cellular growth promoting scaffold disclosed herein is for medical corrective use. In some embodiments, a cellular growth promoting scaffold dermal filler disclosed herein is required as a result of a medical or or dental (gum implants/gum disease) condition. In some embodiments, a cellular growth promoting scaffold dermal filler disclosed herein is required as a result of a medical condition requiring skin augmentation. In some embodiments, medical corrective use includes treating tendinitis. In some embodiments, a cellular growth promoting scaffold disclosed herein is for use in an enhancement procedure, for example but not limited to tissue augmentation.

In some embodiments, tissue augmentation is of a skin tissue.

In some embodiments, use of the dermal fillers including cellular growth promoting scaffolds disclosed herein is in a human. In some embodiments, use of the dermal fillers including cellular growth promoting scaffolds disclosed herein in a human reduces lines, folds, fine lines, wrinkles, or scars, or any combination thereof. In some embodiments, the reduction of lines, folds, fine lines, wrinkles, or scars, or any combination thereof is for cosmetic purposes. In some embodiments, the reduction of lines, folds, fine lines, wrinkles, or scars, or any combination thereof is for cosmetic purposes. In some embodiments, use of the dermal fillers including cellular growth promoting scaffolds disclosed herein in a human augments tissue, for example but not limited to, epidermal or dermal tissue. In some embodiments, tissue augmentation is for cosmetic purposes. In some embodiments, tissue augmentation is for medical treatment. In some embodiments, tissue augmentation is part of an enhancement procedure. In some embodiments, tissue augmentation is part of a skin enhancement procedure.

In some embodiments, tissue augmentation is required as a result of any medical or dental (gum disease/gum implants) condition.

In certain embodiments, a dermal filler for use described herein comprises an interpenetrated (IPN) network or a semi-interpenetrated (Semi-IPN) network, in which the different components may be crosslinked to themselves but are not crosslinked to each other. In some embodiments, an IPN or semi-IPN dermal filler comprises rhCollagen and a filler, such as hyaluronic acid (HA), poly(vinyl alcohol) (PVA), polyethylene glycol (PEG), oxidized cellulose (OC), or a derivative thereof, or a combination thereof. In some embodiments, an IPN or semi-IPN comprises rhCollagen and a crosslinked HA. In some embodiments, an IPN or semi-IPN comprises a rhCollagen derivative, for example but not limited to a methacrylated rhCollagen or a thiol rhCollagen and or a derivative of a filler, for example but not limited to a methacrylated HA, PVA, PEG, or OC, or a thiolated HA, PVA, PEG, or OC, or a combination thereof.

In some embodiments, an IPN or Semi-IPN network or a double crosslinked network comprising a dermal filler comprises a ratio of filler, for example but not limited to HA, PVA, PEG, or OC to rhCollagen of 1:1, 2:1, 3:1, 4:1, 5:1, 6:1, 1:2, 1:3, 1:4, 1:5, 1:6, or 0:1. In some embodiments, an IPN or Semi-IPN network comprising a dermal filler comprises a ratio of MA-filler, for example but not limited to HA, PVA, PEG, or OC to rhCollagen is 1:1, 2:1, 3:1, 4:1, 5:1, 6:1, 1:2, 1:3, 1:4, 1:5, 1:6, or 0:1. In some embodiments, an IPN or Semi-IPN network comprising a dermal filler comprises a ratio of filler, for example but not limited to HA, PVA, PEG, or OC to MA-rhCollagen is 1:1, 2:1, 3:1, 4:1, 5:1, 6:1, 1:2, 1:3, 1:4, 1:5, 1:6, or 0:1. In some embodiments, an IPN or Semi-IPN network comprising a dermal filler comprises a ratio of MA-filler to MA-rhCollagen is 1:1, 2:1, 3:1, 4:1, 5:1, 6:1, 1:2, 1:3, 1:4, 1:5, 1:6, or 0:1.

In some embodiments, an IPN or Semi-IPN or double crosslinked network comprising a dermal filler comprises a ratio of HA to rhCollagen of 1:1, 2:1, 3:1, 4:1, 5:1, 6:1, 1:2, 1:3, 1:4, 1:5, 1:6, or 0:1. In some embodiments, an IPN or Semi-IPN or double crosslinked network comprising a dermal filler comprises a ratio of MA-HA to rhCollagen is 1:1, 2:1, 3:1, 4:1, 5:1, 6:1, 1:2, 1:3, 1:4, 1:5, 1:6, or 0:1. In some embodiments, an IPN or Semi-IPN network comprising a dermal filler comprises a ratio of HA to MA-rhCollagen is 1:1, 2:1, 3:1, 4:1, 5:1, 6:1, 1:2, 1:3, 1:4, 1:5, 1:6, or 0:1. In some embodiments, an IPN or Semi-IPN network comprising a dermal filler comprises a ratio of MA-HA to MA-rhCollagen is 1:1, 2:1, 3:1, 4:1, 5:1, 6:1, 1:2, 1:3, 1:4, 1:5, 1:6, or 0:1.

In some embodiments, an IPN or Semi-IPN or double crosslinked network comprising a dermal filler comprises a ratio of filler to rhCollagen of 1:1, 2:1, 3:1, 4:1, 5:1, 6:1, 1:2, 1:3, 1:4, 1:5, 1:6, or 0:1. In some embodiments, an IPN or Semi-IPN or double crosslinked network comprising a dermal filler comprises a ratio of MA-HA, or MA-PVA, or MA-PEG, or MA-OC to rhCollagen is 1:1, 2:1, 3:1, 4:1, 5:1, 6:1, 1:2, 1:3, 1:4, 1:5, 1:6, or 0:1. In some embodiments, an IPN or Semi-IPN network comprising a dermal filler comprises a ratio of MA-HA, or MA-PVA, or MA-PEG, or MA-OC to MA-rhCollagen is 1:1, 2:1, 3:1, 4:1, 5:1, 6:1, 1:2, 1:3, 1:4, 1:5, 1:6, or 0:1. In some embodiments, an IPN or Semi-IPN network comprising a dermal filler comprises a ratio of MA-HA, or MA-PVA, or MA-PEG, or MA-OC to MA-rhCollagen is 1:1, 2:1, 3:1, 4:1, 5:1, 6:1, 1:2, 1:3, 1:4, 1:5, 1:6, or 0:1.

In some embodiments, an IPN or Semi-IPN network comprising a dermal filler or a double crosslinked dermal filler comprises a cellular growth promoting scaffold.

In certain embodiments, a dermal filler for use described herein comprises an photocurable dermal filler, in which at least one of the component, for example but not limited to rhCollagen comprises a methacrylate-rhCollagen derivative or a thiol-rhCollagen derivative. In some embodiments, a curable dermal filler comprises rhCollagen and a filler, such as hyaluronic acid (HA), poly(vinyl alcohol) (PVA), polyethylene glycol (PEG), oxidized cellulose (OC), or a derivative thereof, or a combination thereof. In some embodiments, photocurable dermal filler comprises MA-rhCollagen and a HA or a derivative thereof. In some embodiments, photocurable dermal filled comprises a rhCollagen derivative, for example but not limited to a methacrylated rhCollagen or a thiol rhCollagen and or a derivative of a filler, for example but not limited to a methacrylated HA, PVA, PEG, or OC, or a thiolated HA, PVA, PEG, or OC, or a combination thereof.

In some embodiments, photocurable dermal filler comprises a ratio of filler, for example but not limited to HA, PVA, PEG, or OC, or a derivative thereof, to rhCollagen of 1:1, 2:1, 3:1, 4:1, 5:1, 6:1, 1:2, 1:3, 1:4, 1:5, 1:6, or 0:1. In some embodiments, a photocurable dermal filler comprises a ratio of filler, for example but not limited to HA, PVA, PEG, or OC, or a derivative thereof, to MA-rhCollagen of 1:1, 2:1, 3:1, 4:1, 5:1, 6:1, 1:2, 1:3, 1:4, 1:5, 1:6, or 0:1. In some embodiments, a photocurable dermal filler comprises a ratio of filler, for example but not limited to HA, PVA, PEG, or OC to Thiol-rhCollagen is 1:1, 2:1, 3:1, 4:1, 5:1, 6:1, 1:2, 1:3, 1:4, 1:5, 1:6, or 0:1. In some embodiments, a photocurable dermal filler comprises a ratio of MA-filler to MA-rhCollagen is 1:1, 2:1, 3:1, 4:1, 5:1, 6:1, 1:2, 1:3, 1:4, 1:5, 1:6, or 0:1.

In some embodiments, a photocurable dermal filler comprises a ratio of HA to MA-rhCollagen of 1:1, 2:1, 3:1, 4:1, 5:1, 6:1, 1:2, 1:3, 1:4, 1:5, 1:6, or 0:1, 1:3, 1:4, 1:5, or 0:1. In some embodiments, a photocurable dermal filler comprises a ratio of MA-HA to MA-rhCollagen is 1:1, 2:1, 3:1, 4:1, 5:1, 6:1, 1:2, 1:3, 1:4, 1:5, 1:6, or 0:1. In some embodiments, a photocurable dermal filler comprises a ratio of PVA, PEG, or OC to MA-rhCollagen is 1:1, 2:1, 3:1, 4:1, 5:1, 6:1, 1:2, 1:3, 1:4, 1:5, 1:6, or 0:1. In some embodiments, a photocurable dermal filler comprises a ratio of MA-PVA, MA-HA-, or OC to MA-rhCollagen is 1:1, 2:1, 3:1, 4:1, 5:1, 6:1, 1:2, 1:3, 1:4, 1:5, 1:6, or 0:1. In some embodiments, the HA components of a photocurable dermal filler comprises a crosslinked HA or a crosslinked MA-HA.

Throughout this application, various embodiments of dermal fillers and their uses, may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1:1 to 6:1 should be considered to have specifically disclosed sub ranges such as from 1.1:1, 1.2:1, 1.3:1 to 5.9:1, from 1:1.1 to 1:1.9, etc., as well as individual numbers within that range and fractions thereof, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

For example, the instant disclosure provides a dermal filler that for a tissue space under an epidermis comprising a cross-linkable, plant-derived human collagen, either alone or together with a filler, such as hyaluronic acid (HA), poly(vinyl alcohol) (PVA), polyethylene glycol (PEG), oxidized cellulose (OC), or a combination thereof, which may be crosslinked, to provide a dermal filler that forms a water insoluble, crosslinked polymer preparation in situ on visible light activation in the presence of a photoinitiator. In some embodiments, the collagen is methacrylated or thiolated.

In some embodiments, the dermal filler provide for uses described herein forms an IPN or semi-IPN network. In some embodiments, the dermal filler provide for uses described herein forms a double crosslinked network.

In certain embodiments, a double crosslinked dermal filler provided for uses described herein comprises rhCollagen that is crosslinked to a crosslinked filler, such as crosslinked hyaluronic acid (HA), crosslinked poly(vinyl alcohol) (PVA), crosslinked polyethylene glycol (PEG), or crosslinked oxidized cellulose (OC), or a crosslinked derivative thereof, or a combination thereof. In certain embodiments, a double crosslinked dermal filler provided for uses described herein comprises rhCollagen that is further crosslinked to methacrylated or thiolated-crosslinked filler, such as HA, PVA, PEG, or OC.

In certain embodiments, in a double crosslinked dermal filler, the ratio of crosslinked filler to rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of MA-filler to rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of crosslinked filler to MA-rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of MA-filler to MA-rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of thiolated-filler to rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of crosslinked filler to thiolated-rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of thiolated-filler to thiolated-rhCollagen is 1:1, 2:1, 3:1, 4:1, 5:1, 6:1, 1:2, 1:3, 1:4, 1:5, 1:6, or 0:1.

In certain embodiments, in a double crosslinked dermal filler, crosslinked HA or crosslinked MA-HA is further crosslinked to rhCollagen or methacrylated rhCollagen or thiol rhCollagen, resulting in a double crosslinked dermal filler. In certain embodiments, in a double crosslinked dermal filler, the ratio of crosslinked HA to rhCollagen or methacrylated rhCollagen or thiol rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of crosslinked MA-HA to rhCollagen or methacrylated rhCollagen or thiol rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of crosslinked MA-HA to rhCollagen or methacrylated rhCollagen or thiol rhCollagen is 1:1, 2:1, 3:1, 4:1, 5:1, 6:1, 1:2, 1:3, 1:4, 1:5, 1:6, or 0:1.

In certain embodiments, in a double crosslinked dermal filler, crosslinked PVA, PEG, or OC or crosslinked MA-PVA, MA-PEG, or MA-OC is further crosslinked to rhCollagen or methacrylated rhCollagen, resulting in a double crosslinked dermal filler. In certain embodiments, in a double crosslinked dermal filler, the ratio of crosslinked PVA, PEG, or OC to rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of crosslinked MA-PVA, MA-PEG, or MA-OC to rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of crosslinked PVA, PEG, or OC to MA-rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of crosslinked MA-PVA, MA-PEG, or MA-OC to MArhCollagen or thiol rhCollagen is 1:1, 2:1, 3:1, 4:1, 5:1, 6:1, 1:2, 1:3, 1:4, 1:5, 1:6, or 0:1.

In certain embodiments, in a double crosslinked dermal filler, crosslinked thiol-PVA, thiol-PEG, or thiol-OC is further crosslinked to rhCollagen or methacrylated rhCollagen, resulting in a double crosslinked dermal filler. In certain embodiments, in a double crosslinked dermal filler, the ratio of crosslinked thiol-PVA, thiol-PEG, or thiol-OC to rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of crosslinked thiol-PVA, thiol-PEG, or thiol-OC to MArhCollagen or thiol rhCollagen is 1:1, 2:1, 3:1, 4:1, 5:1, 6:1, 1:2, 1:3, 1:4, 1:5, 1:6, or 0:1.

In some embodiments, any water-soluble coupling agent may be used that can crosslink hyaluronic acid to collagen. Some non-limiting examples of a coupling agent include carbodimides such as N,N'-dicyclohexylcarbodiimide (DCC), N,N'-diisopropylcarbodiimide (DIC), or 1-ethyl-3-(3-dimethylaminopropyl)carbodiimide (EDC), etc. Carbodiimide coupling agents may facilitate ester or amide bond formation without becoming part of the linkage. In other words, an ester bond or an amide bond may comprise atoms from a carboxylate group from one of hyaluronic acid or collagen, and a hydroxyl group or an amine group from the other. However, other coupling agents that become part of the crosslinking group may be used. The concentration of a coupling agent may vary. In some embodiments, a coupling agent may be present at about 2 mM to about 150 mM, about 2 mM to about 50 mM, about 20 mM to about 100 mM, or about 50 mM. In some embodiments, the coupling agent is EDC that is present at a concentration of about 20 mM to about 100 mM, about 2 mM to about 50 mM, or about 50 mM. In some embodiments, the coupling agent is EDC that is present at an amount of EDC equal to 10 to 100-fold the number of free amines in the rhcollagen. In some embodiments, the coupling agent is EDC that is present at an amount of EDC equal to 50-fold the number of free amines in the rhcollagen. Increasing the carbodiimide concentration up to about 50 mM may result in a crosslinked macromolecular matrix with greater hydrogel stiffness and/or less swelling.

A skilled artisan would appreciate that a dermal filler comprising double crosslinking, wherein the filler is crosslinked to itself and then also crosslinked to the rhCollagen, is distinct from a dermal filler that comprises direct cross linking of collagen and HA using a single type of cross linker in a single reaction. The properties of such dermal fillers differ.

By way of example, the present polymerizable solution can be used to block or fill various lumens and voids just below a skin surface. Thus, the instant technology provides a method of tissue augmentation in a host, such as a human patient, wherein said polymerizable solution of interest is introduced at a site of interest using methods known in the art, such as injecting the polymerizable solution at or in a tissue site in need of augmentation and once applied, exposing the overlying body surface to a visible light to cause polymerization of the deposited polymerizable solution.

"Augmentation" means the repair, prevention or alleviation of defects, particularly defects due to loss or absence of tissue, by providing, augmenting, or replacing such tissue with a polymer or network or interest. Augmentation is also meant to include supplementation of a natural structure or feature, that is, a building of adding to an existing body part, for example, to increase the size thereof, such as lips, nose, breast, ears, portions of organs, chin, cheeks and so on. Thus, tissue augmentation can include the filling or reduction of lines, folds, wrinkles, scars, minor facial depressions, cleft lips, superficial wrinkles and the like, such as, in or on the face, neck, hands, feet, fingers, and toes; the correction of minor deformities due to aging or disease, including in the hands and feet, fingers and toes; the augmentation of the vocal cords or glottis to rehabilitate speech; the dermal filling of sleep lines and expression lines; the replacement of dermal and subcutaneous tissue lost due to aging; the augmentation of lips; the filling of wrinkles and the orbital groove around the eye; the augmentation of the breast; the augmentation of the chin; the augmentation of the cheek and/or nose; the filling of indentations in soft tissue, dermal or subcutaneous, due to, e.g., overzealous liposuction or other trauma; the filling of acne or traumatic scars and rhytids; the filling of nasolabial lines, nasoglabellar lines and infraoral lines and so on.

The polymerizable solution of interest, in some embodiments, encompasses a polymerizable solution which has a viscosity suitable for ready extrusion through a delivery means, such as a fine surgical needle (e.g., needles having a gauge of at least 27 gauge, at least 33 gauge or finer) at the temperature of use. Thus, a solution that is, "injectable" is one having a texture and viscosity which permits flow through a suitable delivery device, such as, a surgical needle, other surgical instrument, or other delivery means such as an equipment used in endoscopic or percutaneous discectomy procedures. The polymerizable solution of interest thus is injectable through a suitable applicator, such as a catheter, a cannula, a needle, a syringe, tubular apparatus and so on, as known in the art.

Once injected into the tissue space, the polymerizable solution can be manipulated, massaged, molded, or sculpted into the desired contours in the tissue space, typically after photoinitiation of polymerization has been triggered. In one embodiment, the manipulation, massage, molding, or sculpting takes place during the gelation process. The polymerizable, polymerizing, or partially polymerized solution can be shaped by external manipulation, using, for example, a shaping means, such as, a surgical depressor or other tool or instrument with a flat or curved surface, fingers, the palm, a knuckle and so on.

Surprisingly, the genetically modified, cross-linkable, plant-derived human collagen of the present method provides an improved collagen-containing dermal filler and improved methods of dermal filling by enabling the use of smaller gauge needles and a decreased force of injection, as well as by its ability to fill smaller tissue spaces.

The "expression force" of an injection (newtons, N) includes the force required for injection from the needle or cannula.

"Absolute viscosity" ("dynamic viscosity") is a fluid's resistance to flow when a force is applied. It is proportional to the force to velocity ratio. The Greek letter—(eta) represents absolute viscosity in calculations. It is commonly measured in cP because many common fluids have viscosities between 0.5 cP and 1000 cP.

A "gel" is a semirigid slab or cylinder of an organic polymer used as a medium for the separation of macromolecules. A gel is a substantially dilute cross-linked system, which exhibits no flow when in the steady-state. Gels are principally liquid by weight yet behave as partly as solids due to a three-dimensional cross-linked network within the liquid while retaining some properties of a liquid, such as deformability. It is the crosslinking within the fluid that gives a gel its structure (hardness) and contributes to the adhesive stick (tack). As a result, gels can be viewed as a dispersion of liquid molecules within a solid, i.e., liquid particles dispersed within a solid medium. "Gelation time" is the time it takes for the polymerizable solution to form a gel.

A "hydrogel" is a network of polymer chains that are hydrophilic, sometimes found as a colloidal gel in which water is the dispersion medium. Hydrogels are highly absorbent (e.g., able to contain over 90% water) polymeric networks and have a flexibility very similar to natural tissue, due to their significant water content.

A "polymer" is a macromolecule composed of a series of repeating subunits. The basic repeating subunit is known as a "monomer." As a group, polymers are known for their tensile strength and elasticity.

A "photoinitiator" is a molecule that creates reactive species (free radicals, cations or anions) when exposed to radiation (UV or visible). The photoinitiator of the present invention induces polymerization of the polymerizable solution. Examples of photoinitiators useful in the present method include, but are not limited to lithium phenyl-2,4, 6-trimethylbenzoylphosphinate (LAP), 1-[4 2-hydroxy-1-[4-(2-hydroxyethoxy)phenyl]-2-methylpropan-1-one (IRGACURE® 2959), Eosin Y+Triethanolamin, or riboflavin.

Methacrylate is an ester or salt derived from methacrylic acid. Methacrylates are common monomers in polymer plastics, forming the acrylate polymers. Addition of methacrylate groups to collagen results in collagen methacrylate (rhCollagen-MA or MA-rhCollagen) which is photocurable. Addition of methacrylate groups to hyaluronic acid (HA) results in hyaluronic acid-methacrylate (HAMA or MA-HA) which is photocurable.

In some embodiments, rhCollagen used in a dermal filler described herein comprises a combination of non-modified rhCollagen and MA-rhCollagen. In some embodiments, the ratio of non-modified rhCollagen to MA-rhCollagen is about 1:0, 1:1, 1:2, 1:3, 1:4, 0:1, 2:1, 3:1, or 4:1. In some embodiments, the final concentration range of MA-rhCollagen comprises between about 0-12 mg/ml. In some embodiments, the final concentration range of non-modified rhCollagen comprises between about 0-12 mg/ml. In some embodiments, the final concentration range of MA-rhCollagen comprises between about 0-12 mg/ml, and the final concentration range of non-modified rhCollagen comprises between about 0-12 mg/ml. In some embodiments, the final concentration range of MA-rhCollagen comprises between about 0 mg/ml-6 mg/ml. In some embodiments, the final concentration range of non-modified rhCollagen comprises between about 0 mg/ml-6 mg/ml. In some embodiments, the final concentration of MA-rhCollagen comprises about 0, 1, 2, 3, 4, 5, 6, 7, 8, 9, 10, 11, or 12 mg/ml. In some embodiments, the final concentration of non-modified-rhCollagen comprises about 0, 1, 2, 3, 4, 5, 6, 7, 8, 9, 10, 11, or 12 mg/ml.

A thiol is an organosulfur compound that contains a carbon-bonded sulfhydryl (R-SH) group (where R represents an alkyl or other organic substituent). Thiolation of collagen can improve cohesion and mucoadhesion properties and affects swelling ability.

Light is a form of electromagnetic radiation. "Visible light" is light having a wavelength in the rangel of 380-800 nm or at least 390-700 nm. "Ultraviolet light" has shorter wavelengths, while "infrared" has longer wavelengths.

An illuminating means can be a light source suitable for activating the photoinitiator used, and which can activate the photoinitiator from outside of the body. While thermal initiators can be used and thus, an infrared source used, and ultraviolet-activated initiators can be used, and thus, a suitable ultraviolet source used, a preferred light source is a white light source. Thus, a suitable photoinitiator is used, so that the maximum absorption of the initiator and the light source are tuned. As mentioned hereinabove, one such visible light source is light-emitting diode (LED). Other suitable light sources can be used so long as gelation occurs in the body, at the site, under the skin surface and so on, such as, by applying the electromagnetic radiation to the body, to the site as needed, or from above the skin surface. The electromagnetic radiation is applied at an intensity, for a time and for a duration that enables gelation. The light source can be situated above the skin surface or directly on the skin surface, typically above the location of the molded or sculpted polymerizable solution.

The monomer solution of some embodiments, can contain any of a variety of other materials, such as, inert materials, such as, preservatives, fillers, excipients or diluents, pharmacologically active molecules or agents, such as a small molecule or a biological, cells and so on, as known in the pharmaceutic arts. Thus, a suitable inert or biologically active agent can be added to the monomer solution. In the case of the latter, the active agent may exert a pharmacologic action locally at the site or in the vicinity of the polymerized or networked structure of interest, or can be released from the formed scaffold, matrix or network to move though the adjoining tissue spaces or may enter the circulatory system for a less local effect.

As discussed above, the polymeriziable solution methods of interest also can be used in combination with other dermatology, orthopedic, cosmetic, and other medical treatments.

In some embodiments, the polymerizable solution is mixed with a known filler to provide a composition which is moldable, contourable, has a long residence time and so on. Examples of fillers include, but are not limited to, hyaluronic acid (HA), poly(vinyl alcohol) (PVA), polyethylene glycol (PEG), oxidized cellulose (OC), or modified derivatives thereof, or a combination thereof. In some embodiments, the polymerizable solution in a semiliquid phase, is independently injected into the dermis as is a known filler also in a semiliquid phase, that together will provide a composition which is moldable, contourable, has a long residence time and so on. Examples of fillers that may be injected independently include, but are not limited to, hyaluronic acid (HA), poly(vinyl alcohol) (PVA), polyethylene glycol (PEG), oxidized cellulose (OC), or modified derivatives thereof, or a combination thereof. In some embodiments, the polymerizable solution in a semiliquid phase, is injected into the dermis as a mixture that together will provide a composition which is moldable, contourable, has a long residence time and so on. Examples of fillers that may be injected mixed with rhCollagen include, but are not limited to, hyaluronic acid (HA), poly(vinyl alcohol) (PVA), polyethylene glycol (PEG), oxidized cellulose (OC), or modified derivatives thereof, or a combination thereof.

In yet another aspect, disclosed herein is methods of inducing a cellular growth promoting scaffold in a tissue space under an epidermis comprising introducing a solution into the tissue space, the solution comprising: (a) a plant-derived human collagen; and (b) at least one growth factor or source thereof.

In one embodiment, the source of the at least one growth factor comprises a plasma or a platelet-rich plasma.

In one embodiment, the cellular growth promoting scaffold promotes healing or replacement due to degradation or injury of a collagen-comprising tissue. In one embodiment, the collagen-comprising tissue is selected from the group consisting of a tendon, a ligament, skin, a cornea, a cartilage, a blood vessel, an intestine, an intervertebral disc, a muscle, a bone, or a tooth. In a particular embodiment, the cellular growth promoting scaffold promotes healing of tendinitis.

In one embodiment, the plant-derived collagen comprises rhCollagen. In one embodiment, the plant-derived collagen is obtained from a genetically modified plant. In various embodiments, the genetically modified plant is a genetically modified plant selected from the group consisting of tobacco, maize, alfalfa, rice, potato, soybean, tomato, wheat, barley, canola, carrot, and cotton. In one embodiment, the genetically modified plant is a tobacco plant.

In one embodiment, the genetically modified plant comprises an expressible sequence of at least one gene sequence of human deoxyribonucleic acid (DNA) selected from the group consisting of: COL1, COL2, P4H-alpha, P4H-beta, and LH3.

In a particular embodiment, the plant-derived human collagen comprises at least modified one human collagen alpha-1 chain as set forth in SEQ ID NO: 3 and as expressed in the genetically modified plant; and at least one modified human collagen alpha-2 chain as set forth in SEQ ID NO: 6 and as expressed in the genetically modified plant; and the genetically modified plant further expresses an exogenous prolyl-4-hydroxylase (P4H).

In another particular embodiment, the method further comprises expressing an exogenous polypeptide selected from the group consisting of lysyl hydroxylase (LH), protease N, and protease C.

In one particular embodiment, the human collagen alpha-1 chain is encoded by a sequence as set forth in SEQ ID NO: 1. In another particular embodiment, the human collagen alpha-2 chain is encoded by a sequence as set forth in SEQ ID NO: 2.

In one embodiment, the exogenous P4H is a mammalian P4H. In one particular embodiment, the exogenous P4H is a human P4H.

In one embodiment, the method further comprises targeting the human collagen alpha-1 to a vacuole of the plant or the genetically modified plant and digesting it with ficin. In one embodiment, the method further comprises targeting the human collagen alpha-2 to a vacuole of the plant or the genetically modified plant and digesting it with ficin.

In one particular embodiment, the plant-derived human collagen is atelocollagen.

A skilled artisan would appreciate that the term "dermal filler" encompasses in some embodiments a solution comprising a plant-derived human collagen, for example a type 1 recombinant human collagen (rhCollagen) or a derivative thereof. The term "dermal filler" also encompass in some embodiments, a solution comprising a plant-derived human collagen, for example a type 1 recombinant human collagen (rhCollagen) or a derivative thereof, and a filler or a derivative thereof, or a crosslinked filler or a derivative thereof, having all the same meanings and qualities, wherein a dermal filler may be used to augment tissue structure, or may be used for reducing lines, folds, fine lines, wrinkles, or scars, or any combination thereof.

A skilled artisan would appreciate that dermal fillers described herein comprise different formulation, for example but not limited to:

An rhCollagen or a MA or Thiol derivative thereof;

an IPN or semi-IPN or double crosslinked network comprising rhCollagen or rhCollagen-MA or rhCollagen-Thiol, and a filler or derivative thereof;

an IPN or semi-IPN or double crosslinked network comprising rhCollagen or rhCollagen-MA or rhCollagen-Thiol, and HA or MA-HA or Thiol-HA;

an IPN or semi-IPN or double crosslinked network comprising rhCollagen or rhCollagen-MA or rhCollagen-Thiol, and PVA or MA-PVA or Thiol-PVA;

an IPN or semi-IPN or double crosslinked network comprising rhCollagen or rhCollagen-MA or rhCollagen-Thiol, and PEG or MA-PEG or Thiol-PEG;

an IPN or semi-IPN or double crosslinked network comprising rhCollagen or rhCollagen-MA or rhCollagen-Thiol, and OC or MA-OC or thiol-OC;

an IPN or semi-IPN or double crosslinked network or a cellular growth promoting scaffold comprising rhCollagen, and an autologous platelet rich plasma (PRP) fraction of blood containing high concentration of platelets;

an IPN or semi-IPN or double crosslinked network or a cellular growth promoting scaffold, each comprising rhCollagen and an autologous platelet rich plasma (PRP) fraction of blood containing high concentration of platelets, wherein the platelets release various types of growth factors (GFs) comprising vasculo-endothelial growth factor (VEGF), transforming beta growth factor (TGF-beta), platelet derived growth factor (PDGF), platelet derived epidermal growth factor (PDEGF), fibroblast growth factors (bFGF), epidermal growth factors (EGF) or hepatocyte growth factors (HGF), or a combination thereof;

a double crosslinked dermal filler comprising rhCollagen or rhCollagen-MA or rhCollagen-Thiol crosslinked to a crosslinked filler or derivative thereof;

a double crosslinked dermal filler comprising a rhCollagen or rhCollagen-MA or rhCollagen-Thiol crosslinked to a crosslinked HA or crosslinked MA-HA or crosslinked Thiol-HA;

a double crosslinked dermal filler comprising a rhCollagen or rhCollagen-MA or rhCollagen-Thiol crosslinked to a crosslinked PVA or crosslinked MA-PVA or crosslinked Thiol-PVA;

a double crosslinked dermal filler comprising a rhCollagen or rhCollagen-MA or rhCollagen-Thiol crosslinked to a crosslinked PEG or crosslinked MA-PEG or crosslinked Thiol-PEG; or a double crosslinked dermal filler comprising a rhCollagen or rhCollagen-MA or rhCollagen-Thiol crosslinked to a crosslinked OC or crosslinked MA-OC or crosslinked thiol-OC.

A skilled artisan would appreciate that in some embodiments, the term "cellular growth promoting scaffold" encompasses dermal fillers comprising collagen and an autologous platelet rich plasma (PRP) fraction of blood or components thereof. In some embodiments, PRP does not include "cells" but membranous vesicles (of cellular origin) containing growth factors and plasma components like fibrinogen and pro-thrombin. in some embodiments, a "cellular growth promoting scaffold" encompasses dermal fillers comprising collagen and an autologous platelet rich plasma (PRP) fraction of blood or components thereof, and an at least additional filler component.

In some embodiments, a cellular growth promoting scaffold comprises a dermal filler that may be an IPN networks, a semi-IPN networks, or a double crosslinked dermal filler that further comprises an autologous platelet rich plasma (PRP) fraction of blood containing high concentration of platelets, wherein the autologous PRP fraction of blood containing high concentration of platelets, wherein the platelets release various types of growth factors (GFs) comprising vasculo-endothelial growth factor (VEGF), transforming beta growth factor (TGF-beta), platelet derived growth factor (PDGF), platelet derived epidermal growth factor (PDEGF), fibroblast growth factors (bFGF), epidermal growth factors (EGF) or hepatocyte growth factors (HGF), or a combination thereof. In some embodiments, a cellular growth promoting scaffold comprises a dermal filler comprising an IPN networks, a semi-IPN networks, or a double crosslinked dermal filler that further comprises, and at least one growth factor comprising vasculo-endothelial growth factor (VEGF), transforming beta growth factor (TGF-beta), platelet derived growth factor (PDGF), platelet derived epidermal growth factor (PDEGF), fibroblast growth factors (bFGF), epidermal growth factors (EGF) or hepatocyte growth factors (HGF), or a combination thereof. In some embodiments, a cellular growth promototing scaffold comprises a dermal filler comprising an IPN networks, a semi-IPN networks, or a double crosslinked dermal filler that further comprises, and a subset or fraction of PRP components.

In some embodiments, a dermal filler described herein comprises a polymerizable solution. In some embodiments, a dermal filler described herein comprises a non-polymerizable solution. In some embodiments, polymerization of a dermal filler solution occurs in vivo. In some embodiments, components of a polymerizable dermal filler solution are injected together and then polymerized to form the cured dermal filler. In some embodiments, components of a polymerizable dermal filler solution are injected independently and then polymerized to form the cured dermal filler. An example of the unique approach of independently injection dermal filler components may in some embodiments comprising, injecting a filler into the skin dermis, for example but not limited to HA or a deriviatives thereof, and separately injecting a methacrylated or thiol-rhCollagen into the skin dermis within close proximity of the first injection, wherein the components are in a semiliquid phase, and then crosslinking in situ. This approach, in some embodiments allows for easier injection and in situ sculturing prior to curing the dermal filler components together by light polymerization.

In some embodiments, a dermal filler provided herein is used in a method of soft tissue augmentation. In some embodiments, a dermal filler provided herein enhances cell proliferation. In some embodiments, a dermal filler provided and used in a method of soft tissue augmentation, degrades over time. In some embodiments, a dermal filler provided herein is used in a method of soft tissue augmentation wherein the dermal filler fills a tissue space under an epidermis. In some embodiments, a dermal filler provided herein is used in a method of soft tissue augmentation, wherein the use reduces lines, folds, fine lines, wrinkles, or scars.

In one embodiment, the solution comprising the plant-derived human collagen has a reduced viscosity at room temperature in comparison with an analogous solution comprising a tissue-extracted human or animal-derived collagen in the same concentration and formulation. In another embodiment, the solution comprising the plant-derived human collagen has a reduced viscosity at 37° C. in comparison with an analogous solution comprising a tissue-extracted human or animal-derived collagen in the same concentration and formulation. In yet another embodiment, the solution comprising the plant-derived human collagen is introduced into the tissue space with a reduced force at room temperature as compared with an analogous solution comprising a tissue-extracted human or animal-derived collagen in the same concentration and formulation. In still another embodiment, the solution comprising the plant-derived human collagen is introduced into the tissue space with a reduced force at 37° C. as compared with an analogous solution comprising a tissued-extracted human or animal-derived collagen in the same concentration and formulation. In one particular embodiment, the solution comprising the plant-derived human collagen has an increased scaffolding formation or promotes an increase in cellular growth as compared with an analogous solution comprising a tissue-extracted human or animal-derived collagen in the same concentration and formulation.

In yet another aspect, disclosed herein is a use of a solution injected into a tissue space under an epidermis to induce a cellular growth promoting scaffold, the solution comprising a plant-derived human collagen and at least one growth factor or source thereof, to promote healing or replacement due to degradation or injury of a collagen-comprising tissue. In a particular embodiment, the source of the at least one growth factor comprises a plasma or a platelet-rich plasma.

In embodiment, the collagen-comprising tissue is selected from the group consisting of a tendon, a ligament, skin, a cornea, a cartilage, a blood vessel, an intestine, an intervertebral disc, a muscle, a bone, or a tooth. In another embodiment, the cellular growth promoting scaffold promotes healing of tendinitis. In embodiment, the collagen-comprising tissue is skin.

In some embodiments, there is provided a genetically modified plant which is capable of expressing at least one type of a collagen alpha chain and accumulating it in a subcellular compartment which is devoid of endogenous P4H activity.

As used herein, the phrase "genetically modified plant" refers to any lower (e.g. moss) or higher (vascular) plant or a tissue or an isolated cell thereof (e.g., of a cell suspension) which is stably or transiently transformed with an exogenous polynucleotide sequence. Examples of plants include tobacco, maize, alfalfa, rice, potato, soybean, tomato, wheat, barley, canola, cotton, carrot as well as lower plants such as moss.

As used herein, the phrase "collagen chain" refers to a collagen subunit such as the alpha 1 or 2 chains of collagen fibers, preferably type I fibers. As used herein, the phrase "collagen" refers to an assembled collagen trimer, which in the case of type I collagen includes two alpha 1 chains and one alpha 2 chain. A collagen fiber is collagen which is devoid of terminal propeptides C and N.

As is used herein, the phrase "subcellular compartment devoid of endogenous P4H activity" refers to any compartmentalized region of the cell which does not include plant P4H or an enzyme having plant-like P4H activity. Examples of such subcellular compartments include the vacuole, apoplast and cytoplasm as well as organelles such as the chloroplast, mitochondria and the like.

Any type of collagen chain can be expressed by the genetically modified plant of the present invention. Examples include fibril-forming collagens (types I, II, III, V, and XI), networks forming collagens (types IV, VIII, and X), collagens associated with fibril surfaces (types IX, XII, and XIV), collagens which occur as transmembrane proteins (types XIII and XVII), or form 11-nm periodic beaded filaments (type VI).

In one embodiment, the collagen chain expressed is an alpha 1 and/or 2 chain of type I collagen. The expressed collagen alpha chain can be encoded by any polynucleotide sequences derived from any mammal. In a particular embodiment, the sequences encoding collagen alpha chains are human and are set forth by SEQ ID NOs: 1 and 4.

Typically, alpha collagen chains expressed in plants may or may not include their terminal propeptides (i.e. propeptide C and propeptide N).

Processing of procollagen by plant proteolytic activity is different then normal processing in human and that propeptide C is removed by plant proteolytic activity although the cleavage site is unknown. Cleavage of the C propeptide may take place on a procollagen peptide before the assembly of trimmer (association of three C-Propeptides is essential for initiating the assembly of trimmers).

N-propeptide cleavage by plant proteolytic activity takes place in mature plants but not in plantlets. Such cleavage removes 2 amino acids from the N telopeptide (2 out of 17).

The C-propeptides (and to a lesser extent the N-propeptides) maintain the procollagen soluble during its passage through the animal cell (Bulleid et al., 2000) and are expected to have a similar effect in the plant cell. Following or during secretion of procollagen molecules into the extracellular matrix, propeptides are removed by procollagen N- and C-proteinases, thereby triggering spontaneous self-assembly of collagen molecules into fibrils. Removal of the propeptides by procollagen N- and C-proteinases lowers the solubility of procollagen by >10000-fold and is necessary and sufficient to initiate the self-assembly of collagen into fibers. Crucial to this assembly process are short non-triple-helical peptides called telopeptides at the ends of the triple-helical domain, which ensure correct registration of the collagen molecules within the fibril structure and lower the critical concentration for self-assembly. Pepsin can cleave the propeptides during production of collagen. However, pepsin damages the telopeptides and as a result, pepsin-extracted collagen is unable to form ordered fibrillar structures.

Protein disulfide isomerase (PDI) that forms the beta subunit of human P4H was shown to bind to the C-propeptide prior to trimmer assembly thereby also acting as a molecular chaperone during chain assembly.

The use of human Procollagen I N-proteinase and Procollagen C-proteinase expressed in different plants may generate collagen that is more similar to the native human collagen and can form ordered fibrillar structures.

In a case where N or C propeptides or both are included in the expressed collagen chain, the genetically modified plant of the present invention can also express the respective protease (i.e. C or N or both). Polynucleotide sequences encoding such proteases are exemplified by SEQ ID NOs: 18 (Protease C) and 20 (Protease N). Such proteases can be expressed such that they are accumulated in the same subcellular compartment as the collagen chain.

Accumulation of the expressed collagen chain in a subcellular compartment devoid of endogenous P4H activity can be effected via any one of several approaches.

For example, the expressed collagen chain can include a signal sequence for targeting the expressed protein to a subcellular compartment such as the apoplast or an organelle (e.g. chloroplast). Examples of suitable signal sequences include the chloroplast transit peptide (included in Swiss-Prot entry P07689, amino acids 1-57) and the mitochondrion transit peptide (included in Swiss-Prot entry P46643, amino acids 1-28). The Examples section which follows provides additional examples of suitable signal sequences as well as guidelines for employing such signal sequences in expression of collagen chains in plant cells.

Alternatively, the sequence of the collagen chain can be modified in a way which alters the cellular localization of collagen when expressed in plants.

As is mentioned hereinabove, the ER of plants includes a P4H which is incapable of correctly hydroxylating collagen chains. Collagen alpha chains natively include an ER targeting sequence which directs expressed collagen into the ER where it is post-translationally modified (including incorrect hydroxylation). Thus, removal of the ER targeting sequence will lead to cytoplasmic accumulation of collagen chains which are devoid of post translational modification including any hydroxylations.

Example 1 of the Examples section which follows describes generation of collagen sequences which are devoid of ER sequences.

Still alternatively, collagen chains can be expressed and accumulated in a DNA containing organelle such as the chloroplast or mitochondria. Further description of chloroplast expression is provided hereinbelow.

As is mentioned hereinabove, hydroxylation of alpha chains is required for assembly of a stable type I collagen. Since alpha chains expressed by the genetically modified plant of the present invention accumulate in a compartment devoid of endogenous P4H activity, such chains must be isolated from the plant, plant tissue or cell and in-vitro hydroxylated. Such hydroxylation can be achieved by the method described by Turpeenniemi-Hujanen and Myllyla (Concomitant hydroxylation of proline and lysine residues in collagen using purified enzymes in vitro. Biochim Biophys Acta. 1984 Jul. 16; 800(1):59-65).

Although such in-vitro hydroxylation can lead to correctly hydroxylated collagen chains, it can be difficult and costly to achieve.

To overcome the limitations of in-vitro hydroxylation, the genetically modified plant of the present invention preferably also co-expresses P4H which is capable of correctly hydroxylating the collagen alpha chain(s) [i.e., hydroxylating only the proline (Y) position of the Gly-X-Y triplets]. P4H is an enzyme composed of two subunits, alpha and beta. Both are needed to form an active enzyme while the Beta subunit also posses a chaperon function.

The P4H expressed by the genetically modified plant of the present invention is preferably a human P4H which is encoded by, for example, SEQ ID NOs:12 and 14. In addition, P4H mutants which exhibit enhanced substrate specificity, or P4H homologues can also be used.

A suitable P4H homologue is exemplified by an *Arabidopsis* oxidoreductase identified by NCBI accession NP_179363. Pairwise alignment of this protein sequence and a human P4H alpha subunit conducted by the present inventors revealed the highest homology between functional domains of any known P4H homologs of plants.

Since P4H needs to co-accumulate with the expressed collagen chain, the coding sequence thereof is preferably modified accordingly (addition of signal sequences, deletions which may prevent ER targeting etc).

In mammalian cells, collagen is also modified by Lysyl hydroxylase, galactosyltransferase and glucosyltransferase. These enzymes sequentially modify lysyl residues in specific positions to hydroxylysyl, galactosythydroxylysyl and glucosylgalactosyl hydroxylysyl residues. A single human enzyme, Lysyl hydroxylase 3 (LH3) can catalyze all three consecutive steps in hydroxylysine linked carbohydrate formation.

Thus, the genetically modified plant of the present invention preferably also expresses mammalian LH3. An LH3 encoding sequence such as that set forth by SEQ ID NO: 22 can be used for such purposes.

The collagen chain(s) and modifying enzymes described above can be expressed from a stably integrated or a transiently expressed nucleic acid construct which includes polynucleotide sequences encoding the alpha chains and/or modifying enzymes (e.g. P4H and LH3) positioned under the transcriptional control of plant functional promoters. Such a nucleic acid construct (which is also termed herein as an expression construct) can be configured for expression throughout the whole plant, defined plant tissues or defined plant cells, or at define developmental stages of the plant. Such a construct may also include selection markers (e.g. antibiotic resistance), enhancer elements and an origin of replication for bacterial replication.

It will be appreciated that constructs including two expressible inserts (e.g. two alpha chain types, or an alpha chain and P4H) preferably include an individual promoter for each insert, or alternatively such constructs can express a single transcript chimera including both insert sequences from a single promoter. In such a case, the chimeric transcript includes an IRES sequence between the two insert sequences such that the downstream insert can be translated therefrom.

Numerous plant functional expression promoters and enhancers which can be either tissue specific, developmentally specific, constitutive or inducible can be utilized by the constructs of the present invention, some examples are provided hereinunder.

As used herein in the specification and in the claims section that follows the phrase "plant promoter" or "promoter" includes a promoter which can direct gene expression in plant cells (including DNA containing organelles). Such a promoter can be derived from a plant, bacterial, viral, fungal or animal origin. Such a promoter can be constitutive, i.e., capable of directing high level of gene expression in a plurality of plant tissues, tissue specific, i.e., capable of directing gene expression in a particular plant tissue or tissues, inducible, i.e., capable of directing gene expression under a stimulus, or chimeric, i.e., formed of portions of at least two different promoters.

Thus, the plant promoter employed can be a constitutive promoter, a tissue specific promoter, an inducible promoter or a chimeric promoter.

Examples of constitutive plant promoters include, without being limited to, CaMV35S and CaMV19S promoters, FMV34S promoter, sugarcane bacilliform badnavirus promoter, CsVMV promoter, *Arabidopsis* ACT2/ACT8 actin promoter, *Arabidopsis* ubiquitin UBQI promoter, barley leaf thionin BTH6 promoter, and rice actin promoter.

Examples of tissue specific promoters include, without being limited to, bean phaseolin storage protein promoter, DLEC promoter, PHS promoter, zein storage protein promoter, conglutin gamma promoter from soybean, AT2S1 gene promoter, ACT11 actin promoter from *Arabidopsis*, napA promoter from *Brassica napus* and potato patatin gene promoter.

The inducible promoter is a promoter induced by a specific stimuli such as stress conditions comprising, for example, light, temperature, chemicals, drought, high salinity, osmotic shock, oxidant conditions or in case of pathogenicity and include, without being limited to, the light-inducible promoter derived from the pea rbcS gene, the promoter from the alfalfa rbcS gene, the promoters DRE, MYC and MYB active in drought; the promoters INT, INPS, prxEa, Ha hsp17.7G4 and RD21 active in high salinity and osmotic stress, and the promoters hsr203J and str246C active in pathogenic stress.

Preferably the promoter utilized by the present invention is a strong constitutive promoter such that over expression of the construct inserts is effected following plant transformation.

It will be appreciated that any of the construct types used in the present invention can be co-transformed into the same plant using same or different selection markers in each construct type. Alternatively, the first construct type can be introduced into a first plant while the second construct type can be introduced into a second isogenic plant, following which the transgenic plants resultant therefrom can be crossed and the progeny selected for double transformants. Further self-crosses of such progeny can be employed to generate lines homozygous for both constructs.

There are various methods of introducing nucleic acid constructs into both monocotyledonous and dicotyledenous plants (Potrykus, I., Annu. Rev. Plant. Physiol., Plant. Mol. Biol. (1991) 42:205-225; Shimamoto et al., Nature (1989) 338:274-276). Such methods rely on either stable integration of the nucleic acid construct or a portion thereof into the genome of the plant, or on transient expression of the nucleic acid construct in which case these sequences are not inherited by a progeny of the plant.

In addition, several methods exist in which a nucleic acid construct can be directly introduced into the DNA of a DNA containing organelle such as a chloroplast.

There are two principle methods of effecting stable genomic integration of exogenous sequences such as those included within the nucleic acid constructs of the present invention into plant genomes:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledenous plants.

There are various methods of direct DNA transfer into plant cells. In electroporation, protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals, tungsten particles or gold particles, and the microprojectiles are physically accelerated into cells or plant tissues.

Following transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different, and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Transient expression methods which can be utilized for transiently expressing the isolated nucleic acid included within the nucleic acid construct of the present invention include, but are not limited to, microinjection and bombardment as described above but under conditions which favor transient expression, and viral mediated expression wherein a packaged or unpackaged recombinant virus vector including the nucleic acid construct is utilized to infect plant tissues or cells such that a propagating recombinant virus established therein expresses the non-viral nucleic acid sequence.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, the constructions can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

The above described transformation approaches can be used to produce collagen chains and/or modifying enzymes as well as assembled collagen (with or without propeptides) in any species of plant, or plant tissue or isolated plants cell derived therefrom.

Preferred plants are those which are capable of accumulating large amounts of collagen chains, collagen and/or the processing enzymes described herein. such plants may also be selected according to their resistance to stress conditions and the ease at which expressed components or assembled collagen can be extracted. examples of preferred plants include tobacco, maize, alfalfa, rice, potato, soybean, tomato, wheat, barley, canola and cotton.

Collagen fibers are extensively used in the food and cosmetics industry. thus, although collagen fiber components (alpha chains) and modifying enzymes expressed by plants find utility in industrial synthesis of collagen, complete collagen production in plants is preferred for its simplicity and cost effectiveness.

Several approaches can be used to generate type I collagen in plants. For example, collagen alpha 1 chain can be isolated from a plant expressing collagen alpha 1 and P4H (and optionally LH3) and mixed with a collagen alpha 2 chain which is isolated from a plant expressing collagen alpha 2 and P4H (and optionally LH3 and protease C and/or N). Since collagen alpha 1 chain self assembles into a triple helix by itself, it may be necessary to denature such a homo-trimer prior to mixing and renaturation with the collagen alpha 2 chain.

Preferably, a first plant expressing collagen alpha 1 and P4H (and optionally LH3 and protease C and/or N) can be crossed with a second (and preferably isogenic) plant which expresses collagen alpha 2 or alternatively, a first plant expressing both alpha chains can be crossed with a second plant expressing P4H and optionally LH3 and protease C and/or N.

It should be noted that although the above described plant breeding approaches utilize two individually transformed plants, approaches which utilize three or more individually transformed plants, each expressing one or two components can also be utilized.

One of ordinary skill in the art would be well aware of various plant breeding techniques and as s such no further description of such techniques is provided herein.

Although plant breeding approaches are preferred, it should be noted that a single plant expressing collagen alpha 1 and 2, P4H and LH3 (and optionally protease C and/or N) can be generated via several transformation events each designed for introducing one more expressible components into the cell. In such cases, stability of each transformation event can be verified using specific selection markers.

In any case, transformation and plant breeding approaches can be used to generate any plant, expressing any number of components. Presently preferred are plants which express collagen alpha 1 and 2 chains, P4H, LH3 and at least one protease (e.g. protease C and/or N). As is further described in the Examples section which follows, such plants accumulate collagen which exhibits stability at temperatures of up to 42° C.

Progeny resulting from breeding or alternatively multiple-transformed plants can be selected, by verifying presence of exogenous mRNA and/or polypeptides by using nucleic acid or protein probes (e.g. antibodies). The latter approach is preferred since it enables localization of the expressed polypeptide components (by for example, probing fractionated plants extracts) and thus also verifies a potential for correct processing and assembly. Examples of suitable probes are provided in the Examples section which follows Once collagen-expressing progeny is identified, such plants are further cultivated under conditions which maximize expression of the collagen chains as well as the modifying enzymes.

Since free proline accumulation may facilitate over production of different proline-rich proteins including the collagen chains expressed by the genetically modified plants of the present invention, preferred cultivating conditions are those which increase free proline accumulation in the cultivated plant.

Free proline accumulates in a variety of plants in response to a wide range of environmental stresses including water deprivation, salinization, low temperature, high temperature, pathogen infection, heavy metal toxicity, anaerobiosis, nutrient deficiency, atmospheric pollution and UV-irradiation (Hare and Cress, 1997).

Free proline may also accumulate in response to treatment of the plant or soil with compounds such as ABA or stress inducing compounds such as copper salt, paraquate, salicylic acid and the like.

Thus, collagen-expressing progeny can be grown under different stress conditions (e.g. different concentrations of NaCl ranging from 50 mM up to 250 mM). In order to further enhance collagen production, the effect of various stress conditions on collagen expression will examined and optimized with respect to plant viability, biomass and collagen accumulation.

Plant tissues/cells are preferably harvested at maturity, and the collagen fibers are isolated using well know prior art extraction approaches, one such approach is detailed below.

Leaves of transgenic plants are ground to a powder under liquid nitrogen and the homogenate is extracted in 0.5 M acetic acid containing 0.2 M NaCl for 60 h at 4° C. Insoluble material is removed by centrifugation. The supernatant containing the recombinant collagen is salt-fractionated at 0.4 M and 0.7 M NaCl. The 0.7 M NaCl precipitate, containing the recombinant heterotrimeric collagen, is dissolved in and dialyzed against 0.1 M acetic acid and stored at −20° C. (following Ruggiero et al., 2000).

In one embodiment, disclosed herein is a method of processing procollagen in order to generate homogeneous, soluble, fibril-forming atelocollagen.

Figure 26:
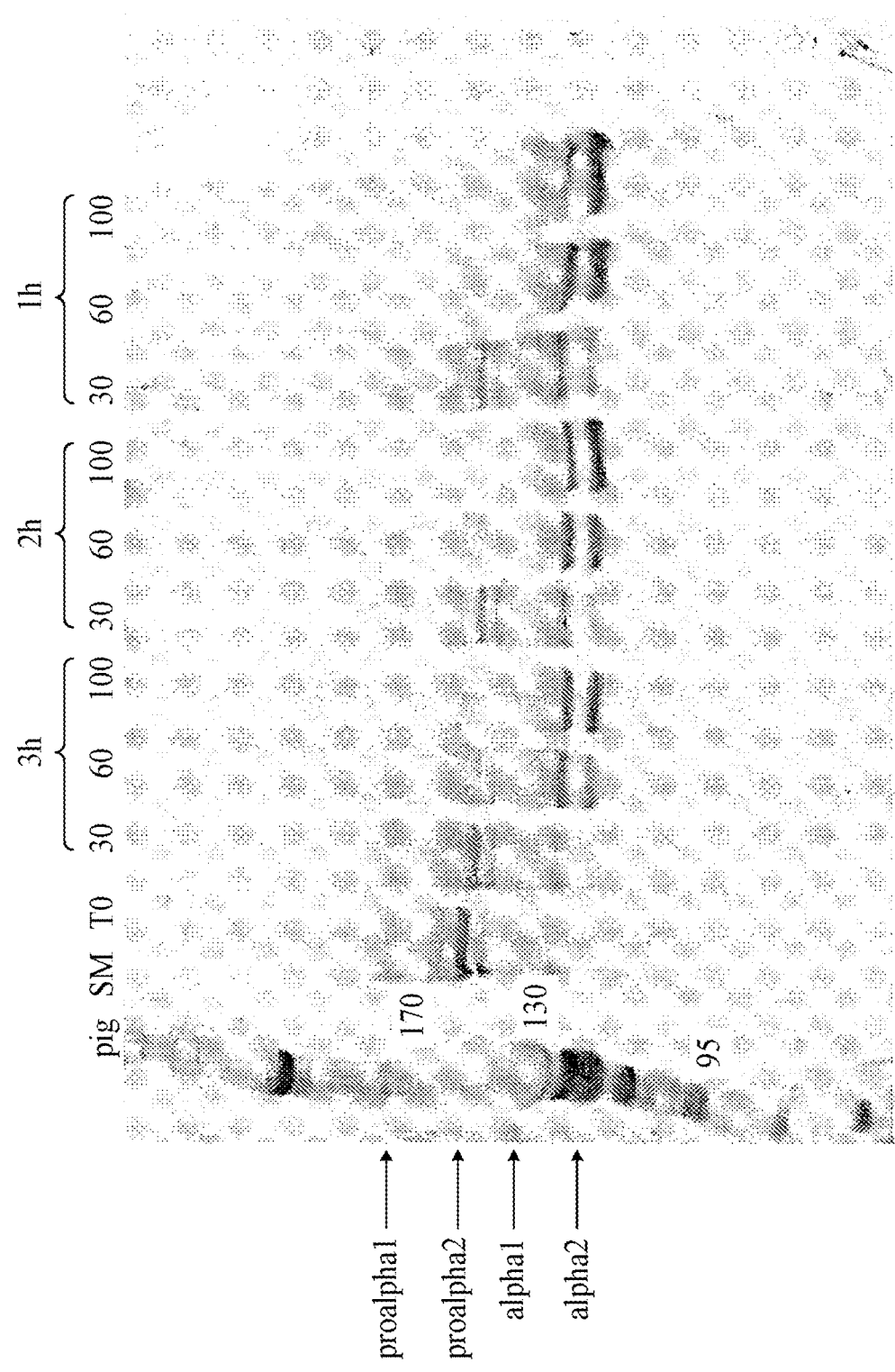
FIG. 26 shows effective procollagen digestion by recombinant trypsin at pH 7.5. AMS-pelleted procollagen-expressing tobacco leaf extracts were resuspended in extraction buffer (pH 7.5) containing L-cystein and EDTA. Samples were then incubated with 30-100 mg/L recombinant trypsin at 15° C. for 1-3 hrs. Cleavage was terminated by centrifugation and protein samples were separated on 8% SDS-PAGE, transferred to nitrocellulose membranes and immunoblotted for alpha-1 and alpha-2 collagen chains with anti-collagen I.

In some embodiments, as shown herein by analysis of proteolysis results by SDS PAGE, certain plant-derived proteases, (e.g. papain), are not capable of cleaving the propeptide portion from soluble procollagen without proteolytic cleavage within the helical region (even though they are capable of removing telopeptides from telocollagen originating from animal sources), while other proteases (e.g. esperase, savinase) do not effectively cleave the propeptide region from soluble procollagen, thereby hindering effective fibrillogenesis. Through meticulous experimentation, the present inventors uncovered that only particular plant-derived proteases such as ficin, and bacterial-derived proteases such as neutrase and subtilisin may be used to correctly cleave the propeptide portion (including the telopeptides) from soluble procollagen to generate a homogeneous preparation of soluble atelocollagen (FIGS. 13, 15, 17, 19, and 20) without digesting the helical region of the non-animal procollagen. In addition, the present inventors showed that a recombinant trypsin is also capable of correct cleavage (FIG. 26). The present inventors further showed that cleavage with ficin allows the resultant atelocollagen to retain its fibrillogenic capacity (Table 5 of the Examples section herein below).

Thus, according to one aspect, there is provided a method of generating atelocollagen. The method comprises contacting a human recombinant telopeptide-comprising collagen with a protease selected from the group consisting of neutrase, subtilisin, recombinant trypsin, recombinant pepsin and ficin, wherein the human recombinant telopeptide-comprising collagen is expressed in a non-animal cell, thereby generating the atelocollagen.

As used herein, the phrase "telopeptide-comprising collagen" refers to a soluble collagen molecule which comprises telopeptides that are longer than the telopeptide remnants comprised in atelocollagen. Thus, the telopeptide-comprising collagen may be procollagen which comprises full length propeptides. Alternatively, the telopeptide-comprising collagen may be a procollagen molecule which comprises partially digested propeptides. Still alternatively, the telopeptide-comprising collagen may be telocollagen.

The term "procollagen" as used herein, refers to a collagen molecule (e.g. human) that comprises either an N-terminal propeptide, a C-terminal propeptide or both. Exemplary human procollagen amino acid sequences are set forth by SEQ ID NOs: 30, 31, 36, and 37.

The term "telocollagen" as used herein, refers to collagen molecules that lack both the N- and C-terminal propeptides typically comprised in procollagen but still contain the telopeptides. As mentioned in the Background section herein above, the telopeptides of fibrillar collagen are the remnants of the N- and C-terminal propeptides following digestion with native N/C proteinases.

Recombinant human telocollagen may be generated in cells which have been transformed to express both exogenous human procollagen and the respective protease (i.e. C or N or both). Polynucleotide sequences encoding such proteases are exemplified by SEQ ID NOs: 39 (Protease C) and 40 (Protease N). Such proteases can be expressed such that they are accumulated in the same subcellular compartment as the collagen chain, as further described herein below.

As used herein, the term "atelocollagen" refers to collagen molecules lacking both the N- and C-terminal propeptides typically comprised in procollagen and at least a portion of its telopeptides but including a sufficient portion of its telopeptides such that under suitable conditions it is capable of forming fibrils.

Any type of atelocollagen may be generated according to the methods disclosed herein. Examples include fibril-forming collagens (types I, II, III, V, and XI), network-forming collagens (types IV, VIII, and X), collagens associated with fibril surfaces (types IX, XII, and XIV), collagens which occur as transmembrane proteins (types XIII and XVII), or form 11-nm periodic beaded filaments (type VI). According to one embodiment, the atelocollagen comprises an alpha-1 and/or alpha-2 chain of type I collagen.

It will be appreciated that in some embodiments, disclosed herein are genetically modified forms of collagen/atelocollagen—for example collagenase-resistant collagens and the like.

The recombinant human procollagen or telocollagen may be expressed in any non-animal cell, including but not limited to plant cells and other eukaryotic cells such as yeast and fungus.

Plants in which the human procollagen or telocollagen may be produced (i.e. expressed) may be of lower (e.g. moss and algae) or higher (vascular) plant species, including tissues or isolated cells and extracts thereof (e.g. cell suspensions). Preferred plants are those which are capable of accumulating large amounts of collagen chains, collagen and/or the processing enzymes described herein below. Such plants may also be selected according to their resistance to stress conditions and the ease at which expressed components or assembled collagen can be extracted. Examples of plants in which human procollagen may be expressed include, but are not limited to tobacco, maize, alfalfa, rice, potato, soybean, tomato, wheat, barley, canola, carrot, lettuce and cotton.

Production of recombinant human procollagen is typically effected by stable or transient transformation with an exogenous polynucleotide sequence encoding human procollagen.

Exemplary polynucleotide sequences encoding human procollagen are set forth by SEQ ID NOs: 32, 33, 41, and 42.

As mentioned, production of human telocollagen is typically effected by stable or transient transformation with an exogenous polynucleotide sequence encoding human procollagen and at least one exogenous polynucleotide sequence encoding the relevant protease.

The stability of the triple-helical structure of collagen requires the hydroxylation of prolines by the enzyme prolyl-4-hydroxylase (P4H) to form residues of hydroxyproline within the collagen chain. Although plants are capable of synthesizing hydroxyproline-containing proteins, the prolyl hydroxylase that is responsible for synthesis of hydroxyproline in plant cells exhibits relatively loose substrate sequence specificity as compared with mammalian P4H. Thus, production of collagen containing hydroxyproline only in the Y position of Gly-X-Y triplets requires co-expression of collagen and human or mammalian P4H genes.

Thus, according to one embodiment, the procollagen or telocollagen is expressed in a subcellular compartment of a plant that is devoid of endogenous P4H activity so as to avoid incorrect hydroxylation thereof. As is used herein, the phrase "subcellular compartment devoid of endogenous P4H activity" refers to any compartmentalized region of the cell which does not include plant P4H or an enzyme having plant-like P4H activity. According to one embodiment, the subcellular compartment is a vacuole.

Accumulation of the expressed procollagen in a subcellular compartment devoid of endogenous P4H activity can be affected via any one of several approaches.

For example, the expressed procollagen/telocollagen can include a signal sequence for targeting the expressed protein to a subcellular compartment such as the apoplast or an organelle (e.g. chloroplast). Examples of suitable signal sequences include the chloroplast transit peptide (included in Swiss-Prot entry P07689, amino acids 1-57) and the Mitochondrion transit peptide (included in Swiss-Prot entry P46643, amino acids 1-28).

Alternatively, the sequence of the procollagen can be modified in a way which alters the cellular localization of the procollagen when expressed in plants.

In some embodiments, disclosed herein are genetically modified cells co-expressing both human procollagen and a P4H, capable of correctly hydroxylating the procollagen alpha chain(s) [i.e. hydroxylating only the proline (Y) position of the Gly-X-Y triplets]. P4H is an enzyme composed of two subunits, alpha and beta as set forth in Genbank Nos. P07237 and P13674. Both subunits are necessary to form an active enzyme, while the beta subunit also possesses a chaperon function.

The P4H expressed by the genetically modified cells of the present invention is preferably a human P4H which is encoded by, for example, SEQ ID NOs: 34 and 35. In addition, P4H mutants which exhibit enhanced substrate specificity, or P4H homologues can also be used. A suitable P4H homologue is exemplified by an *Arabidopsis* oxidoreductase identified by NCBI accession no: NP_179363.

Since it is essential that P4H co-accumulates with the expressed procollagen chain, the coding sequence thereof is preferably modified accordingly (e.g., by addition or deletion of signal sequences).

In mammalian cells, collagen is also modified by Lysyl hydroxylase, galactosyltransferase and glucosyltransferase. These enzymes sequentially modify lysyl residues in specific positions to hydroxylysyl, galactosylhydroxylysyl and glucosylgalactosyl hydroxylysyl residues at specific positions. A single human enzyme, Lysyl hydroxylase 3 (LH3), as set forth in Genbank No. 060568, can catalyze all three consecutive modifying steps as seen in hydroxylysine-linked carbohydrate formation.

Thus, the genetically modified cells disclosed herein, may also express mammalian LH3. An LH3 encoding sequence such as that set forth by SEQ ID NO: 38 can be used for such purposes.

The procollagen (s) and modifying enzymes described above can be expressed from a stably integrated or a transiently expressed nucleic acid construct which includes polynucleotide sequences encoding the procollagen alpha chains and/or modifying enzymes (e.g. P4H and LH3) positioned under the transcriptional control of functional promoters. Such a nucleic acid construct (which is also termed herein as an expression construct) can be configured for expression throughout the whole organism (e.g. plant, defined tissues or defined cells), and/or at defined developmental stages of the organism. Such a construct may also include selection markers (e.g. antibiotic resistance), enhancer elements and an origin of replication for bacterial replication.

It will be appreciated that constructs including two expressible inserts (e.g. two alpha procollagen chain types, or a procollagen alpha chain and P4H) preferably include an individual promoter for each insert, or alternatively such constructs can express a single transcript chimera including both insert sequences under a single promoter. In such a case, the chimeric transcript may include an intraribosomal entry region (IRES) sequence between the two insert sequences such that the downstream insert can be translated therefrom.

Numerous functional expression promoters and enhancers which can be either tissue specific, developmentally specific, constitutive or inducible can be utilized by the constructs of the present invention, some examples are provided herein under.

Regardless of the transformation technique employed, once procollagen-expressing progeny are identified, such plants are further cultivated under conditions which maximize expression thereof. Progeny resulting from transformed plants can be selected, by verifying presence of exogenous mRNA and/or polypeptides by using nucleic acid or protein probes (e.g. antibodies). The latter approach enables localization of the expressed polypeptide components (by for example, probing fractionated plants extracts) and thus also verifies the plant's potential for correct processing and assembly of the foreign protein.

Following cultivation of such plants, the telopeptide-comprising collagen is typically harvested. Plant tissues/cells are preferably harvested at maturity, and the procollagen molecules are isolated using extraction approaches. Preferably, the harvesting is effected such that the procollagen remains in a state that it can be cleaved by protease enzymes. According to one embodiment, a crude extract is generated from the transgenic plants of the present invention and subsequently contacted with the protease enzymes. An exemplary method for generating a plant crude extract is described in the Examples section herein under.

It will be appreciated that the propeptide or telopeptide-comprising collagen may be purified from the genetically engineered cells of the present invention prior to incubation with protease, or alternatively may be purified following incubation with the protease. Still alternatively, the propeptide or telopeptide-comprising collagen may be partially purified prior to protease treatment and then fully purified following protease treatment. Yet alternatively, the propeptide or telopeptide-comprising collagen may be treated with protease concomitant with other extraction/purification procedures.

Exemplary methods of purifying or semi-purifying the telopeptide-comprising collagen of the present invention include, but are not limited to, salting out with ammonium sulfate or the like and/or removal of small molecules by ultrafiltration.

As described in the Background herein above, there is a risk involved in using animal source material for medical purposes. This risk is also relevant when selecting the proteolytic enzymes used in processing the procollagen expressed in plants to atelocollagen. Application of animal-derived source enzymes such as trypsin or pepsin, may in itself contaminate the final preparation with disease carriers. It is therefore desired to devise a production system where all components are free of animal source.

It has been disclosed herein that only particular proteases are capable of correctly cleaving recombinant propeptide or telopeptide-comprising collagen. These include certain plant derived proteases e.g. ficin (EC 3.4.22.3) and certain bacterial derived proteases e.g. subtilisin (EC 3.4.21.62), neutrase. In some embodiments, disclosed herein is a use of recombinant enzymes such as rhTrypsin and rhPepsin Such enzymes are commercially available e.g. Ficin from Fig tree latex (Sigma, catalog #F4125 and Europe Biochem), Subtilisin from *Bacillus licheniformis* (Sigma, catalog #P5459) Neutrase from bacterium *Bacillus amyloliquefaciens* (Novozymes, catalog #PW201041) and TrypZean™, a recombinant human trypsin expressed in corn (Sigma catalog #T3449).

The procollagen or telocollagen is preferably contacted with the proteases under conditions such that the proteases are able to cleave the propeptides or telopeptides therefrom. Typically, the conditions are determined according to the particular protease selected. Thus, for example procollagen may be incubated with a protease for up to 15 hours, at a concentration of 1-25 mg/ml and a temperature of about 10-20° C.

Following protease digestion, the generated atelocollagen may be further purified e.g. by salt precipitation, as described in the Examples section below so that the end product comprises a purified composition of atelocollagen having been processed from plant or plant-cell generated procollagen by a protease selected from the group consisting of neutrase, subtilisin, ficin and recombinant human trypsin and analyzed using methods known in the art (e.g. size analysis via Coomassie staining, Western analysis, etc.).

Following purification, the atelocollagen may be resolubilized by addition of acidic solutions (e.g. 10 mM HCl). Such acidic solutions are useful for storage of the purified atelocollagen.

The present inventors have shown that following digestion with ficin, the atelocollagen maintains its ability to form fibrils upon neutralization of the above described acid solutions. According to one embodiment, at least 70% of the purified and resolubilized atelocollagen generated according to the method of the present invention is capable of forming fibrils. According to one embodiment, at least 88% of the purified and resolubilized atelocollagen generated according to the method of the present invention is capable of forming fibrils.

The ability to form fibrils demonstrates that the generated atelocollagen is useful for medical purposes including, but not limited to cosmetic surgery, healing aid for burn patients, reconstruction of bone and a wide variety of dental, orthopedic and surgical purposes.

As noted in the Background section, Type I collagen is considered a perfect candidate for use as a major component of a building material in 3D-bioprinting. Despite the significant advantages offered by this natural polymer, a number of factors hinder its use for 3D bioprinting. The use of tissue extracted collagen for this purpose is limited due to its sensitivity to temperature and ionic strength which drives spontaneous gel formation at temperatures higher than 20° C., under physiological conditions [see, for example, PureCol, Advanced BioMatrix, Inc.]. The typical temperature-dependent formation of gel of tissue extracted-collagens hampers significantly the precise fluidity during printing. Keeping the printing media at low temperature until application is a possible solution for this phenomenon but implies a serious technical limitation. Another solution is the use of gelatin, the denatured form of collagen which does not become gel-like under these conditions. However, gelatin lacks the genuine tissue and cell interactions of native collagen and thus crucial biological functions are lost.

Recent developments in technology have resulted in the development of a system for the purification of naïve human Type I collagen (rhCollagen) by introducing into tobacco plants, five human genes encoding heterotrimeric type I collagen (COLLPLANT™, Israel; now also available at SIGMA-ALDRICH®, St. Louis, MO., USA). The protein is purified to homogeneity through a cost-effective industrial process taking advantage of collagen's unique properties. See also WO 2006/035442, WO 2009/053985, and patents and patent applications deriving therefrom, all of which are incorporated by reference as if fully set forth herein.

Thus, according to one aspect, disclosed herein is a genetically modified plant which is capable of expressing at least one type of a collagen alpha chain and accumulating it in a subcellular compartment which is devoid of endogenous P4H activity.

Type I collagen and rhCollagen are considered candidates for use as a major component of a building material in 3D-bioprinting. Scaffolding of various types has been used for cosmetic and other reconstructive applications.

In addition, there has been an increase in the use of dermal fillers for soft tissue augmentation, e.g., the reduction of wrinkles. One possible method for the use of dermal fillers includes injection of a polymerizable dermal filler material into the desired area, followed by the contouring or molding of the filler into the desired conformation. Polymerization and cross-linking of the material by one of various methods can transform the monomers in the injected material to form polymers and chains, which can form networks, retaining the desired molded conformation. There are a number of methods to form polymers and to crosslink polymers. One method involves light-reactive reagents and light-induced reactions which create reactive species in a monomer solution.

However, at least some of these approaches continue to focus on tissue-derived collagens or non-collagen polymers (e.g., poly(vinyl alcohol) or hyaluronic acid). Moreover, the use of tissue extracted collagen is limited due to its sensitivity to temperature and ionic strength which drives spontaneous gel formation at temperatures higher than 20° C., under physiological conditions [see, for example, PureCol, Advanced BioMatrix, Inc.]. The typical temperature-dependent formation of gel of tissue extracted-collagens hampers significantly the precise fluidity. Keeping the collagens at low temperature until application is a possible solution for this phenomenon but implies a serious technical limitation. Another solution is the use of gelatin, the denatured form of collagen which does not become gel-like under these conditions. However, gelatin lacks the genuine tissue and cell interactions of native collagen and thus crucial biological functions are lost. Moreover, the viscosity makes it more difficult to be injected under the dermis using fine-gauge needles and also makes it more difficult to spread and mold it into smaller cavities.

Embodiments of dermal fillers and uses thereof disclosed herein, include but are not limited to:

1. A method of filling a tissue space under an epidermis comprising:
   a. introducing a polymerizable solution into the tissue space, the polymerizable solution comprising:
      i. a cross-linkable, plant-derived human collagen; and
      ii. a photoinitiator; and
   b. applying light to the surface of the epidermis superficial to said space to induce polymerization.
2. A method of filling a tissue space under an epidermis, further comprising:
   (a) a step of molding or sculpting the polymerizable solution into a desired configuration in the tissue space, wherein said step is concomitant with, or subsequent to, the step of applying light.
3. A method of filling a tissue space under an epidermis, wherein the molding or sculpting step reduces lines, folds, fine lines, wrinkles, or scars.
4. A method of filling a tissue space under an epidermis, wherein the cross-linkable, plant-derived human collagen is methacrylated or thiolated.
5. A method of filling a tissue space under an epidermis, the polymer solution further comprising a hyaluronic acid (HA) or modified derivative thereof, a poly(vinyl alcohol) (PVA) or modified derivative thereof, a polyethylene glycol (PEG) or modified derivative thereof, oxidized cellulose (OC) or a modified derivate thereof, polymethylmethacrylate (PMMA) microspheres or a modified derivative thereof, tricalcium phosphate (TCP) or a modified derivative thereof, calcium hydroxylapatite (CaHA) or a modified derivative thereof, carboxymethylcellulose or a modified derivative thereof, crystalline nanocellulose (CNC) or a modified derivative thereof, or a combination thereof.
6. A method of filling a tissue space under an epidermis, wherein the modified derivative of hyaluronic acid (HA), a poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a photopolymerizable modified derivative.
7. The method of claim 5, wherein the modified derivative of hyaluronic acid (HA), a poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a methacrylated or thiolated derivative.
8. A method of filling a tissue space under an epidermis, wherein the plant-derived collagen comprises rhCollagen.
9. A method of filling a tissue space under an epidermis, wherein the plant-derived collagen is obtained from a genetically modified plant.
10. A method of filling a tissue space under an epidermis, wherein the genetically modified plant is a genetically modified plant selected from the group consisting of tobacco, maize, alfalfa, rice, potato, soybean, tomato, wheat, barley, canola, carrot, and cotton.
11. A method of filling a tissue space under an epidermis, wherein the genetically modified plant is a tobacco plant.
12. A method of filling a tissue space under an epidermis, wherein the genetically modified plant comprises an expressible sequence of at least one gene sequence of human deoxyribonucleic acid (DNA) selected from the group consisting of: COL1, COL2, P4H-alpha, P4H-beta, and LH3.
13. A method of filling a tissue space under an epidermis, wherein the plant-derived human collagen comprises at least modified one human collagen alpha-1 chain as set forth in SEQ ID NO: 3 and as expressed in the genetically modified plant; and at least one modified human collagen alpha-2 chain as set forth in SEQ ID NO: 6 and as expressed in the genetically modified plant; and wherein the genetically modified plant further expresses an exogenous prolyl-4-hydroxylase (P4H).
14. A method of filling a tissue space under an epidermis, further comprising expressing an exogenous polypeptide selected from the group consisting of lysyl hydroxylase (LH), protease N, and protease C.
15. A method of filling a tissue space under an epidermis, wherein the human collagen alpha-1 chain is encoded by a sequence as set forth in SEQ ID NO: 1.
16. A method of filling a tissue space under an epidermis, wherein the human collagen alpha-2 chain is encoded by a sequence as set forth in SEQ ID NO: 2.
17. A method of filling a tissue space under an epidermis, wherein the exogenous P4H is a mammalian P4H.
18. A method of filling a tissue space under an epidermis, wherein the exogenous P4H is a human P4H.
19. A method of filling a tissue space under an epidermis, further comprising targeting the human collagen alpha-1 to a vacuole of the plant or the genetically modified plant and digesting it with ficin.
20. A method of filling a tissue space under an epidermis, further comprising targeting the human collagen alpha-2 to a vacuole of the plant or the genetically modified plant and digesting it with ficin.
21. A method of filling a tissue space under an epidermis, wherein the plant-derived human collagen is atelocollagen.
22. A method of filling a tissue space under an epidermis, wherein the light source comprises a light-emitting diode (LED), laser, or xenon lamp.
23. A method of filling a tissue space under an epidermis, wherein the photoinitiator induces polymerization of the polymerizable solution in response to visible light.
24. A method of filling a tissue space under an epidermis, wherein the visible light has a wavelength of 390-700 nm.
25. A method of filling a tissue space under an epidermis, wherein the photoinitiator is selected from the group consisting of Eosin Y+triethanolamine or riboflavin.
26. A method of filling a tissue space under an epidermis, wherein the photoinitiator induces polymerization of the polymerizable solution in response to ultraviolet (uv) light.
27. A method of filling a tissue space under an epidermis, wherein the photoinitiator is selected from the group consisting of lithium phenyl-2,4,6-trimethylbenzoylphosphinate (LAP) or 1-[4 2-hydroxy-1-[4-(2-hydroxyethoxy)phenyl]-2-methylpropan-1-one (IRGACURE® 2959).
28. A method of filling a tissue space under an epidermis, wherein the photoinitiator induces polymerization of the polymerizable solution in response to infrared light.
29. A method of filling a tissue space under an epidermis, wherein the polymerizable solution is introduced into the tissue space via a hollow needle or canula in the range of 27-gauge to 33-gauge.
30. A method of filling a tissue space under an epidermis, wherein the polymerizable solution in the tissue space is molded or sculpted into the desired configuration via manual massage.
31. A method of filling a tissue space under an epidermis, wherein the polymerizable solution in the tissue space is molded or sculpted into the desired configuration using a molding or sculpting implement.

32. A method of filling a tissue space under an epidermis, wherein the polymerizable solution in the tissue space is essentially non-gellable at room temperature.

33. A method of filling a tissue space under an epidermis, wherein the polymerizable solution in the tissue space is essentially non-gellable at 37° C.

34. A method of filling a tissue space under an epidermis, wherein the polymerizable solution comprising the plant-derived human collagen has a reduced viscosity at room temperature in comparison with an analogous polymerizable solution comprising a tissue-extracted human or bovine collagen in the same concentration and formulation.

35. A method of filling a tissue space under an epidermis, wherein the polymerizable solution comprising the plant-derived human collagen has a reduced viscosity at 37° C. in comparison with an analogous polymerizable solution comprising a tissue-extracted human or bovine collagen in the same concentration and formulation.

36. A method of filling a tissue space under an epidermis, wherein the polymerizable solution comprising the plant-derived human collagen is introduced into the tissue space with a reduced force at room temperature as compared with an analogous polymerizable solution comprising a tissue-extracted human or bovine collagen in the same concentration and formulation.

37. A method of filling a tissue space under an epidermis, wherein the polymerizable solution comprising the plant-derived human collagen is introduced into the tissue space with a reduced force at 37° C. as compared with an analogous polymerizable solution comprising a tissued-extracted human or bovine collagen in the same concentration and formulation.

38. A method of filling a tissue space under an epidermis, wherein the polymerizable solution comprising the plant-derived human collagen has an increased tissue augmentation as compared with an analogous polymerizable solution comprising a tissue-extracted human or bovine collagen in the same concentration and formulation.

39. Use of a polymerizable solution injected into a tissue space under an epidermis to reduce lines, folds, fine lines, wrinkles, or scars, the polymerizable solution comprising a cross-linkable, plant-derived human collagen and a photoinitiator to induce polymerization prior to, on concomitant with, application of visible light, and molding or sculpting the polymerizable solution into a desired configuration to reduce lines, folds, fine lines, wrinkles, or scars.

40. Use of a polymerizable solution injected into a tissue space under an epidermis to reduce lines, folds, fine lines, wrinkles, or scars, wherein the cross-linkable, plant-derived human collagen is methacrylated or thiolated.

41. Use of a polymerizable solution injected into a tissue space under an epidermis to reduce lines, folds, fine lines, wrinkles, or scars, wherein the polymer solution further comprises a hyaluronic acid (HA) or a modified derivative thereof, a poly(vinyl alcohol) (PVA) or a modified derivative thereof, a polyethylene glycol (PEG) or a modified derivative thereof, polymethylmethacrylate (PMMA) microspheres or a modified derivative thereof, tricalcium phosphate (TCP) or a modified derivative thereof, calcium hydroxylapatite (CaHA) or a modified derivative thereof, carboxymethylcellulose or a modified derivative thereof, crystalline nanocellulose (CNC) or a modified derivative thereof, or a combination thereof.

42. Use of a polymerizable solution injected into a tissue space under an epidermis to reduce lines, folds, fine lines, wrinkles, or scars, wherein the modified derivative of hyaluronic acid (HA), a poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a photopolymerizable modified derivative.

43. Use of a polymerizable solution injected into a tissue space under an epidermis to reduce lines, folds, fine lines, wrinkles, or scars, wherein the modified derivative of hyaluronic acid (HA), a poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a methacrylated or thiolated derivative.

44. A method of filling a tissue space under an epidermis comprising:
introducing a polymerizable solution into the tissue space, the polymerizable solution comprising a cross-linkable, plant-derived human collagen.

45. A method of filling a tissue space under an epidermis, further comprising:
  (a) a step of molding or sculpting the polymerizable solution into a desired configuration in the tissue space.

46. A method of filling a tissue space under an epidermis, wherein the molding or sculpting step reduces lines, folds, fine lines, wrinkles, or scars.

47. A method of filling a tissue space under an epidermis, the polymerizable solution further comprising a hyaluronic acid (HA) or modified derivative thereof, a poly(vinyl alcohol) (PVA) or modified derivative thereof, a polyethylene glycol (PEG) or modified derivative thereof, oxidized cellulose (OC) or a modified derivate thereof, polymethylmethacrylate (PMMA) microspheres or a modified derivative thereof, tricalcium phosphate (TCP) or a modified derivative thereof, calcium hydroxylapatite (CaHA) or a modified derivative thereof, carboxymethylcellulose or a modified derivative thereof, crystalline nanocellulose (CNC) or a modified derivative thereof, or a combination thereof.

48. A method of filling a tissue space under an epidermis, wherein the plant-derived collagen comprises rhCollagen.

49. A method of filling a tissue space under an epidermis, wherein the plant-derived collagen is obtained from a genetically modified plant.

50. A method of filling a tissue space under an epidermis, wherein the genetically modified plant is a genetically modified plant selected from the group consisting of tobacco, maize, alfalfa, rice, potato, soybean, tomato, wheat, barley, canola, carrot, and cotton.

51. A method of filling a tissue space under an epidermis, wherein the genetically modified plant is a tobacco plant.

52. A method of filling a tissue space under an epidermis, wherein the genetically modified plant comprises an expressible sequence of at least one gene sequence of human deoxyribonucleic acid (DNA) selected from the group consisting of: COL1, COL2, P4H-alpha, P4H-beta, and LH3.

53. A method of filling a tissue space under an epidermis, wherein the plant-derived human collagen comprises at least modified one human collagen alpha-1 chain as set forth in SEQ ID NO: 3 and as expressed in the genetically modified plant; and at least one modified human collagen alpha-2 chain as set forth in SEQ ID NO: 6 and as expressed in the genetically modified plant; and wherein the genetically modified plant further expresses an exogenous prolyl-4-hydroxylase (P4H).

54. A method of filling a tissue space under an epidermis, further comprising expressing an exogenous polypeptide selected from the group consisting of lysyl hydroxylase (LH), protease N, and protease C.

55. A method of filling a tissue space under an epidermis, wherein the human collagen alpha-1 chain is encoded by a sequence as set forth in SEQ ID NO: 1.

56. A method of filling a tissue space under an epidermis, wherein the human collagen alpha-2 chain is encoded by a sequence as set forth in SEQ ID NO: 2.

57. A method of filling a tissue space under an epidermis, wherein the exogenous P4H is a mammalian P4H.

58. A method of filling a tissue space under an epidermis, wherein the exogenous P4H is a human P4H.

59. A method of filling a tissue space under an epidermis, further comprising targeting the human collagen alpha-1 to a vacuole of the plant or the genetically modified plant and digesting it with ficin.

60. A method of filling a tissue space under an epidermis, further comprising targeting the human collagen alpha-2 to a vacuole of the plant or the genetically modified plant and digesting it with ficin.

61. A method of filling a tissue space under an epidermis, wherein the plant-derived human collagen is atelocollagen.

62. A method of filling a tissue space under an epidermis, wherein the polymerizable solution is introduced into the tissue space via a hollow needle or canula in the range of 27-gauge to 33-gauge.

63. A method of filling a tissue space under an epidermis, wherein the polymerizable solution in the tissue space is molded or sculpted into the desired configuration via manual massage.

64. A method of filling a tissue space under an epidermis, wherein the polymerizable solution in the tissue space is molded or sculpted into the desired configuration using a molding or sculpting implement.

65. A method of filling a tissue space under an epidermis, wherein the polymerizable solution in the tissue space is essentially non-gellable at room temperature.

66. A method of filling a tissue space under an epidermis, wherein the polymerizable solution in the tissue space is essentially non-gellable at 37° C.

67. A method of filling a tissue space under an epidermis, wherein the polymerizable solution comprising the plant-derived human collagen has a reduced viscosity at room temperature in comparison with an analogous polymerizable solution comprising a tissue-extracted human or bovine collagen in the same concentration and formulation.

68. A method of filling a tissue space under an epidermis, wherein the polymerizable solution comprising the plant-derived human collagen has a reduced viscosity at 37° C. in comparison with an analogous polymerizable solution comprising a tissue-extracted human or bovine collagen in the same concentration and formulation.

69. A method of filling a tissue space under an epidermis, wherein the polymerizable solution comprising the plant-derived human collagen is introduced into the tissue space with a reduced force at room temperature as compared with an analogous polymerizable solution comprising a tissue-extracted human or bovine collagen in the same concentration and formulation.

70. A method of filling a tissue space under an epidermis, wherein the polymerizable solution comprising the plant-derived human collagen is introduced into the tissue space with a reduced force at 37° C. as compared with an analogous polymerizable solution comprising a tissued-extracted human or bovine collagen in the same concentration and formulation.

71. A method of filling a tissue space under an epidermis, wherein the polymerizable solution comprising the plant-derived human collagen has an increased tissue augmentation as compared with an analogous polymerizable solution comprising a tissue-extracted human or bovine collagen in the same concentration and formulation.

72. Use of a polymerizable solution injected into a tissue space under an epidermis to reduce lines, folds, fine lines, wrinkles, or scars, the polymerizable solution comprising a cross-linkable, plant-derived human collagen and molding or sculpting the polymerizable solution into a desired configuration to reduce lines, folds, fine lines, wrinkles, or scars.

73. A method of inducing a cellular growth scaffold in a tissue space under an epidermis comprising introducing a solution into the tissue space, the solution comprising:
    (a) a plant-derived human collagen; and
    (b) at least one growth factor or source thereof.

74. A method of inducing a cellular growth scaffold in a tissue space under an epidermis, wherein the source of the at least one growth factor comprises a plasma or a platelet-rich plasma.

75. A method of inducing a cellular growth scaffold in a tissue space under an epidermis, wherein the cellular growth scaffold promotes healing or replacement due to degradation or injury of a collagen-comprising tissue.

76. A method of inducing a cellular growth scaffold in a tissue space under an epidermis, wherein the collagen-comprising tissue is selected from the group consisting of a tendon, a ligament, skin, a cornea, a cartilage, a blood vessel, an intestine, an intervertebral disc, a muscle, a bone, or a tooth.

77. A method of inducing a cellular growth scaffold in a tissue space under an epidermis, wherein the cellular growth scaffold promotes healing of tendinitis.

78. A method of inducing a cellular growth scaffold in a tissue space under an epidermis, wherein the plant-derived collagen comprises rhCollagen.

79. A method of inducing a cellular growth scaffold in a tissue space under an epidermis, wherein the plant-derived collagen is obtained from a genetically modified plant.

80. A method of inducing a cellular growth scaffold in a tissue space under an epidermis, wherein the genetically modified plant is a genetically modified plant selected from the group consisting of tobacco, maize, alfalfa, rice, potato, soybean, tomato, wheat, barley, canola, carrot, and cotton.

81. A method of inducing a cellular growth scaffold in a tissue space under an epidermis, wherein the genetically modified plant is a tobacco plant.

82. A method of inducing a cellular growth scaffold in a tissue space under an epidermis, wherein the genetically modified plant comprises an expressible sequence of at least one gene sequence of human deoxyribonucleic acid (DNA) selected from the group consisting of: COL1, COL2, P4H-alpha, P4H-beta, and LH3.

83. A method of inducing a cellular growth scaffold in a tissue space under an epidermis, wherein the plant-derived human collagen comprises at least modified one human collagen alpha-1 chain as set forth in SEQ ID NO: 3 and as expressed in the genetically modified plant; and at least one modified human collagen alpha-2 chain as set forth in SEQ ID NO: 6 and as expressed in the genetically modified plant; and wherein the genetically modified plant further expresses an exogenous prolyl-4-hydroxylase (P4H).

84. A method of inducing a cellular growth scaffold in a tissue space under an epidermis, further comprising expressing an exogenous polypeptide selected from the group consisting of lysyl hydroxylase (LH), protease N, and protease C.

85. A method of inducing a cellular growth scaffold in a tissue space under an epidermis, wherein the human collagen alpha-1 chain is encoded by a sequence as set forth in SEQ ID NO: 1.

86. A method of inducing a cellular growth scaffold in a tissue space under an epidermis, wherein the human collagen alpha-2 chain is encoded by a sequence as set forth in SEQ ID NO: 2.

87. A method of inducing a cellular growth scaffold in a tissue space under an epidermis, wherein the exogenous P4H is a mammalian P4H.

88. A method of inducing a cellular growth scaffold in a tissue space under an epidermis, wherein the exogenous P4H is a human P4H.

89. A method of inducing a cellular growth scaffold in a tissue space under an epidermis, further comprising targeting the human collagen alpha-1 to a vacuole of the plant or the genetically modified plant and digesting it with ficin.

90. A method of inducing a cellular growth scaffold in a tissue space under an epidermis, further comprising targeting the human collagen alpha-2 to a vacuole of the plant or the genetically modified plant and digesting it with ficin.

91. A method of inducing a cellular growth scaffold in a tissue space under an epidermis, wherein the plant-derived human collagen is atelocollagen.

92. A method of inducing a cellular growth scaffold in a tissue space under an epidermis, wherein the solution comprising the plant-derived human collagen has a reduced viscosity at room temperature in comparison with an analogous solution comprising a tissue-extracted human or bovine collagen in the same concentration and formulation.

93. A method of inducing a cellular growth scaffold in a tissue space under an epidermis, wherein the solution comprising the plant-derived human collagen has a reduced viscosity at 37° C. in comparison with an analogous solution comprising a tissue-extracted human or bovine collagen in the same concentration and formulation.

94. A method of inducing a cellular growth scaffold in a tissue space under an epidermis, wherein the solution comprising the plant-derived human collagen is introduced into the tissue space with a reduced force at room temperature as compared with an analogous solution comprising a tissue-extracted human or bovine collagen in the same concentration and formulation.

95. A method of inducing a cellular growth scaffold in a tissue space under an epidermis, wherein the solution comprising the plant-derived human collagen is introduced into the tissue space with a reduced force at 37° C. as compared with an analogous solution comprising a tissued-extracted human or bovine collagen in the same concentration and formulation.

96. A method of inducing a cellular growth scaffold in a tissue space under an epidermis, wherein the solution comprising the plant-derived human collagen has an increased scaffolding formation or promotes an increase in cellular growth as compared with an analogous solution comprising a tissue-extracted human or bovine collagen in the same concentration and formulation.

97. Use of a solution injected into a tissue space under an epidermis to induce a cellular growth scaffold, the solution comprising a plant-derived human collagen and at least one growth factor or source thereof, to promote healing or replacement due to degradation or injury of a collagen-comprising tissue.

98. Use of a solution injected into a tissue space under an epidermis to induce a cellular growth scaffold, wherein the source of the at least one growth factor comprises a plasma or a platelet-rich plasma.

Definitions

As used herein, the singular form "a", "an" and "the" include plural references unless the context clearly dictates otherwise. For example, the term "a molecule" also includes a plurality of molecules.

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the phrase "genetically modified plant" encompasses any lower (e.g. moss) or higher (vascular) plant or a tissue or an isolated cell thereof (e.g., of a cell suspension) which is stably or transiently transformed with an exogenous polynucleotide sequence. Examples of plants include but are not limited to tobacco, maize, alfalfa, rice, potato, soybean, tomato, wheat, barley, canola, cotton, carrot as well as lower plants such as moss.

As used herein, the phrase "collagen chain" encompasses a collagen subunit such as the alpha 1 or 2 chains of collagen fibers, preferably type I fibers. As used herein, the phrase "collagen" refers to an assembled collagen trimer, which in the case of type I collagen includes two alpha 1 chains and one alpha 2 chain. A collagen fiber is collagen which is devoid of terminal propeptides C and N.

As used herein, the phrase "telopeptide-comprising collagen" encompasses a soluble collagen molecule which comprises telopeptides that are longer than the telopeptide remnants comprised in atelocollagen. Thus, the telopeptide-comprising collagen may be procollagen which comprises full length propeptides. Alternatively, the telopeptide-comprising collagen may be a procollagen molecule which comprises partially digested propeptides. Still alternatively, the telopeptide-comprising collagen may be telocollagen.

The term "procollagen" as used herein, encompasses a collagen molecule (e.g. human) that comprises either an N-terminal propeptide, a C-terminal propeptide or both. Exemplary human procollagen amino acid sequences are set forth by SEQ ID NOs: 1, 2, 7 and 8.

The term "telocollagen" as used herein, encompasses collagen molecules that lack both the N- and C-terminal propeptides typically comprised in procollagen but still contain the telopeptides. The telopeptides of fibrillar collagen are the remnants of the N- and C-terminal propeptides following digestion with native N/C proteinases. Recombinant human telocollagen may be generated in cells which have been transformed to express both exogenous human procollagen and the respective protease (i.e. C or N or both). Polynucleotide sequences encoding such proteases are exemplified by SEQ ID Nos: 10 (Protease C) and 11 (Protease N). Such proteases can be expressed such that they are accumulated in the same subcellular compartment as the collagen chain, as further described herein below.

As used herein, the term "atelocollagen" encompasses collagen molecules lacking both the N- and C-terminal propeptides typically comprised in procollagen and at least a portion of its telopeptides, but including a sufficient portion of its telopeptides such that under suitable conditions it is capable of forming fibrils. Any type of atelocollagen may be generated according to the method of the present invention. Examples include fibril-forming collagens (types I, II, III, V, and XI), network-forming collagens (types IV, VIII, and X), collagens associated with fibril surfaces (types IX, XII, and XIV), collagens which occur as transmembrane proteins (types XIII and XVII), or form 11-nm periodic beaded filaments (type VI). According to one embodiment, the atelocollagen comprises an alpha 1 and/or 2 chain of type I collagen.

It will be appreciated dermal fillers disclosed herein may in some embodiments comprise genetically modified forms of collagen/atelocollagen—for example collagenase-resistant collagens and the like.

As used herein, the phrase "plant promoter" or "promoter" includes a promoter which can direct gene expression in cells (including DNA-containing organelles) of plants, fungus and yeast. Such a promoter can be derived from a plant, bacterial, viral, fungal or animal origin. Such a promoter can be constitutive, i.e., capable of directing high levels of gene expression in a plurality of tissues, tissue specific, i.e., capable of directing gene expression in a particular tissue or tissues, inducible, i.e., capable of directing gene expression under a stimulus, or chimeric, i.e., formed of portions of at least two different promoters.

As is used herein, the phrase "subcellular compartment devoid of endogenous P4H activity" refers to any compartmentalized region of the cell which does not include plant P4H or an enzyme having plant-like P4H activity. Examples of such subcellular compartments include the vacuole, apoplast and cytoplasm as well as organelles such as the chloroplast, mitochondria and the like.

Herein throughout, the term "building material" encompasses the phrases "uncured building material" or "uncured building material formulation" and collectively describes the materials that are used to sequentially form the layers, as described herein. This phrase encompasses uncured materials which form the final object, namely, one or more uncured modeling material formulation(s), and optionally also uncured materials used to form a support, namely uncured support material formulations. An uncured building material can comprise one or more modeling formulations and can be dispensed such that different parts of the object are made upon curing different modeling formulations, and hence are made of different cured modeling materials or different mixtures of cured modeling materials.

As used herein, "bioprinting" means practicing an additive manufacturing process while utilizing one or more bio-ink formulation(s) that comprises biological components via methodology that is compatible with an automated or semi-automated, computer-aided, additive manufacturing system as described herein (e.g., a bioprinter or a bioprinting system).

Herein throughout, in the context of bioprinting, the term "object" describes a final product of the additive manufacturing which comprises, in at least a portion thereof, biological components. This term refers to the product obtained by a bioprinting method as described herein, after removal of the support material, if such has been used as part of the uncured building material. In some embodiments, the biological components include recombinant human collagen, as described, for example, in WO 2006/035442, WO 2009/053985, and patents and patent applications deriving therefrom, all of which are incorporated by reference as if fully set forth herein.

The term "object" as used herein throughout refers to a whole object or a part thereof.

Herein throughout, a "curable material" is a compound (monomeric or oligomeric or polymeric compound) which, when exposed to a curing condition, as described herein, solidifies or hardens to form a cured modeling material as defined herein. Curable materials are typically polymerizable materials, which undergo polymerization and/or cross-linking when exposed to a suitable energy source. Alternatively, curable materials are thermo-responsive materials, which solidify or harden upon exposure to a temperature change (e.g., heating or cooling). Optionally, curable materials are biological materials which undergo a reaction to form a hardened or solid material upon a biological reaction (e.g., an enzymatically-catalyzed reaction).

A "curing condition" encompasses a curing energy (e.g., temperature, radiation) and/or a material or reagent that promotes curing.

In some of any of the embodiments described herein, a curable material is a photopolymerizable material, which polymerizes or undergoes cross-linking upon exposure to radiation, as described herein, and in some embodiments the curable material is a UV-curable or visible light-curable material, which polymerizes or undergoes cross-linking upon exposure to UV-vis radiation, as described herein.

In some of any of the embodiments described herein, a curable material can be a monomer, an oligomer or a short-chain polymer, each being polymerizable as described herein.

Herein, the term "curable" encompasses the terms "polymerizable" and "cross-linkable".

As used herein, "aeroponics" is the process of growing plants in an air or mist environment without the use of soil or an aggregate medium (known as "geoponics").

As used herein, "hydroponics" is the process of growing plants without soil ("geoponics"), using mineral nutrient solutions in a water solvent.

As used herein, the "endosphere" comprises all endophytes of a plant.

As used herein, an "exudate" is a fluid emitted by an organism through pores or a wound. "Exudation" is the process of emitting an "exudate."

As used herein, "hydroponics" is the process of growing plants without soil ("geoponics"), using mineral nutrient solutions in a water solvent.

As used herein, "integression" or "integression hybridization" is the movement of a gene (i.e., "gene flow") from the gene pool of one species into the gene pool of another species via repeated backcrossing of an interspecific hybrid with one of its parent species, distinct from simple hybridization and resulting in a complex mix of parental genes.

As used herein, the "metabolome" is the complete set of small molecule chemicals found within a "biological sample" (including, but not limited to, a cell, an organelle, an organ, a tissue, a tissue extract, a biofluid, or an organism). The small molecule chemicals of the metabolome may be "endogenous metabolites" or "exogenous chemicals." "Endogenous metabolites" are naturally produced by an organism and include, but are not limited to, amino acids, organic acids, nucleic acids, fatty acids, amines, sugars, vitamins, cofactors, pigments, and antibiotics. "Exogenous chemicals" are not naturally produced by the organism and include, but are not limited to, drugs, environmental contaminants, food additives, toxins, and other xenobiotics. The "endogenous metabolome" is comprised of the endogenous metabolites, while the "exogenous metabolome" is comprised of the "exogenous chemicals." The "endogenous metabolome" is comprised of a "primary metabolome" and a "secondary metabolome," especially with respect to plants, fungi, and prokaryotes. The "primary metabolome" is comprised of "primary metabolites" (i.e., metabolites directly involved in normal growth, development, and reproduction of the organism), while the "secondary metabolome" is comprised of "secondary metabolites (i.e., metabolites not directly involved in the normal growth, development, or reproduction of the organism). Secondary metabolites often have significant ecological functions.

As used herein, a "metabolite" is usually a small molecule having a molecular weight of less than 1500 Da. A "metabolite" can include, but is not limited to, a glycolipid, a polysaccharide, a short peptide, a small oligonucleotide, an organic acid, a taxane, an alkaloid, and strigolactone, while very large macromolecules (e.g., proteins, mRNA, rRNA, and DNA) are not generally not metabolites and are not part of the metabolome.

As used herein, the "SILVA database" is the SILVA ribosomal RNA database.

All samples obtained from an organism, including those subjected to any sort of further processing are considered to be obtained from the organism.

Methods for DNA isolation, sequencing, amplification, and/or cloning are known to a person skilled in the art. Most commonly used method for DNA amplification is PCR (polymerase chain reaction; see, for example, PCR Basics: from background to Bench, Springer Verlag, 2000; Eckert et al., 1991. PCR Methods and Applications 1:17). Additional suitable amplification methods include the ligase chain reaction (LCR), transcription amplification and self-sustained sequence replication, and nucleic acid-based sequence amplification (NASBA). Likewise, methods for RNA and protein isolation, characterization, and the like and for protein expression are known to a person skilled in the art.

The following examples are presented in order to more fully illustrate some embodiments of the dermal fillers and uses thereof, disclosed herein. They should, in no way be construed, however, as limiting the broad scope of dermal fillers disclosed herein nor their uses. One skilled in the art can readily devise many variations and modifications of the principles disclosed herein without departing from the scope of the invention.

EXAMPLES

Example 1. Constructs and Transformation Schemes

Figure 1B:
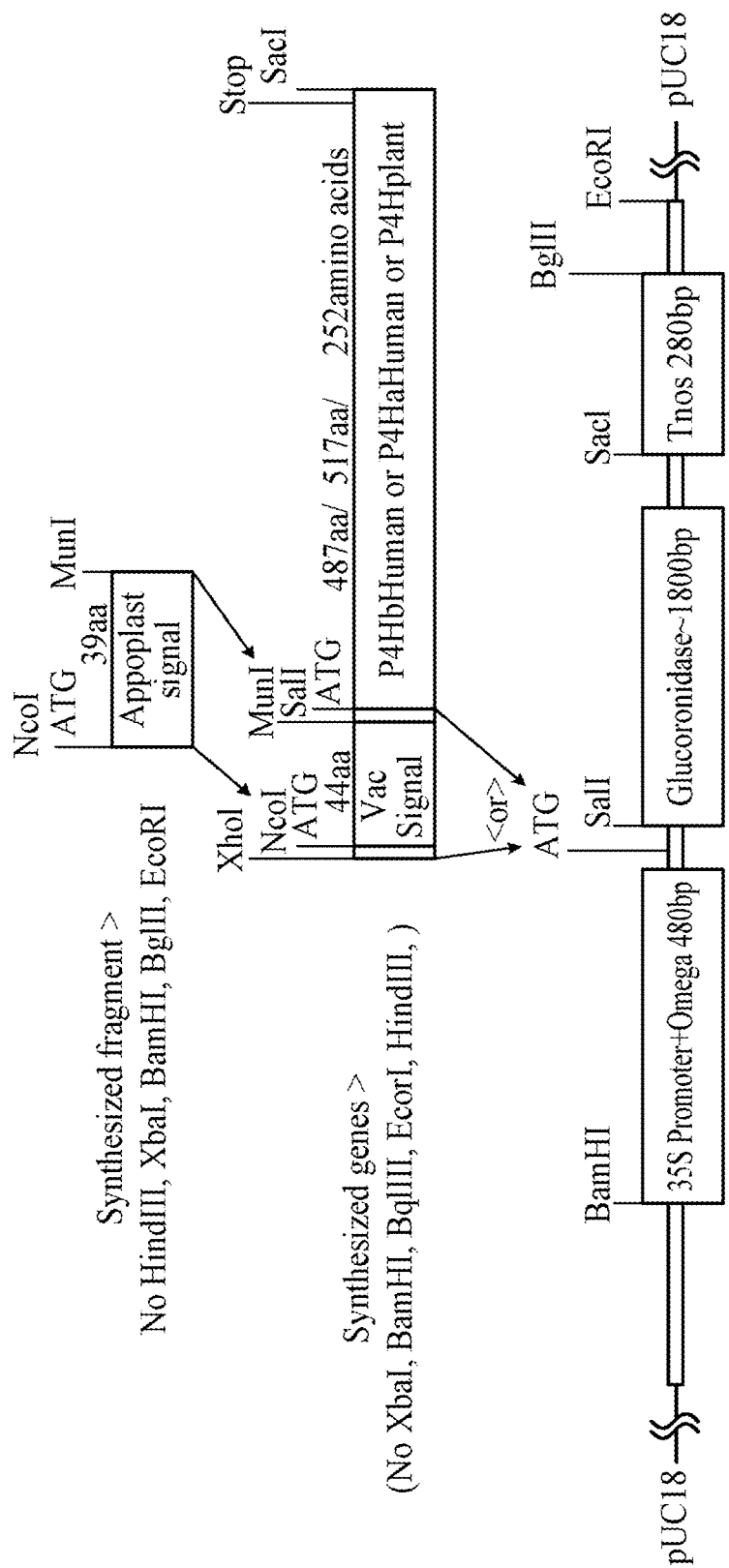
Figure 1C:
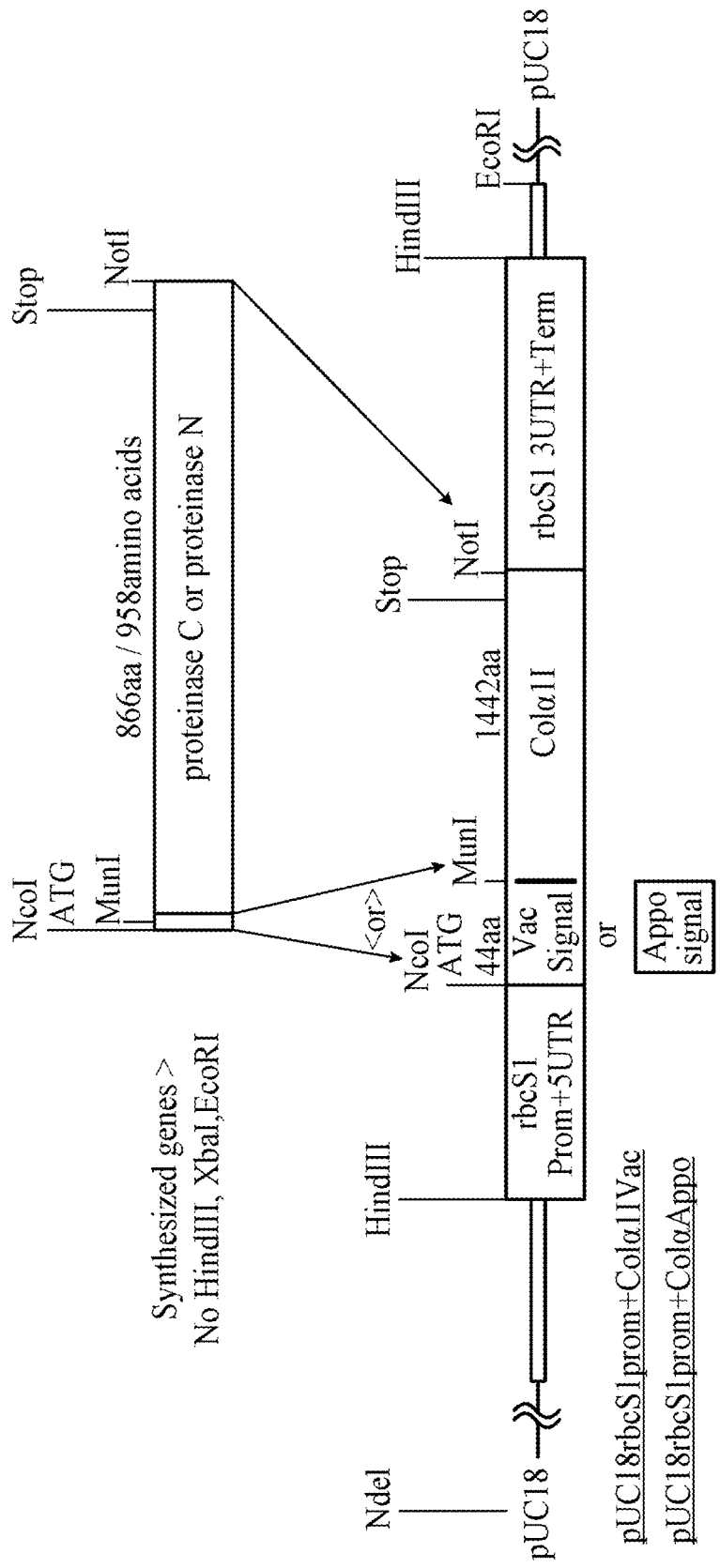
Figure 1D:
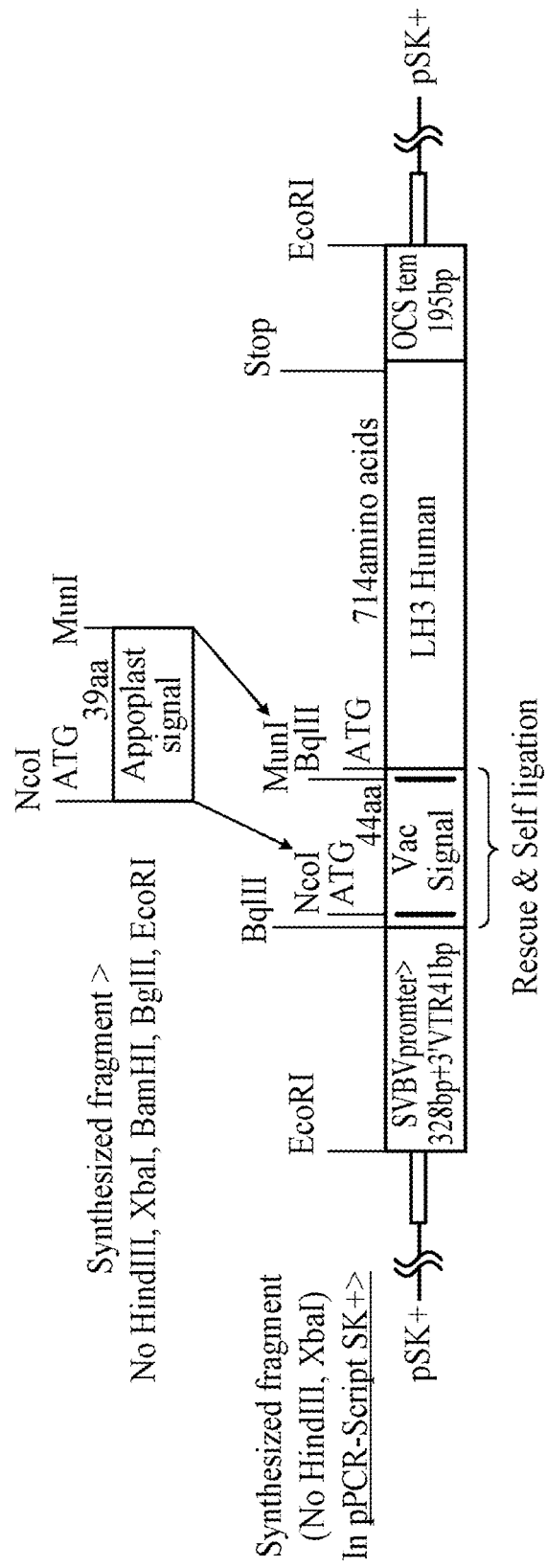

Constructions of expression cassettes and vectors used in this work are illustrated in FIGS. 1a-d (see also U.S. Pat. No. 8,455,717). All of the coding sequences in this work were optimized for expression in tobacco and chemically synthesized with desired flanking regions (SEQ ID NOs: 1, 4, 7, 12, 14, 16, 18, 20.22). FIG. 1A: The synthetic genes coding for Col1 and Col2 (SEQ ID NOs: 1.4) fused either to the vacuolar signal or to the apoplast signal (encoded by SEQ ID NO: 7) or without signals were cloned in expression cassettes composed of a *Chrysanthemum* rbcS1 promoter and 5' UTR (SEQ ID NO: 10) and a *Chrysanthemum* rbcS 3'UTR and terminator (SEQ ID NO: 11). The complete expression cassettes were cloned in the multiple cloning site of the pBINPLUS plant transformation vector (van Engelen et al., 1995, Transgenic Res 4: 288-290). FIG. 1b: The synthetic genes coding for P4H beta-human, P4H alpha-human and P4H-plant (SEQ ID NOs: 12,14 and 16) fused either to the vacuolar signal or to the apoplast signal (encoded by SEQ ID NO: 7) or without signals were cloned in expression cassettes composed of the CaMV 35S promoter and TMV omega sequence and *Agrobacterium* Nopaline synthetase (NOS) terminator carried by the vector pJD330 (Galili et al., 1987, Nucleic Acids Res 15: 3257-3273). The complete expression cassettes were cloned in the multiple cloning site of the pBINPLUS vectors carrying the expression cassettes of Col1 or Col2. FIG. 1c: The synthetic genes coding for Proteinase C and Proteinase N (SEQ ID NOs: 18.20) fused either to the vacuolar signal or to the apoplast signal (encoded by SEQ ID NO: 7) were cloned in expression cassettes composed of a *Chrysanthemum* rbcS1 promoter and 5' UTR (SEQ ID NO: 10) and a *Chrysanthemum* rbcS1 3'UTR and terminator (SEQ ID NO: 11). The complete expression cassettes were cloned in the multiple cloning site of the pBINPLUS plant transformation vector. FIG. 1d: The synthetic gene coding for LH3 (SEQ ID NO: 22) with flanking Strawberry vein banding virus (SVBV) promoter (NCBI accession AF331666 REGION: 623.950 version AF331666.1 GI:13345788) and terminated by *Agrobacterium* octopin synthase (OCS) terminator (NCBI accession Z37515 REGION: 1344.1538 version Z37515.1 GI:886843) fused either to the vacuolar signal or to the apoplast signal (encoded by SEQ ID NO: 7) or without signals was cloned in the multiple cloning site of the pBINPLUS vector carrying the expression cassettes of Col1 and P4H beta.

Co-transformations schemes utilizing the expression cassettes described in FIGS. 1a-d into a host plant are illustrated in FIG. 2. Each expression cassette insert is represented by a short name of the coding sequence. The coding sequences and related SEQ ID NOs. are described in Table 1. Each co-transformation is preformed by two pBINPLUS binary vectors. Each rectangle represents a single pBINPLUS vector carrying one, two or three expression cassettes. Promoters and terminators are specified in FIGS. 1a-d.

Example 2. Plant Collagen Expression

Synthetic polynucleotide sequences encoding the proteins listed in Table 1 below were designed and optimized for expression in tobacco plants.

TABLE 1

List of expressed proteins

| Name: | SwissProt accession | Amino acids | Splicing isoform | Deletions | name | Included in SEQ ID NO. | Encoded by SEQ ID NO. |
|---|---|---|---|---|---|---|---|
| Collagen alpha 1(I) chain [Precursor] | p02452 | 1442 | One version | ER signal | Col1 | 3 | 1 |
| Collagen alpha 2(I) chain [Precursor] | p08123 Two changes done in p08123: D549A and N249I | 1342 | One version | ER signal | Col2 | 6 | 4 |
| Prolyl 4-hydroxylase beta subunit | p07237 | 487 | One version | ER signal, KDEL | P4H betaHuman | 13 | 12 |
| Prolyl 4-hydroxylase alpha-1 subunit | p13674 | 517 | P13674-1 | ER signal | P4H alphaHuman | 15 | 14 |
| Prolyl 4-hydroxylase Plant | No entry in Swissprot. NCBI accession: gi: 15227885 | 252 | One version | Mitochondrial signal predicted as: aa1-39 | P4Hplant | 17 | 16 |
| Procollagen C-proteinase | p13497 | 866 | P13497-1 BMP1-3 | ER signal, propeptide | Proteinase C | 19 | 18 |
| Procollagen I N-protehiase | o95450 | 958 | O95450-1 LpNPI | ER signal, propeptide | Proteinase N | 21 | 20 |
| Lysyl hydroxylase 3 | o60568 | 714 | One version | ER signal | LH3 | 23 | 22 |

Signal Peptides
1. Vacuole signal sequence of barley gene for Thiol protease aleurain precursor (NCBI accession P05167 GI:113603)

(SEQ ID NO: 24)
MAHARVLLLALAVLATAAVAVASSSSFADSNPIRPVTDRAASTLA.

2. Apoplast signal of *Arabidopsis thaliana* endo-1,4-beta-glucanase (Cell, NCBI accession CAA67156.1 GI:2440033); SEQ ID NO. 9, encoded by SEQ ID NO. 7.

Construction of Plasmids

Plant expression vectors were constructed as taught in Example 1, the composition of each constructed expression vector was confirmed via restriction analysis and sequencing.

Expression vectors including the following expression cassettes were constructed:
1. Collagen alpha 1
2. Collagen alpha 1+human P4H beta subunit
3. Collagen alpha 1+human P4H beta subunit+human LH3
4. Collagen alpha 2
5. Collagen alpha 2+with human P4H alpha subunit
6. Collagen alpha 2+with *Arabidopsis* P4H
7. Human P4H beta subunit+human LH3
8. Human P4H alpha subunit Each of the above described coding sequences was either translationally fused to a vacuole transit peptide or to an apoplasm transit peptide or was devoid of any transit peptide sequences, in which case cytoplasmic accumulation is expected.

Plant Transformation and PCR Screening

Tobacco plants (*Nicotiana tabacum*, Samsun NN) were transformed with the above described expression vectors according to the transformation scheme taught in FIG. 2.

Figure 3:
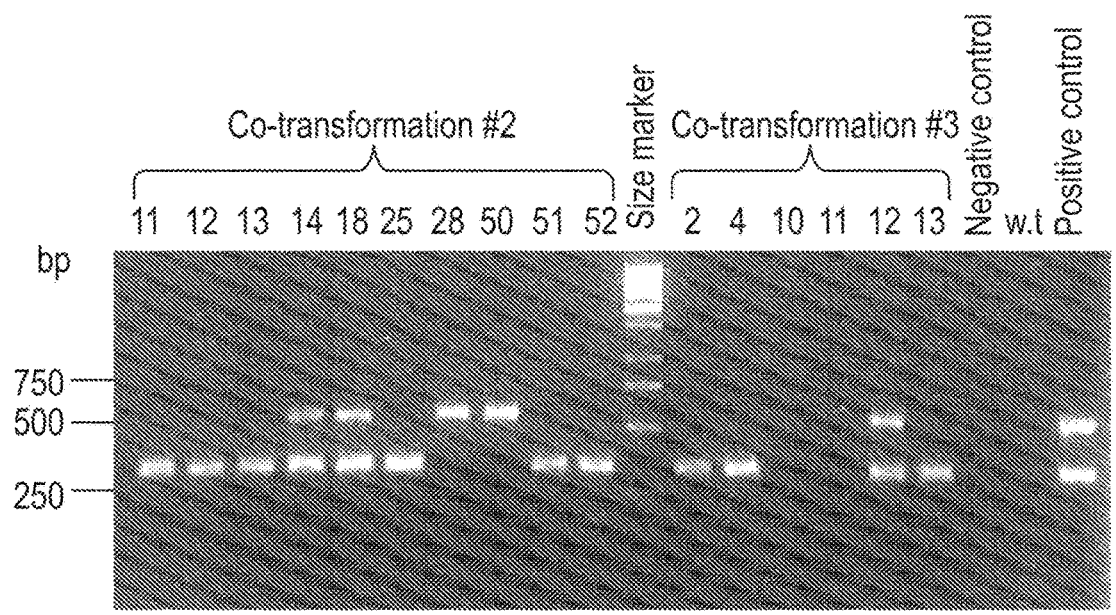
FIG. 3 is a previous multiplex PCR screening of transformants showing plants that were positive for Collagen alpha 1 (324 bp fragment) or Collagen alpha 2 (537 bp fragment) or both.

Resultant transgenic plants were screened via multiplex PCR using four primers which were designed capable of amplifying a 324 bp fragment of Collagen alpha 1 and a 537 bp fragment of Collagen alpha 2 (Table 2). FIG. 3 illustrates the results of one multiplex PCR screen.

TABLE 2

List of primers for multiplex PCR for amplification of a 324 bp fragment of Collagen alpha 1 and a 537 bp fragment of Collagen alpha 2

| Col1 forward primer (24-mer): | 5' ATCACCAGGAGAACAGGGACCATC 3' | SEQ ID 25 |
|---|---|---|
| Col1 reverse primer (29-mer): | 5' TCCACTTCCAAATCTCTATCCCTAACAAC 3' | SEQ ID 26 |

TABLE 2-continued

List of primers for multiplex PCR for amplification of a
324 bp fragment of Collagen alpha 1 and a 537 bp fragment
of Collagen alpha 2

| | | |
|---|---|---|
| Col2 forward primer (23-mer): | 5' AGGCATTAGAGGCGATAAGGGAG 3' | SEQ ID 27 |
| Col2 reverse primer (27-mer): | 5' TCAATCCAATAATAGCCACTTGACCAC 3' | SEQ ID 28 |

Example 3. Detection of Human Collagen in Transgenic Tobacco Plants

Figure 4:
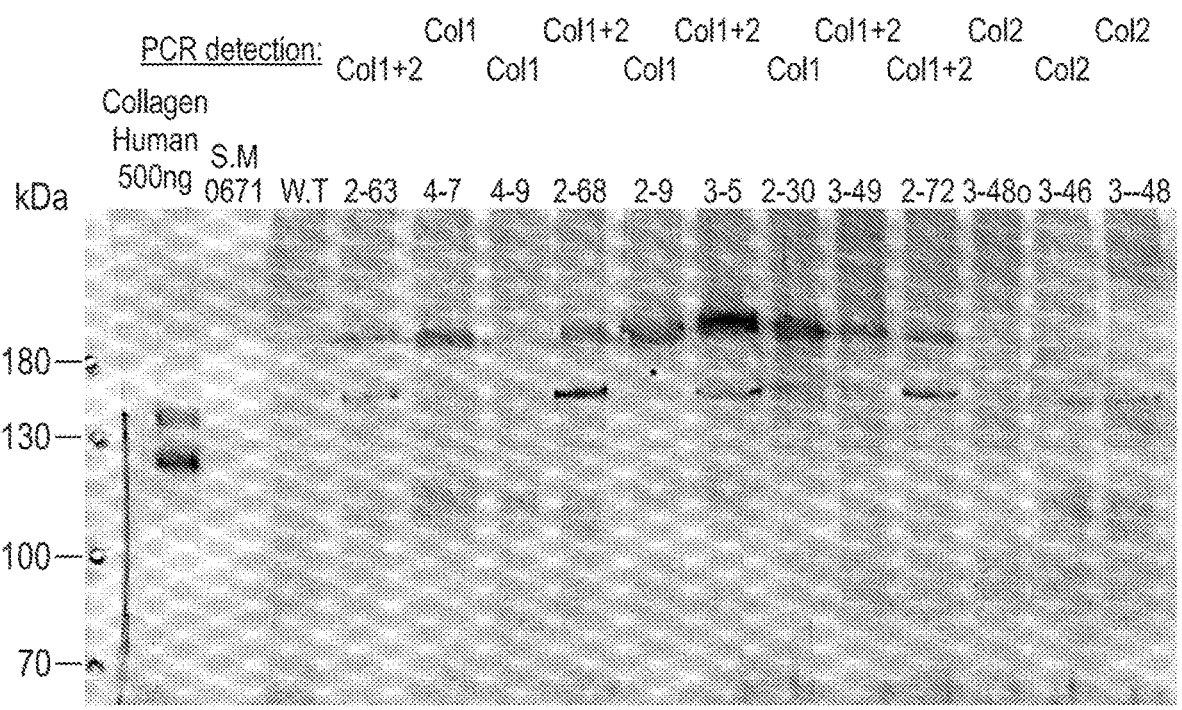
FIG. 4 is a previous Western blot analysis of transgenic plants generated by co-transformations 2, 3 and 4. Total soluble proteins were extracted from tobacco co-transformants #2, #3 and #4 and tested with anti-Collagen I antibody (#AB745 from Chemicon Inc.). Size markers were #SM0671 from Fermentas Inc. W.T. is a wild type tobacco. Positive collagen bands are visible in plants that are PCR positive for collagen typeI alpha 1 or alpha 2 or both. Positive control band of 500 ng collagen type I from human placenta (#CC050 from Chemicon Inc., extracted from human placenta by pepsin digestion) represents about 0.3% of the total soluble proteins (about 150 µg) in the samples from the transgenic plants. The larger band at about 140 kDa in the human collagen sample is a procollagen with its C-propeptide as detected by anti carboxy-terminal propeptide of collagen type I antibody (#MAB1913 from Chemicon Inc.). The smaller band at about 120 kDa in the human collagen sample is a collagen without propeptides. Due to their unusual composition, proline rich proteins (including collagens) consistently migrate on polyacrylamide gels as bands with molecular mass higher than expected. Therefore, the collagen chains without propeptides with a molecular weight of about 95 kDa migrate as a band of about 120 kDa.

Total soluble proteins were extracted from tobacco transformants 2, 3 and 4 by grinding 500 mg of leaves in 0.5 ml 50 mM Tris-HCl pH=7.5 with a "Complete" protease inhibitor cocktail (product #1836145 from Roche Diagnostics GmbH, 1 tablet per 50 ml buffer). The crude extract was mixed with 250 µl 4×. Sample application buffer containing 10% beta-mercapto-ethanol and 8% SDS, the samples were boiled for 7 minutes and centrifuged for 8 minutes in 13000 rpm. 20 µl of the supernatant were loaded in a 10% polyacrylamide gel and tested with anti-Collagen I (denatured) antibody ((#AB745 from Chemicon Inc.) in a standard Western blot procedure (FIG. 4). W.T. is a wild type tobacco. Positive collagen bands are visible in plants that are PCR positive for collagen typeI alpha 1 or alpha 2 or both. Positive control band of 500 ng collagen type I from human placenta (#CC050 from Chemicon Inc.) represents about 0.3% of the total soluble proteins (about 150 µg) in the samples from the transgenic plants.

Figure 5:
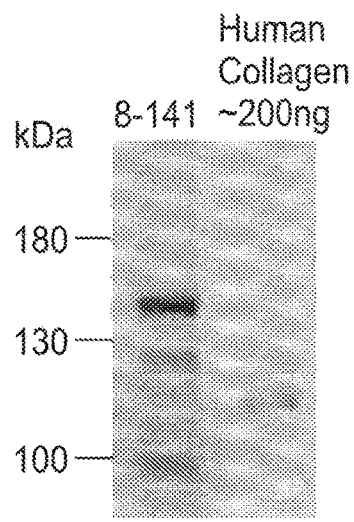
FIG. 5 is a previous Western blot analysis of transgenic plant generated by co-transformation #8 (carrying apoplast signals translationally fused to the collagen chains). Total soluble proteins were extracted from transgenic tobacco leaves and tested with anti-Collagen I antibody (#AB745 from Chemicon Inc.) Positive collagen alpha 2 band is visible in plant 8-141. Collagen type I from human placenta (#CC050 from Chemicon Inc.) served as control.

Plants expressing collagen at the expected molecular weight up to about 1% of the total soluble proteins were detected when collagen was targeted to the vacuole (FIG. 4). Subcellular targeting of full length collagen to the apoplast was successfully achieved (FIG. 5). Plants expressing collagen in the cytoplasm (i.e. no targeting peptide) did not accumulate collagen to detectable levels showing that subcellular targeting of collagen in plants is critical for success.

In addition, in contrast to the studies of Ruggiero et al. 2000 and Merle et al. 2002 which showed that collagen lacking the N-propeptide was subjected to significant proteolysis, using the present approach full length collagen proteins with C-propeptide and N-propeptide accumulated in subcellular compartments at high levels.

The present data also clearly shows that crossing two plants each expressing a different collagen chain type is advantageous in that it enables selection of plants expressing optimal levels of each chain type and subsequent plant crossing to achieve the desired collagen producing plant.

Collagen produced by the plants of the present invention includes the native propeptides and therefore is expected to form a larger protein then the human control that was purified by proteolysis. The calculated molecular weight of Collagen alpha 1 and alpha 2 chains without hydroxylations or glycosylations are the following: Col1 with propeptides—136 kDa, Col1 without propeptides—95 kDa, Col2 with propeptides—127 kDa, Col2 without propeptides—92 kDa.

As can be seen in FIG. 4, the Col1 bands in transformants 3-5 and 3-49 appears larger then Col1 bands in other plants. This indicates prolines hydroxylation in collagen chains by human proline-4-hydroxylase holoenzyme composed of alpha and beta subunits that were coexpressed in these plants and targeted to the same subcellular compartment as the human collagen chains (e.g., vacuole).

Example 4. Collagen Triple Helix Assembly and Thermal Stability in Transgenic Plants Assembly of collagen triple helix and the helix thermal stability in transgenic plants were tested by thermal denaturation followed by trypsin or pepsin digestion of the total crude protein extract of transgenic plants (FIGS. 6a-b).

In a first experiment, total soluble proteins from tobacco 2-9 (expressing only col alfa1 and no P4H) and 3-5 (expressing both col alpha1+2 and P4H) were extracted by grinding 500 mg leaves in 0.5 ml of 50 mM Tris-HCl pH=7.5, centrifuging for 10 minutes in 13000 rpm and collecting the supernatant. 0 µl of the supernatant were subjected to heat treatment (15 minutes in 33° C. or 43° C.) and then immediately placed on ice. Trypsin digestion was initiated by adding to each sample 6 mu.l of 1 mg/ml Trypsin in 50 mM Tris-HCl pH=7.5. The samples were incubated for 20 minutes at room temperature (about 22° C.). The digestion was terminated by addition of 20 µl 4× sample application buffer containing 10% betamercaptoethanol and 8% SDS, the samples were boiled for 7 minutes and centrifuged for 7 minutes at 13000 rpm. 50 µl of the supernatant were loaded onto a 10% polyacrylamide gel and tested with anti-Collagen I antibody ((#AB745 from Chemicon Inc.) using a standard Western blot procedure. Positive controls were samples of 500 ng human collagen I (#CC050 from Chemicon Inc., extracted from human placenta by pepsin digestion) which was added to 50 µl total soluble proteins extracted from w.t. tobacco.

Figure 6A:
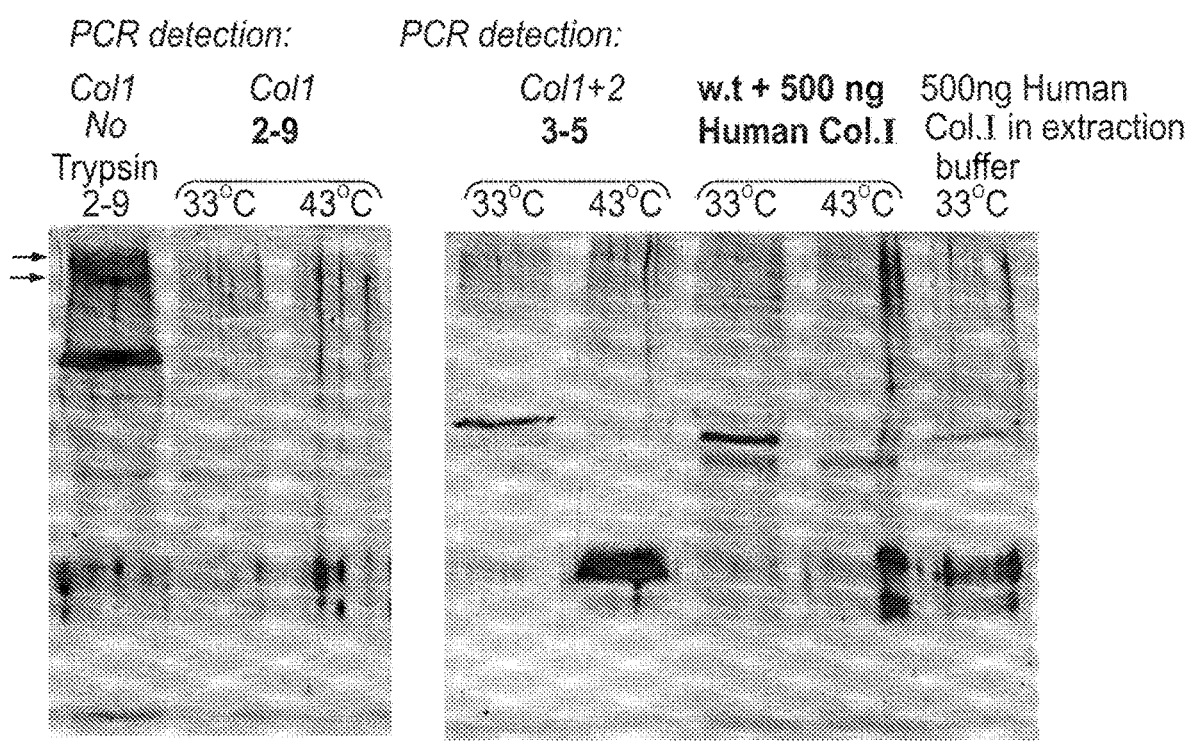
FIGS. 6a and 6b illustrate collagen triple helix assembly and thermal stability as qualified previously by heat treatment and Trypsin or Pepsin digestion.
Figure 6B:
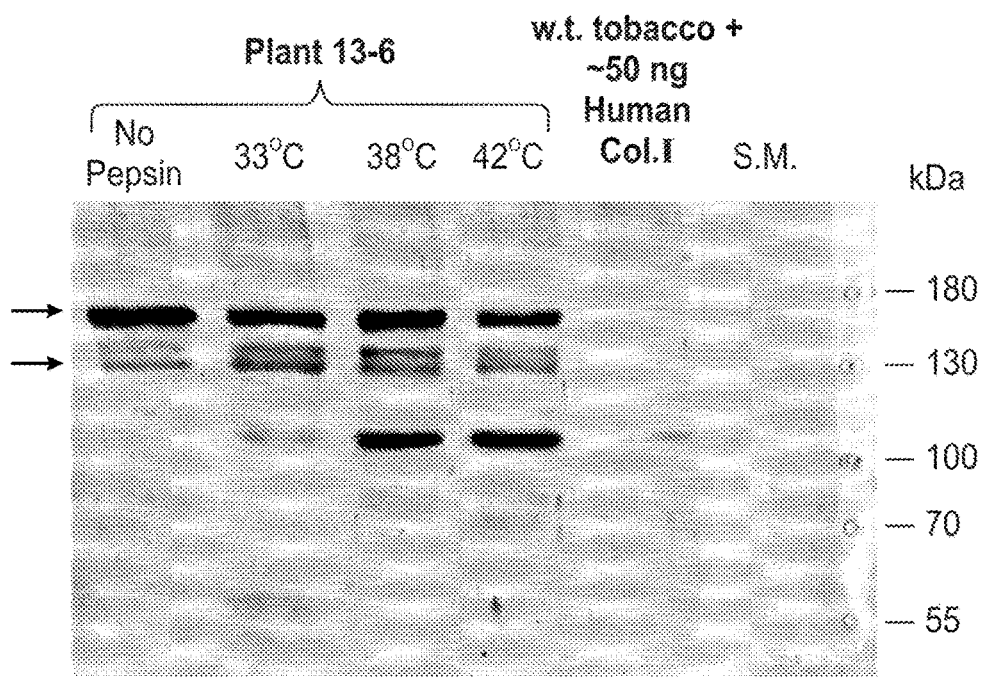

As shown in FIG. 6a, collagen triple helix that formed in plants #3-5 as well as control human collagen was resistant to denaturation at 33° C. In contrast, collagen formed by plants #2-9 denatured at 33° C. This difference in thermal stability indicates a successful triple helix assembly and post translational proline hydroxylation in transformants #3-5 which express both collagen alpha 1 and collagen alpha 2 as well as P4H beta and alpha subunits.

Two bands in transformants #2-9 may represent dimers or trimers, which are stable following 7 minutes of boiling with SDS and mercaptoethanol. Similar bands are visible in human collagen (upper panel) and in transformants #3-5. A possible explanation is a covalent bond between two peptides in different triple helixes (cross link), formed following oxidative deamination of two lysines by Lysine oxidase.

In a second experiment, total soluble proteins from transgenic tobacco 13-6 (expressing collagen I alpha 1 and alpha 2 chains—pointed by arrows, human P4H alpha and beta subunits and human LH3) were extracted by grinding 500 mg of leaves in 0.5 ml of 100 mM Tris-HCl pH=7.5 and 300 mM NaCl, centrifuging for 7 minutes at 10000 rpm and collecting the supernatant. 50 μl of the supernatant was subjected to heat treatment (20 minutes in 33° C., 38° C., or 42° C.) and then immediately placed on ice. Pepsin digestion was initiated by adding to each sample 4.5 μl of 0.1M HCl and 4 μl of 2.5 mg/ml Pepsin in 10 mM acetic acid. The samples were incubated for 30 minutes at room temperature (about 22° C.). The digestion was terminated by adding 5 μl of unbuffered 1 M Tris. Each sample was mixed with 22 μl 4× Sample application buffer containing 10% beta-mercapto-ethanol and 8% SDS, boiled for 7 minutes and centrifuged for 7 minutes in 13000 rpm. 40 μl of the supernatant were loaded in a 10% polyacrylamide gel and tested with anti-Collagen I antibody ((#AB745 from Chemicon Inc.) in a standard Western blot procedure. Positive control was sample of about 50 ng human collagen I(#CC050 from Chemicon Inc., extracted from human placenta by pepsin digestion) added to total soluble proteins from w.t. tobacco.

As is illustrated in FIG. 6b, collagen triple helix that formed in plant #13-6 was resistant to denaturation at 42° C. Cleavage of the propetides is first visible at 33° C. and gradually increases in efficiency when the temperature is raised to 38° C. and again to 42° C. The cleaved collagen triple helix domain shows a similar migration on the gel to the migration of the pepsin treated human collagen. The human collagen that was used in this experiment was extracted from human placenta by pepsin proteolysis and therefore lacks the propetides and some of the telopeptides.

Example 5. Plant P4H Expression

Induction of Native Plant P4H

Figure 7:
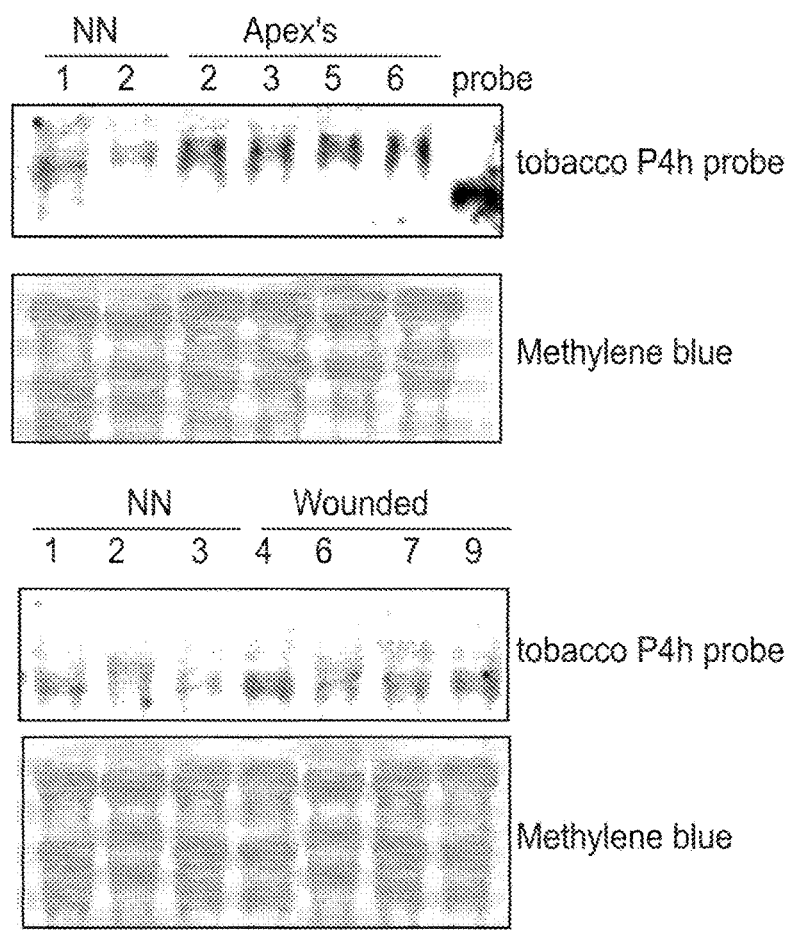
FIG. 7 illustrates previous Northern blot analysis conducted on wild type tobacco. Blots were probed with tobacco P4H cDNA.

Tobacco P4H cDNA was cloned and used as a probe to determine conditions and treatments that would induce endogenous P4H expression. Northern blot analysis (FIG. 7) clearly shows that P4H is expressed at relatively high levels in the shoot apex and at low levels in leaves. P4H level was induced significantly in leaves 4 hours following abrasion treatment ("wounded" in the lower panel). Similar results were achieved using other stress conditions (not shown).

Detection of Human P4H Alpha and Beta Subunits and Collagen Alpha 1 and Alpha 2 Chains in Transgenic Tobacco Plants Detection of human P4H alpha and beta subunits and collagen type I alpha 1 and alpha 2 chains in transgenic tobacco plants was effected using anti-human P4H alpha subunit antibody (#63-163 from ICN Biomedicals Inc.), anti-human P4H beta subunit antibody (#NMAB2701 from Chemicon Inc.) and anti-Collagen I antibody (#AB745 from Chemicon Inc.). The results of a Western blot probed with these antibodies are shown in FIG. 8.

Expression of P4H alpha, P4H beta and collagen 1 alpha 1 and alpha 2 bands was confirmed in plant 13-6 (also transformed also with human LH3). The calculated molecular weights of P4H alpha and beta including the vacuolar signal peptide are 65.5 kDa and 53.4 kDa respectively. The calculated molecular weights of Collagen alpha 1 and alpha 2 chains with propetides, without hydroxylations or glycosylations are 136 kDa and 127 kDa respectively.

Example 6. Vacuolar Targeted Collagen is Stably Expressed in Dark-Grown Plants

Collagen Expressing Plants:

The 20-279 parental tobacco plant line was generated by co-transformation with an expression vector expressing P4Hbeta+LH3 and another expression vector expressing P4Halpha. Each gene is preceded by a vacuolar targeting determinant of aleurain, a plant vacuolar thiol protease, The 2-300 parental tobacco plant line was generated by co-transformation with an expression vector expressing col1 and another expression vector expressing col2. Each gene is preceded by a vacuolar targeting determinant of aleurain, a plant vacuolar thiol protease.

The 13-652 plant was generated by co-transformation of tobacco plant with an expression vector encoding Col1, P4Hbeta and LH3 and a second expression vector encoding Col2 and P4H alpha. Each gene is preceded by a vacuolar targeting determinant of aleurain, a plant vacuolar thiol protease, Cassette sequences included in the vectors are described in Example 1 above.

Light and Darkness Trial

Analysis of six 13-6/52 homozygote plants. Samples from leaf #4+5/6 were taken daily at the same time (12:30) for 8 days, from 3 plants that were grown at regular conditions (16 hours under light conditions and 8 hours in the dark) and from 3 plants that were grown only in the dark.

Total Protein Extraction and Western Blot Analysis

Ninety mg of tobacco leaves were homogenized by mixer mill Type MM301 (Retsch) in an extraction buffer (100 mM Tris HCl pH=7.5, protease inhibitor cocktail available from Roche Catalog Number, 04-693-116-001) at 4° C. Following 30 min of centrifugation (20,000×g at 4° C.), the supernatant was collected. Protein samples were fractionated on 8% SDS-PAGE (Laemmli 1970) and transferred to a nitrocellulose membrane using BIO-RADM Protein TRANSBLO™ apparatus. The membrane was blocked for 30 min at room temperature in 3% (g/v) skim milk (Difco), and then reacted with either commercial rabbit anti-human collagen type I polyclonal antibodies (Chemicon), for overnight (o.n.) at room temperature. The membrane was rinsed with water 3-5 times and then washed for 30 min in TBS. Following incubation with a secondary antibody [goat anti rabbit-IgG antibody conjugated to alkaline phosphatase (AP) (Chemicon)] for 2 hours at room temperature, the membrane was rinsed with water for 3-5 times and washed for 30 min in TBS. Immunodetection was effected with nitrotetrazolium blue chloride (NBT, Sigma) and 5-bromo-4-chloro-3-indolyl phosphate p-toluidine salt (BCIP, Sigma), at room temperature for 2 hour-o.n.

Results

As shown in FIG. 9, tobacco plants transgenic for vacuolar targeted collagen express Pro-alpha-1 and Pro-alpha-2 (lane 1). Collagen from dark grown vacuolar targeted plants exhibited similar stability (lane 2), substantiating the exceptional stability of collagen generated according to the teachings of the present invention Examples 7-13.

General Materials and Methods

Collagen extraction and enzymatic reaction: In a blender, 300 g of tobacco leaves were blended in a chilled extraction buffer (600 ml of 100 mM Tris-HCl pH 7.5 containing 360 mg potassium-meta-bisulfite, 530 mg L-Cysteine and 1 g EDTA) supplemented with 5 g PVPP and 2 g of activated carbon (see also U.S. Pat. No. 8,759,487). Blending was performed 5 times for 1-minute intervals to keep temperatures below 15° C. Crude extract was filtered through a gauze pad and centrifuged for 30 min, 25000 g, 5° C. The supernatant was collected; CaCl$_2$ was added to a final concentration of 10 mM. The supernatant was divided into 10 ml samples. The desired enzyme was added to each 10 ml sample, according to the conditions set forth in Table 3 herein below.

TABLE 3

Procollagen digestion reaction conditions

| # Sample | Protease: | Concentration of protease (mg/Liter): | Incubation time (Hours): | Incubation temperature (degrees Celcius): |
|---|---|---|---|---|
| 1 | Desired enzyme | 1 | 3 | 15 |
| 2 | Desired enzyme | 5 | 3 | 15 |
| 3 | Desired enzyme | 25 | 3 | 15 |
| 4 | Desired enzyme | 1 | 6 | 15 |
| 5 | Desired enzyme | 5 | 6 | 15 |
| 6 | Desired enzyme | 25 | 6 | 15 |
| * | Control-no protease | 0 | 3 | 15 |
| * | Control-no protease | 0 | 6 | 15 |

Enzyme description: Ficin from Fig tree latex (Sigma, catalog #F4125), Subtilisin from *Bacillus licheniformis* (Sigma, catalog #P5459-5 gr), Bromelain from pineapple stem (Sigma, catalog #B4882-10 gr), Papain from *Carica papaya* (Fluka, Catalog #76220-25 gr), Savinase 6.0 t type W from the alkalophilic bacterium *Bacillus lentus* (Novozymes, catalog #PX92500501), Neutrase 1.5 MG from bacterium *Bacillus amyloliquefaciens* (Novozymes, catalog #PW201041), Protamex, a commercial *Bacillus* proteinase complex (Novozymes, catalog #PW2A1021), Alcalase 3.0 T, *Bacillus subtilis* alkaline proteinase (Novozymes, catalog #PJ90000901), Esperase 6.0 T, alkalophilic bacterium *Bacillus lentus* (Novozymes, catalog #PE90110401), Alcalase 2.4 L FG, *Bacillus subtilis* alkaline proteinase (Novozymes, catalog #PLN05330), Esperase 8.0 L, alkalophilic bacterium *Bacillus lentus* (Novozymes, catalog #PE00077) were all donated by Novozymes. Trypsin, pancreatic trypsin 6.0 S type saltfree, from animal pancreas (Novozymes, catalog #P245-D20). TRYPZEAN™, a recombinant trypsin expressed in corn was purchased from Sigma Chemical Co. (catalog #: T3449).

Determination of atelocollagen concentration: The concentration of atelocollagen generated according to Examples 9-10 was assayed by two methods as follows:

SIRCOL™ assay: SIRCOL™ collagen assay kit was purchased from Biocolor Ltd. (Cat. No 85000). This assay is based on the interaction of the Sirius Red dye with the collagen triple helix. The analysis was performed according to the supplier's instruction manual, 4th edition, 2002. Bovine collagen standard was used to prepare a calibration curve (0 to 50 μg collagen). Three samples of 10-50 μl of the collagen solution in 10 mM HCl were placed into a 1.5 ml Eppendorf tube, and the volume was brought to 100 μl with 0.5 M acetic acid. 1 ml SIRCOL™ dye reagent was added to each tube and the tubes were shaken for 30 min at room temperature. Tubes were centrifuged at 12,000 rpm for 10 min at room temperature, the supernatant was aspirated and the tubes were inverted over an absorbing paper to remove the remaining supernatant. Cotton buds were used to remove any access drops from the walls of the tubes. 1 ml of Alkali reagent was added to each tube, mixed well and incubated for 10 min at room temperature. Absorption at 540 nm was measured using a spectrophotometer and the concentration of collagen was calculated against the calibration curve, using 10 mM HCl as a blank sample.

SDS-PAGE Instant Blue assay: Samples were boiled for 5 min in SAB buffer (reducing conditions) and centrifuged at 12,000 rpm for 5 min, prior to loading on a SDS PAGE, 8% acrylamide. The gel was run in a Mini Protean 3 unit (BioRad #165-3301, 165-3302). Instant Blue reagent (Novexin #ISB01L) was applied to the gel until the protein was visualized as blue bands on the gel. The gel was rinsed with water and dried. Concentration of the collagen bands was calculated by densitometry, against a human standard loaded on the same gel.

Coomassie analysis: Samples of collagen (in 10 mM HCl) were titered to pH 7.5 using 1M Tris. Sample Application Buffer containing 10% beta-mercaptoethanol and 8% SDS was added by diluting it fourfold in the 30 μl of pH titered samples. The samples were boiled for 7 minutes. 30 μl of the supernatant were loaded on to a 10% polyacrylamide gel and separated for 2 hours at 100 volts. The gel was transfer to a Coomassie-based solution for 1 hour with shaking. The Coomassie dye was removed using a standard destain solution.

SDS-PAGE and Western blot analysis of alpha-1 and alpha-2 collagen chains: Samples were boiled for 7 minutes in reducing sample application buffer (2.5% beta-mercaptoethanol and 2% SDS) and then centrifuged for 15 minutes at 13,000 rpm. 30 μl of the supernatant were separated on a 10% polyacrylamide gel. Following separation, standard Western blot protocols were employed to blot samples onto nitrocellulose membranes. Following transfer, the membranes were incubated with anti-Collagen I antibody (Chemicon Inc. catalogue #AB745) for immunodetection of alpha-1 and alpha-2 collagen chains. Molecular weight markers were purchased from Fermentas Inc. (catalogue #SM0671).

Controls: A positive control of Human Skin Collagen Type I purchased from Calbiochem (#234138) was employed as a marker for Western blot analyses. The grinding control sample reflects pellets derived from tobacco leaves immediately prior to resuspension in extraction buffer. The "D" control samples reflect the same pellets following resuspension in extraction buffer. "K" control samples include ficin-digested procollagen in 10 mM HCl. To monitor background ficin-independent protease activity, ficin-free cleavage samples were always prepared in parallel to all ficin digestion tests.

Purification of collagen from transgenic plants: Digestion of propeptides in the collagen-containing extract was initiated by the addition of 30 mg/L trypsin or 5 mg/L (50 μl/L) Subtilisin (Sigma #P5459) or 5 mg/L Ficin (Sigma #F4125). Proteolysis was performed at 15° C. for 4 hours. Elimination of non-soluble contaminants was performed by centrifugation for 30 min, 22,000 g, 15° C. The supernatant was recovered, and the collagen was precipitated by slowly adding crystalline NaCl to a final concentration of 3.13 M with constant stirring for 20 min at R.T. The solution was incubated in a cold room O.N. without stirring. Collection of the collagen was effected by centrifugation at 25,000 g, for 2 hours at 5° C.

The supernatant was carefully poured through four layers of gauze pad. The pellets were resuspended in 200 ml of 250 mM acetic acid and 2M NaCl for 5 minutes using a magnetic stirrer. The suspension was centrifuged at 25,000 g, for 40 min at 5° C. Traces of supernatant were eliminated from the glass vials. The pellets were redissolved in 200 ml of 0.5 M acetic acid at room temperature for 1 hour. Elimination of nonsoluble matter was performed by centrifugation at 16,000 g, 30 min, 15° C. The supernatant was poured through 12 layers of gauze pad. Collagen was precipitated by slowly adding NaCl to a final concentration of 3M with constant stirring for 20 min at R.T. The solution was incubated at 4° C. for 8 hours up to O.N. Collection of collagen was performed by centrifugation at 25,000 g, for 2 hours at 5° C. Following aspiration of the supernatant, the pellet was redissolved in 200 ml of 0.5 M acetic acid using a magnetic stirrer at R.T. for 1 hour. Elimination of non-soluble matter was performed by centrifugation at 16,000 g, 30 min, 15° C. The supernatant was poured through 12 layers of gauze pad. Collagen was precipitated by slowly adding NaCl to a final concentration of 3M with constant stirring for 20 min at R.T. The solution was incubated at 4° C. for 8 hours. Collagen was collected by centrifugation at 2,000 g, for 2 hours at 5° C. Supernatant was aspirated. The pellet was redissolved in 40 ml of 10 mM HCl by pipetation and vortexing for 5 min at R.T. The solution was transferred to a dialysis bag (MWCO 14,000 Da) and dialyzed for 4 hours against 4 L of 10 mM HCl at 4° C. This dialysis was repeated O.N.

Sterilization of the collagen was performed by filtering the solution first through a 0.45 μm filter, then through a 0.2 μM filter using a 30 ml syringe. Collagen was further concentrated via ultrafiltration using a Vivaspin PES 20 ml filtration tube (Vivascience, #VS2041, MWCO 100,000). Centrifugation was performed for 45 min at 5000 g at 5° C. until the volume was reduced to 0.75 ml.

Optimization of digestion kinetics and conditions of procollagen cleavage by food-grade ficin: Pellets (collected as described in Example 10), up to saturation in 25% ammonium sulfate (AMS)) were resuspended in a buffer (Buffer A: 4.5 mM potassium metadisulfite, 12.5 mM L-cystein, 7.5 mM EDTA dissolved in 0.1 M sodium phosphate buffer, titrated to pH 7.5 with 10 M NaOH or 6 N HCl) at a ratio of 4.36 g pellet:200 mL ice cold buffer. Samples were then stirred for 20 min at 15° C. Aliquots of 10 mL per 15 mL test tube were then prepared, followed by administration of increasing concentrations (5-15 mg/L) of ficin (Fig tree latex, Biochem Europe food grade ficin). Samples were incubated at 15° C. for 1-3 hours and separated by SDS-PAGE and then analyzed by Western blot for presence of collagen migrating at lower molecular weights than procollagen.

Tobacco leaf-derived pellets resuspended in phosphate Buffer A (27.2 g:800 mL buffer) of varying pH values (5.5, 7.5, or 8.5) were treated with 10 mg/L ficin in the presence of 0-3 M NaCl for 1 h at 15° C. The reaction was terminated by centrifuging 1 mL samples from each reaction mixture (10 min, 15000 g, 4° C.). Pellets were resuspended in 1 mL Buffer A (pH 7.5), separated by SDS-PAGE and analyzed by means of Western blot.

Optimization of digestion kinetics and conditions of procollagen cleavage by pharmaceutical-grade ficin: Tobacco leaf pellets were resuspended in a pharmaceutical-grade (Biochem-Europe Pharm grade) ficin-containing extraction buffer (10 mg/L) of varying pH values (7.5.8.5.9.5) along with increasing NaCl concentrations (0-3 M) for 5-45 minutes. Further experiments studied the necessity and optimal conditions and concentrations of EDTA and L-cystein as additives to the extraction buffer. Samples were incubated in the digestion mixture in the presence of 0-100 mM EDTA with 0-80 mM L-cystein for 1-3 h at 15° C., at pH 7.5 and without NaCl.

Fibrillogenesis: Fibrillogenesis is regarded as a collagen functionality test. Hence, the ability of purified collagen digested by ficin to form fibrils is an essential property of the obtained product. Test method: The pH of the collagen-containing solution (duplicate samples) was neutralized to pH 6.7 with sodium phosphate, pH 11.2, and then incubated at 27+/−2 μC for 6 hours. Samples were centrifuged to sediment the hydrogel which was formed. Protein concentration of both pre and post-neutralization (supernatant) samples was determined via the Lowry method. PURECOL™ (Purchased from NUTACON, Cat No. 5409) was employed as positive control and gelatin as a negative control.

Example 7. Extraction and Purification of Collagen from Transgenic Plants in the Presence of Trypsin and Pepsin The production of human collagen in plants was initiated in order to avoid the use of collagen from mammalian sources since the use of mammalian proteins in human cosmetics or medical applications may be risky to human health as the evolutionary proximity is relativity close. The known disease Creutzfeldt-Jakob disease (CJD) is an example of one which is caused by consumption of infected mammal proteins by humans.

Initially, the purification of collagen from transgenic plants was performed using bovine pancreatic Trypsin and the digestive protease Pepsin, both of which catalyze the hydrolysis of proteins in the animal digestive system. The following examples illustrate the identification of a protease from a non-animal source suitable for use in the collagen purification process.

Results

Figure 10:
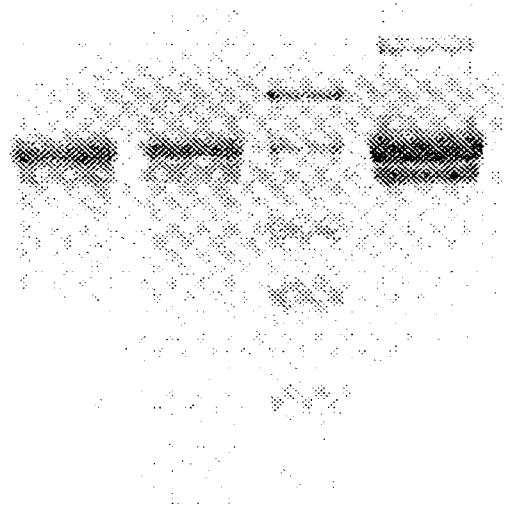
FIG. 10 shows tobacco-leaf derived purified collagen following digestion with trypsin. Collagen was purified from the tobacco plant transgenic leaf line number 13-6 ground in 100 mM Tris buffer, centrifuged, proteolyzed and precipitated in a high salt concentration buffer, as detailed in the Material and Methods section. Following resuspension, collagen-containing pellets were washed, dialyzed and concentrated to the final product. This gel depicts a Coomassie stain analysis of the collected collagen samples where lanes 1 and 2 are the resulting collagen following digestion of procollagen with 300 mg/L Trypsin. Propeptide-free pig-derived collagen (0.5 mg/ml) was loaded and run as a positive control for collagen type 1 alpha 1 and alpha 2 chains.
Figure 11:
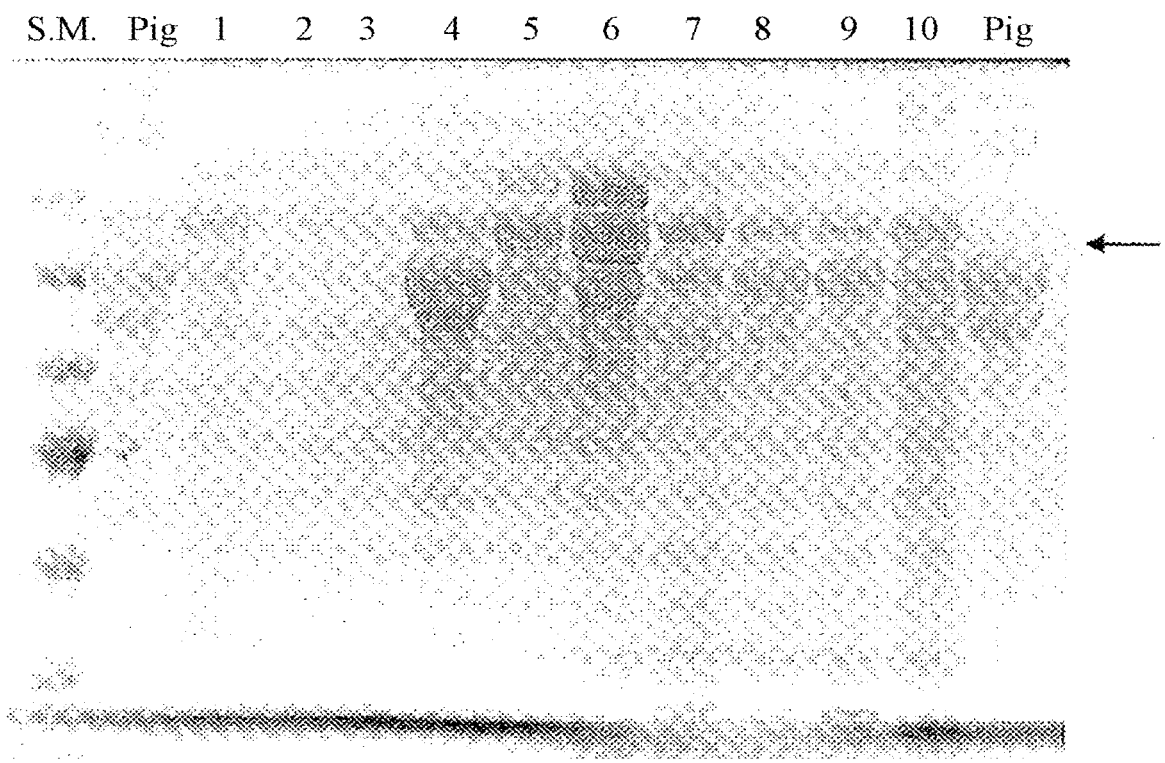
FIG. 11 shows tobacco-leaf derived purified collagen following digestion with varying concentrations of trypsin. Collagen was extracted and purified as in FIG. 10 following digestion with 20 mg/L Trypsin (lanes 1-7) or 30 mg/L (lanes 8-10). Products were separated on a 10% SDS PAGE and analyzed with a Coomassie-based staining solution. Propeptide-free pig-derived collagen (0.5 mg/ml) was loaded and run as a positive control for collagen type 1 alpha 1 and alpha 2 chains.

Propeptide digestion during the purification of collagen was first performed by the pancreatic enzyme Trypsin. Trypsin, at 300 mg/L digested the collagen propeptides, however collagen yield was very low at the end of the purification process (FIG. 10). When the concentration of trypsin was lowered to 20 mg/L or 30 mg/L, the yield was higher, however procollagen digestion was only partial and inconsistent between identical samples (FIG. 11).

Figure 12:
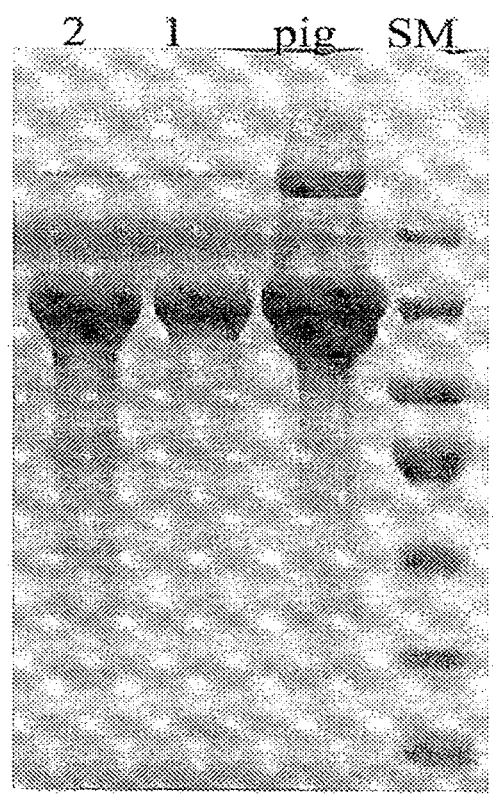
FIG. 12 shows tobacco-leaf derived purified collagen following digestion with trypsin and pepsin. Collagen was extracted and purified as in FIG. 10 following digestion with 30 mg/L Trypsin and 1 µg/200 ml Pepsin (lanes 1-2). Products were separated on a 10% SDS PAGE and analyzed with a Coomassie-based staining solution. Propeptide-free pig-derived collagen (0.5 mg/ml) was loaded and run as a positive control for collagen type 1 alpha 1 and alpha 2 chains.
Figure 13:
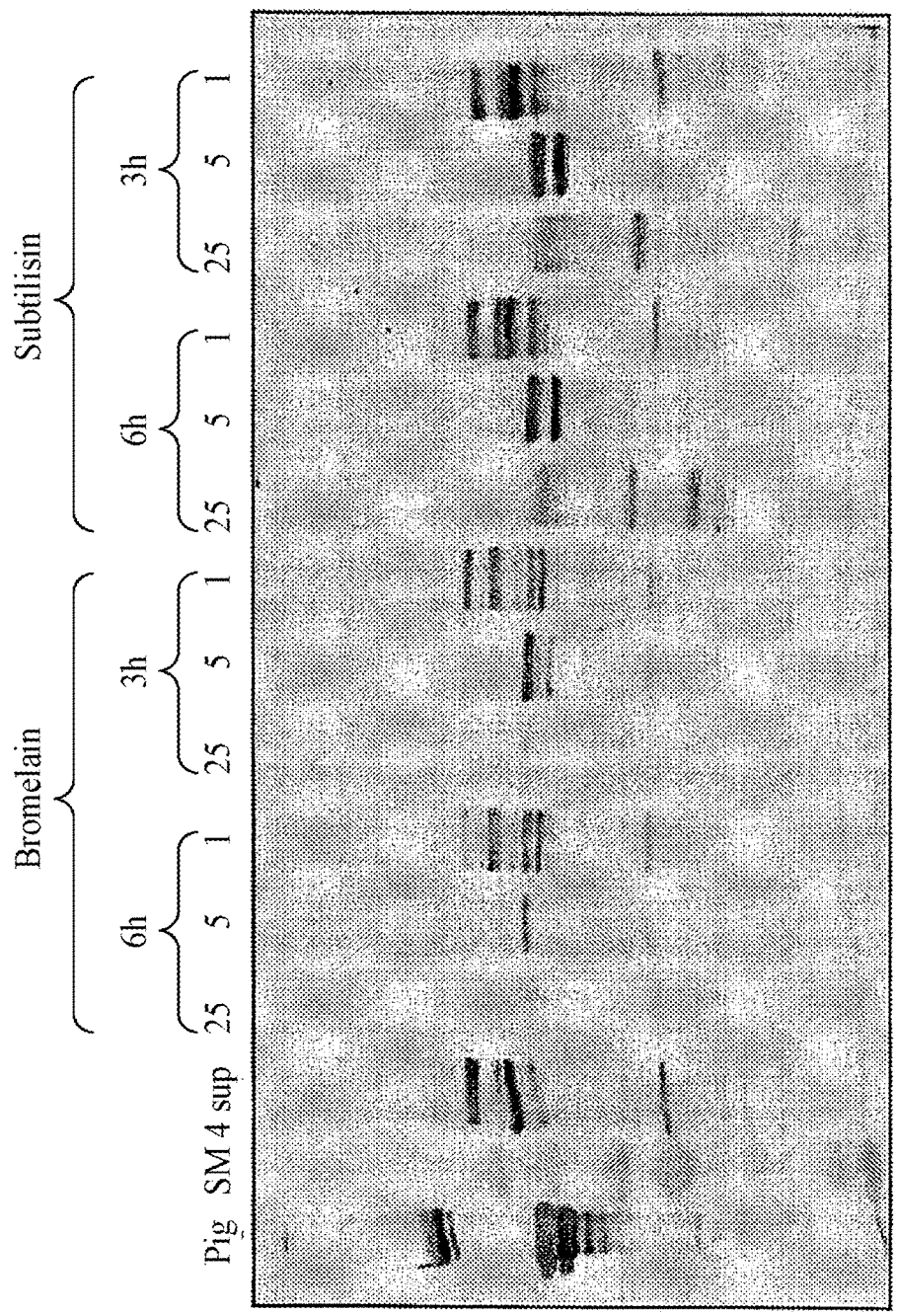
FIG. 13 shows collagen chains obtained upon digestion of procollagen with Subtilisin or Bromelain. Collagen was purified from the tobacco plant transgenic leaf line number 13-361 ground in 100 mM Tris buffer, centrifuged and proteolyzed with either Subtilisin (1-25 mg/L) or Bromelain (1-25 mg/L) incubated for 3 or 6 hrs. Samples were separated on a 10% SDS PAGE and blotted to nitrocellulose membranes. Collagen chains were immunodetected using anti-collagen I. Untreated supernatants collected following homogenization and centrifugation served as collagen-free negative controls (lane 3-4 sup). Propeptide-free pig-derived collagen (2.5 µg) served as a positive control for alpha 1 and alpha 2 chains (lane 1).

In an attempt to overcome this problem, varying incubation temperatures and times were tried; however, the results did not lead to a change in yield (data not shown). The addition of Pepsin enzyme later on in the purification process resolved the partial digestion problem (FIG. 12) and yielded alpha-1 and alpha-2 collagen which co-migrated with pig-derived collagen control samples.

Example 8. Collagen Extraction and its Enzymatically-Induced Digestion

Figure 14:
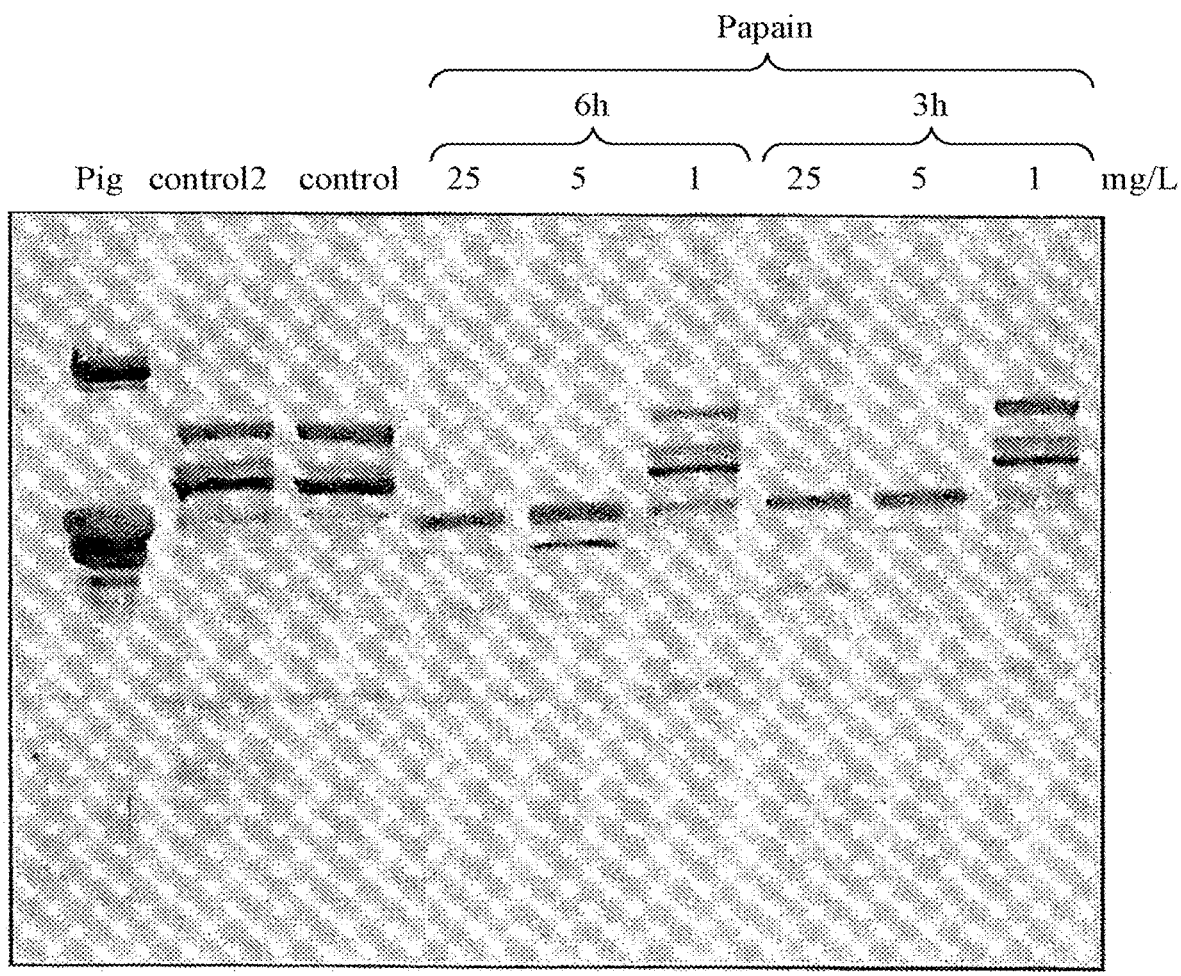
FIG. 14 shows collagen chains obtained upon digestion of procollagen with Papain. Collagen was purified from the tobacco plant transgenic leaf line number 13-361 ground in 100 mM Tris buffer, centrifuged and proteolyzed with Papain (1-25 mg/L) over a 3 or 6 hrs incubation period. Samples were separated on a 10% SDS PAGE and blotted to nitrocellulose membranes. Collagen chains were immunodetected using anti-collagen I. Untreated supernatants collected following homogenization, centrifugation and incubation at 15° C. for 3 hrs (lane 3) or 6 hrs (lane 2) with no enzyme served as collagen-free negative controls. Propeptide-free pig-derived collagen (2.5 µg) served as a positive control for alpha 1 and alpha 2 chains (lane 1).
Figure 15:
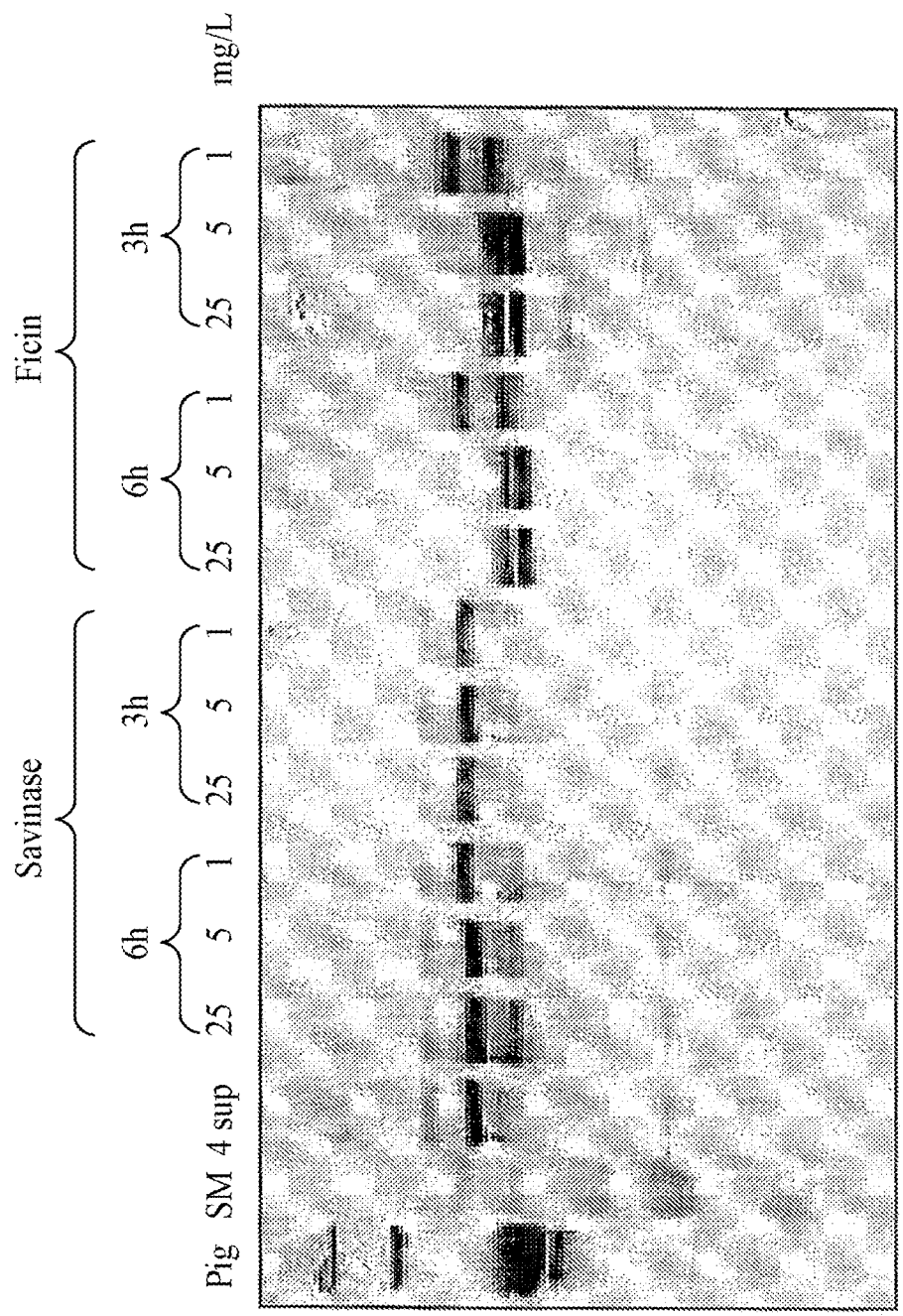
FIG. 15 shows collagen chains obtained upon digestion of procollagen with Ficin or Savinase. Collagen was purified from the tobacco plant transgenic leaf line number 13-361 ground in 100 mM Tris buffer, centrifuged and proteolyzed with Ficin (1-25 mg/L) or Savinase (1-25 mg/L) over a 3 or 6 hrs incubation period. Samples were separated on a 10% SDS PAGE and blotted to nitrocellulose membranes. Collagen chains were immunodetected using anti-collagen I. Untreated supernatants collected prior to proteolysis served as a collagen-free control sample (lane 3). Propeptide-free pig-derived collagen (2.5 µg) served as a positive control for alpha 1 and alpha 2 chains (lane 1).
Figure 16:
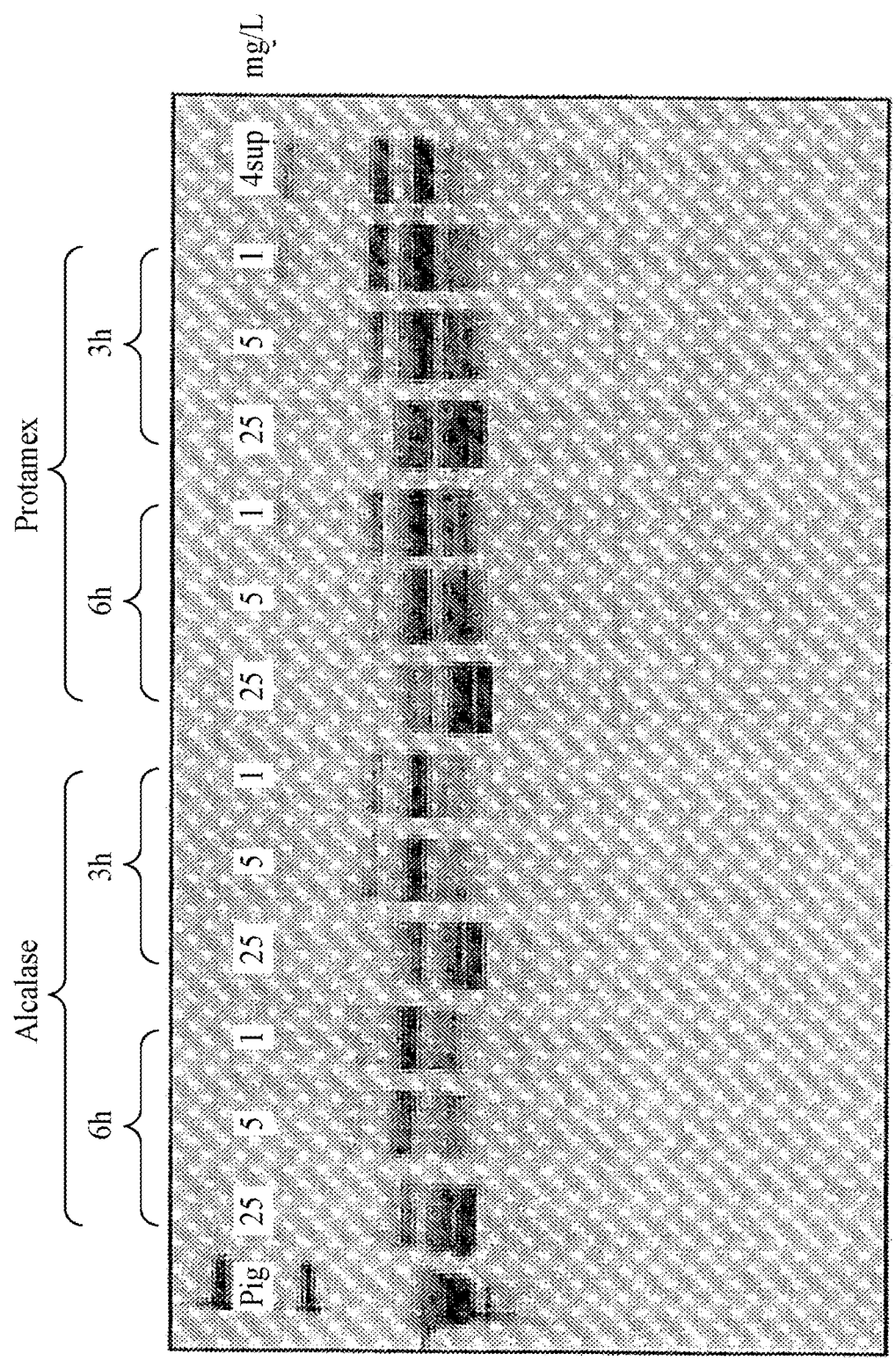
FIG. 16 shows collagen chains obtained upon digestion of procollagen with Protamex or Alcalase. Collagen was purified from the tobacco plant transgenic leaf line number 13-361 ground in 100 mM Tris buffer, centrifuged and proteolyzed with Protamex (1-25 mg/L) or Alcalase (1-25 mg/L) over a 3 or 6 hrs incubation period. Samples were separated on a 10% SDS PAGE and blotted to nitrocellulose membranes. Collagen chains were immunodetected using anti-collagen I. Untreated supernatants collected prior to proteolysis served as a collagen-free control sample (lane 14). Propeptide-free pig-derived collagen (2.5 µg) served as a positive control for alpha 1 and alpha 2 chains (lane 1).
Figure 17:
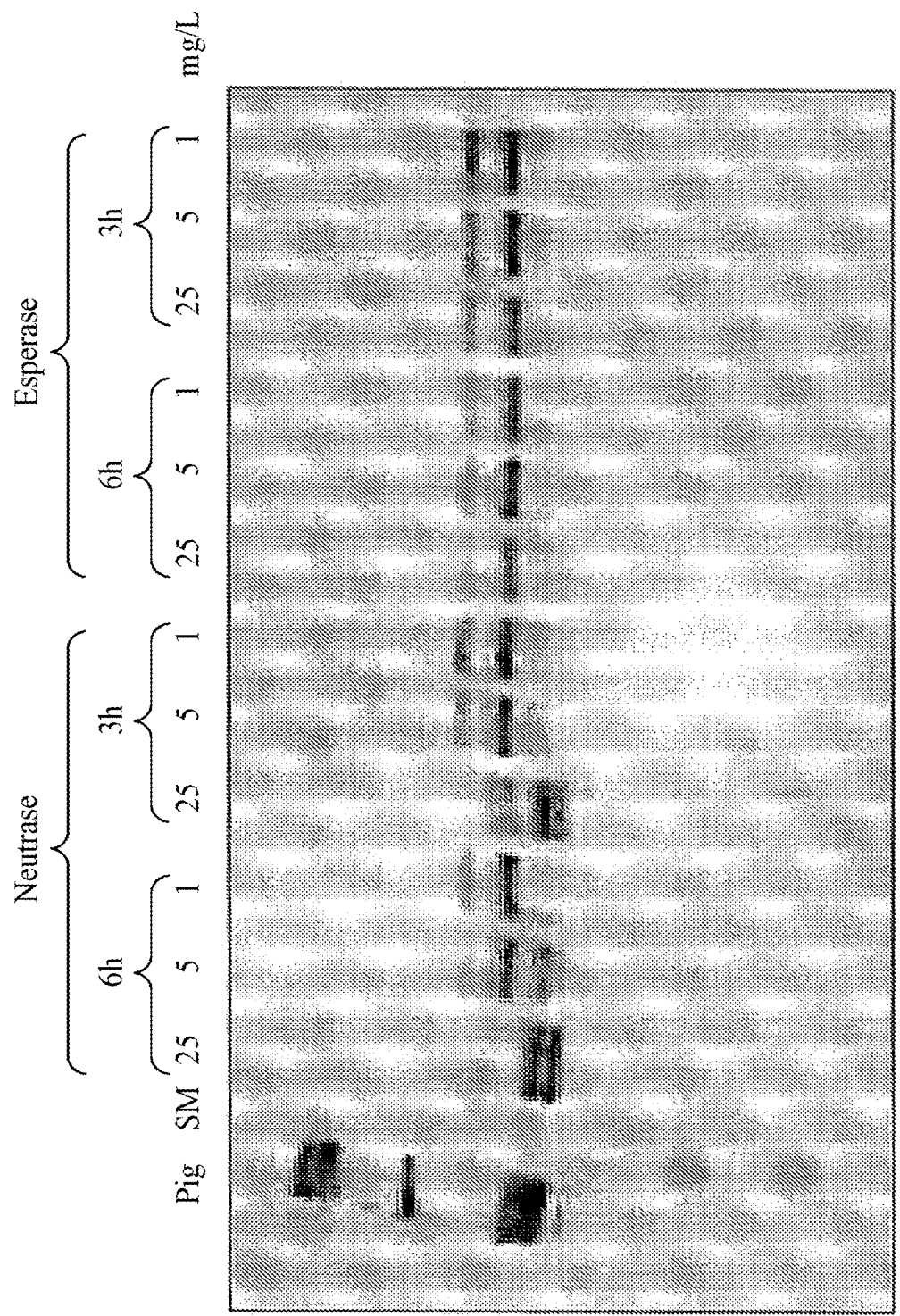
FIG. 17 shows collagen chains obtained upon digestion of procollagen with Esperase or Neutrase. Collagen was purified from the tobacco plant transgenic leaf line number 13-361 ground in 100 mM Tris buffer, centrifuged and proteolyzed with Esperase (1-25 mg/L) or Neutrase (1-25 mg/L) following a 3 or 6 hrs incubation period. Samples were separated on a 10% SDS PAGE and blotted to nitrocellulose membranes. Collagen chains were immunodetected using anti-collagen I. Propeptide-free pig-derived collagen (2.5 µg) served as a positive control for alpha 1 and alpha 2 chains (lane 1).
Figure 18:
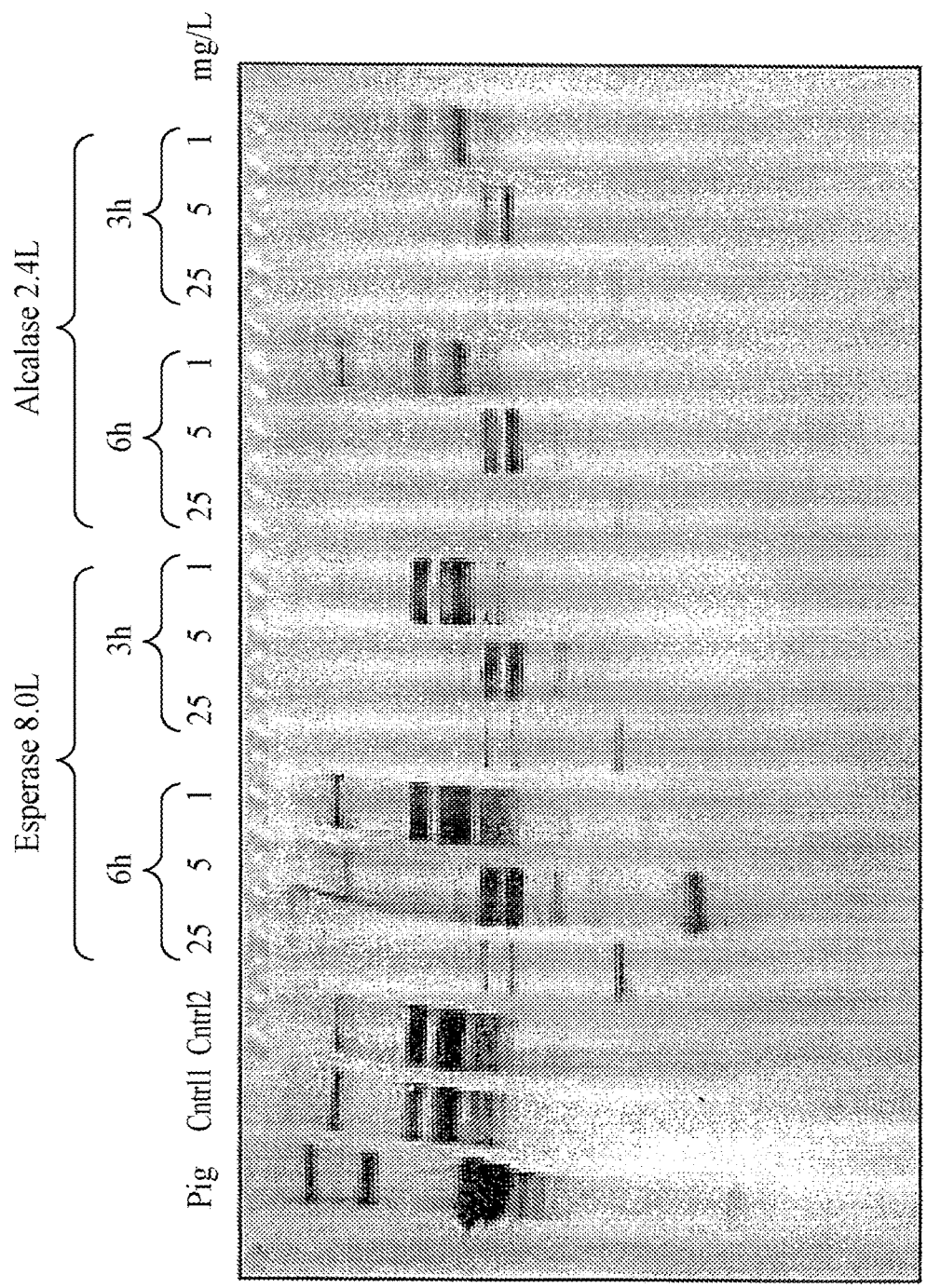
FIG. 18 shows collagen chains obtained upon digestion of procollagen with Esperase 8.0 L or Alcalase. Collagen was purified from the tobacco plant transgenic leaf line number 13-361 ground in 100 mM Tris buffer, centrifuged and proteolyzed with Esperase (1-25 mg/L) or Neutrase (1-25 mg/L) following a 3 or 6 hrs incubation period. Samples were separated on a 10% SDS PAGE and blotted to nitrocellulose membranes. Collagen chains were immunodetected using anti-collagen I. Untreated supernatants collected following homogenization, centrifugation and incubation at 15° C. for 3 h (lane 3) or 6 h (lane 2) with no proteolytic enzyme served as collagen-free negative controls. Propeptide-free pig-derived collagen (2.5 µg) served as a positive control for alpha 1 and alpha 2 chains (lane 1).

However, the trypsin-pepsin solution was not optimal since it required two different enzymes, lengthening the purification process. Furthermore, both enzymes are from animal sources. In order to overcome these issues, a screen of different protease enzymes of non-animal origin, was performed. Varying digestion patterns were obtained by the different enzymes screened. Very little or no observable digestion of the propeptides resulted from the incubation of collagen with the Savinase (FIG. 15) and Esperase (FIG. 17) enzymes. Incubation with Papain (FIG. 14), Bromelain (FIG. 13), Alcalase 2.4 L and Esperase 8.0 L (FIG. 18), led to over- or under-digestion of the propeptides. Alcalase and Protamex enzymes (FIG. 16) led to the desired digestion pattern and level (25 mg/L, 6 hr), with alpha 1 and alpha 2 chains migrating similar to the pig-derived collagen sample. However, not all the molecules were fully digested and may require longer incubation periods. Optimal results were obtained upon procollagen incubation with Ficin (5 mg/L and 25 mg/L) (FIG. 15) where the bands of alpha 1 and alpha 2 chains comigrated with the pig-derived collagen control sample, with no apparent overdigestion. Similar results were demonstrated with Subtilisin 5 mg/L for 3 h (FIG. 13) and Neutrase 25 mg/L for 6 h (FIG. 17).

Figure 19:
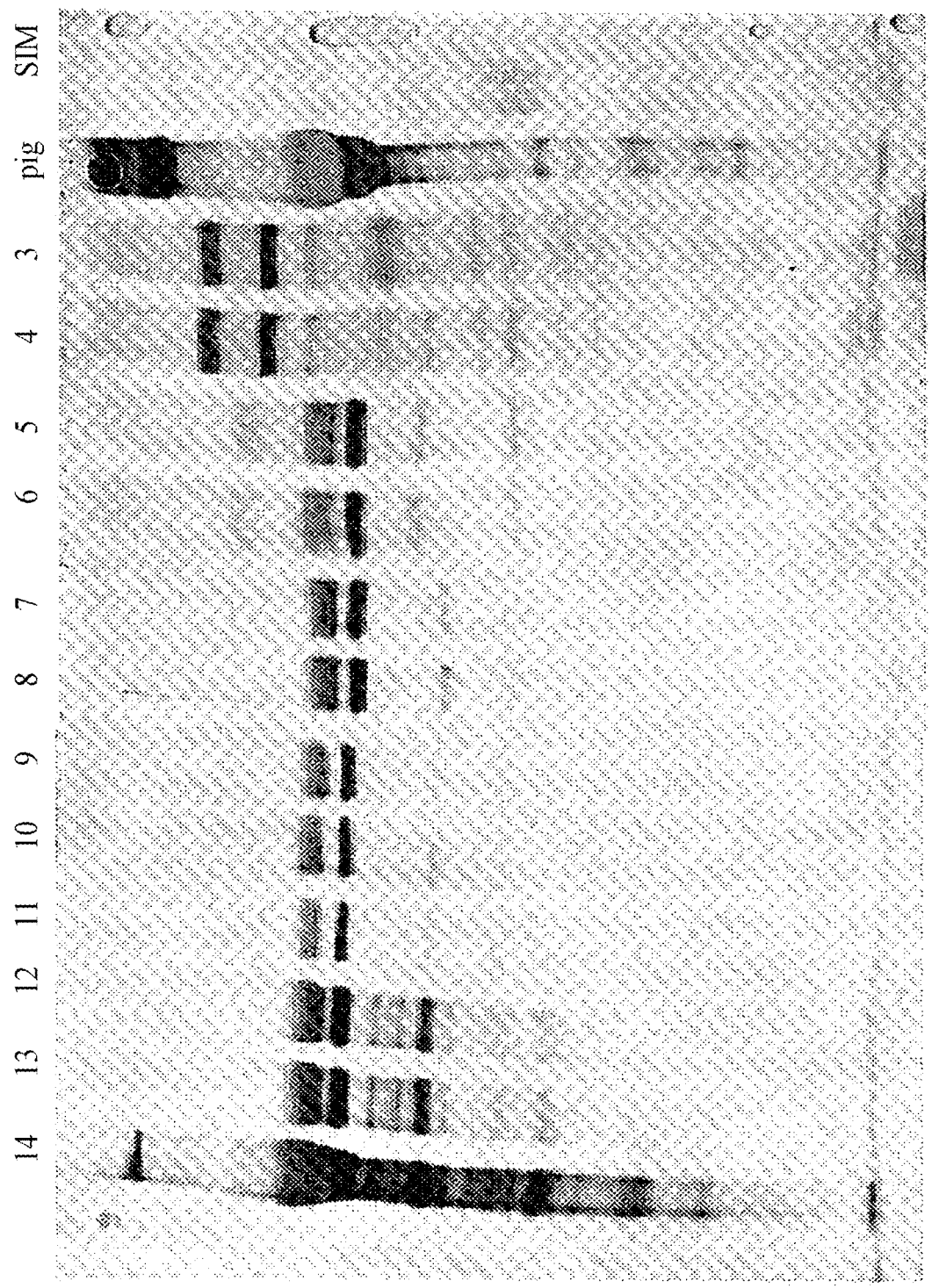
FIG. 19 shows collagen chains obtained at various purification stages following digestion of procollagen with Ficin. Collagen was purified from the tobacco plant transgenic leaf line number 13-361 ground in 100 mM Tris buffer, centrifuged and proteolyzed with Ficin (5 mg/L) following a 3 hrs incubation period at 15° C. Samples were separated on a 10% SDS PAGE and blotted to nitrocellulose membranes. Collagen chains was immunodetected using anti-collagen I. Samples collected after grinding, centrifugation and incubation of supernatant with Ficin were loaded in lane 5. Lanes 6-14 depict samples of ficin-treated collagen at different stages in purification process: lane 6: sample post-ficin incubation and centrifugation; lane 7: following salt precipitation and resuspension in 0.5M acetic acid; lane 8: sample as in lane 7 with an added centrifugation step; lane 9: sample as in lane 8 following resuspension in 0.5 M acetic acid and centrifugation; lane 10: mature collagen following resuspension in 10 mM HCl and dialysis; lane 11: sample as in lane 10 with an additional filtration step; lane 12: sample as in lane 11 with an additional 5× concentration step; lane 13: sample as in lane 11 with an additional 20× concentration step; lane 14: sample as in lane 13 with additional 5× concentration step. Untreated procollagen samples (lanes 3-4) served as negative controls. Propeptide-free pig-derived collagen (2.5 µg) served as a positive control for alpha 1 and alpha 2 chains (lane 1).
Figure 20:
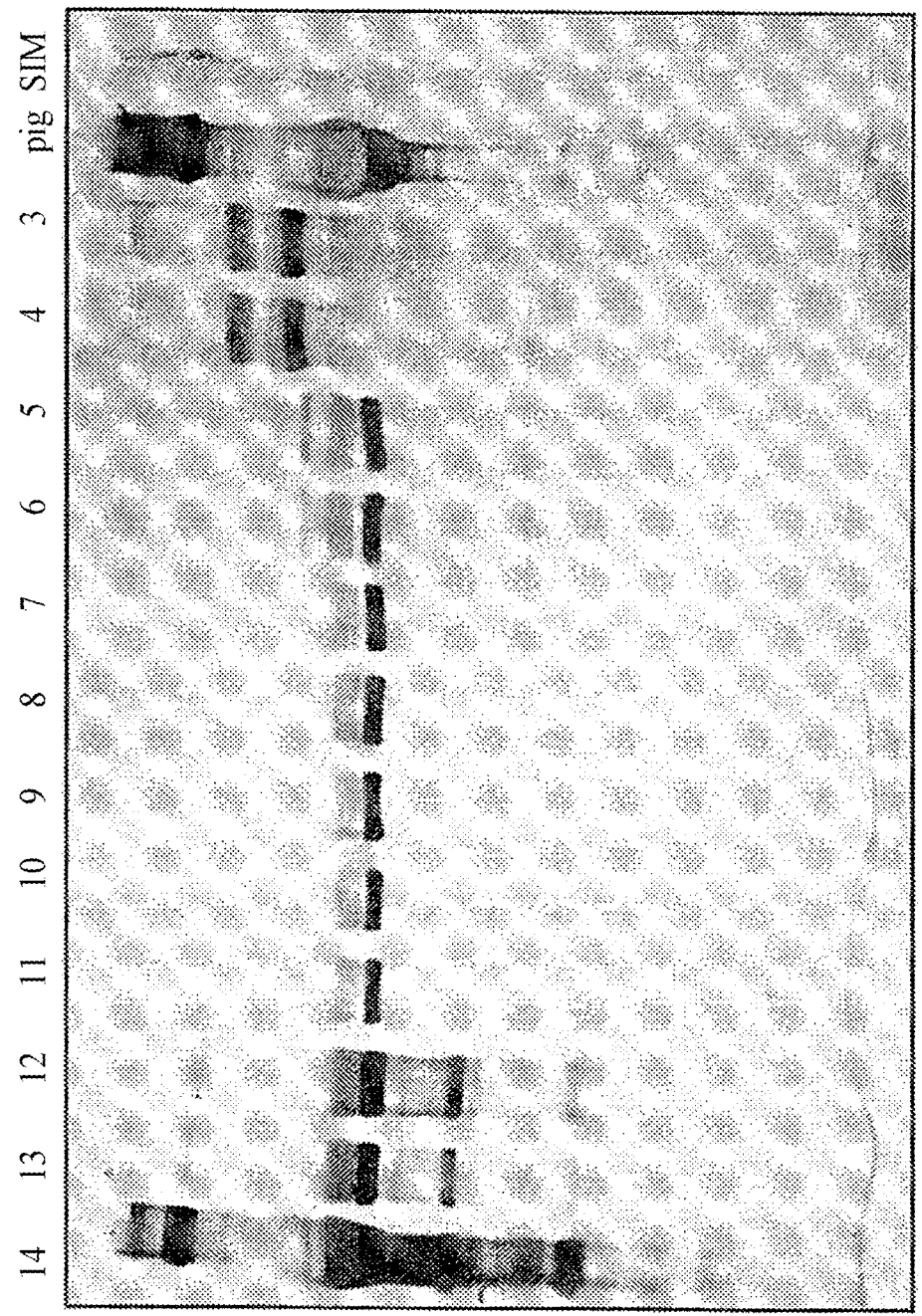
FIG. 20 shows collagen chains obtained at various purification stages following digestion of procollagen with Ficin. Collagen was purified from the tobacco plant transgenic leaf line number 13-361 ground in 100 mM Tris buffer, centrifuged and proteolyzed with Ficin (5 mg/L) following a 3 hrs incubation period at 15° C. Samples were separated on a 10% SDS PAGE and blotted to nitrocellulose membranes. Collagen chains were immunodetected using anti-collagen I. Samples collected after grinding, centrifugation and incubation of supernatant with Ficin were loaded in lane 5. Lanes 6-14 depict samples of ficin-treated collagen at different stages in purification process: lane 6: sample post-ficin incubation and centrifugation; lane 7: following salt precipitation and resuspension in 0.5M acetic acid; lane 8: sample as in lane 7 with an added centrifugation step; lane 9: sample as in lane 8 following resuspension in 0.5 M acetic acid and centrifugation; lane 10: mature collagen following resuspension in 10 mM HCl and dialysis; lane 11: sample as in lane 10 with an additional filtration step; lane 12: sample as in lane 11 with an additional 5× concentration step; lane 13: sample as in lane 11 with an additional 20× concentration step; lane 14: sample as in lane 13 with additional 5× concentration step. Untreated procollagen samples (lanes 3-4) served as negative controls. Propeptide-free pig-derived collagen (2.5 µg) served as a positive control for alpha 1 and alpha 2 chains (lane 1).
Figure 21:
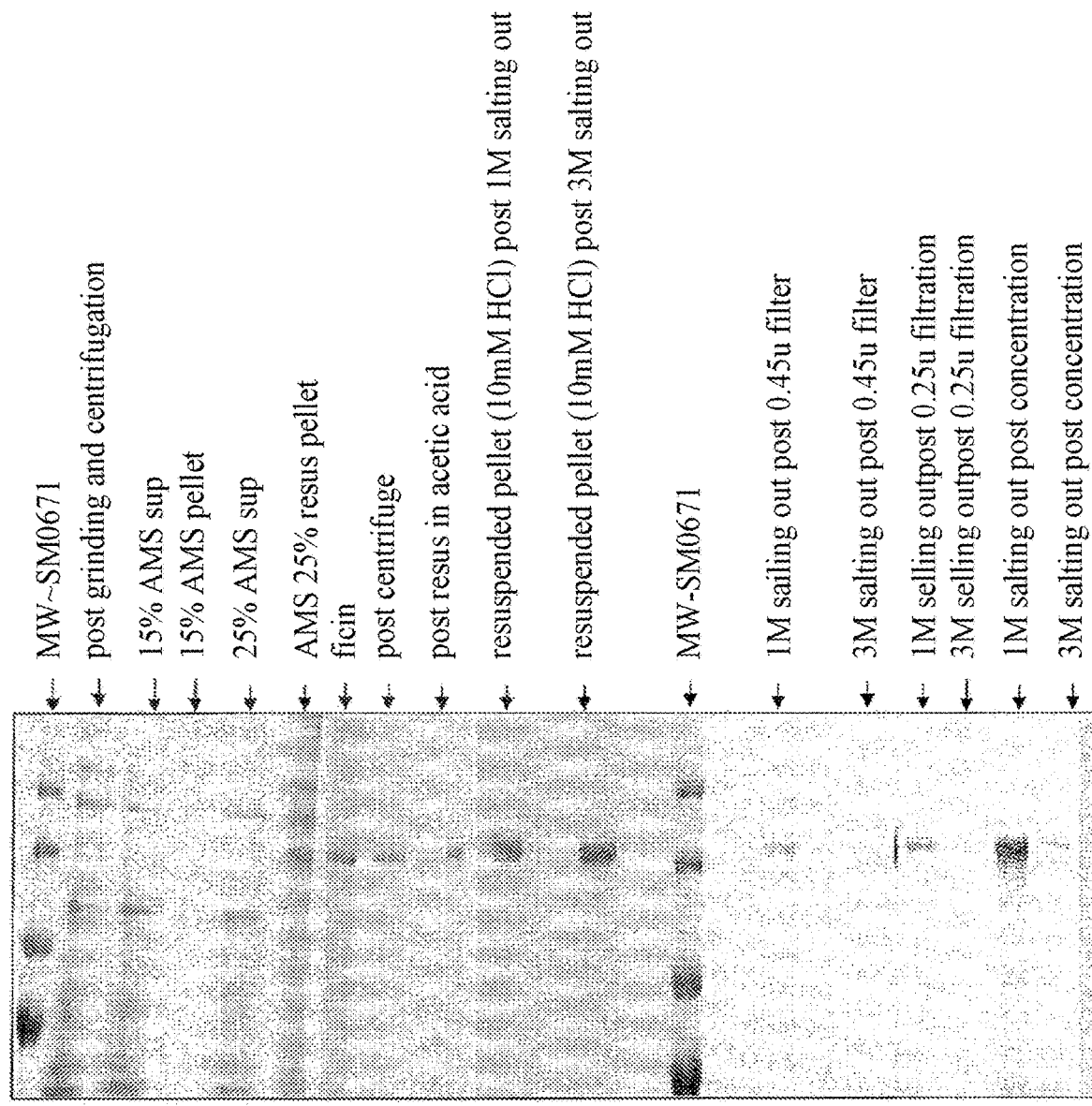
FIG. 21 shows collagen content of post-ficin treated samples at the various stages of purification. Collagen-containing samples were collected at each extraction and purification stage of a reactor size AMS-based purification procedure described in the Material and Methods section. Samples were treated with ficin (5 mg/L, 15° C., 3 h) for propeptide removal, separated on a 10% SDS PAGE and stained with a Coomassie-based staining solution.

Example 9. Extraction and Purification of Collagen from Transgenic Plants Following Digestion with Subtilisin or Ficin Collagen purifications from 450 gr leaves of transgenic plants (13-361 or 13-6-52) were performed followed by procollagen digestion with Ficin (FIG. 19) or Subtilisin (FIG. 20). Samples of the collagen at the various stages of the purification process were analyzed by Western analysis. Propeptide digestion by ficin and subtilisin led to the desirable degree of processing of Collagen 1 and Collagen 2. Bands of lower molecular weight were observed on the Western blots throughout the purification process, however, these bands appeared in the plant extracts prior to the incubation with the enzyme (lanes 3-4) and also in the pig-derived collagen control sample (positive control) (FIG. 19).

Example 10. Scaled Up Extraction and Purification of Collagen from Transgenic Plants Following Digestion with FICIN 1 kg of transgenic tobacco leaves were ground with pre-chilled 2 L extraction buffer (100 mM sodium phosphate buffer pH 7.5, 4.5 mM potassium Meta disulfite, 12.23 mM L-cystein and 7.5 mM EDTA) in a 4 L reactor (ESCO model EL-3) for 20 minutes (5° C., 50% scraper speed and 100% homogenizer blade rpm). 6.68 g charcoal and 16.67 g of PVPP were added to the extract and continuously stirred for 20 minutes (5° C. and 50% scraper speed). Extract was centrifuged (11000 rpm, 5° C., 0.5H) and supernatant was saturated with 15% ammonium sulfate (1 hour stirring, 5° C.). Following a 6880 rpm, 5° C., 30 min, the supernatant was saturated to 25% ammonium sulfate and stirred for 1 hour (5° C.). Following recentrifugation, the pellet (6880 rpm, 5° C., 30 min) was resuspended (in extraction buffer) in 15% of the volume collected after the first centrifugation step. Removal of propeptides was enabled by a 3 hr digestion, 15° C. with 5 mg/L ficin (Biochem Europe). The sample was centrifuged (11,000 rpm, 15° C., 30 min) and the mature collagen was precipitated using 3 M NaCl (NaCl was added slowly while stirring and left O.N. at 4° C.). Following precipitation (13,000 rpm, 5° C., 2 hours), the supernatant was discarded, and the pellet was resuspended in 0.5M acetic acid. Another round of 3M salting out (O.N) and centrifugation was followed by the resuspension of the pellets in 40 ml of 10 mM HCl. The sample was transferred to a dialysis bag (12-14 kDa) and dialyzed against 4 L 10 mM HCl, at 4° C., for 4 hours. The dialysis was repeated with fresh 4 L 10 mM HCl, O.N. The dialyzed solution was filtered through a 0.45 micron filter (previously washed with 10 mM HCl) and then through a 0.25 micron filter. The samples were finally concentrated in a Vivaspin (Vivascience) filtration tube (100 kDa).

Example 11. Solubility of Atelocollagen Produced as Recombinant Human Procollagen in Transgenic Tobacco Plants The concentration of atelocollagen generated according to Examples 9-10 was assayed by two methods as follows as described in the Methods section. The resulting concentrations obtained for several typical preparations digested with ficin, are listed in Table 4, herein below:

TABLE 4

| | Collagen concentrations as determined via the Instant blue or Sircol staining methods | |
|---|---|---|
| Lot No. | mg/ml collagen by Instant blue | mg/ml collagen by Sircol ™ |
| UPEK1 | 15.7 | 9.3 |
| UPEK2 | 5.8 | 4.78 |
| PEK052 | 6.8 | 5.5 |
| UPEK3 | 3.4 | 3.54 |
| UPEK4 | NA | 3.3 |
| UPEK6-1 | 5.9 | 4.7 |
| UPEK6-2 | 4.3 | 3.7 |

Example 12. Ficin-Dependent Proteolysis of Tobacco Leaf-Derived Procollagen

Figure 22:
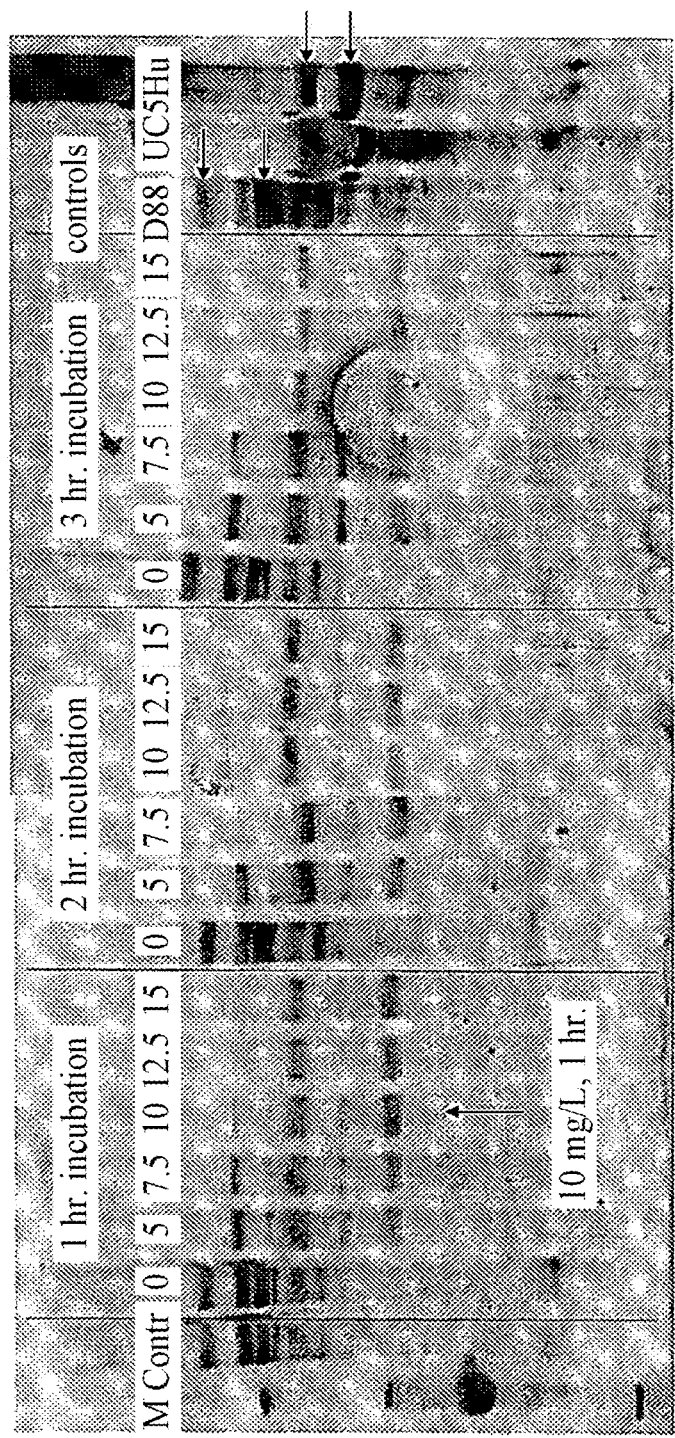
FIG. 22 shows optimization of procollagen cleavage by food-grade ficin: optimization of ficin concentration and reaction time. AMS-pelleted procollagen-expressing tobacco leaf extracts were resuspended in extraction buffer and then incubated with increasing concentrations of food-grade ficin (5-15 mg/L). Reaction mixtures were then incubated at 15° C. for 1-3 hours. Cleavage was terminated by centrifugation and protein samples were separated on 8% SDS-PAGE, transferred to nitrocellulose membranes and immunoblotted for alpha-1 and alpha-2 collagen chains with anti-collagen I. Procollagen bands are indicated by white arrows, while the red arrows indicate cleaved collagen bands.

Digestion kinetics of procollagen by food-grade ficin: To calibrate appropriate ficin concentrations and incubation times allowing for highest collagen yields, procollagen-expressing tobacco leaf pellets were incubated with increasing concentrations of food-grade ficin (5-15 mg/L) at 15° C. for 1-3 hours. Samples were then analyzed by immunodetection of alpha-1 and alpha-2 collagen chains on Western blots. Increased ficin concentrations offered improvement in collagen chain yield following a 1-hour incubation period (FIG. 22, lane 5 vs. 6). However, upon extension of reaction time, increased ficin concentrations led to overdigestion of collagen (FIG. 22, lane 11 vs. 12-14 and lane 17 vs. 18-20). Thus, optimal conditions for digestion of procollagen to collagen were set at addition of 10 mg/L food-grade ficin for 1 hour at 15° C.

Figure 23A:
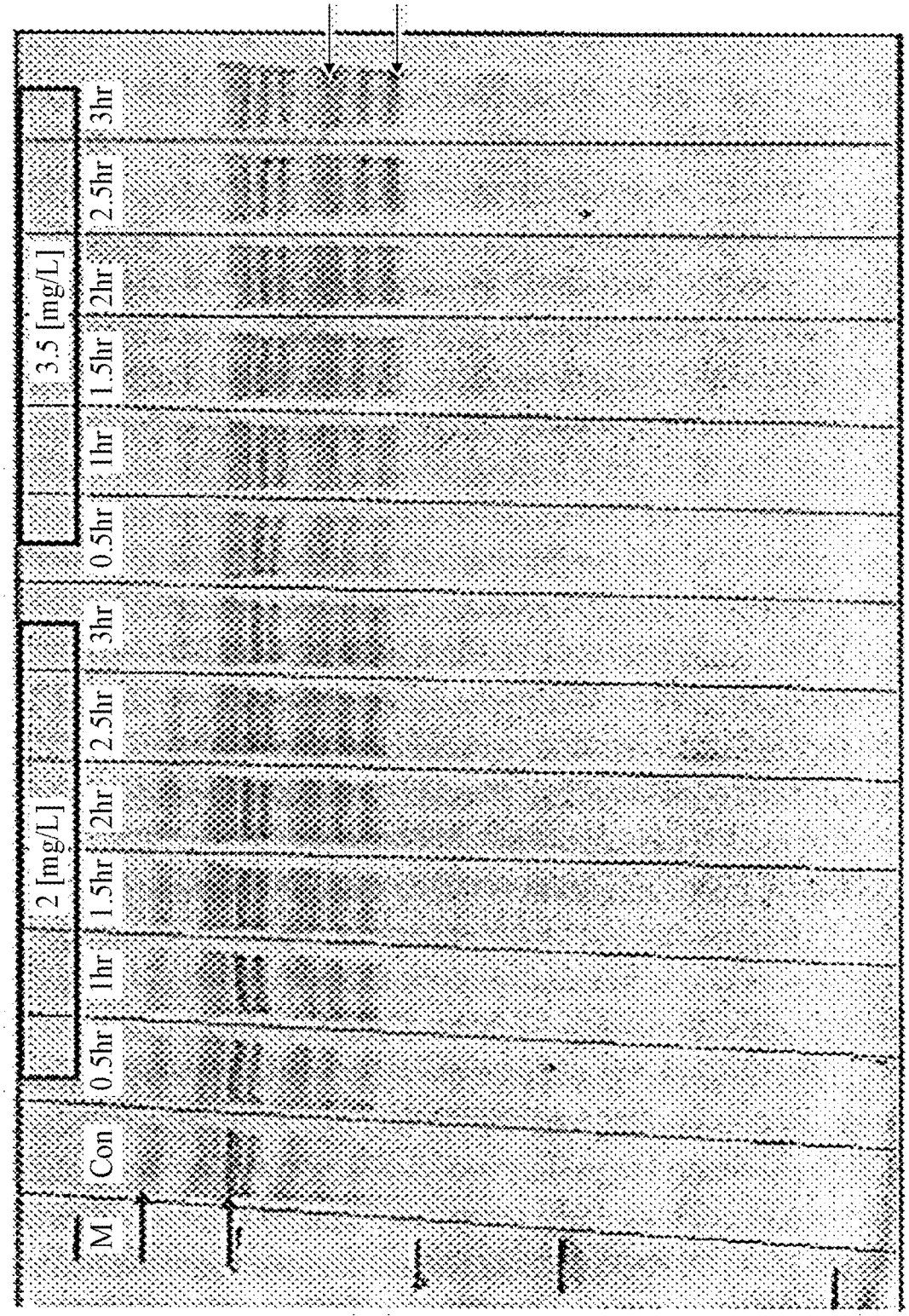
FIGS. 23a-c show optimization of procollagen cleavage by pharmaceutical-grade ficin: optimization of ficin concentration and reaction time. AMS-pelleted procollagen-expressing tobacco leaf extracts were resuspended in extraction buffer and then incubated with increasing concentrations of pharmaceutical-grade ficin (2.5-10 mg/L). Reaction mixtures were then incubated at 15° C. for 0.5-3 hours. Cleavage was terminated by centrifugation and protein samples were separated on 8% SDS-PAGE, transferred to nitrocellulose membranes and immunoblotted for alpha-1 and alpha-2 collagen chains with anti-collagen I. Arrows indicate procollagen band and collagen bands.
Figure 23B:
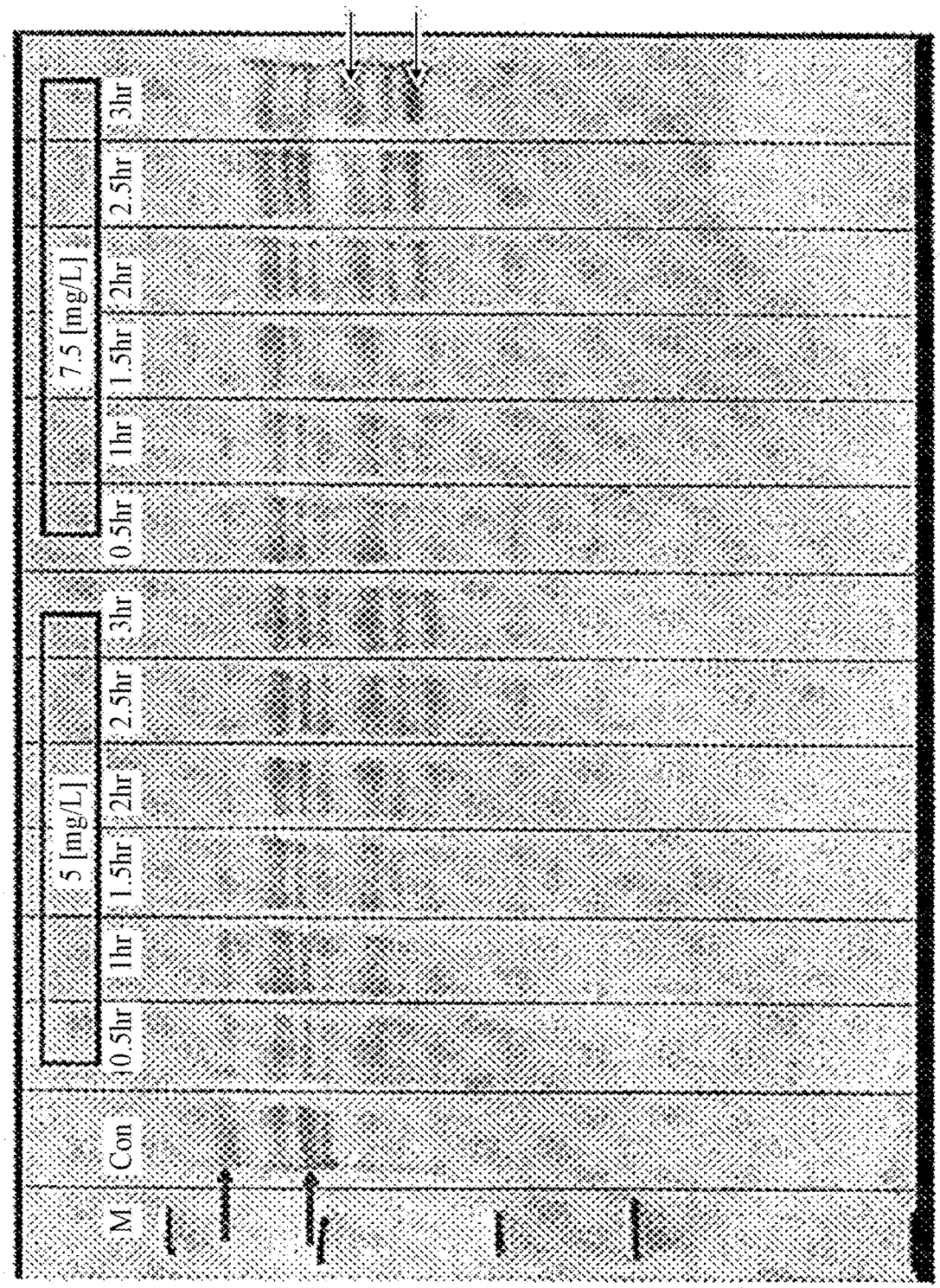
Figure 23C:
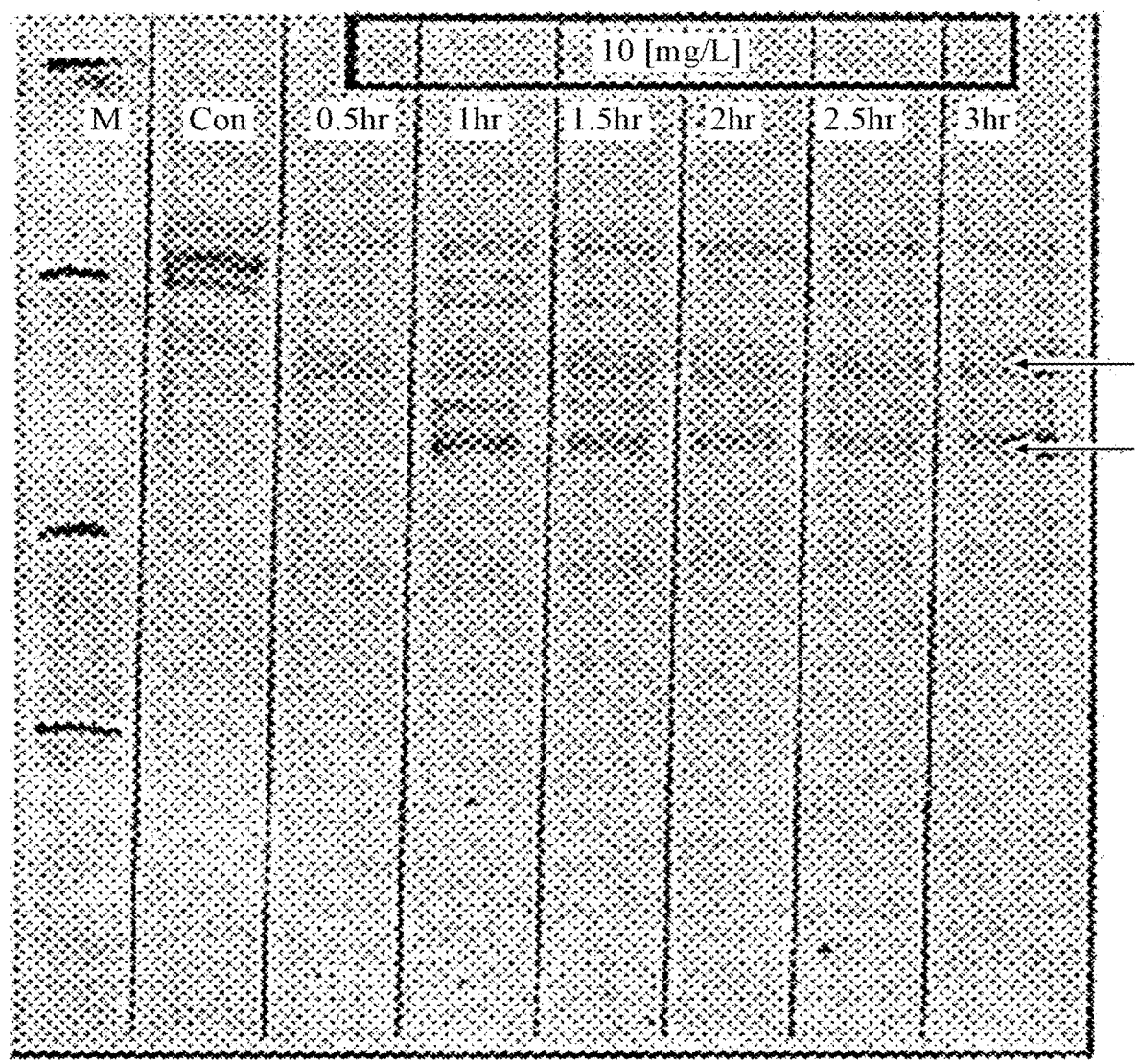

Digestion kinetics of procollagen by pharmaceutical-grade ficin: Similar experiments were carried out on procollagen-expressing tobacco leaf pellets to determine the appropriate conditions for procollagen digestion by pharmaceutical-grade ficin. Pellets were resuspended and incubated with increasing concentrations of pharmaceutical-grade ficin (2.5-10 mg/L), at 15° C. for 0.5-3 hrs. Digestion efficiency was determined by immunodetection of collagen chains on Western blots. As is shown in FIGS. 23A-C, increasing ficin concentrations led to increased collagen yield and decreased procollagen levels. The most effective digestion of procollagen with pharma-grade ficin was seen at 10 mg/L, after a 1-hour reaction time.

Figure 24A:
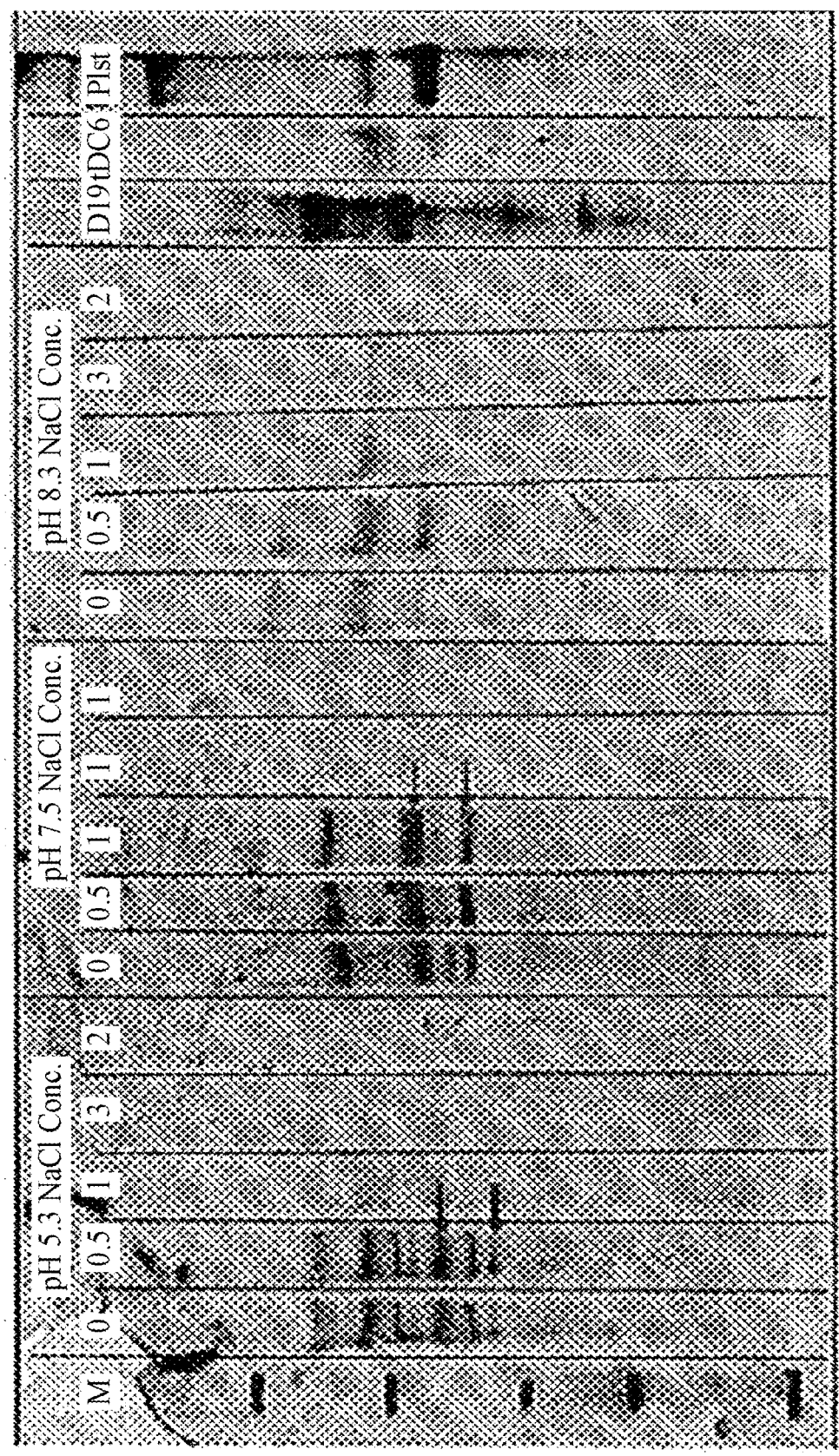
FIGS. 24a-b show optimization of procollagen cleavage by pharmaceutical-grade ficin: optimization of pH and salt concentrations in reaction buffer. AMS-pelleted procollagen-expressing tobacco leaf extracts were resuspended in extraction buffer containing 10 mg/L pharmaceutical-grade ficin at varying pH values (5.5-9.5) and with increasing NaCl concentrations (0.5-3 M). Reaction mixtures were then incubated at 15° C. for 1 hour. Cleavage was terminated by centrifugation and protein samples of both resulting pellets and supernatants were separated on 8% SDS-PAGE, transferred to nitrocellulose membranes and immunoblotted for alpha-1 and alpha-2 collagen chains with anti-collagen I. Arrows indicate collagen bands.
Figure 24B:
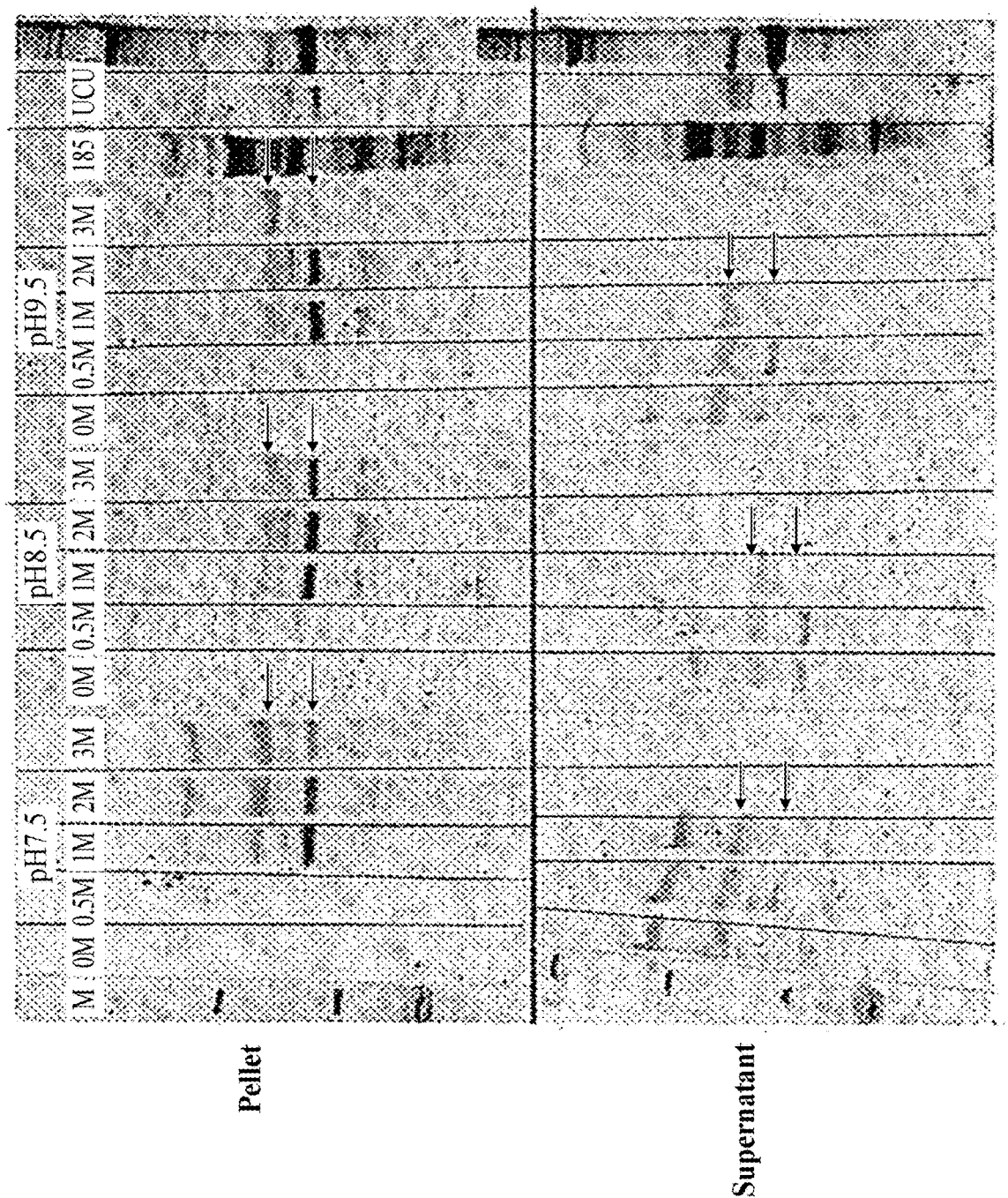

Optimization of pH values and salt concentrations for ficin-dependent procollagen cleavage: The contribution of both digestion buffer pH and salt concentrations were then evaluated. Similar tobacco leaf post-AMS pellets were resuspended in extraction buffer titrated to pH 5.5, 7.5, 8.5, or 9.5 with salt content ranging from 0.5-3 M NaCl. Samples were then incubated with 10 mg/L pharmaceutical-grade ficin at 15° C. for 1 hour prior to immunoanalysis on Western blots. Acidic assay conditions (pH 5.5) led to insufficient collagen yield (FIG. 24A, lanes 2-6), while increases in pH values demonstrated a correlative rise in ficin-dependent collagen content, with peak values observed at pH 8.5 in the presence of 2 M NaCl (FIG. 24B, lane 10). These results were further supported in a scale up extraction and purification experiment performed on two 15 kg pellets pooled for ficin-induced procollagen digestion. Aside from increased collagen chain yield as viewed by immunoblotting, samples digested in buffer of pH 8.5 in the presence of 2 M NaCl fibrillated just as efficiently as those digested in buffer A (pH 7.5, 0 mM NaCl) (see Table 5, herein below—batches YC1 and YC2). Thus, both higher pH and salt concentrations afford improved collagen yield following ficin-induced digestion of procollagen.

Figure 25:
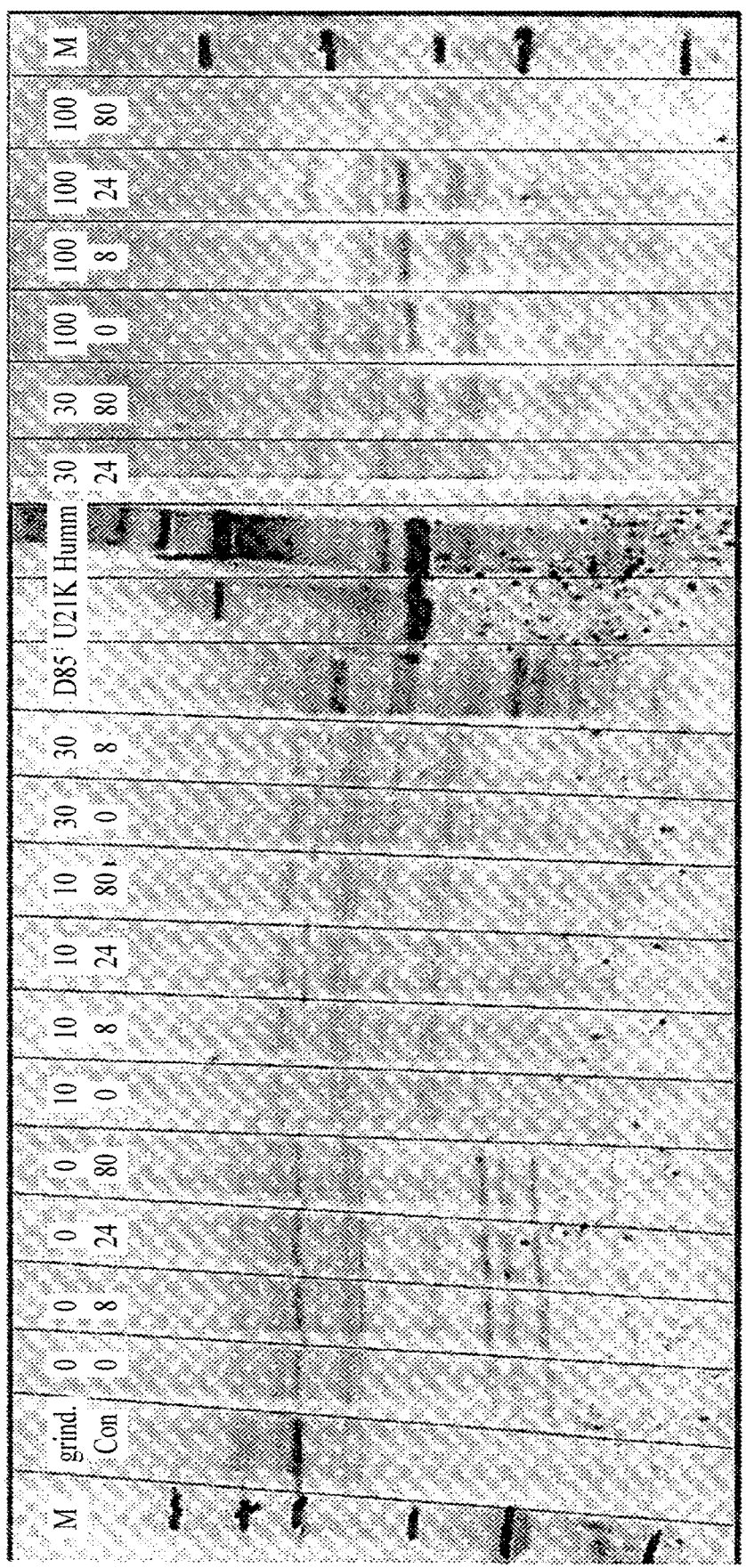
FIG. 25 shows Optimization of procollagen cleavage by pharmaceutical-grade ficin: optimization of EDTA and L-cystein concentrations in reaction buffer. AMS-pelleted procollagen-expressing tobacco leaf extracts were resuspended in extraction buffer (pH 7.5) containing varying concentrations of L-cystein (10-100 mM—upper panel of concentrations) and of EDTA (8-80 mM—lower panel of concentrations). Samples were then incubated with 1 mg/L pharmaceutical-grade ficin at 15° C. for 1 hr. Cleavage was terminated by centrifugation and protein samples were separated on 8% SDS-PAGE, transferred to nitrocellulose membranes and immunoblotted for alpha-1 and alpha-2 collagen chains with anti-collagen I.

Determination of vitalness of EDTA and L-cystein in digestion reaction mixture: Both EDTA and L-cystein are additives present in the extraction buffer at early stages of the collagen purification process. Herein, the essentiality of these two components to effective ficin-dependent collagen cleavage was determined. Procollagen post-AMS pellets were resuspended in extraction buffer containing increasing concentrations of EDTA (8-80 mM) and L-cystein (10-100 mM), and incubated with ficin (10 mg/L) at 15° C. for 1 hour, at pH 7.5. A pronounced enhancing effect was observed on digestion efficiency in the presence of 10 mM L-cystein (FIG. 25, lanes 7-10), with no apparent contribution of EDTA to ficin-dependent collagen output (FIG. 25, lanes 7 vs. 8-10).

Optimization of temperature conditions for ficin-induced procollagen digestion: Procollagen-expressing tobacco leaf pellets were incubated with ficin for 1.5 hours at 15° C. and then transferred to a 30° C. bath for an additional 1.5 hours. Western blot and fibrillogenesis assays did not identify any improvement in collagen yield or sample purity related to increased reaction temperatures.

Fibrillogenesis of collagen extracted from ficin-induced cleavage of procollagen: Following ficin-induced digestion, fibrillogenesis assays were performed to determine the resultant collagen's ability to form fibrils, the ultimate method of determining the collagen's functionality. Table 5, herein below summarizes fibrillogenesis results as determined following ficin cleavage of procollagen using two variant protocols. Both protocols A and B, differing in reaction buffer pH and salt content yielded significant percentage of collagen fibrils. Thus, the proteolysis reaction parameters developed and optimized herein, lead to functional collagen at high yields.

TABLE 5

Percent fibrillogenesis observed by collagen obtained via digestion under varying conditions

| Batch # | Digestion conditions: | % Fibrillogenesis |
|---|---|---|
| C39 | Protocol A: 10 mg/L ficin, 1 hr, pH 7.5 | 94.1 |
| P100 | Protocol B: 10 mg/L ficin, pH 8.5, 2M NaCl, 1 hr | 87.2 |
| P101 | Protocol A | 73.1 |
| YC1 | Protocol A | 95.4 |
| YC2 | Protocol B | 98.4 |
| YC3 | Protocol A | 96 |
| YC4 | Protocol A | 93.1 |
| YC5 | Protocol A | 93.2 |
| YC7-8 | Protocol B | 94.2 |

Example 13. Determination of TRYPZEAN™ Protease Efficacy in Procollagen Cleavage Procollagen-expressing tobacco leaf pellets resuspended in extraction buffer (pH 7.5) enriched with EDTA (7.5 mM) and L-cystein (12.5 mM), were incubated with TRYPZEAN™ (30-100 mg/L) for 1-3 hours at 15° C. Within 1 hour, doses of 60 and 100 mg/L TRYPZEAN™ efficiently cleaved procollagen to yield two distinct alpha collagen chains, with no detectable over-digestion (FIG. 26). Thus, procollagen treatment with TRYPZEAN™ at pH 7.5 lead to its effective digestion to collagen chains alpha-1 and alpha-2.

Discussion

The above Examples 7-13 describe the identification of a non-mammalian protease suitable for use in the process of purification of collagen derived from plants. Proteases from bacterial and plant sources were examined and three enzymes were found suitable for the collagen propeptides digestion, namely, neutrase, subtilisin, TRYPZEAN™ and ficin.

Neutrase and Subtilisin are both secreted by the bacteria *Bacillus* sp. Subtilisin is primarily (>90%) used in detergents and household cleaning products. Approximately 10% of subtilisin use is towards technical applications such as protein hydrolysis, leather treatment, and in the textile and cosmetics industries. Standard use of subtilisin in the collagen purification process at higher concentration is problematic due to overdigestion of collagen. Neutrase is mainly used in the beverage alcohol industry and in cheese ripening. In Examples 7-13, described herein above, neutrase was only effective in digesting the propeptides at high concentrations and at least 6 hours were required for desirable digestion results.

Under the presently described experimental conditions, recombinant trypsin and ficin were found to be the most suitable among the four, since there was no overdigestion of collagen at either high enzyme concentrations or after extended incubation periods. Furthermore, these enzymes apparently did not digest the helical region of the collagen, as determined by SDS PAGE analysis. Ficin, being a natural enzyme extracted for Fig latec plant (*Ficus carica*), is available commercially at several grades including a pharmaceutical grade from several sources at low cost. It is used in the food industries: alcohol and beer industries, hydrolisation of proteins, meat processing, baking industry, and in the preparation of pet food and health food. It is also applied in the pharmaceutical industry in contact lens cleansers, cancer treatment, anti-arthritis treatments, and digestive aids as well as in the cosmetic and textile industries.

Example 14. Further Analysis of rhCollagen Properties

Materials and Methods

Materials

Human recombinant collagen (rhCollagen) type I expressed and isolated from transgenic tobacco plants was produced and supplied by CollPlant Ltd (Israel). Type I Bovine Collagen (PureCol) was purchased from Advanced Biomatrix, USA. Methacrylic anhydride, glycidyl methacrylate, triethylamine, tetrabutylammonium bromide, 2,4,6-Trinitrobenzenesulfonicacid (TNBS),2-Hydroxy-4'-(2-hydroxyethoxy)-2-methylpropiophenone (Irgacure 2959), sodium phosphate monobasic anhydrous, HCl 1N, HCl≥37%, sodium bicarbonate and NaOH were purchased from Sigma Aldrich Ltd, Israel. Phosphate buffered saline (PBS), ×10 PBS, Foetal Bovine Serum (FBS), DMEM high glucose and penicilin/streptomicin were purchased from Biological Industries Ltd, Israel. Sodium phosphate dibasic anhydrous was purchased from Canton, India. Ethanol absolute and acetone were purchased from Bio-Lab Ltd, Israel. Hyaluronic acid was purchased by Lifecore, USA.

Buffers and Photoinitiator Stock Solution Preparation

Fibrillogenesis buffer (FB): sodium phosphate dibasic was dissolved in double distilled water (DDW) to final concentration of 162 mM. The solution was titrated to pH 11.2 with 1ON NaOH.

Medium preparation: 50 ml of foetal bovine serum and 5 ml of penicillin/streptomycin (10,000 units/mL and 10 mg/mL respectively) were added under aseptic conditions to 500 ml of DMEM high glucose medium. The medium was gently mixed and kept in fridge.

Phosphate Buffer Saline preparation: 39 ml of 0.1M Sodium phosphate monobasic solution were mixed with 61 ml of 0.1M sodium phosphate dibasic solution and final volume adjusted to 200 ml with DDW. Final pH was adjusted to 7 with concentrated NaOH or HCl as needed. NaCl was added to final concentration of 150 mM.

Washing buffer: HCl was added to the fibrillogenesis buffer to reach a final concentration of 16.2 mM sodium phosphate dibasic and 10 mM HCl. pH was adjusted to 7.2-7.4 with ION NaOH.

Photoinitiator 10% (v/v) stock solution: Irgacure 2959 was dissolved in ethanol absolute/PBS 1:1 solution to a final concentration of 100 mg/mL.

Methacrylation of rhCollagen

Fibrillar rhCollagen-methacrylamide and monomeric rhCollagen-methacrylamide were prepared by reaction of lysine and hydroxylysine collagen residues with methacrylic anhydride in aqueous medium as described below and stored at 4° C. light protected until further use.

Fibrillar rhCollagen-Methacrylamide 3 to 10 mg/mL fibrillar rhCollagen-methacrylamide was synthesized either in washing buffer, fibrillogenesis buffer or DDW, at room temperature (R.T.) or at 12° C. For example, in brief, fibrillar collagen-MA was synthesized in DDW as follow: monomeric rhCollagen 3-4 mg/mL solution in 10 Mm HCl, (COLLAGEm) was mixed with fibrillogenesis buffer at 9:1 v/v ratio and stirred for 1 hr at R.T, receiving fibrils. The solution was centrifuge at 7500 rpm at 4° C. for 30 minutes, discarding the supernatant. The pellet was re-suspended in equal volume of washing buffer and centrifuged at the same conditions. After that, the sediment fibrils were re-suspended in DDW to 10 mg/mL. Concentration was confirmed by percent solid measurements. Methacrylic anhydride (MA) was added drop-wise under nitrogen flow at room temperature at 10 to 20 molar ratio with respect to collagen lysines, and the reaction solution pH was monitored over time and adjusted to pH 7 with ION NaOH. After 24 hours reaction, the mixture was dialyzed against washing buffer (pH 7) using 10 kDa cutoff dialysis tubing (Spectrum Laboratories Inc, CA, US) for 3 days at 4° C. with at least 6 changes of the dialysate (washing buffer in this case), to remove reaction by-products and eventually lyophilized for 3-4 days.

Monomeric rhCollagen-Methacrylamide 200 mM MOPS, phosphate, or Tris buffers with the addition of 150 mM NaCl were used. For example, 200 mM MOPS and 150 mM NaCl were added to 3-4 mg/mL COLLAGE™ and stirred at RT until clear solution was obtained. Thereafter, 10 to 20-fold excess of methacrylic anhydride was added drop-wisely under nitrogen flow at 12° C., and the pH was adjusted over time to pH 7 with ION NaOH. After 24 hours reaction, the mixture was dialyzed against 10 mM HCl and 20 mM NaCl (pH 2) with 10 kDa cutoff dialysis tubing for 3 days at 4° C. with at least 6 changes of the dialysate, followed by 3-4 days lyophilization.

Methacrylation of Hyaluronic Acid (HA)

500 mg of HA were functionalized as described by Leach et al. [Leach et. al. 2002, Biotechnology and Bioengineering, vol. 82, no. 5]. Briefly, 1.8 ml of triethylamine, 1.8 ml of glycidyl methacrylate, and 1.8 g of tetrabutyl ammonium bromide were added separately to 50 ml of 10 mg/mL HA solution in DDW and thoroughly mixed before the next component was added. The reaction was mixed overnight at room temperature and the HAMA precipitated in 20-fold volume of acetone and re-dissolved in DDW. The precipitation process was repeated twice to eliminate all the reaction residues. The material was eventually lyophilized.

Solutions Preparation for Viscosity Measurements

PureCol and Collage™ in PBS: 8 m of monomeric collagen solutions (3 mg/mL in 10 mM HCl), either rhCollagen (COLLAGE™) or bovine collagen (PureColl) were neutralized by adding 1 ml of PBS×10. The solution was then brought to pH 7-7.5 by titration with 0.1N NaOH. Eventually double distilled water was added to reach a final volume of 10 ml. Samples were incubated at 37° C. for at least 90 min before measurements were performed (either at 37° C. or 4° C.).

COLLAGE™ in fibrillogenesis buffer: 9 ml of monomeric rhCollagen (COLLAGE™) solution (3.79 mg/mL in 10 mM HCl) was neutralized by adding 1 ml of fibrillogenesis buffer. Samples were incubated at 37° C. for at least 90 min before measurements were performed (either at 37° C. or 4° C.).

Fibrillar rhCollagen-methacrylamide in PBS: Lyophilized fibrillar rhCollagen-MA prepared in DDW and dialyzed vs. washing buffer (according to what described above with 10-fold excess of MA) were dissolved in PBS to a concentration of 10 mg/mL. Samples were incubated at 37° C. for at least 90 min before measurements were performed (either at 37° C. or 4° C.).

rhCollagen-methacrylamide in DMEM: Lyophilized fibrillar rhCollagen-methacrylamide (15-fold excess of MA, prepared and dialyzed in washing buffer, according to the description above) was dissolved in DMEM medium to final concentrations of 20 and 26 mg/mL.

rhCollagen-methacrylamide/Hyaluronic Acid in DMEM: Hyaluronic Acid was added to a solution of fibrillar rhCollagen-MA to obtain final concentrations of 10 mg/mL HA and 20 mg/mL rhCollagen-MA in DMEM medium.

rhCollagen-methacrylamide/Hyaluronic Acid methacrylate (HA-MA) in DMEM: Hyaluronic Acid methacrylate (see above) was added to a solution of fibrillar rhCollagen-MA to obtain final concentrations of 10 mg/mL HA-MA and 20 mg/mL rhCollagen-MA in DMEM medium.

rhCollagen-MA photocrosslinking for loss and storage moduli measurements rhCollagen-MA crosslinked scaffolds were formed in two different preparations, aimed to be examined in two individual experiments. In the first preparation, 1-2 wt % fibrillar rhCollagen-MA synthesized with 10-fold excess of the methacrylic reagent were dissolved in PBS 0.1 M at R.T, then Irgacure 2959 0.1% was added and 1 mL final volume of solutions was injected into a discoid mold. Following that, curing process was performed from a distance of 1.5 cm for 7 and 10 seconds at an averaged intensity of 670 mW/cm2 using mercury light source, ending up in crosslinked scaffolds. The second preparation included 2 different batches of fibrillar rhCollagen-MA, synthesized with 15- and 20-fold excess of the methacrylic reagent. 1-2 wt % were dissolved in PBS 0.1 M, and Irgacure 2959 0.1% was added to achieve a final volume of 1.5 mL. In order to obtain highly crosslinked scaffolds, curing process was performed from a distance of 2 cm for 60 seconds at an averaged intensity of 420 mW/cm$^2$.

TNBS Assay

The assay protocol was similar to the one reported by Sashidhar et al. [Sashidhar R. B., Capoor, A. K., Ramana, D, Journal of Immunological Methods. 1994, 167, 121-127], and based on Habeeb [Habeeb A. F. S. A, Analytical Biochemistry. 1966, 14, 328-336]. Briefly, freshly prepared 0.4 mL of 0.01% (v/v) TNBS was added to 0.4 mL of 0.1-2 mg/mL fibrillar rhCollagen-MA in sodium bicarbonate 4%. After 2 hours reaction at 40° C., 0.2 mL of 1N HCl and 0.4 mL of 10% (v/v) SDS were added. The absorbance was measured at 335 nm in a spectrophotometer in a 1 mL polystyrene cuvette. A control (blank) was prepared with the same procedure except that sodium bicarbonate buffer was added instead of rhCollagen-MA solution. The absorption of 1-2 mg/mL native fibrillar rhCollagen prepared with the same conditions was recorded for calibration.

Rheological Characterization

Viscosity: Viscosity measurements were performed on a HAAKE RHEOSTRESS600™ rheometer (Thermo Electron Corporation) with a temperature-controlled cell chamber, using a C60/1° Ti cone-plate set up. Viscosity was measured on 1 mL sample in a rotational ramp mode, shear rate ranging from 0.0001 to 1000 sec-1 at 4° C., 25° C. and 37° C.

Scaffolds' storage and loss moduli: The rheological behavior of rhCollagen crosslinked discs was investigated using parallel plate system employing PP20 serrated spindle and 20 mm serrate plate set up. In order to characterize the non-crosslinked rhCollagen-MA, C60/1° Ti cone-plate elements were used. In order to evaluate the rheological behavior of rhCollagen-MA, two sets of experiments were performed individually. In the first, 1 mL samples were subjected to oscillation forces at controlled stress mode, recording storage modulus G' and loss modulus G" values while applying 5 Pa shear stress at 1 Hz frequency and 37° C. for 300 seconds. The gap was adjusted to 90% of the original sample height and G' and G" values were averaged at the range of 150-300 seconds. In the second experiment, 1.5 mL crosslinked discs were tested in frequency sweep oscillations at 37° C., where G' was recorded under 1 Pa shear stress at frequency range of 0.01-100 Hz. To initiate measurement, the spindle was lowered to contact the hydrogel surface, and then further lowered until the axial force of the instrument was equaled to 0.4 N. Prior to all measurements, samples were kept on the plate covered with humidity lid for 1 minute, in order to reach temperature equilibrium.

Results

TNBS Assay

The extent of modification of rhCollagen was quantified using TNBS colorimetric assay. The assay quantifies the molar content of free, non-reacted ε-amino groups derived from lysine and hydroxyl lysine, and subsequently the degree of functionalization. The degree of functionalization of fibrillar rhCollagen 10, 15 and 20-fold different batches was determined by TNBS assay, as shown in Table 6.

TABLE 6

The degree of functionalization of fibrillar rhCollagen from different preparations, as determined by TNBS assay.

| Fibrillar rhCollagen-MA batch | Degree of methacrylation [%] |
| --- | --- |
| 10-fold | 98.1 |
| 15-fold | 95.5 |
| 20-fold | 92.9 |

The results indicate on high modification capability of the fibrillary rhCollagen and imply that adding the methacrylic reagent in molar ratio of 10 may be preferable for receiving maximal functionalization of the fibrillar collagen.

Rheology

1. Viscosity

Temperature Dependence of rhCollagen/Bovine Collagen Viscosity

Figure 27:
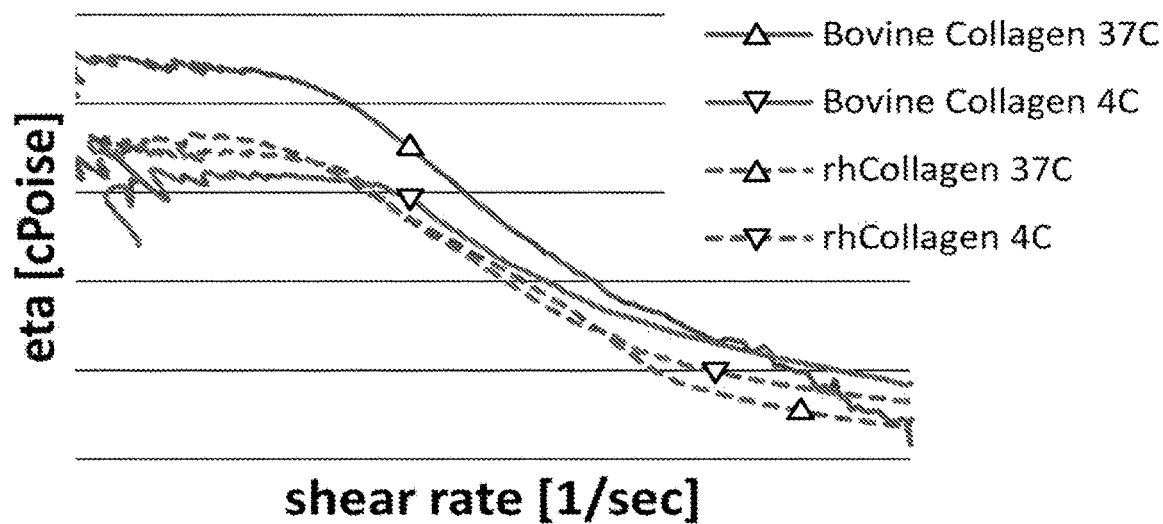
FIG. 27 shows viscosity (eta [η], cP) as a function of shear rate, solid line-2.7 mg/mL bovine collagen in phosphate buffered saline (PBS), dashed line 2.79 mg/mL rhCollagen in PBS. ▼: measurements at 4° C., ▲: measurements at 37° C.
Figure 28:
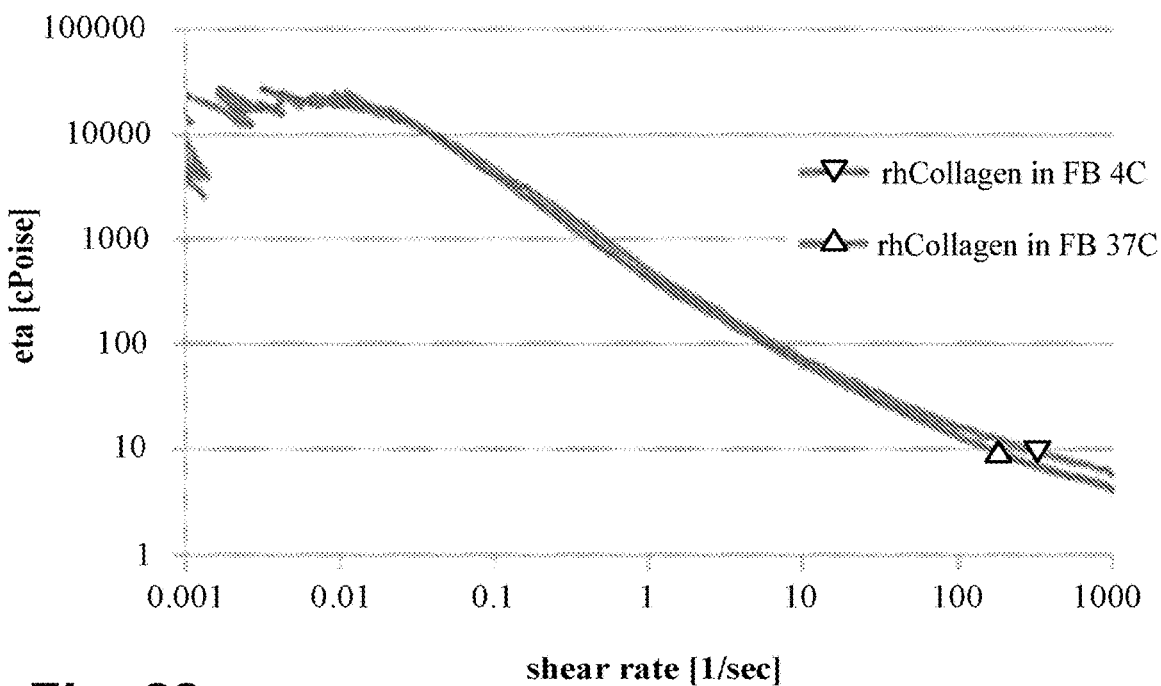
FIG. 28 shows viscosity as a function of shear rate, 3.4 mg/mL bovine collagen in FB. ▼: measurements at 4° C., ▲: measurements at 37° C.
Figure 29:
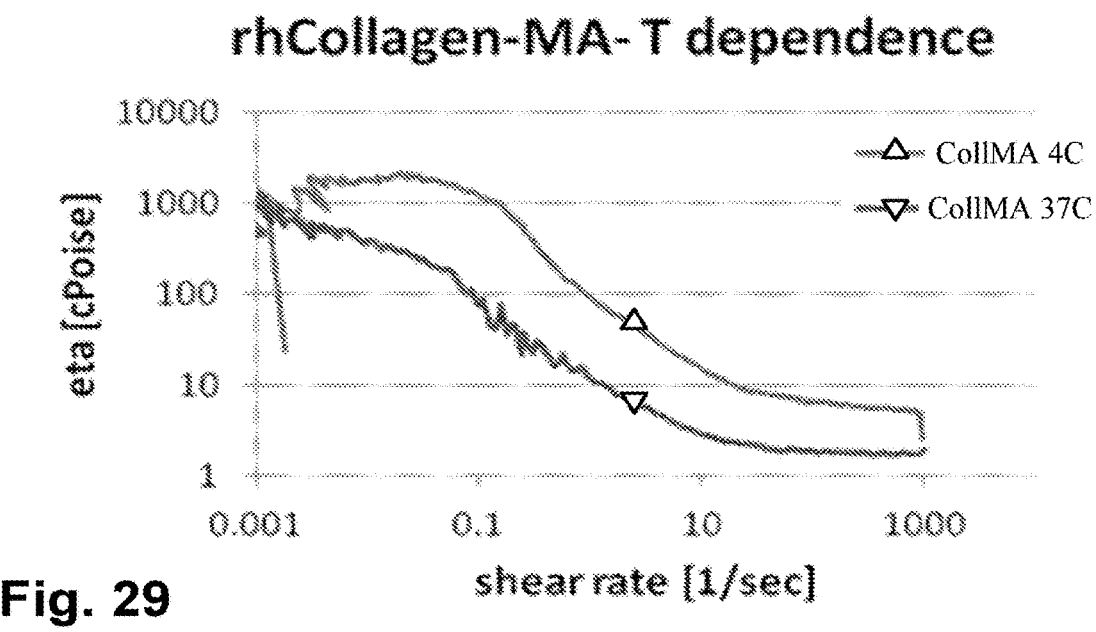
FIG. 29 shows viscosity as a function of shear rate, 10 mg/mL rhCollagen-MA in PBS. ▲: measurements at 4° C., ▼: measurements at 37° C.

FIG. 27 shows the viscosity of rhCollagen (COL-LAGE™) and Bovine Collagen (PureCol) in PBS expressed as a function of shear rate at T=4° C. (blue, dashed and solid line respectively) and T=37° C. (red, dashed and solid line respectively). Bovine collagen (solid lines) shows clear temperature dependence of the zero-shear rate viscosity ($\eta 0$) i.e. the viscosity plateau at low shear rate values, having at 37° C. (red) $\eta 0$ values that are more than one order of magnitude higher than the values at 4° C. (blue). On the contrary rhCollagen (dashed lines) shows no significant difference between $\eta 0$ values at 4° C. and 37° C. rhCollagen neutralized in FB (see methods) shows a very similar behavior (FIG. 28), i.e. the viscosity at 4° C. and 37° C. is almost identical. FIG. 29 shows the viscosity of fibrillar rhCollagen-MA at 4° C. (blue line) and 37° C. (red line). Although the profiles are not identical the zero shear rate values are around 1000 cP at both temperatures.

Viscosity of rhCollagen-Methacrylamide

Figure 30:
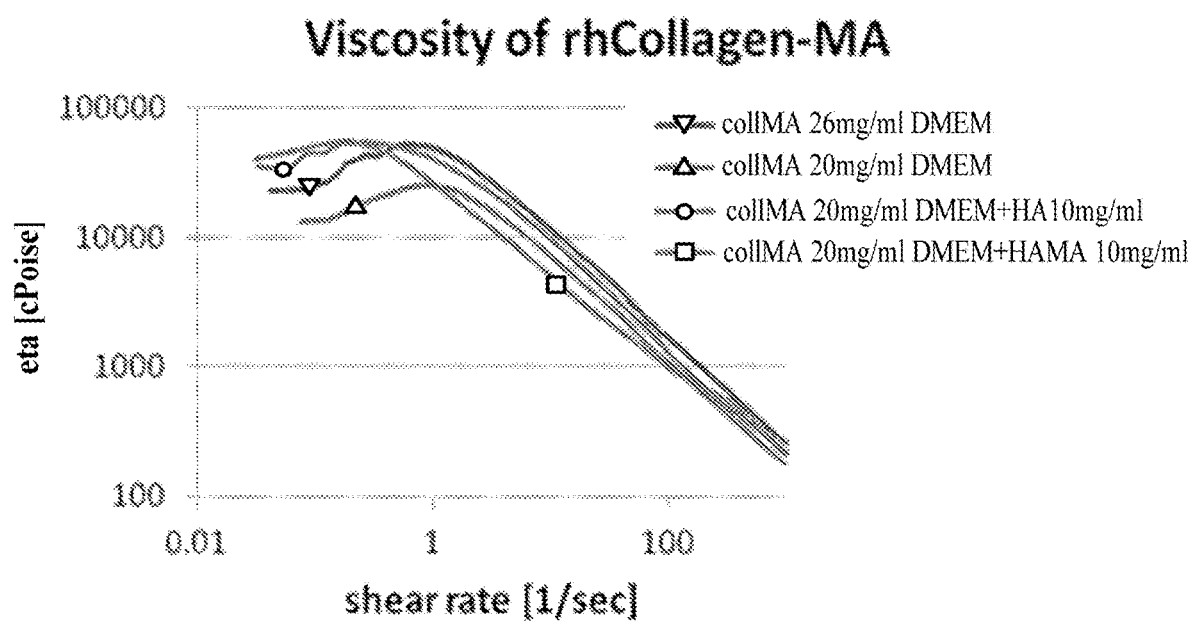
FIG. 30 shows viscosity measurements of rhCollagen-MA in DMEM with and without addition of HA/HAMA.

FIG. 30 shows the viscosity of rhCollagen-MA dissolved in DMEM at 25° C. The typical shear thinning behavior of the rhCollagen seen in FIGS. 27 and 28 is maintained also for the rhCollagen-MA with and without the addition of HA/HA-MA. Increasing the concentration of rhCollagen from 20 to 26 mg/mL (green and red line respectively) the zero-shear viscosity increases as well as by the ulterior addition of 10 mg/mL HA or HAMA which leads to final polymer concentration of 30 mg/mL.

The skilled artisan would recognize that rhCollagen-MA is not crosslinked and that in order to achieve crosslinking, one needs to add a photoinitiator and light.

2. Scaffolds' Loss and Storage Moduli

Rheological analysis of 1 mL discs over time at 37° C. performed in the first experiment are presented in FIG. 31. The upper graph reports loss and storage moduli and the tan (delta) before UV curing while the lower graph reports the values after UV curing (upon addition of photoinitiator). The data demonstrates that the storage modulus of the rhCollagen-MA increases by 2-fold upon illumination in the presence of photoinitiator. Moreover, the results point on the capability of controlling the scaffold properties by changing the rhCollagen-MA concentration. High differences between G' and G" values, and close-to-zero tan (delta) values of the crosslinked discs indicate on their elastic-like behavior. (G'—storage moduli; G"—loss moduli; G', the "storage/elastic modulus," represents the energy fraction of G* stored by the gel during deformation and used to recover the original shape afterwards. G' measures the elastic behavior of a gel or how much it can recover its shape after shear deformation. For example, vulcanized rubber is a purely elastic material as it deforms instantly under stress and completely recovers its shape after the stress is removed (i.e., G*≈G'). G", the "loss/viscous modulus," represents the energy fraction of G* lost on shear deformation through internal friction. G" is not directly related to viscosity because HA filler is not purely viscous. Instead, this term reflects the inability of the gel to recover its shape completely after the shear stress is removed.)

Figure 32:
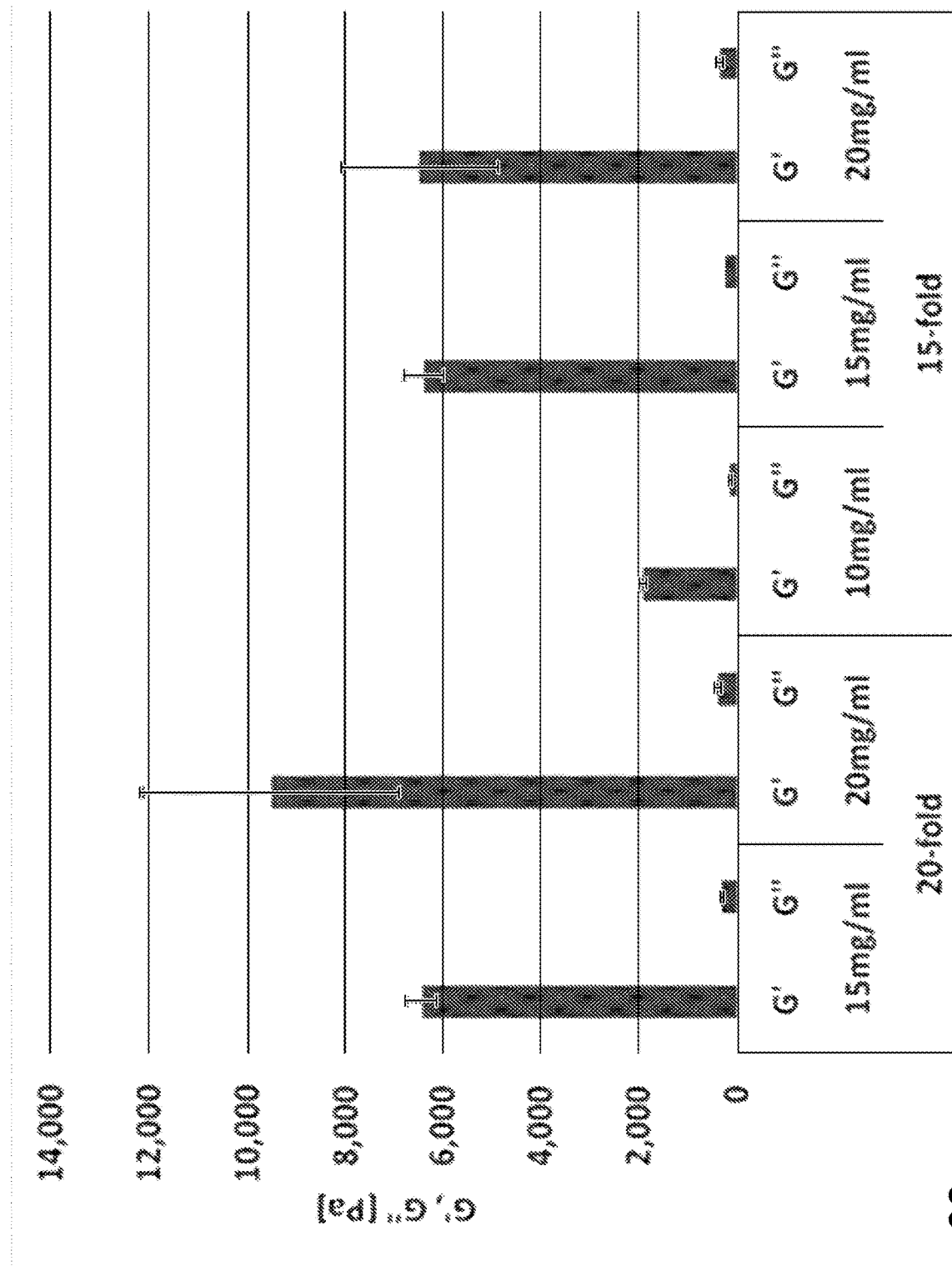
FIG. 32 shows G' and G" values at 37° C. recorded in frequency sweep test and plotted at 1 Hz.

In the second experiment, 1.5 mL discs illuminated for 60 seconds present higher G' values, as shown in FIG. 32. The data shows that G' increases with the rhCollagen-MA concentration and the degree of methacrylation, indicating on capability of controlling the scaffolds properties.

Figure 33A:
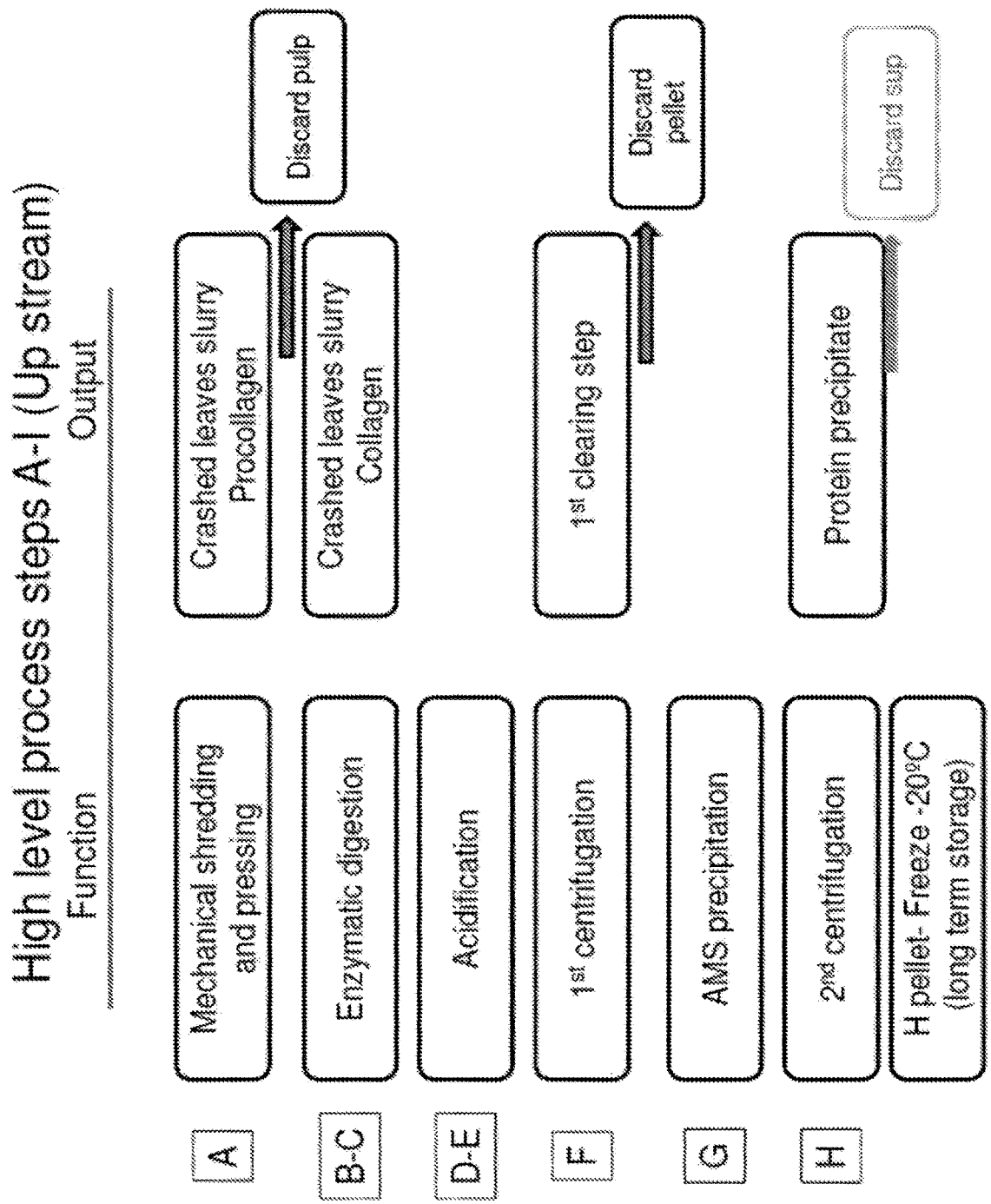
FIGS. 33A-33C provide a flow chart for the processing of rhCollagen and rhCollagen Methacrylate.
Figure 33B:
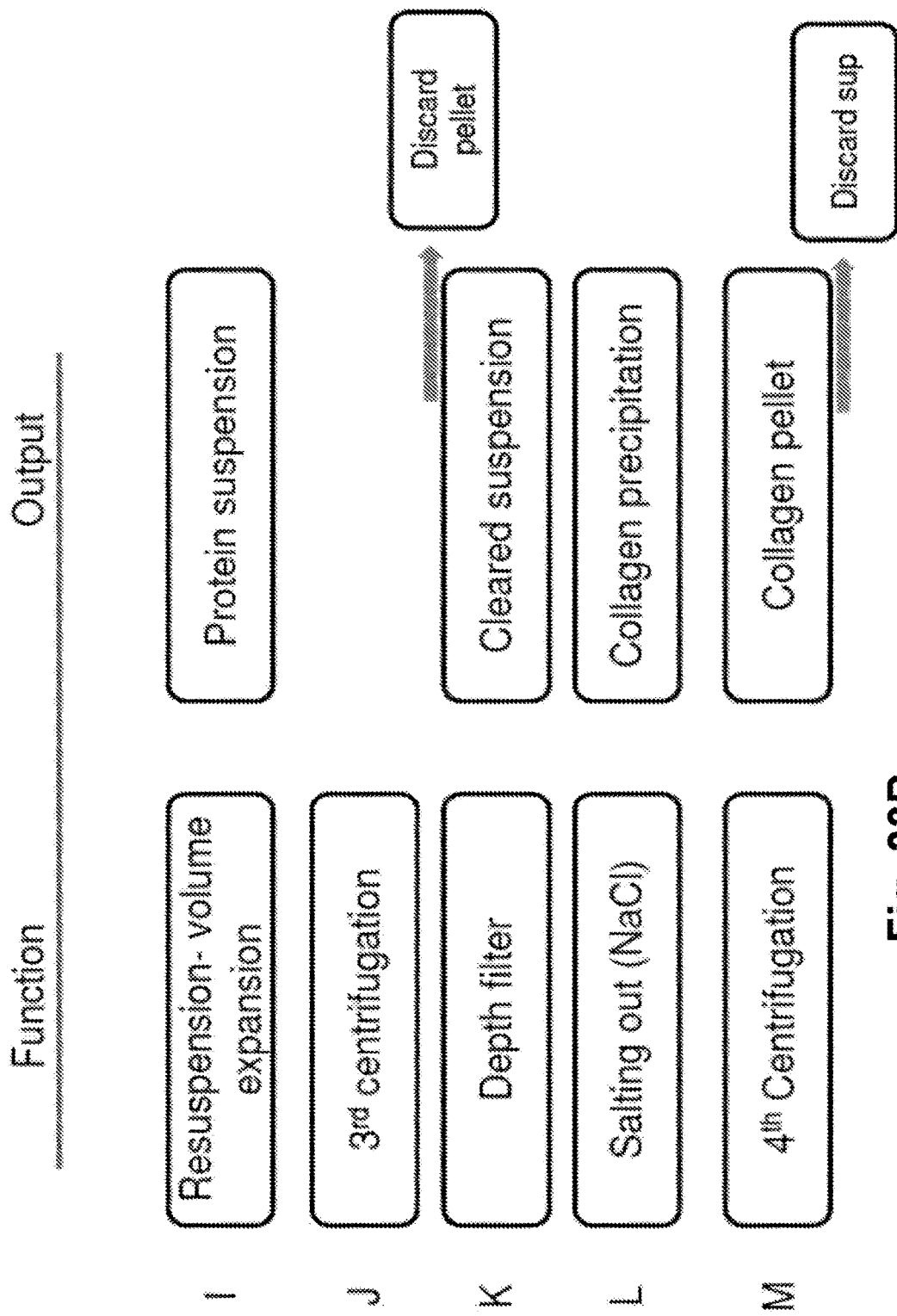
Figure 33C:
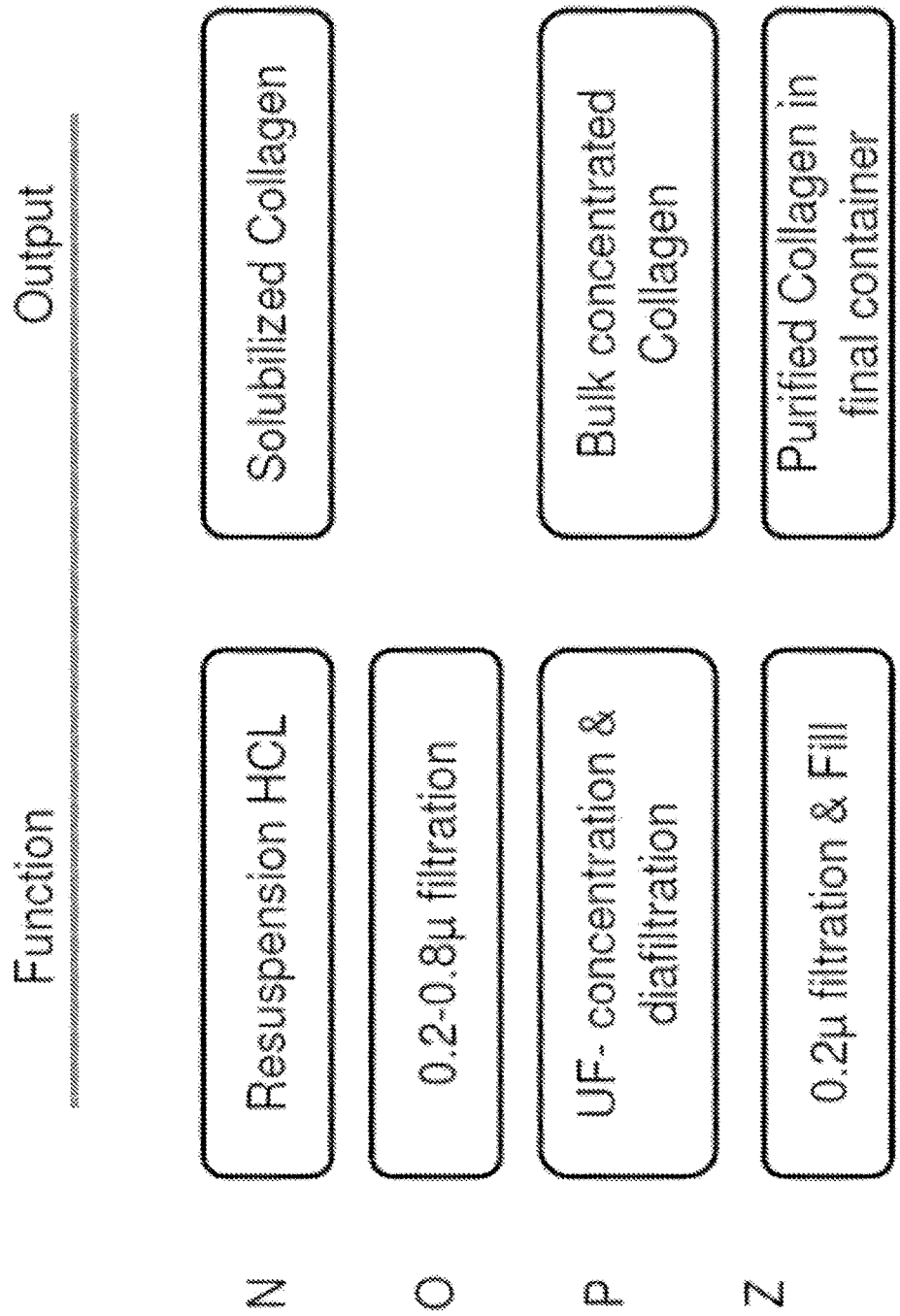
Figure 34:
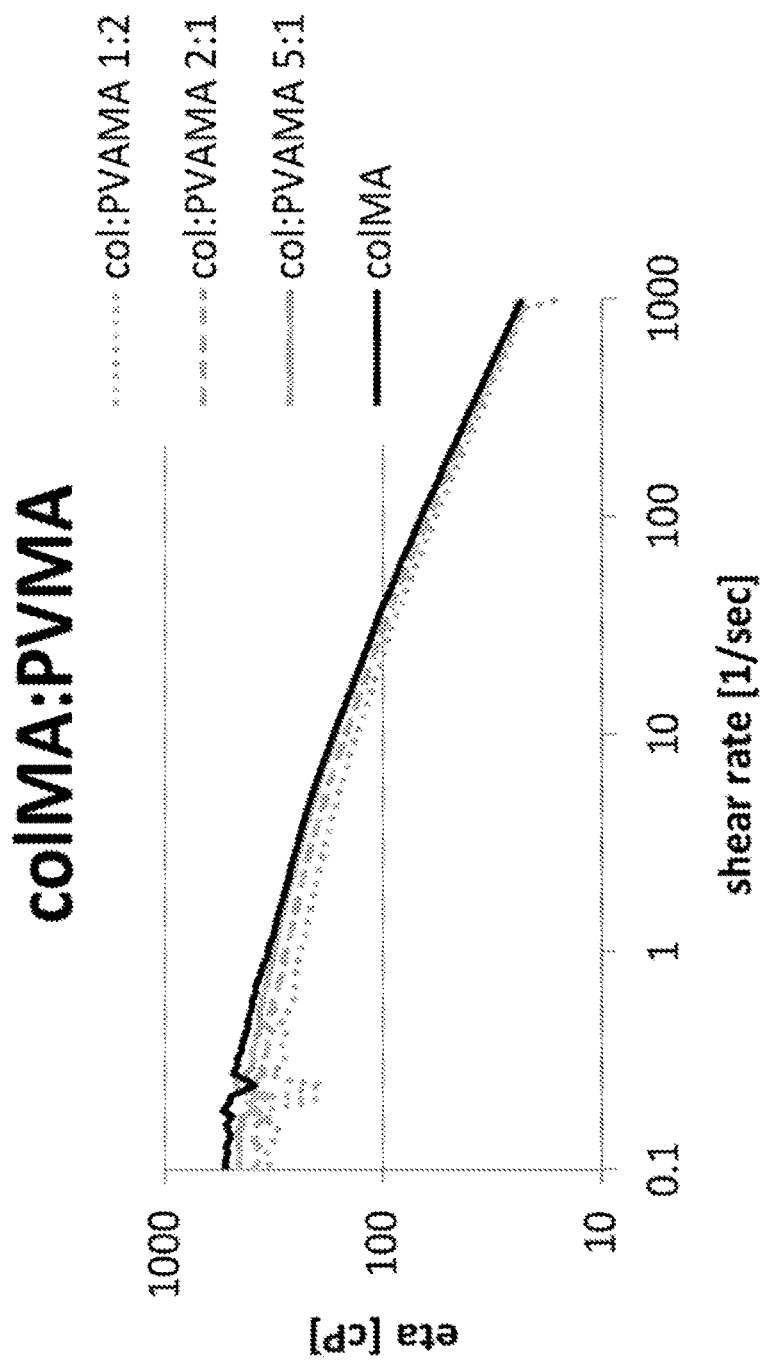
FIG. 34 shows the viscosity (eta [η], cP) of 5 mg/ml rhCollagen Methacrylate (CollMA) (solid black curve) and 5 mg/ml Collagen MA+polyvinyl alcohol methacrylate (PVMA) (light grey curves) at collMA:PVAMA ratio of 5:1 (solid curve), 2:1 (dashed curve), 1:2 (dotted curve). The viscosity of 5 mg/ml rhCollagen methacrylate is reported for comparison (black curve).
Figure 35:
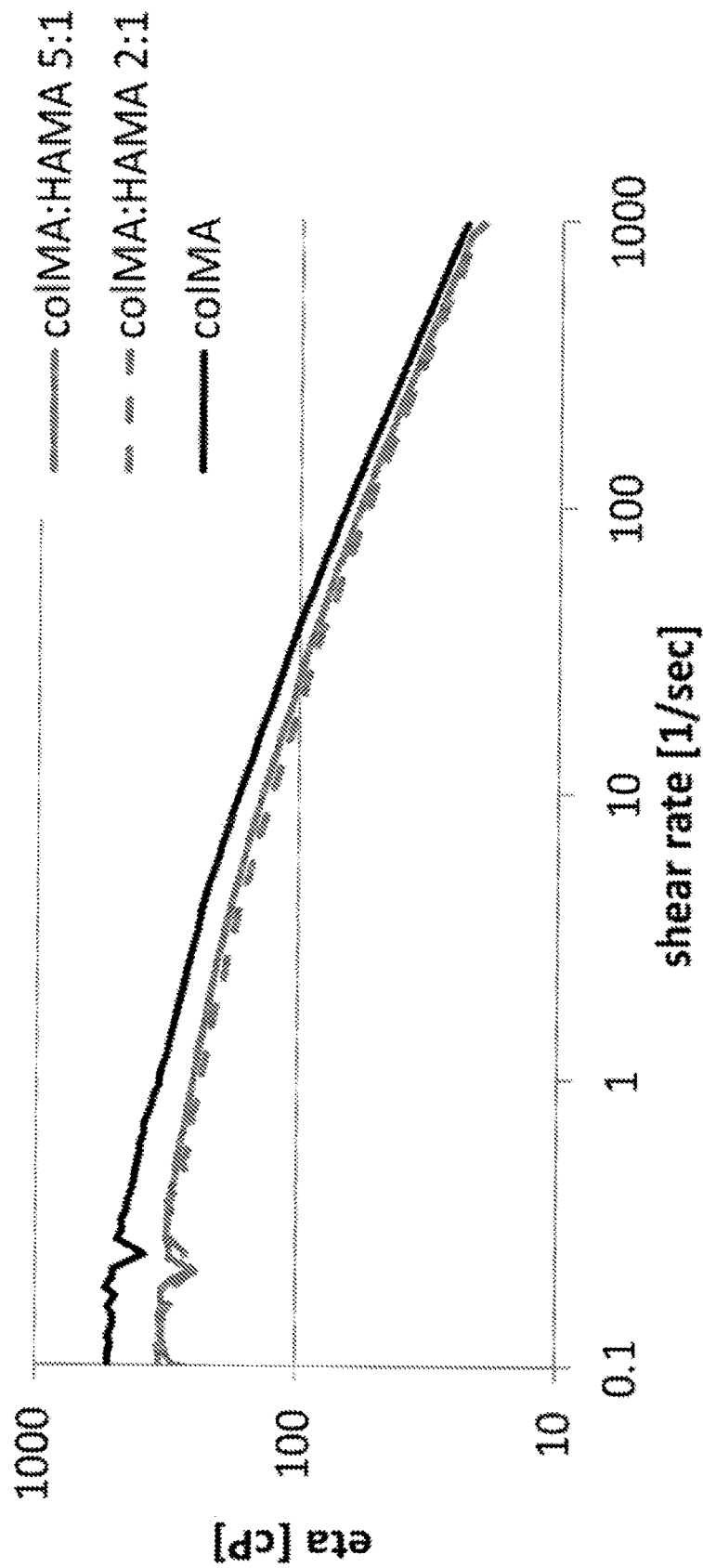
FIG. 35 shows the viscosity of 5 mg/ml CollMA (solid black curve) and 5 mg/ml Collagen MA+hyaluronic acid methacrylate (HAMA) (grey curves) at collMA:HAMA ratio of 5:1 (solid curve), 2:1 (dashed curve). The viscosity of 5 mg/ml rhCollagen methacrylate is reported for comparison (solid black curve). These materials are not yet crosslinked but would be crosslinked after injection. The visocisty is representatibe of the injectability of the materials. (HAMA—HA methacrylate; Collagen MA (ColMA)—rhCollagen methyacrylate.)
Figure 36:
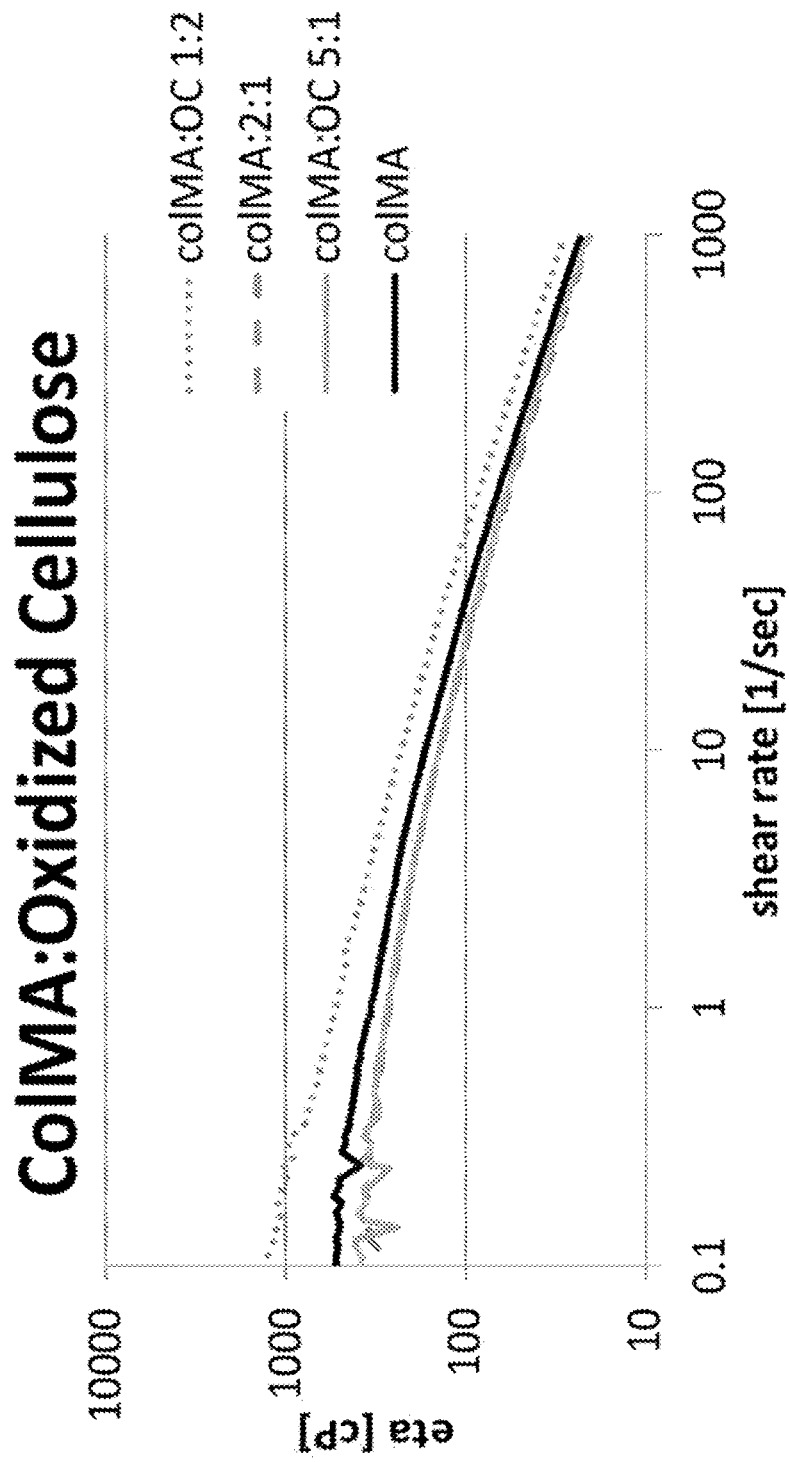
FIG. 36 shows the viscosity of 5 mg/ml CollMA (solid black curve) and 5 mg/ml Collagen MA+oxidized cellulose (OC) (grey curves) at collMA:OC ratio of 5:1 (solid curve), 2:1 (dashed curve), 1:2 (dotted curve). The viscosity of 5 mg/ml rhCollagen methacrylate is reported for comparison (solid black curve).
Figure 37:
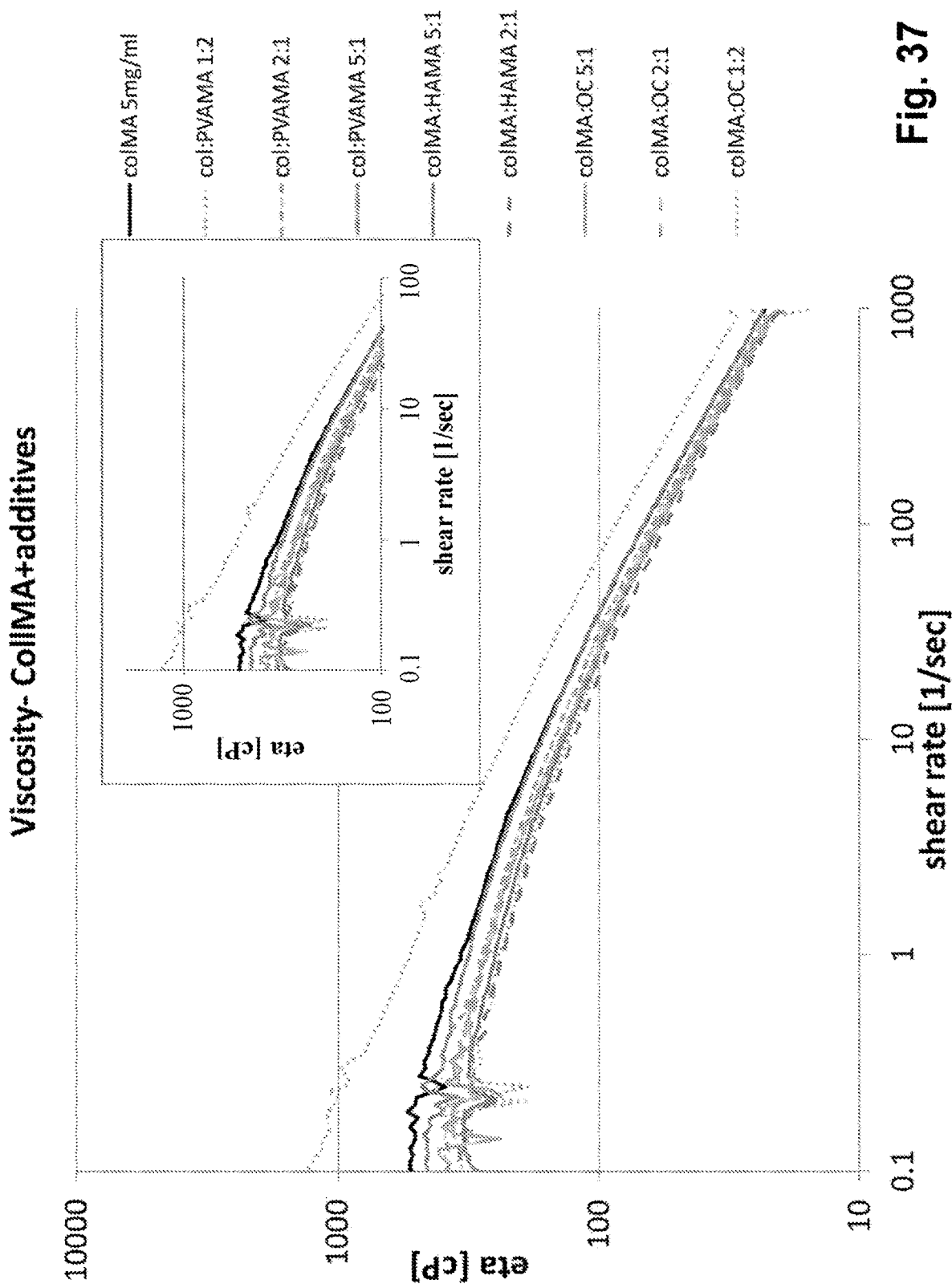
FIG. 37 provides a comparison of the data from FIGS. 33-35. It shows the viscosity of 5 mg/ml CollMA (solid black curve) and 5 mg/ml Collagen MA+different additives (light through dark grey curves as indicated in Figure) at ratio of 5:1 (solid curves), 2:1 (dashed curves), 1:2 (dotted curves). The viscosity of 5 mg/ml rhCollagen methacrylate is reported for comparison (solid black curve).

Example 15. Procedure for Obtaining and Processing rhCollagen from Tobacco Plants Tobacco plants genetically modified as described above are grown, and the leaves are harvested and prepared for initial upstream extraction and purification (FIGS. 33A-C). As shown in FIG. 33A, the leaves are subject to mechanical shredding (step A), and the pulp is removed from the slurry, while the procollagen containing moiety is retained and subjected to enzymatic digestion to convert procollagen to collagen (steps B-C). The pulp is again discarded, and the collagen containing moiety is retained from the slurry (step C). Following an acidification step, the sample undergoes a first centrifugation for a first clearing step, after which the pellet is discarded (steps D-F). After AMS precipitation and a second centrifugation, the protein is precipitated (H pellet), and the supernatant is discarded (steps G-H). The H pellet can be frozen at −20° C. for storage.

As shown in FIG. 33B, the H pellet is resuspended to yield a protein suspension, followed by a third centrifugation, after which the pellet is discarded (steps I-J). A depth filter is used to clear the suspension, which is subjected to salting out with NaCl to precipitate the collagen (steps K-L). A fourth centrifugation yields a collagen pellet, and the supernatant is discarded (step M).

As shown in FIG. 33C, the collagen pellet is resuspended in HCl to yield solubilized collagen (step N). After 0.2-0.8 micron filtration, ultrafiltration (UF) (concentration and diafiltration) results in bulk concentrated collagen (steps O-P). After 0.2 micron filtration and fill, the purified collagen is stored in its final container (step Z).

Example 16. Viscosity and Polymerization of rhCollagen Methacrylate with Additives The viscosity of 5 mg/ml rhCollagen methacrylate enriched with different additives (polyvinyl alcohol methacrylate (PVAMA) (FIGS. 34 and 37), hyaluronic acid methacrylate (HAMA) (FIGS. 35 and 37), and oxidized cellulose (OC) (FIGS. 36 and 37) at collagenMA:additive ratios of 5:1, 2:1 and 1:2 is shown in FIGS. 31-37. The viscosity of 5 mg/ml rhCollagen methacrylate is reported in each FIG. for comparison (black curve). All the samples were prepared in 0.1M Phosphate buffer pH 7.4+11.3 mM NaCl (physiological osmolarity) and measurement done at T=22° C. The data is compared and summarized in FIG. 37.

Figure 38:
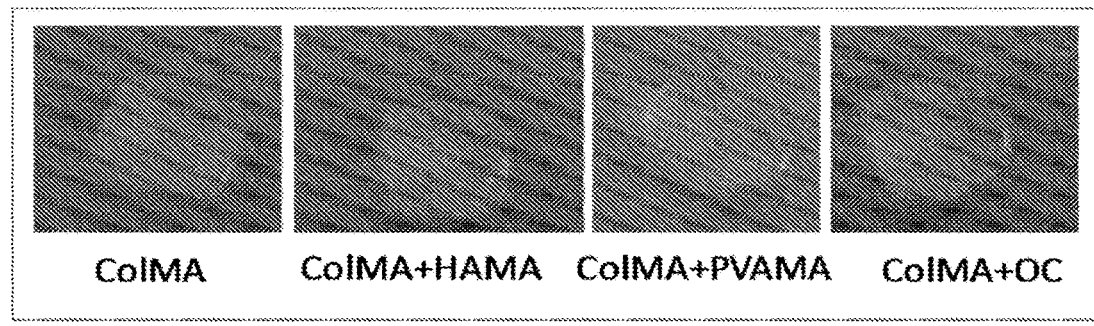
FIG. 38 shows polymerized scaffolds of rhCollagen Methacrylate (Co1MA)+additives at collMA:additive ratio of 2:1. ColMA alone was compared with CoMA combined with Polyvinyl alcohol methacrylate (PVMA), hyaluronic acid methacrylate (HAMA), or oxidized cellulose (OC). Solutions were mixed with the photoinitiator 2-hydroxy-4'-(2-hydroxyethoxy)-2-methylpropiophenone (0.1%) and illuminated for 20 sec with ultraviolet (uv) light (365 nm).

The polymerization of rhCollagen methacrylate enriched with different additives is also shown with respect to typical scaffolds of 5 mg/ml collagenMA+different additives at a ratio of collMA:additive 2:1 (FIG. 38). ColMA alone was compared with ColMA combined with Polyvinyl alcohol methacrylate (PVMA), hyaluronic acid methacrylate (HAMA), or oxidized cellulose (OC). The solutions were mixed with the photoinitiator 2-hydroxy-4'-(2-hydroxyethoxy)-2-methylpropiophenone (0.1%) and illuminated for 20 see with ultraviolet (uv) light (365 nm).

Example 17. Injectable rhCollagen/Platelet Rich Plasma Scaffold

Injectable rhCollagen/Platelet Rich Plasma (PRP) scaffold was investigated as a scaffold and healing implement for tendonophathy. A slow-degrading rhCollagen matrix combined with a source of growth factors (GFs), such as platelet rich plasma (PRP), was injected at the vicinity of the injured tendon in an effort to provide the required support to enhance the healing of injured tendon. The treatment used a matrix made of plant derived recombinant human Type I collagen (rhCollagen) mixed with PRP, which supports extended release of growth factors at the injured site and promotes healing. The effect of the rhCollagen-PRP matrix was compared to PRP, in vitro and in vivo, in supporting proliferation of fibroblasts, clot degradation, release of GFs and tendon healing in a collagenase-induced Achilles tendon tendinopathy rat model. rhCollagen-PRP demonstrated a superior performance compared to PRP alone in vitro and in vivo. These results are encouraging with respect to the use of the rhCollagen matrix combined with PRP in a clinical trial for a tendinopathy indication.

Materials and Methods
rhCollagen Matrix
Monomeric solution of rhCollagen in 10 mM HCl (CollPlant, Ness Ziona, Israel) was fibrillated by pH neutralization in phosphate solution and cross-linked in 18 mM 1-Ethyl-3-(3-dimethylaminopropyl) carbodiimide (Sigma Aldrich, Israel). The cross-linked collagen was then washed by repeated centrifugations in double distilled water and Calcium Chloride ($CaCl_2$)) (Merck, Israel) was added, calculated to a final concentration of 20 mM. Syringes filled with rhCollagen slurry were lyophilized and terminally sterilized with Ethylene Oxide.

Platelet Rich Plasma (PRP) Preparation
Granulocyte free PRP was prepared using Tropocell PRP kit (ESTAR, Israel) according to the manufacturer instructions. For the in vitro cell proliferation assay, human blood was collected from healthy human volunteers (Helsinky permission number 2012068). For the in vivo animal studies blood was withdrawn from Hsd:Sprague DawleySD rats (Harlan).

RhCollagen Matrix/PRP and Control Preparation
RhCollagen matrix/PRP: syringes containing lyophilized cross-linked rhCollagen were hydrated with PRP or saline to obtain a final concentration of 20 mg/ml rhCollagen.

Thrombin activated PRP (control): human PRP was mixed with purified Thrombin (Sigma Aldrich, Israel) to obtain final concentration of 100 IU/ml.

CaCl2) activated PRP (control): rat PRP was mixed with CaCl2) (Merck, Israel) to obtain a final concentration of 20 Mm In Vitro Cell Proliferation Assay
In this study the effect of GFs on normal human dermal fibroblasts (nHDF) viability and proliferation was assessed. Cell viability and proliferation were compared upon GFs diffusion from either a matrix composed of the crosslinked rhCollagen matrix combined with PRP or from a clot composed of thrombin activated PRP. The rhCollagen matrix combined with PRP or thrombin activated PRP (200 µl each), were injected into transwells (Thincerts™ 24 well 8.0 µm, Greiner bio-one, Israel) placed on top of a 24 well plate (Thermo scientific, Israel) and incubated at 37° C. for 20 minutes to enable clot formation. Normal human dermal fibroblasts (nHDF) (5,000 cells per 0.5 ml), were seeded on the bottom of each well in serum deprived medium (Dulbecco's Modified Eagle's Medium, DMEM, with 1% Fetal Bovine Serum, FBS, Biological Industries, Israel). The transwells containing the matrices (either the rhCollagen matrix combined with PRP or thrombin activated PRP) were placed on top of the seeded well and additional 0.2 ml of medium were added on top of the samples. nHDF in 0.5 ml DMEM, 1% FBS were seeded as control. Samples were tested in triplicates 7 and 10 days after seeding using cell proliferation kit WST-1 (Roche, Israel) according to the manufacturer instructions.

In Vivo Studies

Animals

Hsd:Sprague Dawley SD rats weighing 230 g±20% were chosen for the animal experiments. Animals were given a unique animal identification ear number and randomly assigned to a specific group. Animals were housed in individually ventilated (IVC) cages in dedicated heat, ventilation, air conditioning (HVAC) animal facility. Temperature and humidity were monitored continuously. Animals were provided ad libitum a commercial rodent diet (Harlan Teklad TRM Ra/Mouse Diet) and allowed free access to autoclaved water. The facility had no exposure to outside light and is maintained on automatic alternating cycles of 12 hours light and 12 hours dark. All animals were treated according to the guidelines for laboratory animal treatment and care, and all protocols were approved by the local Institutional Animal Care and Use Committee. No abnormalities were detected in any of the animals throughout the entire study period. No statistically significant differences were found in mean group body weight values and gain. All gains were within the range of normally expected values at termination.

In Vivo Clot Degradation and Growth Factors Release

Degradation time and GFs content over time of rhCollagen matrix combined with PRP, rhCollagen matrix alone or $CaCl_2$) activated PRP were compared in a subcutaneous (SC) rat model (Science in Action Ltd., Ness Ziona, Israel)

Injection sites on the backs of 34 female Sprague Dawley rats (Harlan Laboratories, Ness Ziona Israel) were shaved and marked. Each rat was injected at four distanced locations with 0.5 ml of the same formulation on the dorsal plane, two sites in the anterior portion and two sites in the posterior portion of the rat's back. Animals were sacrificed at time-points 1, 7, 14, 21, 30, and 45 days post-treatment (10 or 12 animals per group, 2 animals per time point). At each time point, the injection sites were exposed and assessed macroscopically. The skin at the injection sites was gently separated from the muscle using scissors, the sites washed with 0.25 ml DMEM, 1% FBS (Biological Industries, Israel) and the clot extracted and weighed. The washing medium was transferred to an Eppendorf tube (1.5-2 ml) while the extracted clot was transferred to a 6 or 12 wells plate. Once weighed, the clot was combined with the respective washing medium, cut with scissors and minced with a pestle to promote the release of GFs from the clot to the surrounding medium. The Eppendorf tubes were then centrifuged for at least 5 minutes to separate between the clot's pellet and the medium. Supernatants were collected and stored at −80° C. until assayed. A control (TO) containing ~0.5 ml of the respective formulation was formed in vitro following the same procedure as described above without injecting into the animal. At the end of the study, PDGF and VEGF contents in the preserved supernatants were assessed by ELISA (Quantikine ELISA Mouse/rat PDGF and Quantikine ELISA Rat VEGF, R&D Systems, Israel).

In Vivo Tendinopathy Induced in Rats

The healing properties of the rhCollagen matrix combined with PRP and of PRP alone were compared in a collagenase induced tendonopathy model in 36 male Sprague Dawley rats (18 rats per group, 6 animals per time point). The experiment was performed at Harlan Laboratories Israel Ltd. (Ness Ziona, Israel).

A skin incision was made over the proximal portion of the right posterior leg of the rat over the Common Calcaneal tendon. Under appropriate magnification, the middle branch of the tendon was identified and isolated and tendinopathy was induced by injecting 0.3 mg collagenase (10 mg/ml, Sigma) under the Common Calcaneal tendon sheath using a 0.5 ml insulin syringe. Eventually the skin was closed with interrupted subcutaneous sutures using 4/0 Vicryl. One week following tendinopathy induction, a stab incision was created in the tendon sheath using an ophthalmic corneal/scleral knife. A tunnel was then created under the tendon sheath using a cannula and 50 µl of rhCollagen combined with PRP or PRP alone were injected into the pre-created canal. Animals were sacrificed at 3, 7, and 14 days post-treatment. The treated tendons were excised and preserved for histopathological evaluation.

Histology

Tissues were embedded in paraffin and serially cut into 4-5 microns thick samples. The slides were stained with Hematoxilyn & Eosin (H&E) for histopathological examination and blinded evaluated by a pathologist.

Results

In Vitro Cell Proliferation Assay

Figure 39:
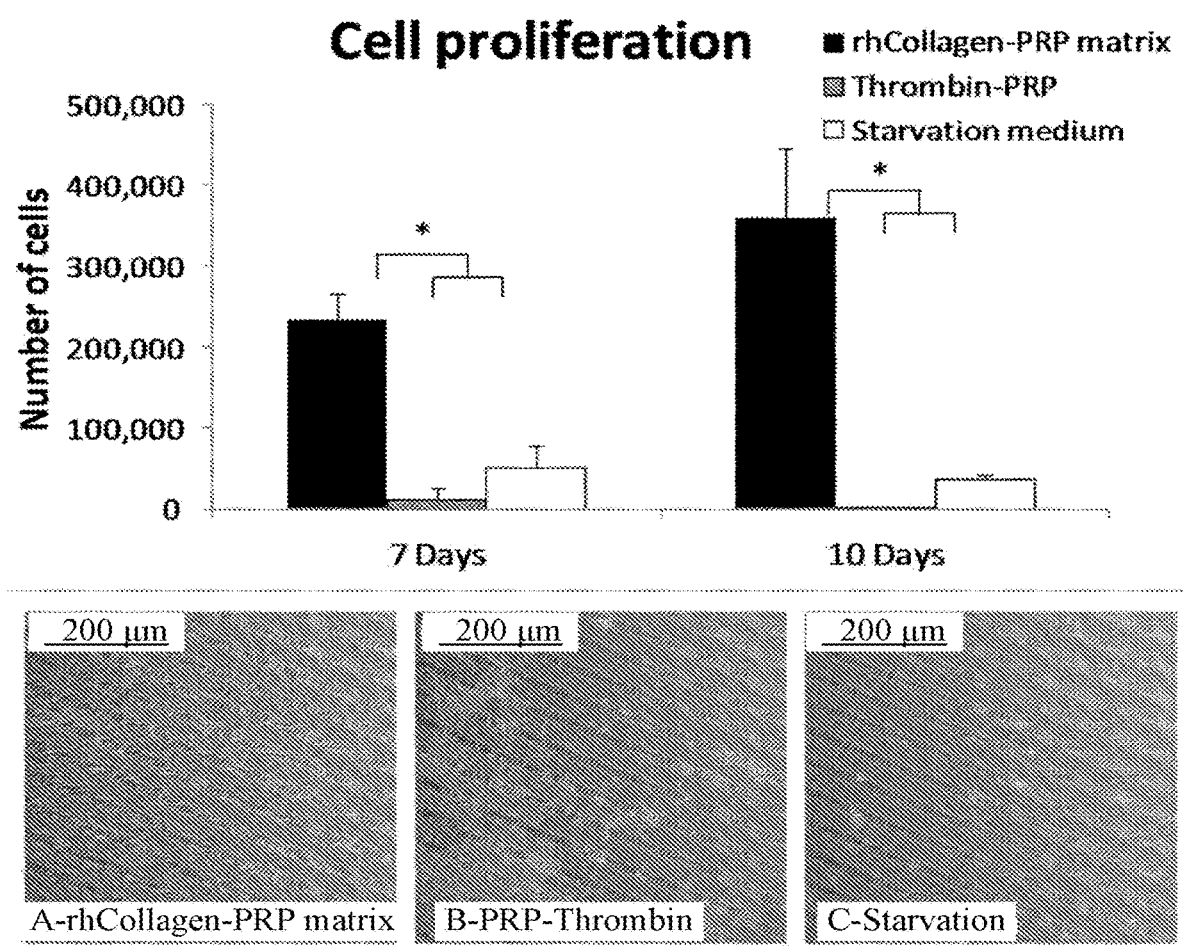
FIG. 39 shows viability studies. Upper graph: Comparison of normal human fibroblasts (nHDF) viability (and proliferation) when cultured in the presence of GFs released from the rhCollagen-PRP matrix (black), in the presence of GFs released from activated PRP (gray) and cultured under starvation conditions (white). The data is an average of two different fibroblasts proliferation assays performed with PRP extracted from 2 different donors. Significant difference (p<0.0002). Lower inset: microscope images of nHDF cells proliferated in the presence of GFs released from the rhCollagen matrix combined with PRP (A), in the presence of GFs released from activated PRP (B) and cultured under starvation conditions (C). Images were taken 7 days after cells were seeded.

In this study viability and proliferation of cells seeded in the vicinity of a matrix composed of rhCollagen combined with PRP and a clot composed of thrombin activated PRP were compared. Cells seeded in untreated wells were used as control. The matrices (either composed of rhCollagen combined with PRP or thrombin activated PRP) were placed in transwells on top of the seeded wells in order to allow the diffusion of GFs from the matrices to the well without being in direct contact with the cell layers. The number of live cells on days 7 and 10 are reported (FIG. 39 Upper) as an average of two different experiments (3 repetitions for experiment) where PRP was extracted from two different blood donors. As shown in FIG. 39, cell viability (on days 7 and 10) in the presence of GFs released from the rhCollagen matrix combined with PRP is significantly higher than in the thrombin activated PRP clot or in the control. Moreover, while in the presence of the rhCollagen matrix combined with PRP the cell number increased from day 7 to day 10, in the presence of thrombin activated PRP and in the control group the number of cells decreased, showing that both cell viability and proliferation are considerably superior in the presence of the rhCollagen matrix. The data was confirmed by microscopy analysis (FIG. 39 Lower). Cells cultured in the presence of the rhCollagen matrix combined with PRP (FIG. 39 Lower, panel A) show an elongated shape and already arrived to full confluence 7 days after seeding while cells cultured in the presence of thrombin activated PRP were hardly alive, which may point to toxic effect of the thrombin in this experimental setup. (FIG. 39 Lower, panel B). Cells cultured in the presence of only medium showed very limited viability (FIG. 39 Lower, panel C).

In Vivo Matrices Degradation Profile and Growth Factors Release

Matrices Degradation Profile

The degradation profile of the injected formulations was determined by weighing the matrices at different time points following subcutaneous injections into rats.

Upon injection of activated PRP, the material disappeared already at day 1 (FIG. 40), suggesting complete degradation of the fibrin clot during the first 24 hours. On the other hand, the rhCollagen matrix alone or combined with PRP had a two-phases degradation profile (FIG. 40) starting with a steep weight decrease during the first day followed by relatively slower degradation rate leading to complete elimination after 30-45 days (final weight<0.5% of initial weight).

Growths Factors Content

Figure 40:
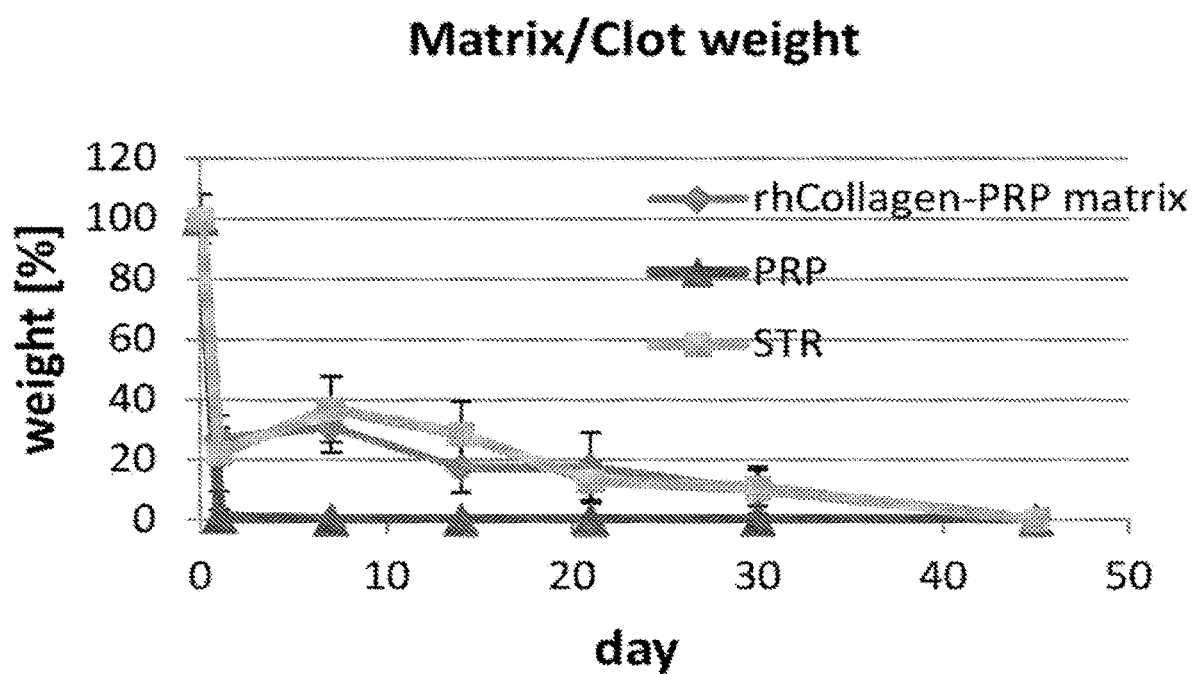
FIG. 40 shows scaffold weight as a function of time (each point is an average of 6 scaffolds, 2 rats per time point, 3 injections per rat).
Figure 41A:
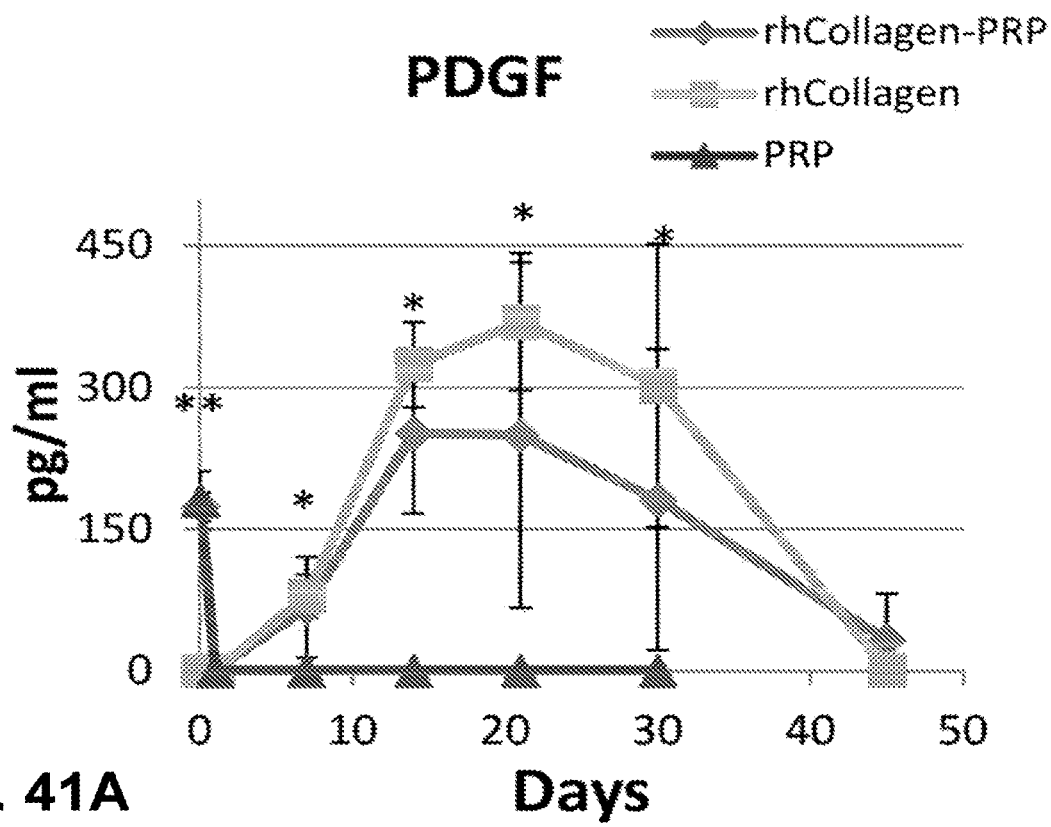
FIGS. 41A-41B show two studies using a subcutaneous rat model. (A) PDGF content as a function of time (B) VEGF content as a function of time in a subcutaneous rat model. Significant difference between rhCollagen matrix combined with PRP and PRP alone ($p<0.038$) and between the rhCollagen matrix alone and PRP alone ($p<0.004$). * Significant difference ($p<0.021$) between rhCollagen matrix alone and PRP alone and between rhCollagen matrix alone and rhCollagen matrix combined with PRP (A), and between rhCollagen matrix combined with PRP and PRP alone and rhCollagen matrix combined with PRP and rhCollagen matrix alone ($p<0.007$) (B).
Figure 41B:
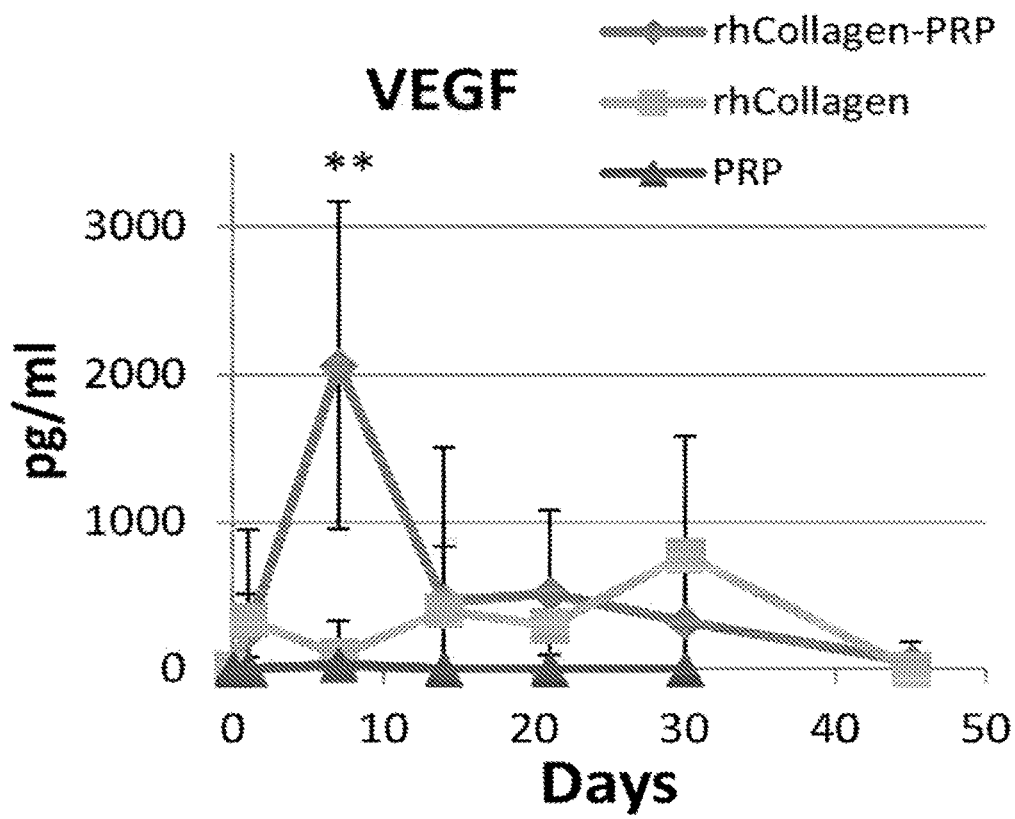
Figure 42:
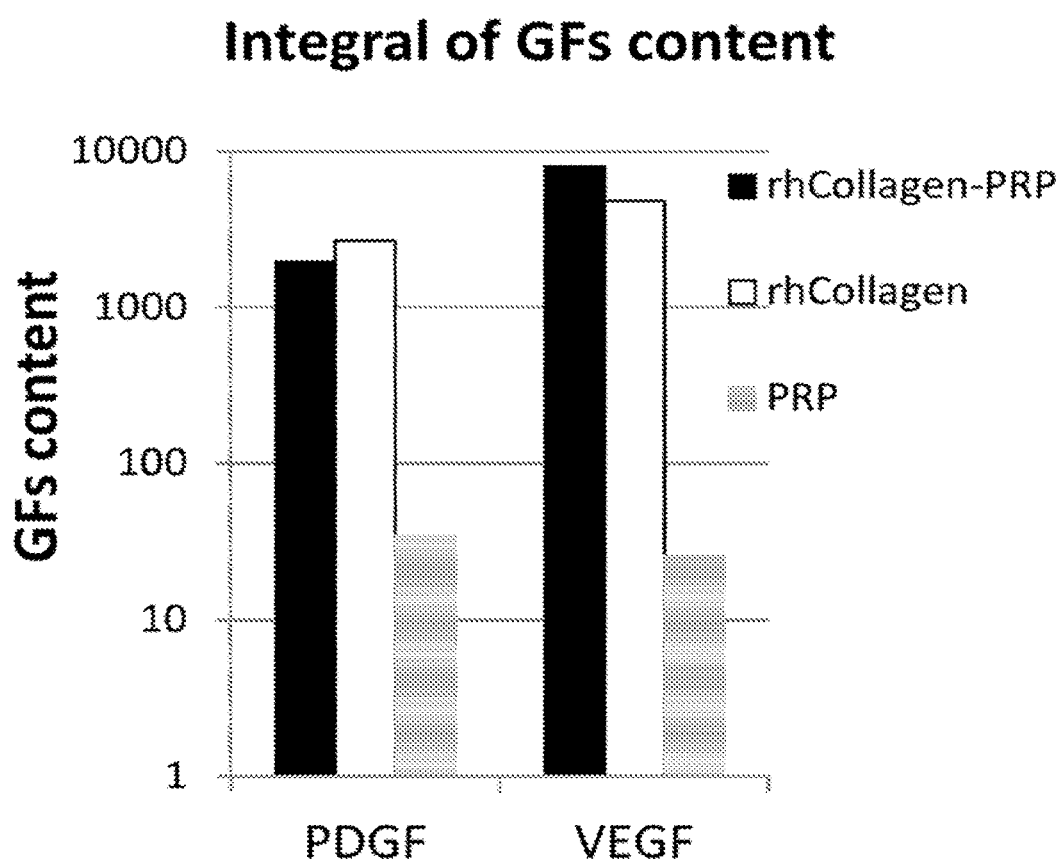
FIG. 42 shows integration of the nominal PDGF and VEGF content in the injected matrices over 45 (or 30) days in a rat model.

GFs content in the injection site as a function of time was assessed by ELISA for PDGF and VEGF (FIGS. 41A-B). PDGF content at time 0 was similar in the rhCollagen matrix in combination with PRP and in the activated PRP treatments (FIG. 41A), suggesting that the PDGFs content at day 0 is a sole contribution of the GFs rich platelets brought by PRP. However, upon injection of PRP alone the PDGF content at the injection site was lower than the detection limit already 1 day after injection and remained undetectable along the whole study, in agreement with the rapid clot degradation (FIG. 40). A different picture is shown when PRP was incorporated in the rhCollagen matrix (FIG. 41A). PDGF content gradually increased from day 1 to day 14 and decreased again until completely eliminated towards day 45, in concomitance with the scaffolds degradation (FIG. 40). Interestingly, the PDGF content in the rhCollagen matrix alone group increased starting from day 7 and followed the pattern shown by the matrix combined with PRP group. The VEGF content at day 0 was lower than the detection limit for all formulations and remained at baseline level in the activated PRP group (FIGS. 41A-B and 42). The VEGF profile of the rhCollagen matrix combined with PRP shows a brisk increase in VEGF content around day 7 followed by a steep decrease to day 14 and a plateau until day 30, VEGF eventually decreases at day 45 in concomitance with scaffold degradation (FIG. 41B).

The GFs increase seen from day 1 to 14 in the PDGF analysis and from day 0 to day 7 in the VEGF analysis testifies the capability of the rhCollagen scaffold to enable GFs accumulation, likely reflecting cells that migrate and proliferate in the scaffold. The integration of the nominal content of PDGF and VEGF over the whole study for each formulation is summarized in FIG. 42. It is clear that the GFs content at the injection site is much higher upon injection of the rhCollagen matrix alone or combined with PRP compared to activated PRP alone.

In Vivo Tendinopathy Induced in Rats

The healing properties of the rhcollagen matrix combined with PRP in comparison to PRP alone were assessed in a rat model for tendinopathy and evaluated by histopathological analysis at different time points. Tendon healing and inflammation were quantified by scoring the level of mature fibrosis, the presence of mononuclear inflammatory cells and the presence of immature granulation tissue (score 0-5 as described in Table 7).

TABLE 7

Histopathological scoring

| Score | Description |
|---|---|
| 0 | No change |
| 1 | Up to 10% of the area of sectioned tissue is involved by the lesion |
| 2 | Up to 25% of the area of sectioned tissue is involved by the lesion |
| 3 | Up to 50% of the area of sectioned tissue is involved by the lesion |
| 4 | Up to 75% of the area of sectioned tissue is involved by the lesion |
| 5 | More than 75% of the area of sectioned tissue is involved by the lesion |

Figure 43A:
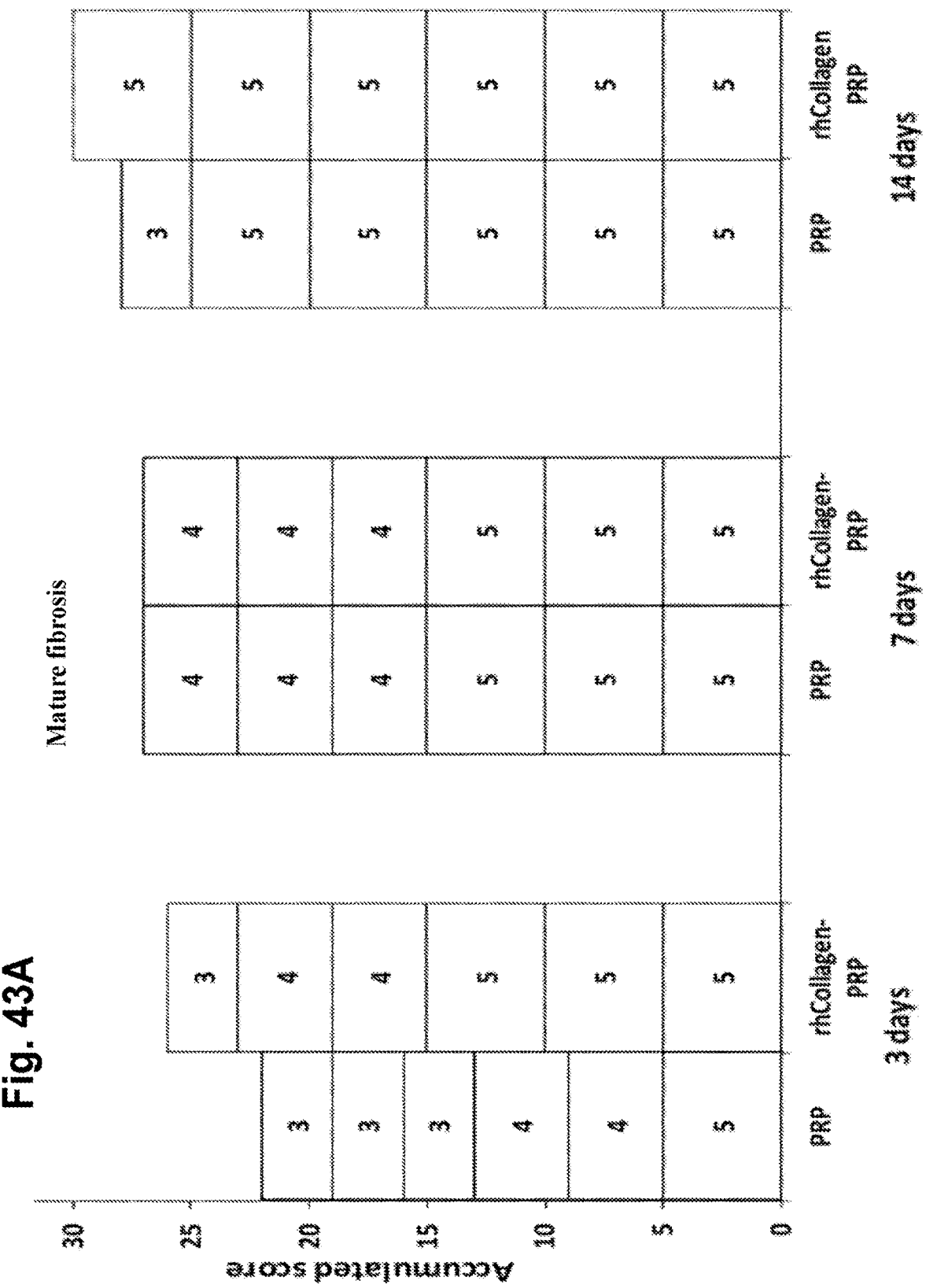
Figure 43C:
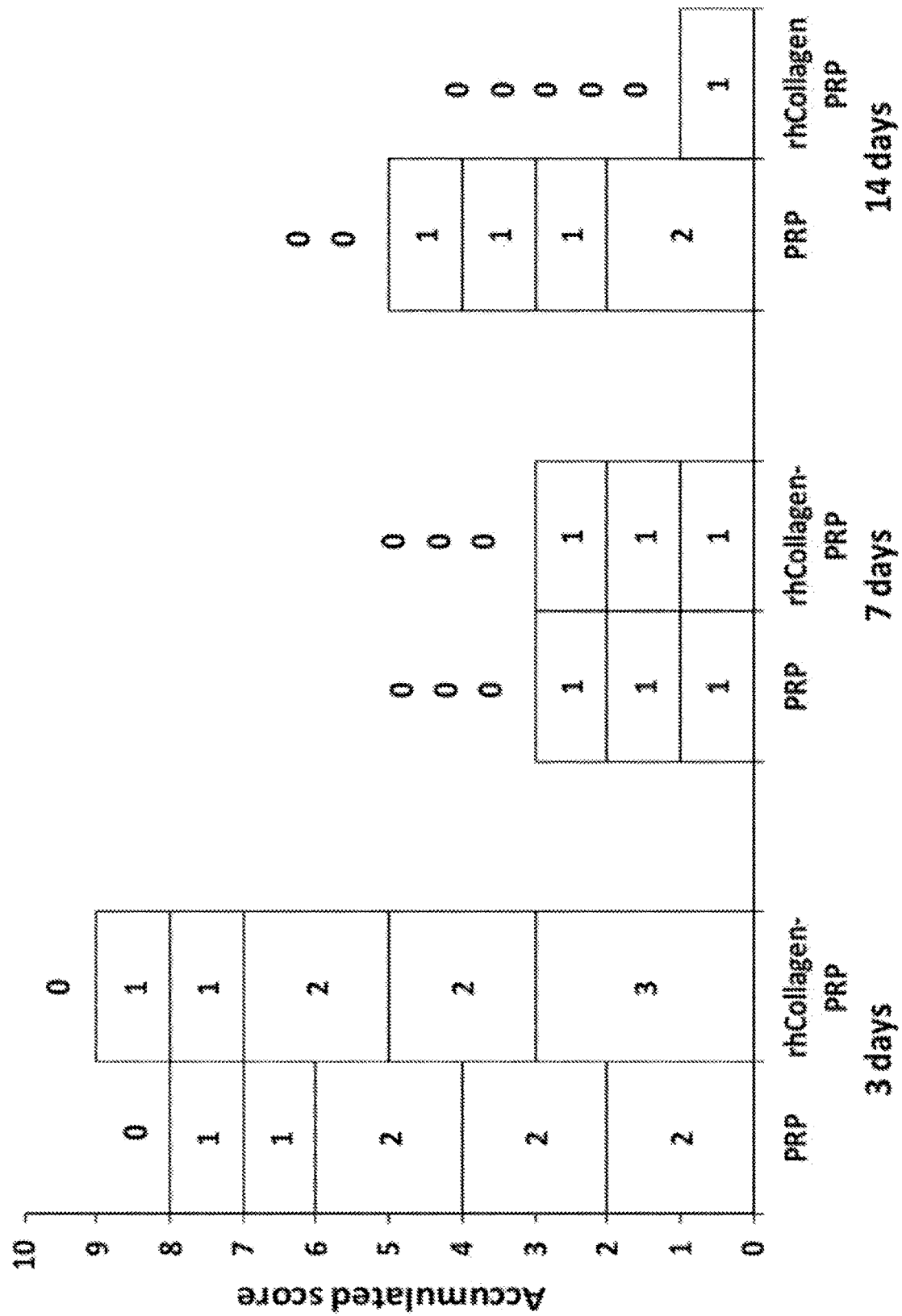

The cumulative values of the histopathological scores associated with each treatment are depicted in FIGS. 43A-C. The group treated with the rhCollagen matrix combined with PRP displayed a slightly more mature fibrosis when compared to the PRP treated group, specifically at day 3 and 14. This is consistent and correlated to the lower level of immature granulation displayed by the group treated with the rhCollagen matrix combined with PRP at day 14 (FIG. 43C). Moreover in FIG. 43B the group treated with the rhCollagen matrix combined with PRP displays a decrease in inflammation as indicated by the low presence of mononuclear inflammatory cells at all time points, especially at day 3 and 14. Overall, the data demonstrates that treating the injured tendon with the rhCollagen matrix combined with PRP promotes faster healing as shown by the higher level of mature fibrosis and lower level of immature granulation tissue accompanied by a major decrease in inflammatory mononuclear cells when compared to the standard PRP injection treatment.

Discussion

Damages to soft tissues, including injuries in tendons and ligaments are very common and cause a significant clinical burden. Although several treatments are available, their clinical benefit is still limited. This encouraged the search for new alternatives with the intent of improving healing and reducing recovery time. An injectable matrix composed of human recombinant type I collagen was developed that, once mixed with PRP, forms a collagen-fibrin-PRP composite that degrades slowly, attracts cell migration and proliferation into the collagen scaffold and allows extended release of GFs at the injured site, thus better supporting the healing process. In vitro experiments (FIG. 39) showed considerably superior nHDF viability and proliferation in the surrounding of the rhCollagen matrix combined with PRP as compared with thrombin activated PRP. The results demonstrated that the sustained growth factors released from the collagen matrix promote and enhance cell proliferation. Type I rhCollagen, when combined to PRP, still provides supportive environment that promotes and enhances cell proliferation even when not in direct contact with the cell layer. SC injections in rats showed for the first time that the GFs containing fibrin-clot formed in situ upon PRP injection, degrades already within twenty-four hours and consequently, the GFs content in the injection site is lower than the ELISA detection limit (FIGS. 41A-B). Once platelets are complexed with the rhCollagen matrix, GFs are released over 45 days, time that coincides with the scaffold degradation (FIGS. 40 and 41A-B). It is interesting to notice that the GFs content profile is not monotonic as it would have been expected by a standard release profile. The PDGF profile in the rhCollagen matrix with PRP treatment (FIGS. 41A-B) demonstrated a first steep decrease in the first day, very similar to the case of PRP alone, followed however, by a gradual increase up to day 21 and a final decrease to reach undetectable levels in concomitance with the scaffold degradation. Interestingly, rhCollagen alone showed a similar pattern of gradual increase in PDGF content during the first couple of weeks and decrease towards the complete degradation of the scaffold. The rhCollagen with PRP scaffold therefore combines the benefits provided by the trapped PRP (early GFs release) to those provided by the rhCollagen scaffold itself which highly promotes and enhances cells recruitment and proliferation. As for the VEGF content profile, while upon PRP injection the VEGF level remained extremely low along the whole study, injection of the rhCollagen matrix combined with PRP resulted in an increase in the VEGF level within the first week to eventually decrease in concomitance with the scaffold degradation. Interestingly, in contrast to PDGF, the VEGF level in the group treated with the rhCollagen matrix alone was still higher than in the PRP alone group but showed a different profile than in that of the rhCollagen matrix with PRP, especially at day 7. This observation stresses the contribution of PRP to the GFs level once combined with the collagen scaffold. The healing properties of rhCollagen and PRP were eventually compared to PRP in a rat model for Common Calcaneal tendon (Achilles tendon) tendinopathy. The histological evaluation confirmed the faster ability of the rhCollagen matrix combined with PRP to build mature fibrotic tissue which is consistent to the scaffold ability to promote cells recruitment and proliferation as anticipated in the previous experiments. Moreover, the histological analysis also demonstrates that once the injured site is treated with rhCollagen matrix combined with PRP, the inflammation substantially decreases in comparison to the standard treatment with PRP alone.

This study demonstrates the biological effects in vitro and in vivo, of an injectable scaffold composed of crosslinked human recombinant type I collagen. Once combined with an autologous source of GFs such as PRP, the formed scaffold accelerates the healing of soft tissue injuries, by controlling the inflammatory response and promoting faster formation of new healthy tissue. The results suggest that the enhanced healing properties reside in the unique combination of rhCollagen and autologous PRP which extends the release of GFs. The data supports the use of the rhCollagen matrix combined with PRP in a clinical trial for tendinopathy.

Example 18. Use of a Plant-Derived Human Recombinant Collagen as a Dermal Filler In order to reduce immunogenicity, to promote tissue regeneration, and to provide a more uniform and potentially longer lasting dermal filler with improved rheological properties, in comparison with tissue-derived human and bovine collagens, a human transgenic collagen (rhCollagen) is produced and isolated from a plant (e.g., a genetically engineered tobacco plant) and then used as a dermal filler. Typically, the genetically modified plant comprises an expressible sequence of at least one gene sequence of human deoxyribonucleic acid (DNA) selected from the group consisting of: COL1, COL2, P4H-alpha, P4H-beta, and LH3. Typically, the plant-derived human collagen comprises at least modified one human collagen alpha-1 chain as set forth in SEQ ID NO: 3 and as expressed in the genetically modified plant; and at least one modified human collagen alpha-2 chain as set forth in SEQ ID NO: 6 and as expressed in the genetically modified plant; and the genetically modified plant further expresses an exogenous prolyl-4-hydroxylase (P4H) (e.g., a human or other mammalian P4H). Optionally, the genetically modified plant further expresses an exogenous polypeptide selected from the group consisting of lysyl hydroxylase (LH), protease N, and protease C. For example, the human collagen alpha-1 chain is encoded by a sequence as set forth in SEQ ID NO: 1, and/or the human collagen alpha-2 chain is encoded by a sequence as set forth in SEQ ID NO: 2. Optionally, the human collagen alpha-1 chain and/or alpha-2 chain is targeted to a vacuole of the plant or the genetically modified plant and digesting it with ficin, resulting in human atelocollagen.

Optionally, the rhCollagen is modified or is formulated with other substances, including those known in the art for dermal fillers. Examples of modification include, but are not limited to, methacrylation and/or thiolation. Examples of other substances include, but are not limited to, hyaluronic acid (HA) or a modified derivative thereof, poly(vinyl alcohol) (PVA) or a modified derivative thereof, polyethylene glycol (PEG) or a modified derivative thereof, oxidized cellulose (OC) or a modified derivative thereof, or a combination of any of these. Examples of other substance include, but are not limited to, hyaluronic acid (HA), poly (vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, crystalline nanocellulose (CNC) or a combination thereof. Modified derivatives of HA, PVA, PEG, or OC include, but are not limited to, photopolymerizable derivatives. Modifications of HA, PVA, PEG, or OC include, but are not limited to, methacrylation and/or thiolation. Examples of other substances include, but are not limited to, polymerizing agents or initiators, such as a photoinitiator (e.g., sensitive to visible, ultraviolet (uv), or infrared light). Examples of visible light photoinitiators include, but are not limited to, Eosin Y+triethanolamine or riboflavin. Examples of ultraviolet photoinitiators include, but are not limited to, lithium phenyl-2,4,6-trimethylbenzoylphosphinate (LAP) or 1-[4 2-hydroxy-1-[4-(2-hydroxyethoxy)phenyl]-2-methylpropan-1-one (IRGACURE® 2959).

An inherent property of tissue-extracted collagen is gelation at room temperature. At relative low concentrations (e.g., 5-15 mg/ml) in physiological buffer, tissue-extracted collagen forms a gel when transformed from cold (approximately 4° C.) to room temperature.

In contrast, rhCollagen has a relatively low viscosity (in the same concentration and formulation) that allows injection through narrow gauge needles or cannulae (27-gauge to 33-gauge) using a relatively decreased expression force, as well as better penetration into tinier spaces, and greater flexibility in post-injection modulation (sculpting).

The rhCollagen is placed in a syringe having a fine-gauge needle or cannula (27-gauge to 33-gauge) and is injected into a cavity or space below the dermis. The injected rhCollagen is then molded, sculpted, or otherwise manipulated into the desired position (e.g., via manual massage or with a molding or sculpting implement, such as a surgical depressor). Polymerization may be initiated before, during, or after this process by exposure to a light source (e.g., a light-emitting diode (LED), laser, or xenon lamp) located on or above the dermis overlying the injected formulation.

Example 19. Use of a Modified Plant-Derived Human Recombinant Collagen Formulated with a Photoinitiator and Additive The rhCollagen is modified by methacrylation, as described in Example 18. The modified rhCollagen is prepared as a polymerizable solution formulation with a photoinitiator (e.g., Eosin Y+triethanolamine or riboflavin). Hyaluronic acid (HA), poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, crystalline nanocellulose (CNC) or some combination thereof are included.

The formulation is placed in a syringe having a fine-gauge needle or a cannula (27-gauge to 33-gauge and is injected into a cavity or space below the dermis. The injected formulation is then molded, sculpted, or otherwise manipulated, either manually or with an appropriate surgical instrument, into the desired position during or after exposure to a light source (e.g., a visible light source), as described in Example 18.

Example 20. Use of a Modified Plant-Derived Human Recombinant Collagen Formulated with a Photoinitiator and Modified Additive The rhCollagen is modified by methacrylation or thiolation as in Example 19. The modified rhCollagen is prepared as a polymerizable solution formulation with a photoinitiator (e.g., Eosin Y+triethanolamine or riboflavin), as described in Example 18. A modified derivative of hyaluronic acid (HA), poly(vinyl alcohol) (PVA), polyethylene glycol (PEG), oxidized cellulose (OC), or some combination thereof is included and is modified by methacrylation or thiolation.

The formulation is placed in a syringe having a fine-gauge needle or a cannula (27-gauge to 33-gauge and is injected into a cavity or space below the dermis. The injected formulation is then molded, sculpted, or otherwise manipulated, either manually or with an appropriate surgical instrument, into the desired position during or after exposure to a light source (e.g., a visible light source), as described in Example 18.

Figure 44:
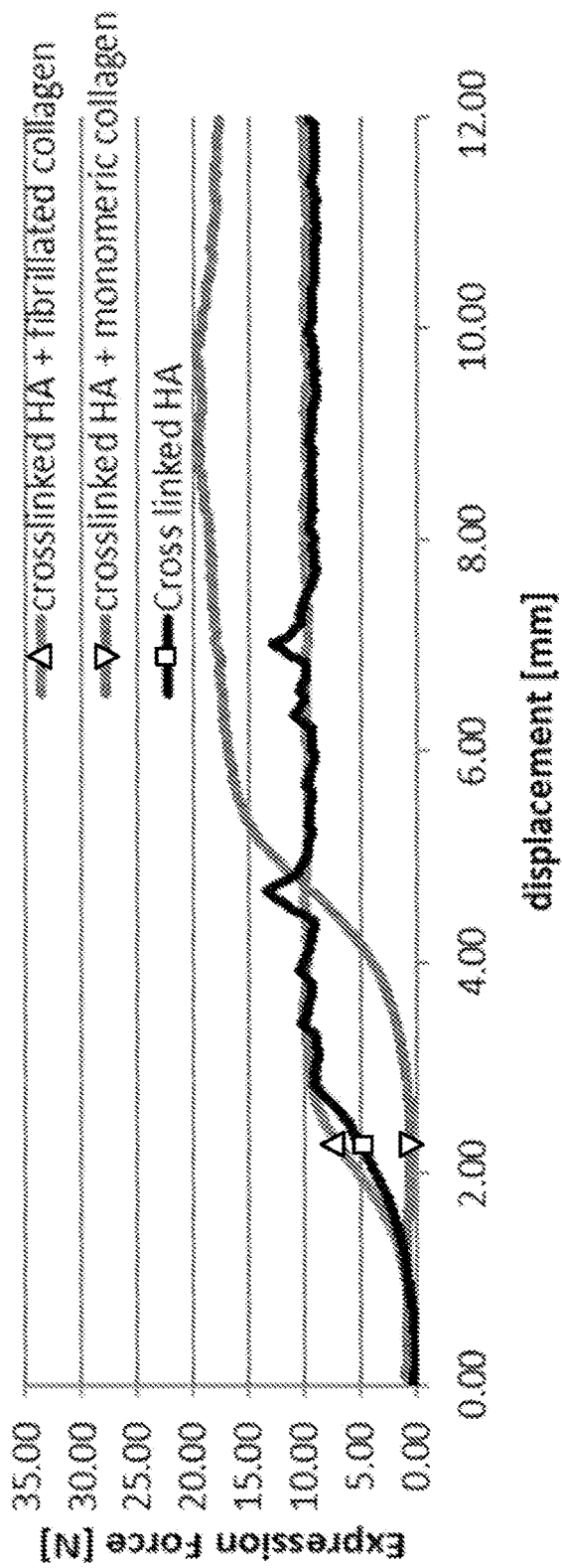
FIG. 44 shows a comparison of the expression force (newtons, N) needed for injections of crosslinked hyaluronic acid (HA) (black curve—□), crosslinked hyaluronic acid (HA)+monomeric collagen (▼), or crosslinked hyaluronic acid (HA)+fibrillated collagen (▲) from a 32-gauge needle and 1 ml syringe (Becton Dickinson [BD], ref. 309628). Crosslinked HA+monomeric collagen and crosslinked HA+fibrillated collagen are semi-Interpenetrated networks, wherein the collagen is not crosslinked to anything.
Figure 45:
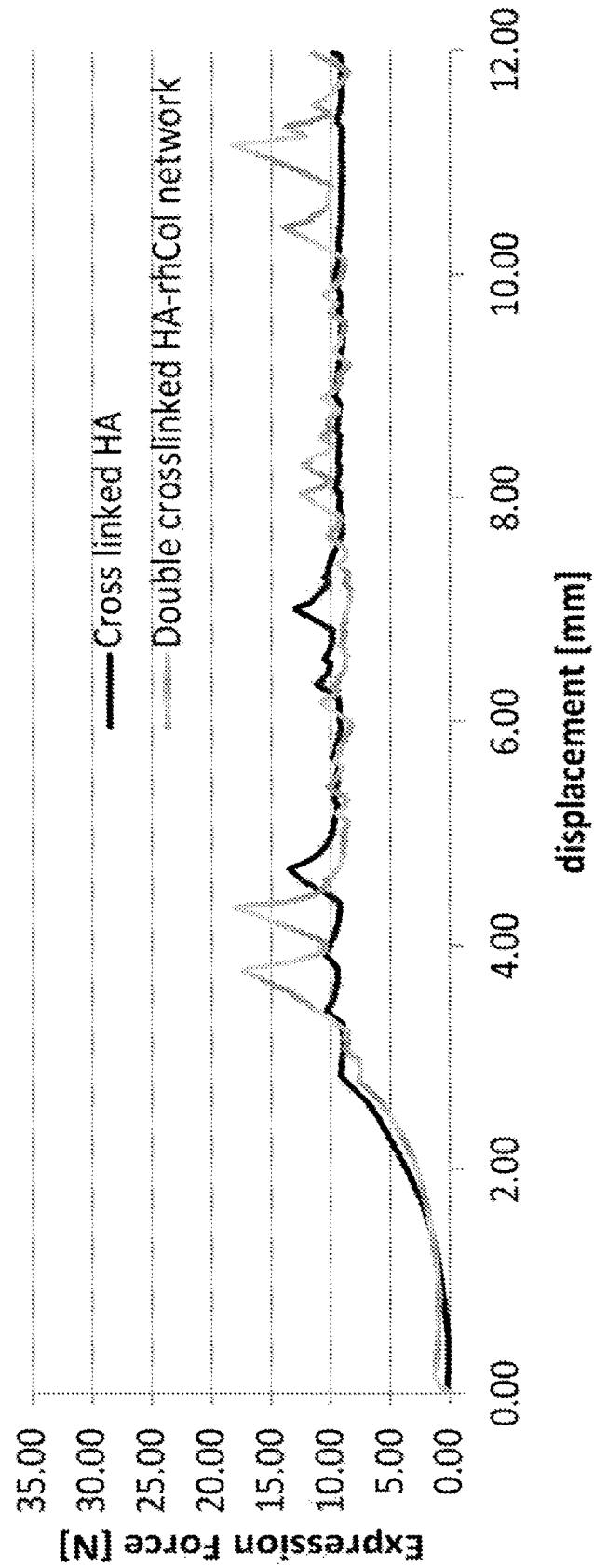
FIG. 45 shows a comparison of the expression force (newtons, N) needed for injections of crosslinked hyaluronic acid (HA) (black) or a double crosslinked network of crosslinked hyaluronic acid (HA) and collagen (grey) from a 32-gauge needle and 1 ml syringe (Becton Dickinson [BD], ref. 309628).

Example 21. Comparative Injectability and Viscosity of Crosslinked Hyaluronic Acid with Collagens As shown in FIG. 44, the expression force (newtons, N) needed for injecting crosslinked hyaluronic acid (HA) (black □ curve) was compared to the expression force needed for injecting crosslinked hyaluronic acid (HA) with monomeric collagen (▼ curve) or fibrillated collagen (▲ curve). (Crosslinked HA 20 ml/ml; Crosslinked HA 20 mg/ml, monomeric rhCol 7.5 mg/ml; Crosslinked HA 20 mg/ml, fibrillated collagen 10 mg/ml As shown in FIG. 45, the expression force (newtons, N) needed for injecting crosslinked HA was compared to the force needed for injecting a formulation of double crosslinked HA—collagen (grey curve). The two curves were largely similar.

Figure 46:
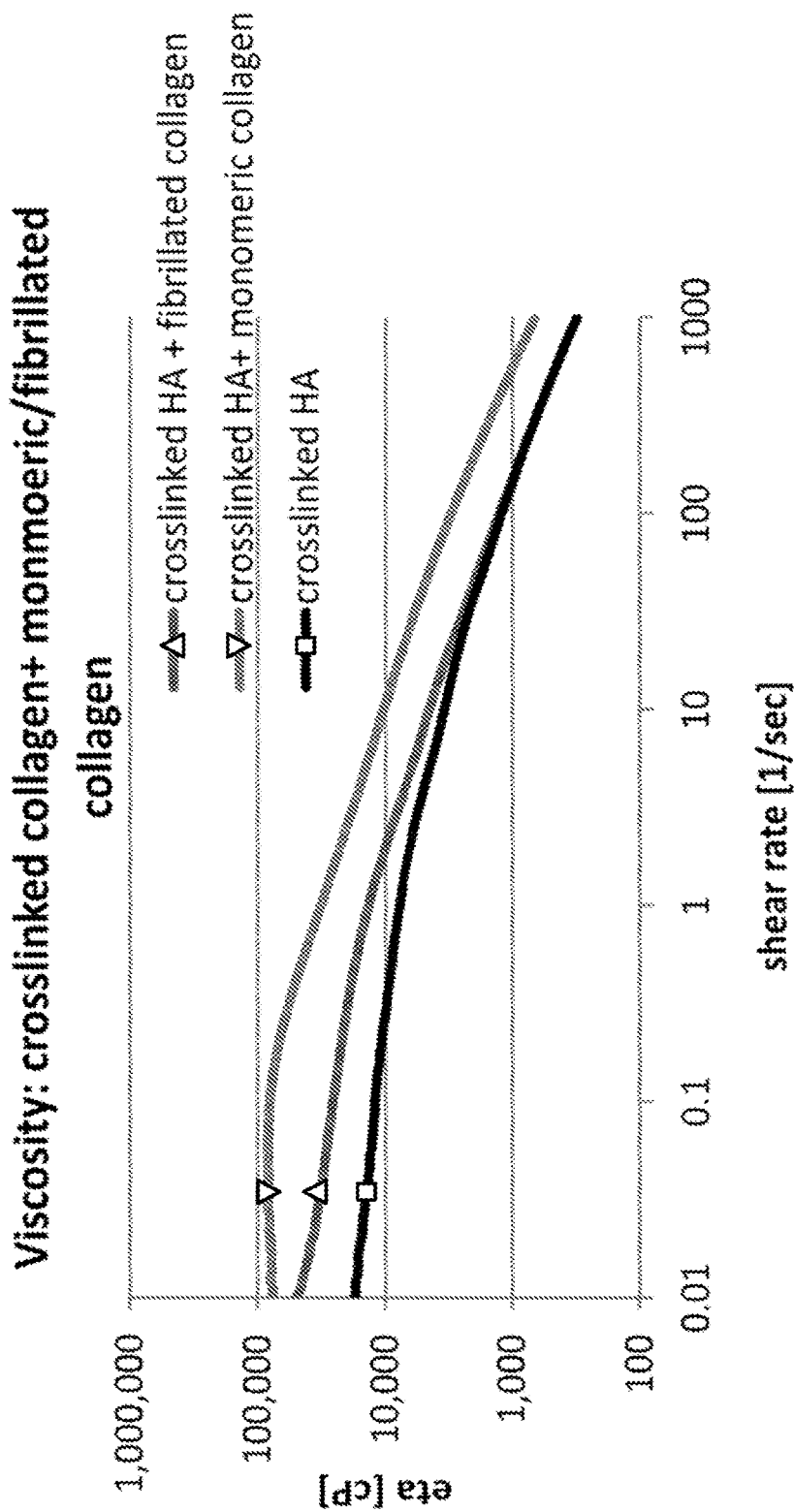
FIG. 46 shows a comparison of the viscosity (eta [η], cP) of crosslinked hyaluronic acid (HA) (black), crosslinked hyaluronic acid (HA)+monomeric collagen (▼), or crosslinked hyaluronic acid (HA)+fibrillated collagen (▲).

As shown in FIG. 46, the viscosity of crosslinked hyaluronic acid (HA) (black Ecurve) was compared to the viscosity of crosslinked hyaluronic acid (HA) with monomeric collagen (▲ curve) or fibrillated collagen (▼ curve). The viscosity for crosslinked HA with fibrillated collagen was lower than that of crosslinked HA with monomeric collagen, but still greater than that of crosslinked HA alone. Concentrations were as for FIG. 44.

Figure 47:
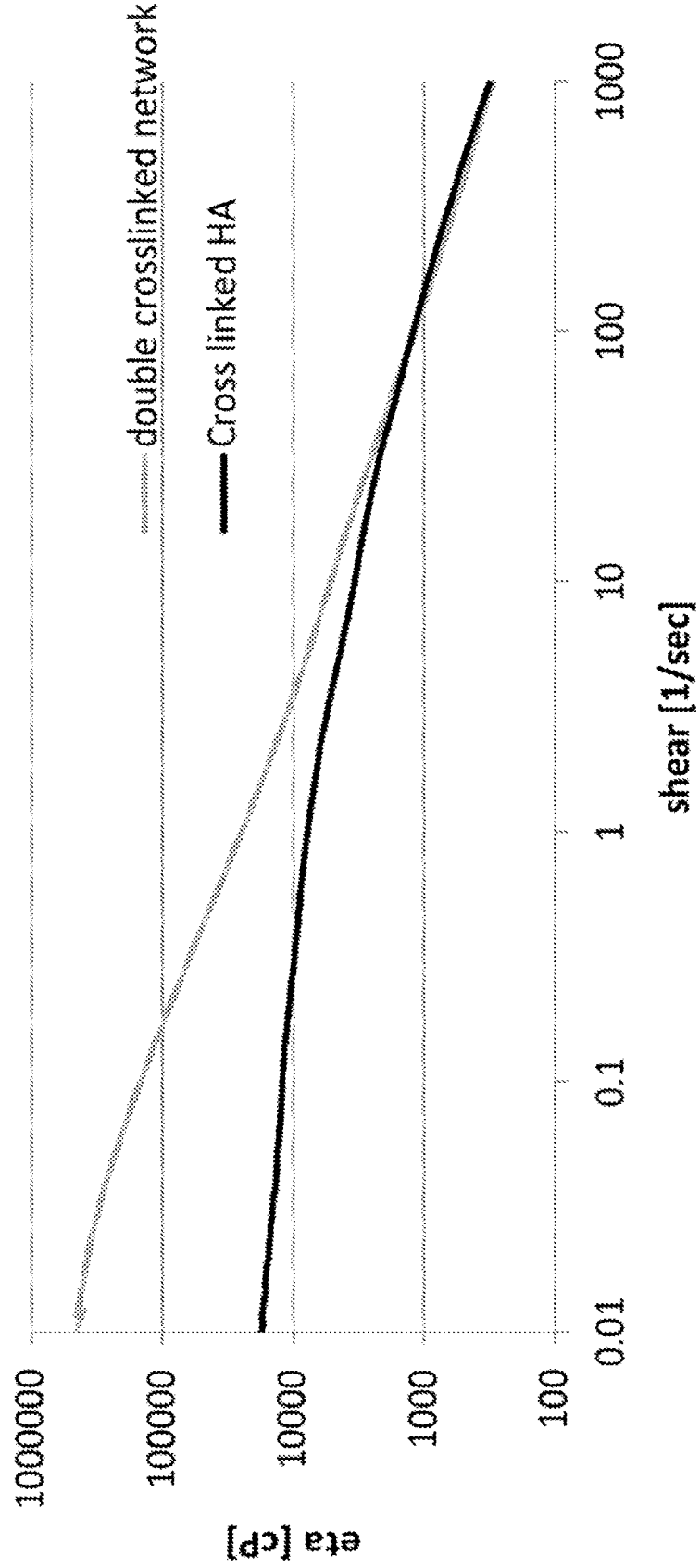
FIG. 47 shows a comparison of the viscosity (eta [η], cP) of crosslinked hyaluronic acid (HA) (black) or a double crosslinked network of crosslinked hyaluronic acid (HA) and collagen (grey).

As shown in FIG. 47, the viscosity of crosslinked hyaluronic acid (HA) was compared to the viscosity of a formulation of double crosslinked hyaluronic acid (HA)-collagen (grey curve). The viscosity for double crosslinked HA-collagen was greater than that of crosslinked HA alone.

The addition of rhCollagen, either monomeric or fibrillated, crosslinked or not crosslinked, to a crosslinked HA dermal filler did not significantly increase the expression force, allowing similar performance to the physician, but on the other hand it significantly increased the material viscosity, allowing better skin lifting upon injection.

Example 22. Transdermal Polymerization of Recombinant Human Collagen Methacrylate (rhCollagenMA)

Figure 48A:
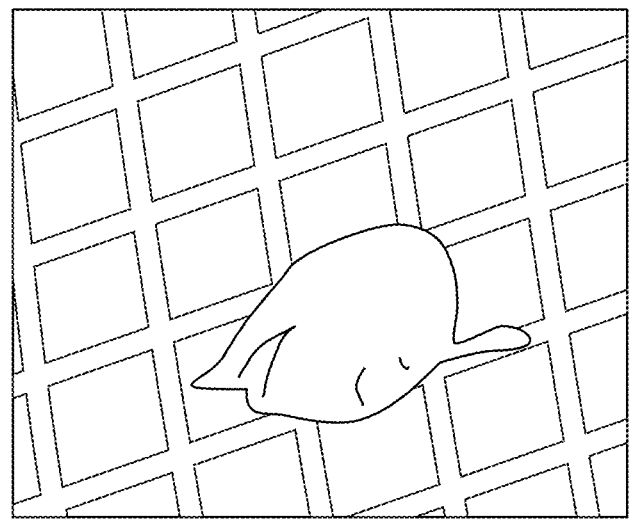
FIGS. 48A-B show photographs of (A) a mouse patch laid on top of a methacrylated collagen (collMA/rhCollagenMA) solution and (B) methacrylated collagen (collMA/rhCollagenMA) polymerized and integrated into the skin tissue upon illumination with a white light-emitting diode (LED) torch through the skin.
Figure 48B:
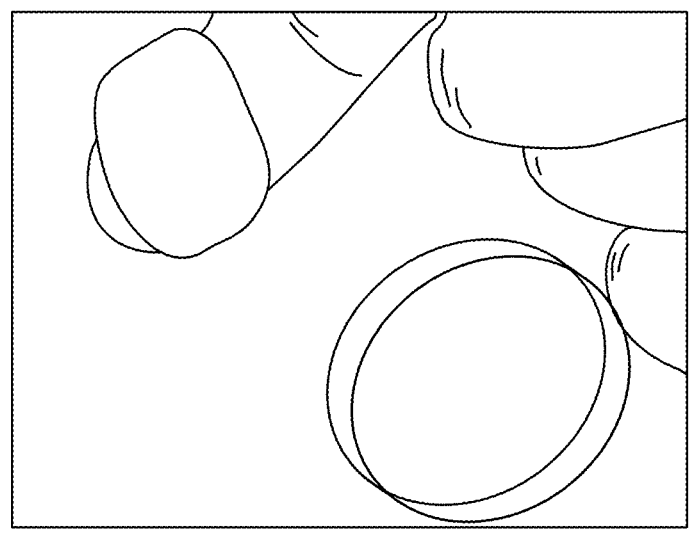

As shown in FIGS. 48A-B, a liquid solution of recombinant human collagen methacrylate (rhCollagenMA) with Eosin Y/TEA as photoinitiator, injected underneath a mouse skin patch (FIG. 48A), was transdermally polymerized by illuminating the skin with LED white light from a white LED torch for 6 minutes. The rhcollagenMA polymerized and was integrated into the skin tissue (FIG. 48B).

The rhCollagenMA polymerizes under the skin when illuminated for 6 minutes with a small LED torch in the presence of eosinY/TEA as photoinitiator.

Example 23. Formulation of Double Crosslinked Dermal Fillers: Two-Step Synthesis Objective: To develop injectable dermal fillers for use improving the appearance of the skin surface for either aesthetic or clinical purposes. The dermal fillers are composed of type I recombinant human Collagen (rhCollagen) or its modified form, methacrylated rhCollagen (MA-rhCol) and crosslinked hyaluronic acid (HA).

The double crosslinked product, wherein crosslinked-HA is further crosslinked to rhCollagen (FIG. 49), is designed to be a scaffold wherein hyaluronic acid provides the structural support and void filling, while the rhCollagen enhances cell proliferation promoting tissue regeneration. The scaffold will eventually degrade leaving the newly formed tissue. Another objective is to analyze the double crosslinked dermal filler, examining the lifting effect (tissue augmentation) provided by crosslinked-HA, with tissue regeneration promoted by type I rhCollagen.

Methods:
Double Crosslinking
—HA Crosslinking—

High Molecular Weight Hyaluronic Acid (range 700 KDa-3 MDa, preferably 1.5M Da) was dissolved under alkaline conditions (pH 12-13, e.g. in 0.3N Na(OH)) at a concentration ranging between 50 to 200 mg/ml (preferably 100 mg/ml). Crosslinker 1.4-butanediol diglycidyl ether (BDDE) was added to the solvent in a ratio ranging between 1 to 50% of the HA disaccharides amounts (preferably 6, 8, 10%) prior to dissolving the HA. In some embodiments of this formulation, the HA comprises methacrylated-HA (MA-HA).

HA crosslinking was done at room Temp for 24 h.
Addition of Lower MW HA and Neutralization Lower molecular weight HA (50 KDa to 1000 KDa, preferably 300 to 700 KDa) ranging between 1 to 30% of the total HA amount (preferably 5-10%) was dissolved in water at a concentration ranging between 10 to 100 mg/ml (preferably 30 mg/ml). In some embodiments of this formulation, the HA comprises methacrylated-HA (MA-HA).

Prior to mixing the non-crosslinked HA with the crosslinked HA, HCl is added to the non-crosslinked HA in an amount necessary to neutralize the pH of the crosslinked HA. Phosphate buffer (PB) and NaCl are added to a final concentration of 0.1M PB and 0.2M NaCl.

Neutralization of rhCollagen

Prior to mixing the rhCollagen with HA, rhCollagen is brought to 0.1M in PB+0.2M NaCl.

Mixing HA+rhCollagen

HA (crosslinked+non-crosslinked HA) is mixed with rhCollagen in a ratio HA:rhColalgen ranging between (6:1, 5:1, 4:1, 3:1, 2:1, 1:1, 1:2, 1:3, 1:4, 1:5, 1:6) and kept at 2-8° C. The final concentration of HA is between about 5-50 mg/ml. The final concentration of rhCollagen or MA-rhCollagen is between about 1-50 mg/ml.

Second Crosslinking

When HA and rhCollagen were well mixed, a second crosslinking was performed with 1-[3-(Dimethylamino)propyl]-3-ethylcarbodiimide methiodide (EDC): an amount of EDC equal to 10 to 100 fold (preferably 50 fold) the amount of free amines in the rhCollagen was dissolved in (0.1

MPB+0.2M NaCl), added to the crosslinked HA-rhCollagen mixture and mixed. The second crosslinking is performed in the dark for 2-3 h at 2-8° C.

Dialysis

The double crosslinked material was then dialyzed vs. either PBS, 1 mM HCl or vs. low phosphate buffer (Low phosphate buffer preparation: (a) Stock solution: 162 mM Sodium phosphate dibasic brought to pH 11.2 with 10 N Na(OH); (b) dilute the stock solution 1:1000 in 0.1 mM HCL.

Rheological and Mechanical Evaluation

Storage and loss moduli were measured, e.g., using a HAAKE-RHEO STRESS 600™ instrument (THERMO SCIENTIFIC™) using a cone (1-degree) vs. plate configuration (C35/1). Frequency sweep measurements were performed at a constant deformation (e.g., 0.8%) with a range of frequencies (e.g., 0.02-100 Hz). Optionally various ratios or crosslinking ratios of one or both components were tested. First and second crosslinking can be tuned to control the final product storage and loss moduli.

Injectability measurements were taken, e.g., using a MULTITEST 1-/i MECMESIN™ machine as a function of plunger displacement (mm) to observe expression force.

Injectability

Injectability measurements were taken using a MULTITEST 1-/i MECMESIN™ machine, as described above. 1 ml LUER-LOK™ syringes (BECTON-DICKINSON™) and 30G needles were used for Formulations 2.2A, and 3 (Table 8). Expression force as a function of plunger displacement of representative double crosslinked Formulations 2.2A, and 3 (Table 8) was compared to a commercially available dermal filler, also using a 30G needle.

Animal Studies 200 microlitres of Formulation 2, or 2A, or control were injected subcutaneously into the back of Sprague dawley rats. Histology was performed after 1 week.

TABLE 8

Formulations of compositions.

| Formulation | HA crosslinking ratio | HA:rhCollagen ratio | Comments |
| --- | --- | --- | --- |
| 1 | 10% | 2:1 | Dialyzed vs. phosphate buffer saline |
| 1A | 10% | 2:1 | Dialyzed vs. 1 mM HCl and neutralized |
| 2 | 6% | 2:1 | Dialyzed vs. phosphate buffer saline |
| 2A | 6% | 2:1 | Dialyzed vs. 1 mM HCl and neutralized |
| 3 | 8% | 2:1 | Dialyzed vs. phosphate buffer saline |

Rheological and Mechanical Evaluation

Figure 50:
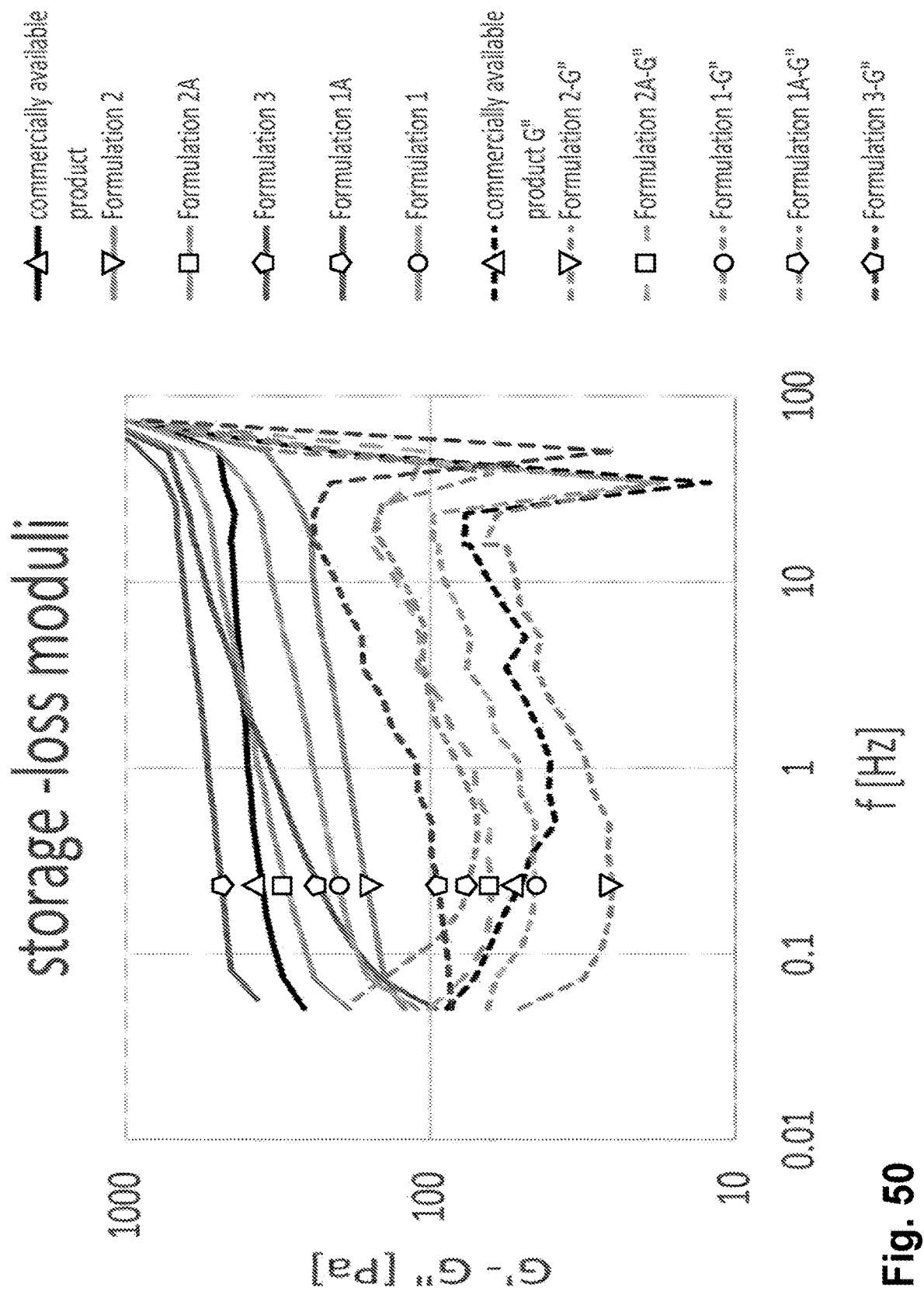
FIG. 50 shows a graph depicting rheological measurements of storage and loss moduli for various double crosslinked formulations measured using a HAAKE-RHEO STRESS 600™ instrument (THERMO SCIENTIFIC™) using a cone (1-degree) vs. plate configuration (C35/1). Frequency sweep measurements were performed at a constant deformation of 0.8% and a frequency ranging from 0.02-100 Hz. Storage (solid lines) and loss (dashed lines) moduli of representative double crosslinked formulations (see Table 7) compared to a commercially available dermal filler (solid and dashed lines: solid black—commercially available product; solid ▼—formulation 2; solid □—formulation 2A; solid upward pentagon—Formulation 3; solid downward pentagon—Formulation 1A; solid ○—Formulation 1; dashed ▲—commercially available product G"; dashed ▼—Formulation 2G"; dashed □—Formulation 2A-G"; dashed ○—Formulation 1G"; dashed downward pentagon—Formulation 1A G"; dashed upward pentagon—Formulation 3").
Figure 51:
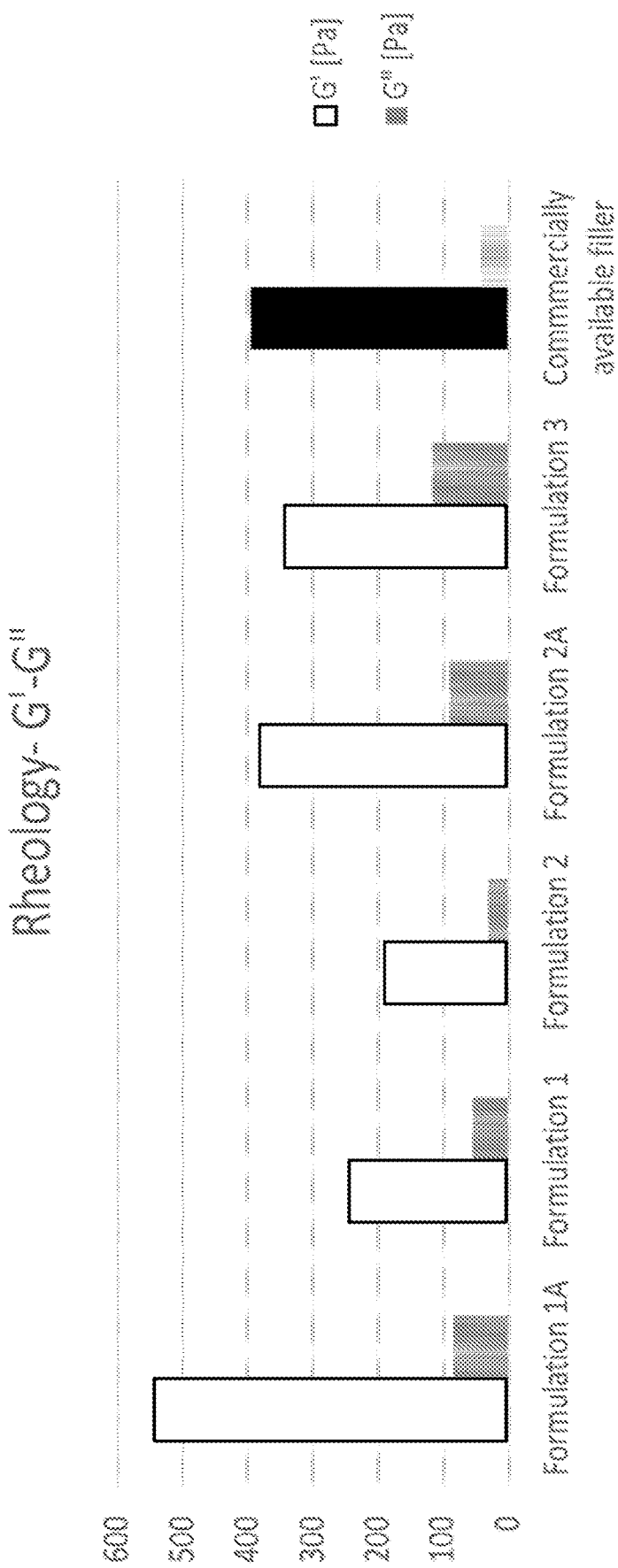
FIG. 51 shows a graph depicting a comparison at $f=1$ Hz of the storage and loss moduli of formulations reported in FIG. 50. (open barsG' [Pa]; grey bars G" [Pa])

As shown in FIG. 50, storage (solid lines) and loss (dashed lines) moduli of the representative double crosslinked formulations (Table 8) were comparable to the commercially available dermal filler. A comparison of the storage and loss moduli of these formulations and this commercial filler at f=1 Hz is shown in FIG. 51.

Figure 52:
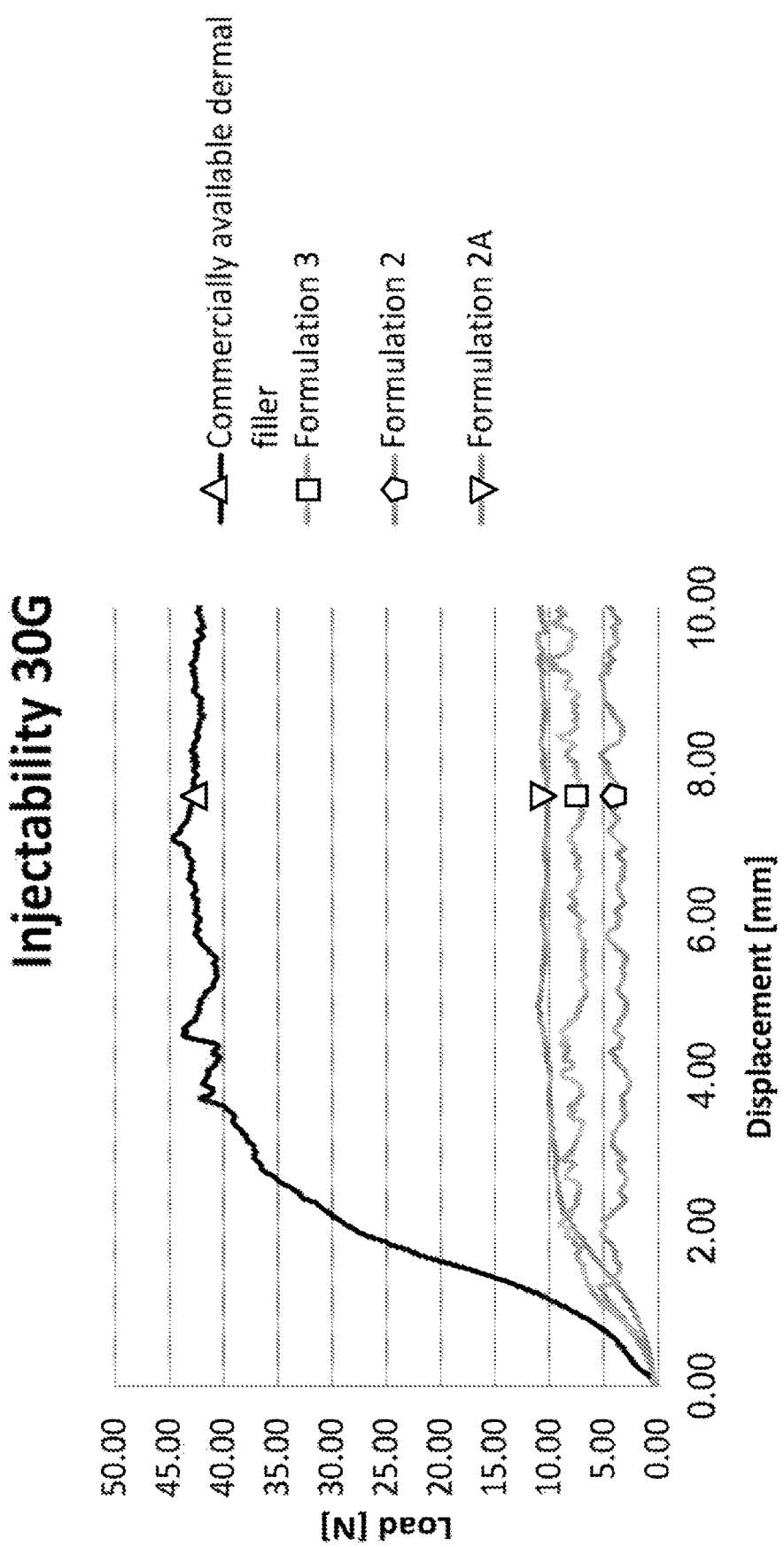
FIG. 52 shows a graph depicting injectability of selected double crosslinked formulations measured using a MULTI-TEST 1-i MECMESIN™ compression tester machine with 1 ml LUER-LOK™ syringes (BECTON-DICKINSON™) and 30G needles used for Formulations 2.2A, and 3 (Table 8). The commercially available dermal filler is included for comparison with the double crosslinked formulations. Express force as a function of plunger displacement (12 mm/min) of representative double crosslinked formulations was compared to a commercially available dermal filler. (Black ▲ Commercially available dermal filler; Grey □-Formulation 3; Grey upward pentagon—Formulation 2; Grey ▼—Formulation 2A)

The first and second crosslinking can be adjusted to control the final product storage and loss moduli. As shown in FIG. 52, the expression force required to inject the double crosslinked formulations through a 30G needle was significantly lower than the expression foce required to inject the commercially available dermal filler.

Histology and Animal Studies

Animal studies were conducted as described above. Formulations 2 and 2A (see Tables 8 and 9) were compared with a commercially available dermal filler product following subcutaneous injections. Inflammation is the first step in the regeneration process, as long as it is not too severe.

The average histology scores at day 7 post subcutaneous injections are compared to the commercially available dermal filler in Table 9.

TABLE 9

Day 7 Histology Scores.

| | Inflammation score | % Lymphocytes | % Macrophages | % Neutrophils | Necrosis score | Fibrosis Score |
| --- | --- | --- | --- | --- | --- | --- |
| Formulation 2 | 2 | 50 | 40 | 10 | 0 | 2 |
| Formulation 2A | 2.25 | 42.5 | 42.5 | 15 | 0 | 2 |
| Commercially available material/control | 1.333333 | 36.66667 | 53.33333 | 10 | 0 | 1.333 |

Results:

A skilled artisan would appreciate that the two-step double cross linking here uses two-types of crosslinker. The 1st step includes HA and BDDE as crosslinker. In the second step collagen and non-crosslinked HA are added and cross linking is achieved using EDC. It is expected that the difference in cross linking chemistry and sequence of actions, as compared to all other methods of dermal filler preparation, should result in dermal filler compositions having different properties including mechanical properties, tissue interaction, and degradation rate.

Formulations of HA:rhCollagen were made using the above methods, with representative formulations shown in Table 8.

As shown in Table 9, double crosslinked formulations have a higher fibrosis score and a higher inflammation level than the commercially available dermal filler, indicating a more advanced process of tissue regeneration.

Figure 56:
FIG. 56 presents representative histology images at day 7 following subcutaneous injection of Formulations 2.2A, and control (commercially available dermal filler) into the back of Sprague Dawley rats. In each case, the arrow points to an enhanced inflammation reaction in Formulations 2 and 2A (not severe) indicating initiation of tissue regeneration.

FIG. 56. shows representative histology images at day 7 post subcutaneous injection of formulations 2.2A, or control. Arrows point to the enhanced inflammation reaction in formulation 2 and 2A (but still not severe) indicating initiation of tissue regeneration. "Blebs" refer to bullae formed by the injected material.

Figure 57:
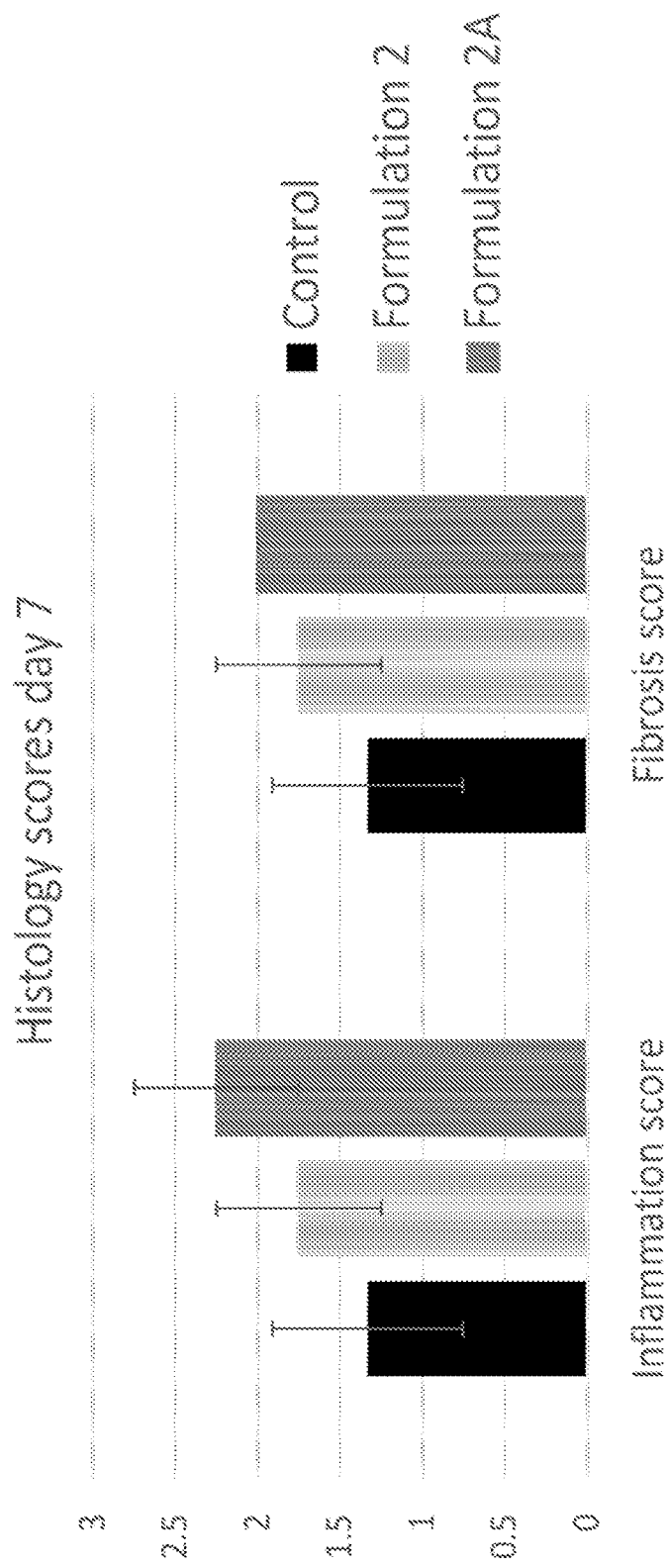
FIG. 57 presents the histology score at day 7 of formulation 2.2A and control from the tissue analyzed in FIG. 56. (Blacl—control; Light Grey Formulation 2; Dark Grey Formulation 2A)

Histology scores for the samples shown in FIG. 56 are presented as a bar graph in FIG. 57, wherein the higher inflammation scores and fibrosis scores for double crosslinked Formulations 2 and 2A indicate they shown improved tissue regeneration compared with control.

Summary/Conclusion

Double Crosslinked formulations have been developed to have easy injection through 27 to 32 G needles and a wide range of stiffness G'-G". Histology results following one-week injection show enhanced initiation of the tissue regeneration process.

Example 24. Photocurable Dermal Filler

Objective: To analyze the properties of a photocurable dermal filler. The photocurable formulation is a semi IPN before curing and ends up being an IPN (interpenetrated network) after curing. Meaning two entangled networks, each one crosslinked to itself and not crosslinked to the other.

Methods:

A mixture of rhCollagen and Methacrylated rhCollagen was added to already crosslinked HA, crosslinked as in Example 23, to a final concentration of 1-10 mg/ml wherein the ratio between the methacrylated to non-methacrylated rhCollagen is 1:0, 1:1, 1:2, 1:3, 1:4, 0:1, 2:1, 3:1, or 4:1. The final concentration range of MA-rhCollagen is 0-12/mg/ml and the final concentration range of non-modified rhCollagen is 0-12 mg/ml. The ratio of the crosslinked HA To MA-rhCollagen is 1:1, 2:1, 3:1, 4:1, 5:1, 6:1, 1:2, 1:3, 1:4, 1:5, 1:6, or 0:1. The final concentration of HA is 12-25 mg/ml, the final concentratil of rhCollagen (MA+non-modified) is 1-24 mg/ml.

Visible light photoinitiator was added to the mixture (e.g. compositions of Eosin Y, triethanolamine and N-vinylpyrrolidone).

Rheological Studies 1.6 ml samples of each of representative Formulations 4, 5, and 6 and the Control (see Table 10 below) were poured into cylindrical molds and cylinders of 2 cm diameter and 0.5 mm height and were cured by a constant amount of visible light illumination using a white LED flashlight for 6 minutes.

Formulations of highly crosslinked hyaluronic acid (HA) were mixed with combinations of rhCollagen and/or rH Collagen methacrylate at 3 different representative ratios with a constant amount of visible light photoinitiator, using the above methods, as shown in Table 10. Highly BDDE crosslinked HA (but could be any other crosslinker as well, or even a standard commercial filler made of only crosslinked HA) was mixed with rhCol and rhColMA in different ratios. The result is a crosslinking of the HA and a crosslinking of the entangled rhCoMA after curing. This forms an interpenetrated network where the HA is crosslinked to itself and the collagen is crosslinked to itself within the HA network.

TABLE 10

Formulations tested before and after photocuring.

| | Crosslinked HA | rhCollagen MA | rhCollagen |
|---|---|---|---|
| Control (crosslinked HA) | 23 mg/ml | — | — |
| Formulation 4 | 19 mg/ml | 2.5 | — |
| Formulation 5 | 19 mg/ml | 1.25 | 1.25 |
| Formulation 6 | 19 mg/ml | 0.64 | 1.83 |

Storage and loss moduli were measured before and after illumination as described below.

a. Before Curing

Storage and loss moduli were measured using a HAAKE-RHEO STRESS 600™ instrument (THERMO SCIENTIFIC™) using a cone (1) vs. plate configuration (C35/1). Frequency sweep measurements were performed at a constant deformation of 0.8% with a frequency ranging from 0.02 Hz to 100 Hz.

b. After Curing

Storage and loss moduli of photocured cylinders were measured using a HAAKE-RHEO STRESS 600™ instrument (THERMO SCIENTIFIC™) using a serrated plate vs. plate configuration (PP20). Frequency sweep measurements were performed at a constant shear stress of 3 Pa with a frequency ranging from 0.02 Hz to 100 Hz, under a constant normal load of 0.3 N.

Injectability

Injectability measurements were taken using a MULTITEST 1-i MECMESIN™ machine, as described above for Formulations 4, 5, and 6 and for highly crosslinked HA as a control. 1 ml LUER-LOK™ syringes (BECTON-DICKINSON™) and 30G needles were used for all samples (Table 10). Expression force as a function of plunger displacement (12 mm/min) of representative Formulations 4, 5, and 6 (Table 10) was compared to highly crosslinked HA.

Animal Studies

Animal studies were conducted as described above. Formulation 4 (see Tables 10 and 11) was compared with highly crosslinked HA following subcutaneous injections into the back of rats.

Results:

Rheololigal and Mechanical Evaluation

Figure 53:
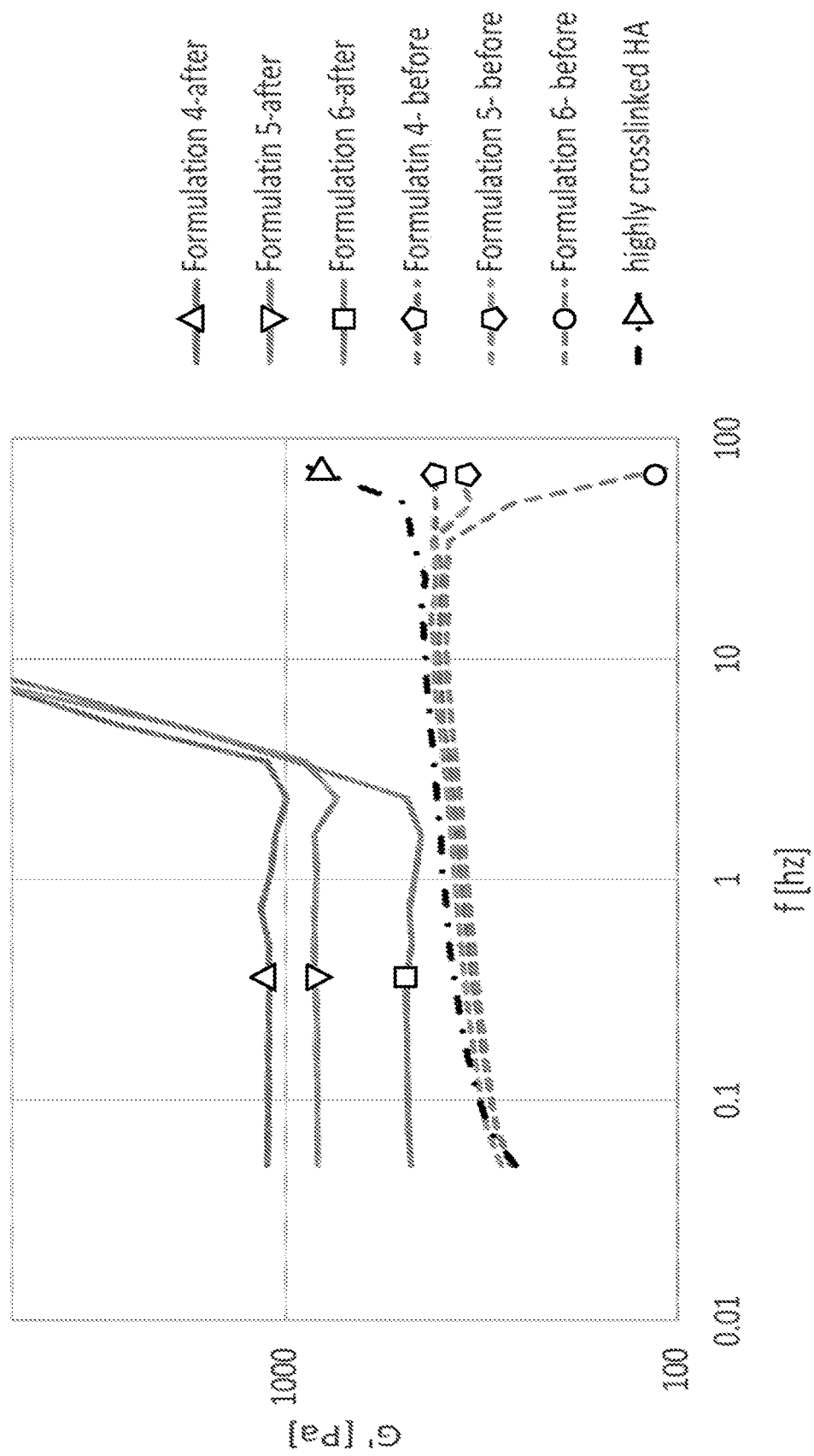
FIG. 53 shows a graph depicting rheological measurements of storage and loss moduli for various combinations (see Table 10) of highly crosslinked hyaluronic acid (HA), rhCollagen methacrylate (MA), and/or rhCollagen before (dashed lines) and after (solid lines) photocuring with visible light, as a comparison with highly crosslinked HA (black intermittent line sideways triangle). Before photocuring, storage and loss moduli were measured using a HAAKE-RHEO STRESS 600™ instrument (THERMO SCIENTIFIC™) using a cone (1-degree) vs. plate configuration (C35/1). Frequency sweep measurements were performed at a constant deformation of 0.8%, frequency ranging 0.02-100 Hz. After photocuring (visible light illumination with a white LED flashlight for 6 minutes), storage and loss moduli were measured using a HAAKE-RHEO STRESS 600™ instrument (THERMO SCIENTIFIC™) using a serrated plate vs. plate configuration (PP20). Frequency sweep measurements were performed at a constant shear stress of 3 Pa, frequency ranging 0.02-100 Hz, under a constant normal load of 0.3 N. (Solid ▲-Formulation 4-after; Solid ▼—Formulation 5-after; Solid □—Formulation 6-after; Dashed upward pentagon—Formulation 4-before; Dashed downward pentagon—Formulation 5-before; Dashed ○—Formulation 6-before; Dashed-dot Black sideways triangle—highly crosslinked HA)
Figure 54:
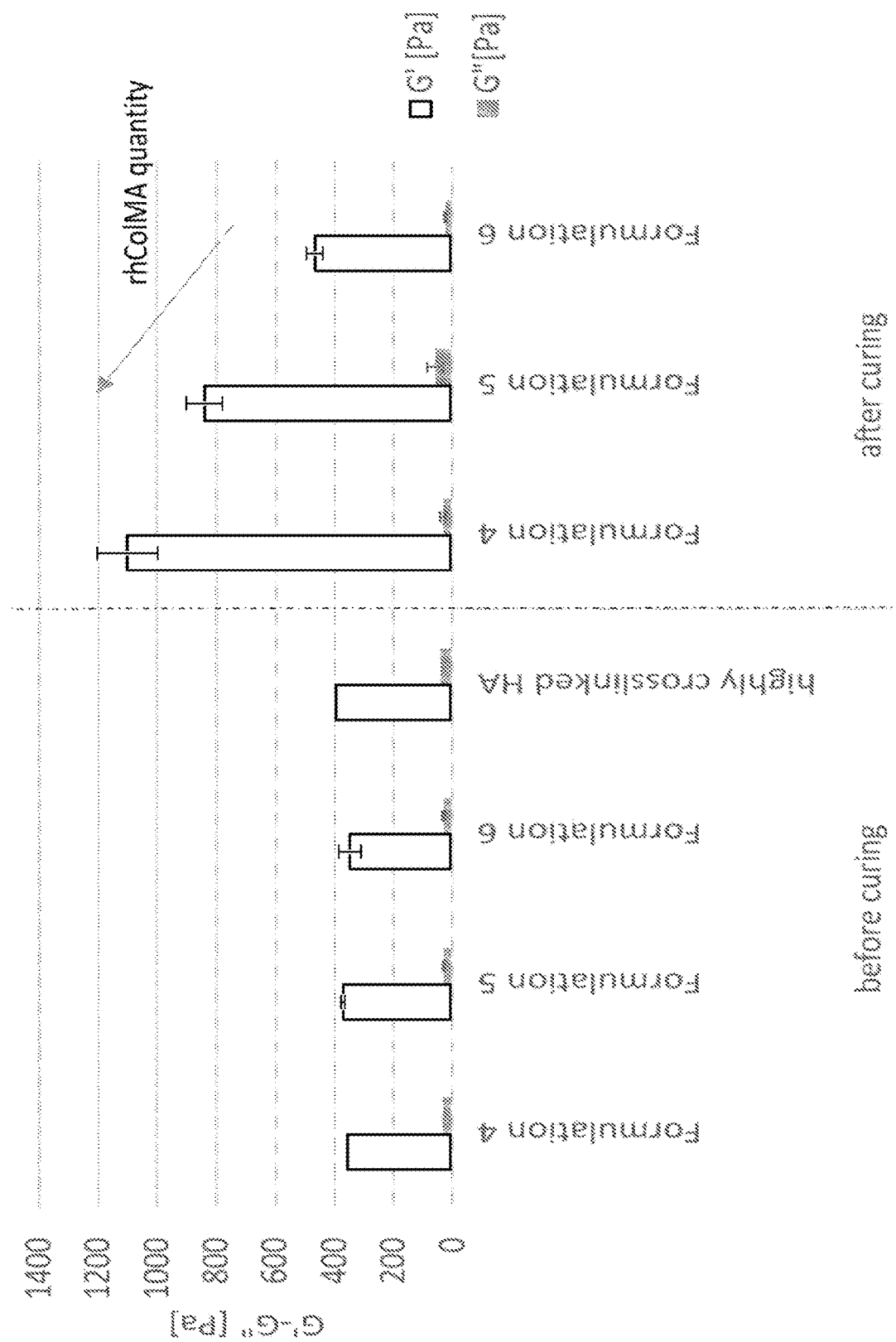
FIG. 54 shows a graph depicting a comparison of the storage and loss moduli before and after photocuring of the formulations 4, 5, and 6 in Table 10, as well as non-curable highly crosslinked HA, at a frequency of $F=1$ Hz. (Open bar G' [Pa]; Grey bar G" [Pa])

FIG. 53 shows a comparison of storage moduli before and after photocuring of Formulations 4, 5, and 6 with highly crosslinked HA (see Table 10). A comparison of the storage and loss moduli of these formulations, both before and after photocuring, and highly crosslinked HA (not curable) at a frequency of f=1 Hz is shown in FIG. 54. The arrow represents "Trend": the stiffness increase as the quantity of rhCoMA increases.

Injectability

Figure 55:
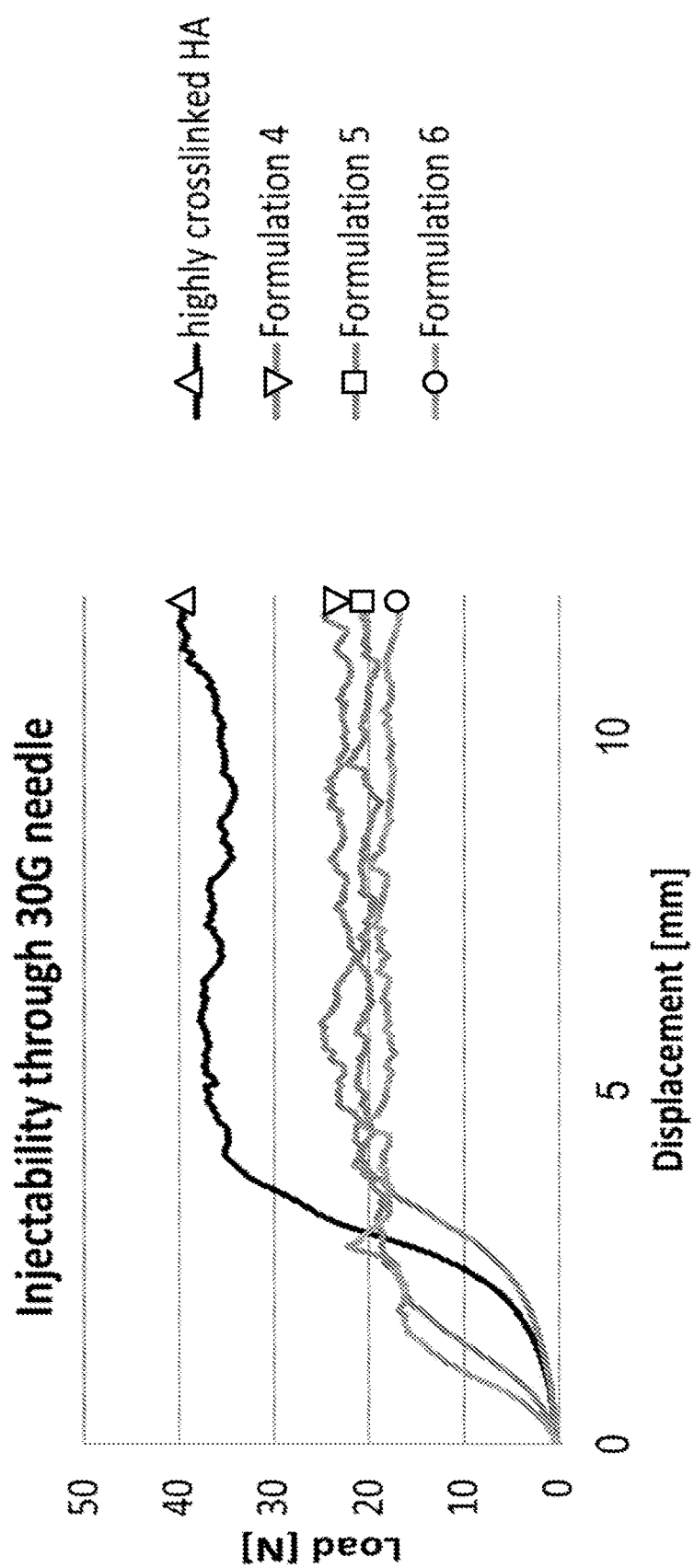
FIG. 55 shows a graph depicting injectability of selected double crosslinked formulations measured using a MULTI-TEST 1-i MECMESIN™ compression tester machine with 1 ml LUER-LOK™ syringes (BECTON-DICKINSON™) and 30G needles used for all samples. Express force as a function of plunger displacement (12 mm/min) of representative double crosslinked formulations was compared to highly crosslinked HA. (Black ▲—Highly crosslinked HA; Grey ▼—Formulation 4; Grey ☐—Formulation 5; Grey ○—Formulation 6)

As shown in FIG. 55, the expression force required for the injection of Formulations 4, 5, and 6 through a 30G needle was lower than the expression force required for the crosslinked HA alone, allowing easier usability for the physician and easier injection at fine lines and delicate areas of the patient. However, after in situ photocuring (following injection), the material stiffness can be adjusted to be significantly higher than crosslinked HA alone (see FIGS. 53 and 54).

Histology and Animal Studies

The average histology score for Formulation 4 at day 7 of subcutaneous injections was compared to highly crosslinked HA in Table 11.

TABLE 11

Day 7 Histology Scores.

| | Inflammation score | % Lymphocytes | % Macrophages | % Neutrophils | Necrosis score | Fibrosis Score |
|---|---|---|---|---|---|---|
| Formulation 4 | 1.5 | 42.5 | 50 | 7.5 | 0 | 1.5 |
| Commercially available material/control | 1.333333 | 36.66667 | 53.33333 | 10 | 0 | 1.333 |

As shown in Table 11, Formulation 4 has a higher fibrosis score and a higher inflammation level than the highly crosslinked HA, indicating a more advanced process of tissue regeneration.

Figure 58:
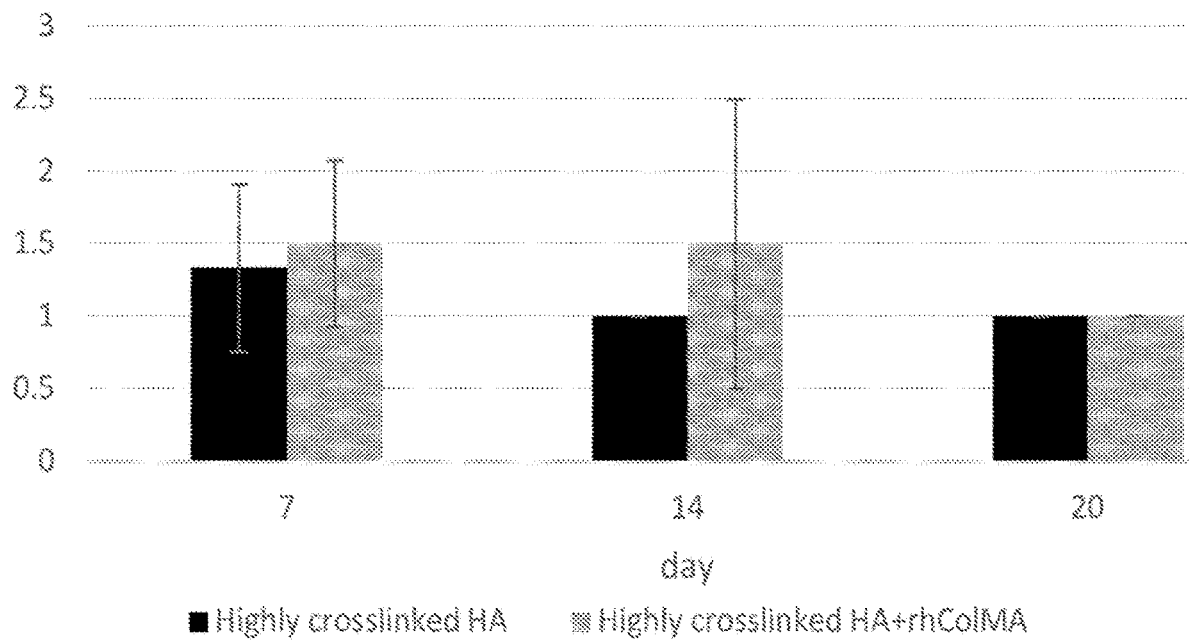
FIG. 58 presents photocurable histology scoring results of photocurable dermal fillers on day 7, day 14, and day 20. (Black—Control highly crosslinked HA; Grey—Formulation 4 highly crosslinked HA and rhColMA)
Figure 59:
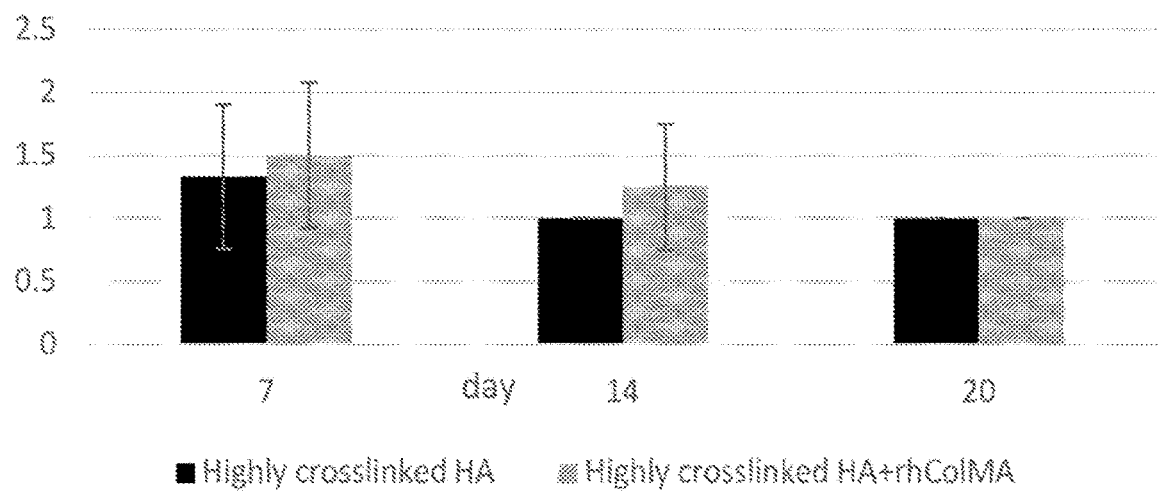
FIG. 59 presents fibrosis score results at day 7 and day 14 following injections of formulation 4 (Grey—highly crosslinked HA+rhColMA) vs. control (Black—highly crosslinked HA).

FIG. 58 and FIG. 59 show that Formula 4 has a higher inflammation score and fibrosis score than control dermal filler, indicating improved initiation of tissue regeneration process with the dermal filler of Formula 4.

Conclusion/Summary

The photo curable filler was developed to have a relative low stiffness before injection allowing easy injection through 27-32G needles but a significant improve in stiffness (tunable) following photocuring. Stiffness can be tuned by controlling the final ratio between rhCol and rhColMA. This technology allows the physician to sculpture the filler to the desired shape before fixing it with the photocuring illumination. The injected material strongly adheres to the sourroundy tissue. Preliminary in vivo results indicate initiation of regeneration process.

Example 25. In Vivo Animal Studies: Independent Injection of Dermal Filler Components Objective: To separately inject HA or its methacrylated derivative, and methacrylated rhCollagen into the subcutaneously at a semiliquid phase and crosslink them in situ (crosslinking is rhColMA to rhColMA), post injection, by white light illumination through the skin. This approach allows easier injection and in situ sculpturing of the material shape, just before fixing it by light polymerization. Using a subcutaneous rat model, the cell proliferation, tissue augmentation, and characteristics of matrix degradation overtime will be assessed.

Methods: In this model, sample formulation components (HA or its methacrylated derivative, and methacrylated rhCollagen and photoinitiator) for evaluation will be injected subcutaneously to the back of male Sprague Dawley rats and the injection sites followed for up to 20 days. Injections will be at about the same time (immediately one after the other), at the same location. Component solutions may be massaged in situ prior to or concurrent with or following crosslinking. The subcutaneous rat model is chosen as it is the simplest model to estimate biocompatibility, lifting effect and persistence. Moreover, Hillel at al. published a validation study for this specific model (Dermatol Surg 2012; 38:471-478).

Animals will be sedated with Ketamine/Xylasine prior to each treatment. The animal's back will be shaved, and the injection sites marked on the shaved skin. Each rat will be injected with 0.2 ml of the formulation using 27.5-32G needle at distanced locations on the dorsal plane, over all, 6 injections per rat.

The formulations will be crosslinked post injection by transdermal illumination of the injection site with a white light LED torch for 2 minutes.

All animals will be observed for morbidity and mortality twice daily throughout the entire study period. Every three days (time points 0, 1, 4, 7, 11, 14, 18, and 21 days post injections) the height, width, and length of each bleb will be measured with caliper, and the ellipsoid volume of each bleb [(4/3)(7)(½ height)(½ length)(½ width)] calculated.

Animals will be sacrificed at time-points for example but not limited to 7, 14, and 21 days post-treatment.

At each scarification point, injections sites will be exposed and assessed macroscopically, and the blebs collected for histological assessment. Injections sites (including the blebs) will be excised with the overlying skin and, fixed in 4% formalin and embedded in paraffin.

Histology

Slides Preparation

Paraffin blocks will be sectioned at approximately 3-5 microns thickness, put on a glass slide, stained with Hematoxylin & Eosin (H&E) and Masson trichrome and covered by an automated machine. The histology evaluation of all the slides will be performed using a light microscope (Olympus BX60, serial NO. 7D04032).

Images will be taken at magnification of ×4. Image acquisition will be performed only on pathological changes and of representative animals.

Results:

Similar results to those obtained in Example 24 are expected, wherein the separate, independent injection of components of the photocurable dermal filler may provide increased ease of injection, for example due to decreased viscosity of the components compared with the formulation mix.

Although the dermal fillers, including cellular growth promoting scaffolds, and uses thereof have been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art.

What is claimed is:

1. A method of filling a tissue space under an epidermis comprising:
   (a) introducing a polymerizable solution into the tissue space, wherein the polymerizable solution comprises:
      (i) a methacrylated or thiolated derivative of a plant-derived type 1 recombinant human collagen (rhCollagen); and
      (ii) a photoinitiator; and
   (b) applying light to the surface of the epidermis superficial to said space to induce polymerization.

2. The method of claim 1, wherein said polymerizable solution further comprises a hyaluronic acid (HA), a poly(vinyl alcohol) (PVA), a polyethylene glycol (PEG), oxidized cellulose (QC), polymethylmethacrylate (PMMA) microspheres, tricalcium phosphate (TCP), calcium hydroxylapatite (CaHA), carboxymethylcellulose, crystalline nanocellulose (CNC), modified derivatives thereof, or a combinations thereof.

3. The method of claim 2, wherein said polymerizable solution components are introduced into the tissue space together as a mixture or independently at about the same location and about the same time, wherein when introduced into the tissue space independently:
   (a) the methacrylated or thiolated derivative of a plant derived type 1 recombinant human collagen and the photoinitiator are introduced together and independently from
   (b) said hyaluronic acid (HA), said poly(vinyl alcohol), said polyethylene glycol (PEG), oxidized cellulose (OC), polymethylmethacrylate (PMMA) microspheres, tricalcium phosphate (TCP), calcium hydroxylapatite (CaHA), carboxymethylcellulose, crystalline nanocellulose (CNC), said modified derivatives thereof, or said combinations thereof, which are introduced into the tissue space independently at about the same time.

4. The method of claim 2, further including a step of molding or sculpting the polymerizable solution or the components of the polymerizable solution, into a desired configuration in the tissue space, wherein said step is concomitant with, or subsequent to, the step of applying light and wherein the method is non-therapeutic, and the molding or sculpting step reduces lines, folds, fine lines, wrinkles, or scars, or a combination thereof, or the method is required as a result of any medical or dental condition, said dental condition comprising a gum disease or gum replacement.

5. The method of claim 2, wherein
   (a) the modified derivative of hyaluronic acid (HA), poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a methacrylated or thiolated derivative; or
   (b) the hyaluronic acid (HA), poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a crosslinked hyaluronic acid (HA), crosslinked poly(vinyl alcohol) (PVA), crosslinked polyethylene glycol (PEG), crosslinked oxidized cellulose (OC), crosslinked polymethylmethacrylate (PMMA) microspheres, crosslinked tricalcium phosphate (TCP), crosslinked calcium hydroxylapatite (CaHA), crosslinked carboxymethylcellulose, or crosslinked crystalline nanocellulose (CNC).

6. A method of filling a tissue space under an epidermis comprising introducing a double crosslinked dermal filler into the tissue space, wherein the double crosslinked dermal filler comprises:
   (a) a plant-derived human collagen comprising a methacrylated or thiolated derivative of type 1 recombinant human collagen (rhcollagen): and
   (b) a crosslinked hyaluronic acid (HA) or modified crosslinked derivative thereof, a crosslinked poly(vinyl alcohol) (PVA), a crosslinked polyethylene glycol (PEG), crosslinked oxidized cellulose (OC), crosslinked polymethylmethacrylate (PMMA) microspheres, crosslinked tricalcium phosphate (TCP), crosslinked calcium hydroxylapatite (CaHA), crosslinked carboxymethylcellulose, crosslinked crystalline nanocellulose (CNC), modified crosslinked derivatives thereof, or combinations thereof;
   wherein the plant-derived human collagen is crosslinked to the crosslinked hyaluronic acid (HA), the crosslinked poly(vinyl alcohol) (PVA), the crosslinked polyethylene glycol (PEG), the crosslinked oxidized cellulose (OC), the crosslinked polymethylmethacrylate (PMMA) microspheres, the crosslinked tricalcium phosphate (TCP), the crosslinked calcium hydroxylapatite (CaHA), crosslinked carboxymethylcellulose, the crosslinked crystalline nanocellulose (CNC), or the modified crosslinked derivatives thereof.

7. The method of claim 6, wherein
the modified derivative of hyaluronic acid (HA), poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a methacrylated or thiolated derivative;
and wherein when crosslinked HA is selected, the ratio of crosslinked HA to the plant-derived human collagen is 1:1, 2:1, 3:1, 4:1, 5:1, 6:1, 1:2, 1:3, 1:4, 1:5, 1:6, or 0:1.

8. The method of claim 6, wherein the method is nontherapeutic, and said method reduces lines, folds, fine lines, wrinkles, or scars, or a combination thereof.

9. A method of inducing a cellular growth promoting scaffold in a tissue space under an epidermis comprising introducing a solution into the tissue space, the solution comprising:
(a) a plant-derived human collagen which comprises a methacrylated or thiolated derivative of plant-derived type 1 recombinant human collagen (rhCollagen); and
(b) at least one growth factor or source thereof;
wherein said method promotes healing or replacement of a collagen-comprising tissue.

10. The method of claim 9, wherein
(a) the source of the at least one growth factor comprises a plasma or a platelet-rich plasma; or
(b) the collagen-comprising tissue comprises skin; or
(c) any combination thereof.

11. The method of claim 9, wherein said solution further comprises
(a) a hyaluronic acid (HA), a poly(vinyl alcohol) (PVA), a polyethylene glycol (PEG), oxidized cellulose (OC), polymethylmethacrylate (PMMA) microspheres, tricalcium phosphate (TCP), calcium hydroxylapatite (CaHA), carboxymethylcellulose, crystalline nanocellulose (CNC), modified derivatives thereof, or combinations thereof, and a photoinitiator to induce polymerization prior to, on concomitant with, application of visible light; or
(b) a crosslinked HA or a crosslinked PVA, or a crosslinked PEG, or a crosslinked OC, or crosslinked PMMA microspheres, or a crosslinked TCP, or a crosslinked CaHA, or a crosslinked carboxymethylcellulose, or a crosslinked CNC, wherein the plant-derived human collagen is crosslinked to the crosslinked HA or crosslinked PV A, or a crosslinked PEG, or a crosslinked OC, or crosslinked PMMA microspheres, or crosslinked TCP, or crosslinked CaHA, or crosslinked carboxymethylcellulose, or crosslinked CNC.

12. The method of claim 9, wherein said method is nontherapeutic and the cellular growth promoting scaffold fills in tissue space reducing lines, folds, fine lines, wrinkles, or scars, or a combination thereof.

\* \* \* \* \*